US012583817B2

(12) United States Patent
Anderson et al.

(10) Patent No.: US 12,583,817 B2
(45) Date of Patent: Mar. 24, 2026

(54) IONIZABLE LIPIDS AND COMPOSITIONS AND USES THEREOF

(71) Applicant: Massachusetts Institute of Technology, Cambridge, MA (US)

(72) Inventors: Daniel Griffith Anderson, Framingham, MA (US); Luke Hyunsik Rhym, Cambridge, MA (US); Allen Jiang, Boston, MA (US); Jacob Witten, Cambridge, MA (US); Idris Raji, Boston, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 590 days.

(21) Appl. No.: 18/080,299

(22) Filed: Dec. 13, 2022

(65) Prior Publication Data

US 2023/0183168 A1 Jun. 15, 2023

Related U.S. Application Data

(60) Provisional application No. 63/289,343, filed on Dec. 14, 2021.

(51) Int. Cl.

| | |
|---|---|
| ***C07D 237/16*** | (2006.01) |
| ***C07C 237/16*** | (2006.01) |
| ***C07D 207/09*** | (2006.01) |
| ***C07D 207/12*** | (2006.01) |
| ***C07D 211/82*** | (2006.01) |
| ***C07D 211/86*** | (2006.01) |
| ***C07D 231/12*** | (2006.01) |

(52) U.S. Cl.

CPC .......... *C07C 237/16* (2013.01); *C07D 207/09* (2013.01); *C07D 207/12* (2013.01); *C07D 211/82* (2013.01); *C07D 211/86* (2013.01); *C07D 231/12* (2013.01)

(58) Field of Classification Search

CPC .................................................... C07C 237/16

See application file for complete search history.

(56) References Cited

FOREIGN PATENT DOCUMENTS

| | | |
|---|---|---|
| WO | WO 2015/095346 A1 | 6/2015 |
| WO | WO 2018/170306 A1 | 9/2018 |
| WO | WO 2021/055835 A1 | 3/2021 |

OTHER PUBLICATIONS

Hajj et al., Tools for translation: non-viral materials for therapeutic mRNA delivery. Nat Rev Mater. Sep. 12, 2017;2:17056. doi: 10.1038/natrevmats.2017.56.

Han et al., An ionizable lipid toolbox for RNA delivery. Nat Commun. Dec. 13, 2021;12(1):7233. doi: 10.1038/s41467-021-27493-0.

Kowalski et al., Delivering the Messenger: Advances in Technologies for Therapeutic mRNA Delivery. Mol Ther. Apr. 10, 2019;27(4):710-728. doi: 10.1016/j.ymthe.2019.02.012. Epub Feb. 19, 2019.

Qiu et al., Lipid nanoparticle-mediated codelivery of Cas9 mRNA and single-guide RNA achieves liver-specific in vivo genome editing of Angptl3. Proc Natl Acad Sci U S A. Mar. 9, 2021;118(10):e2020401118. doi: 10.1073/pnas.2020401118.

International Search Report and Written Opinion, mailed May 9, 2023 for International Application No. PCT/US2022/052667.

International Preliminary Report on Patentability, mailed Jun. 27, 2024 for International Application No. PCT/US2022/052667.

Andries et al., Comparison of the gene transfer efficiency of mRNA/GL67 and pDNA/GL67 complexes in respiratory cells. Mol Pharm. Aug. 6, 2012;9(8):2136-45. doi: 10.1021/mp200604h. Epub Jun. 25, 2012.

Bahl et al., Preclinical and Clinical Demonstration of Immunogenicity by mRNA Vaccines against H10N8 and H7N9 Influenza Viruses. Mol Ther. Jun. 7, 2017;25(6):1316-1327. doi: 10.1016/j.ymthe.2017.03.035. Epub Apr. 27, 2017. Erratum in: Mol Ther. Aug. 3, 2022;30(8):2874. doi: 10.1016/j.ymthe.2022.07.013.

Ball et al., Achieving long-term stability of lipid nanoparticles: examining the effect of pH, temperature, and lyophilization. Int J Nanomedicine. Dec. 30, 2016;12:305-315. doi: 10.2147/IJN.S123062.

Barbier et al., The clinical progress of mRNA vaccines and immunotherapies. Nat Biotechnol. Jun. 2022;40(6):840-854. doi: 10.1038/s41587-022-01294-2. Epub May 9, 2022.

Billingsley et al., Ionizable Lipid Nanoparticle-Mediated mRNA Delivery for Human CAR T Cell Engineering. Nano Lett. Mar. 11, 2020;20(3):1578-1589. doi: 10.1021/acs.nanolett.9b04246. Epub Feb. 5, 2020. Author Manuscript, 26 pages.

Billingsley et al., Orthogonal Design of Experiments for Optimization of Lipid Nanoparticles for mRNA Engineering of CAR T Cells. Nano Lett. Jan. 12, 2022;22(1):533-542. doi: 10.1021/acs.nanolett.1c02503. Epub Oct. 20, 2021. Author Manuscript, 22 pages.

(Continued)

*Primary Examiner* — Yong S. Chong

(74) *Attorney, Agent, or Firm* — Wolf, Greenfield & Sacks, P.C.

(57) ABSTRACT

Provided herein are compounds, such as compounds of Formula (I), and pharmaceutically acceptable salts, hydrates, solvates, polymorphs, co-crystals, tautomers, stereoisomers, and isotopically labeled derivatives thereof, and compositions, methods, uses, and kits thereof. The compounds provided herein are lipids useful for delivery of polynucleotides, such as mRNA, for the treatment and/or prevention of various diseases and conditions (e.g., genetic disease, proliferative disease, hematological disease, neurological disease, liver disease, spleen disease, lung disease, painful condition, psychiatric disorder, musculoskeletal disease, a metabolic disorder, inflammatory disease, or autoimmune disease).

25 Claims, 54 Drawing Sheets

(56) References Cited

OTHER PUBLICATIONS

Chen et al., Rapid discovery of potent siRNA-containing lipid nanoparticles enabled by controlled microfluidic formulation. J Am Chem Soc. Apr. 25, 2012;134(16):6948-51. doi: 10.1021/ja301621z. Epub Apr. 10, 2012.
Cheng et al., Selective organ targeting (SORT) nanoparticles for tissue-specific mRNA delivery and CRISPR-Cas gene editing. Nat Nanotechnol. Apr. 2020;15(4):313-320. doi: 10.1038/s41565-020-0669-6. Epub Apr. 6, 2020. Author Manuscript, 22 pages.
Cornebise et al., Discovery of a Novel Amino Lipid That Improves Lipid Nanoparticle Performance through Specific Interactions with mRNA. Adv Funct Mater. Nov. 12, 2021;32(8):2106727. doi: 10.1002/adfm.202106727.
Eastman et al., Optimization of formulations and conditions for the aerosol delivery of functional cationic lipid:DNA complexes. Hum Gene Ther. Feb. 10, 1997;8(3):313-22. doi: 10.1089/hum.1997.8.3-313.
Espeseth et al., Modified mRNA/lipid nanoparticle-based vaccines expressing respiratory syncytial virus F protein variants are immunogenic and protective in rodent models of RSV infection. NPJ Vaccines. Feb. 14, 2020;5(1):16. doi: 10.1038/s41541-020-0163-z.
Feldman et al., mRNA vaccines against H10N8 and H7N9 influenza viruses of pandemic potential are immunogenic and well tolerated in healthy adults in phase 1 randomized clinical trials. Vaccine. May 31, 2019;37(25):3326-3334. doi: 10.1016/j.vaccine.2019.04.074. Epub May 10, 2019.
Fenton et al., Synthesis and Biological Evaluation of Ionizable Lipid Materials for the In Vivo Delivery of Messenger RNA to B Lymphocytes. Adv Mater. Sep. 2017;29(33). doi: 10.1002/adma.201606944. Epub Jul. 6, 2017.
Heyes et al., Cationic lipid saturation influences intracellular delivery of encapsulated nucleic acids. J Control Release. Oct. 3, 2005;107(2):276-87. doi: 10.1016/j.jconrel.2005.06.014.
Hou et al., Lipid nanoparticles for mRNA delivery. Nat Rev Mater. 2021;6(12):1078-1094. doi: 10.1038/s41578-021-00358-0. Epub Aug. 10, 2021.
John et al., Multi-antigenic human cytomegalovirus mRNA vaccines that elicit potent humoral and cell-mediated immunity. Vaccine. Mar. 14, 2018;36(12):1689-1699. doi: 10.1016/j.vaccine.2018.01.029. Epub Feb. 15, 2018.
Kauffman et al., Optimization of Lipid Nanoparticle Formulations for mRNA Delivery in Vivo with Fractional Factorial and Definitive Screening Designs. Nano Lett. Nov. 11, 2015;15(11):7300-6. doi: 10.1021/acs.nanolett.5b02497. Epub Oct. 20, 2015.
Kauffman et al., Rapid, Single-Cell Analysis and Discovery of Vectored mRNA Transfection In Vivo with a loxP-Flanked tdTomato Reporter Mouse. Mol Ther Nucleic Acids. Mar. 2, 2018;10:55-63. doi: 10.1016/j.omtn.2017.11.005. Epub Nov. 21, 2017.
Kim et al., Barriers to inhaled gene therapy of obstructive lung diseases: A review. J Control Release. Oct. 28, 2016;240:465-488. doi: 10.1016/j.jconrel.2016.05.031. Epub May 16, 2016. Author Manuscript, 68 pages.
Krishnamurthy et al., Manipulation of Cell Physiology Enables Gene Silencing in Well-differentiated Airway Epithelia. Mol Ther Nucleic Acids. Aug. 28, 2012;1(8):e41. doi: 10.1038/mtna.2012.36.
Liu et al., Fast and Efficient CRISPR/Cas9 Genome Editing In Vivo Enabled by Bioreducible Lipid and Messenger RNA Nanoparticles. Adv Mater. Aug. 2019;31(33):e1902575. doi: 10.1002/adma.201902575. Epub Jun. 19, 2019. Author Manuscript, 13 pages.
Lokugamage et al., Optimization of lipid nanoparticles for the delivery of nebulized therapeutic mRNA to the lungs. Nat Biomed Eng. Sep. 2021;5(9):1059-1068. doi: 10.1038/s41551-021-00786-x. Epub Oct. 6, 2021. Author Manuscript, 23 pages.
Maier et al., Biodegradable lipids enabling rapidly eliminated lipid nanoparticles for systemic delivery of RNAi therapeutics. Mol Ther. Aug. 2013;21(8):1570-8. doi: 10.1038/mt.2013.124. Epub Jun. 25, 2013.
Miao et al., Delivery of mRNA vaccines with heterocyclic lipids increases anti-tumor efficacy by STING-mediated immune cell activation. Nat Biotechnol. Oct. 2019;37(10):1174-1185. doi: 10.1038/s41587-019-0247-3. Epub Sep. 30, 2019.
Numata et al., Phosphatidylglycerol provides short-term prophylaxis against respiratory syncytial virus infection. J Lipid Res. Aug. 2013;54(8):2133-2143. doi: 10.1194/jlr.M037077. Epub Jun. 6, 2013.
Oberli et al., Lipid Nanoparticle Assisted mRNA Delivery for Potent Cancer Immunotherapy. Nano Lett. Mar. 8, 2017;17(3):1326-1335. doi: 10.1021/acs.nanolett.6b03329. Epub Dec. 5, 2016. Author Manuscript, 20 pages.
Paunovska et al., A Direct Comparison of in Vitro and in Vivo Nucleic Acid Delivery Mediated by Hundreds of Nanoparticles Reveals a Weak Correlation. Nano Lett. Mar. 14, 2018;18(3):2148-2157. doi: 10.1021/acs.nanolett.8b00432. Epub Mar. 5, 2018. Author Manuscript, 20 pages.
Riley et al., Ionizable lipid nanoparticles for in utero mRNA delivery. Sci Adv. Jan. 13, 2021;7(3):eaba1028. doi: 10.1126/sciadv.aba1028.
Robinson et al., Lipid Nanoparticle-Delivered Chemically Modified mRNA Restores Chloride Secretion in Cystic Fibrosis. Mol Ther. Aug. 1, 2018;26(8):2034-2046. doi: 10.1016/j.ymthe.2018.05.014. Epub Jun. 15, 2018.
Ryals et al., The effects of PEGylation on LNP based mRNA delivery to the eye. PLoS One. Oct. 29, 2020;15(10):e0241006. doi: 10.1371/journal.pone.0241006.
Sabnis et al., A Novel Amino Lipid Series for mRNA Delivery: Improved Endosomal Escape and Sustained Pharmacology and Safety in Non-human Primates. Mol Ther. Jun. 6, 2018;26(6):1509-1519. doi: 10.1016/j.ymthe.2018.03.010. Epub Mar. 14, 2018.
Smith et al., Synthesis and convenient functionalization of azide-labeled diacylglycerol analogues for modular access to biologically active lipid probes. Bioconjug Chem. Sep. 2008;19(9):1855-63. doi: 10.1021/bc8001002. Epub Aug. 7, 2008.
Swingle et al., Lipid Nanoparticle-Mediated Delivery of mRNA Therapeutics and Vaccines. Trends Mol Med. Jun. 2021;27(6):616-617. doi: 10.1016/j.molmed.2021.03.003. Epub Apr. 6, 2021.
Whitehead et al., In vitro-in vivo translation of lipid nanoparticles for hepatocellular siRNA delivery. ACS Nano. Aug. 28, 2012;6(8):6922-9. doi: 10.1021/nn301922x. Epub Jul. 6, 2012. Author Manuscript, 16 pages.
Wilson, C., Future therapies for cystic fibrosis. Lancet Respir Med. Aug. 2022;10(8):e75-e76. doi: 10.1016/S2213-2600(22)00253-3. Epub Jun. 30, 2022.
Zhang et al., Functionalized lipid-like nanoparticles for in vivo mRNA delivery and base editing. Sci Adv. Aug. 21, 2020;6(34):eabc2315. doi: 10.1126/sciadv.abc2315.

Amines

Tails

From Tail 11 (Oleic acid)

1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33

From Tail 12 (Linoleic acid)

34

35

36

37

38

39

40

41

42

43

44

45

46

47

48

49

50

51

52

53

54

55 (117-17)

56

From Tail 10 (octadecanoic series)

62

63

64

65

66

67

68

From Tail 8 (palmitic acid series)

69

70

71

72

73

117-17 analogs 117-17-$C_9$

74

117-17-$C_{10}$

75

117-17-$C_{11}$

76

117-17-$C_{12}$

77

117-17-$C_{13}$

78

117-17-$C_{14}$

79

117-17-$C_{15}$

80

117-17-$C_{16}$

81

117-17-$C_{17}$

82

117-17-$C_{18}$

83

117-17-Linolenic

84

19-Pyrazole analogs

19-Pyrazole-$C_9$

85

19-Pyrazole-$C_{10}$

86

19-Pyrazole-$C_{11}$

87

19-Pyrazole-$C_{12}$

88

19-Pyrazole-$C_{13}$

89

19-Pyrazole-$C_{14}$

90

19-Pyrazole-$C_{15}$

91

19-Pyrazole-$C_{16}$

92

19-Pyrazole-$C_{17}$

93

19-Pyrazole-$C_{18}$

94

19-Pyrazole-linoleic

95

117-7 analogs 117-7-$C_9$

96

117-7-$C_{10}$

97

117-7-$C_{11}$

98

117-7-$C_{12}$

99

117-7-$C_{13}$

100

117-7-$C_{14}$

101

117-7-$C_{15}$

102

117-7-$C_{16}$

103

117-7-$C_{17}$

104

117-7-$C_{18}$

105

117-7-Linolenic

106

IR-117-17

IR-19-Py

IR-117-17 variant

IR-01-97_25

IR-01-97_26

IR-01-97_27

IR-01-117_22

IR-01-117_23

IR-01-158_1

IR-01-158_2

IR-01-158_3

IR-01-158_6

IR-19-Py variant

IR-01-97_28

IR-01-97_29

IR-01-117_24

IR-01-117_25

IONIZABLE LIPIDS AND COMPOSITIONS AND USES THEREOF

CROSS-REFERENCE TO RELATED APPLICATIONS

This application claims the benefit of and priority under 35 U.S.C. § 119(e) to U.S. Provisional Application No. 63/289,343, filed Dec. 14, 2021, titled IONIZABLE LIPIDS AND COMPOSITIONS AND USES THEREOF, the contents of which are incorporated herewith by reference in their entirety.

GOVERNMENT SUPPORT

This invention was made with government support under Grant No. HL147367 awarded by the National Institutes of Health. The government has certain rights in the invention.

STATEMENT OF SPONSORED RESEARCH

Research for this invention was supported by awards from the Cystic Fibrosis Foundation.

BACKGROUND

RNA based therapies are highly sought as they present an opportunity to treat the root cause of many diseases. Their potential for clinical success requires that efficient delivery systems be developed to facilitate such therapies in patients. Of all the delivery systems currently being studied, lipid nanoparticles (LNPs) are promising mRNA delivery vehicles to target cells in vivo. RNA encapsulation into LNPs is facilitated by complexation with ionizable lipids, which has a reversible positive charge. In addition to complexing with RNA, ionizable lipids can drive organ-selective uptake and facilitate endosomal escape, which is required for RNA to reach the cytoplasm and become active. As RNA based therapies are administered repeatedly, concerns over toxicity due to accumulation of ionizable lipids in target organs have been raised. Accordingly, new compounds capable of forming delivery vehicles capable of specific mRNA delivery to tissues are needed.

SUMMARY OF THE INVENTION

The present disclosure relates in part to new compounds that can deliver agents to a subject or a cell, and compositions and methods of using and preparing such compounds.

Provided herein are compounds (e.g., compounds of Formula (I)), and pharmaceutically acceptable salts, solvates, tautomers, stereoisomers, and isotopically labeled derivatives thereof, and compositions thereof. In certain embodiments, the compounds provided herein can form particles for delivery of various agents and can therefore be useful for the treatment and/or prevention of diseases (e.g., genetic disease, proliferative disease, hematological disease, neurological disease, liver disease, spleen disease, lung disease, painful condition, psychiatric disorder, musculoskeletal disease, a metabolic disorder, inflammatory disease, or autoimmune disease).

The present disclosure also provides methods of using the compounds and compositions provided herein, e.g., for delivering an agent to a subject or a cell or for treating or preventing a disease, disorder, or condition in a subject. Also provided herein are methods of preparing the compounds provided herein (e.g., compounds of Formula (I)), and pharmaceutically acceptable salts, solvates, tautomers, stereoisomers, and isotopically labeled derivatives thereof. The present disclosure also provides kits comprising a compound provided herein (e.g., a compound of Formulae (I)), or a pharmaceutically acceptable salt, solvate, tautomer, stereoisomer, or isotopically labeled derivative thereof, or a composition thereof.

In one aspect, the disclosure provides a compound of Formula (I):

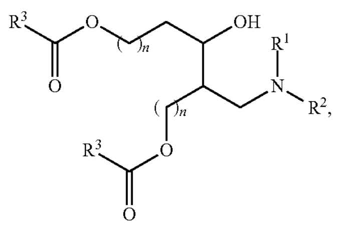

(I)

or a pharmaceutically acceptable salt, solvate, tautomer, stereoisomer, or isotopically labeled derivative thereof, wherein $R^1$, $R^2$, $R^3$, and n are as defined herein.

In another aspect, the present disclosure provides compositions comprising a compound provided herein (e.g., a compound of Formula (I)), or a pharmaceutically acceptable salt, solvate, tautomer, stereoisomer, or isotopically labeled derivative thereof, and an agent. In certain embodiments, the agent is a polynucleotide. In some embodiments, the polynucleotide is mRNA.

In yet another aspect, the present disclosure provides methods of delivering a polynucleotide to a subject, comprising administering to the subject a composition comprising a polynucleotide and a compound provided herein (e.g., a compound of Formula (I)), or a pharmaceutically acceptable salt, solvate, tautomer, stereoisomer, or isotopically labeled derivative thereof. In some embodiments, the delivery is to the lung or nasal epithelium of the subject. In certain embodiments, the delivery is to a lung cell or nasal epithelium cell.

In another aspect, the present disclosure provides methods for treating and/or preventing a disease, disorder, or condition (e.g., a genetic disease, proliferative disease, hematological disease, neurological disease, liver disease, spleen disease, lung disease, painful condition, psychiatric disorder, musculoskeletal disease, a metabolic disorder, inflammatory disease, or autoimmune disease) in a subject, comprising administering to the subject a composition provided herein. In certain embodiments, the disease, disorder, or condition is a genetic disease, proliferative disease, hematological disease, neurological disease, liver disease, spleen disease, lung disease, painful condition, psychiatric disorder, musculoskeletal disease, a metabolic disorder, inflammatory disease, or autoimmune disease. In some embodiments, the disease, disorder, or condition is a lung disease. In certain embodiments, the lung disease is cystic fibrosis, sepsis, or lung cancer.

In another aspect, the present disclosure provides kits comprising a compound provided herein (e.g., a compound of Formula (I)), or a pharmaceutically acceptable salt, solvate, tautomer, stereoisomer, or isotopically labeled derivative thereof; or a composition thereof; and instructions for using the compound, or pharmaceutically acceptable salt, solvate, tautomer, stereoisomer, or isotopically labeled derivative thereof, or composition (e.g., for treating and/or preventing a disease or condition in a subject or delivering a polynucleotide to a subject).

In another aspect, the disclosure provides a method of preparing a compound of Formula (I), the method comprising reacting a compound of Formula (II):

(II)

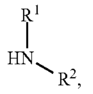

or a salt, solvate, tautomer, stermoisomer, or isotopically labeled derivative thereof, with a compound of Formula (III):

(III)

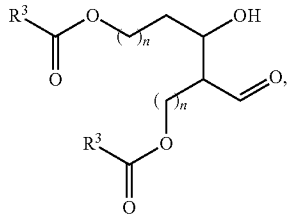

or a salt, solvate, tautomer, stereoisomer, or isotopically labeled derivative thereof, wherein $R^1$, $R^2$, $R^3$, and n are as defined herein.

The details of certain embodiments of the invention are set forth in the Detailed Description of Certain Embodiments, as described below. Other features, objects, and advantages of the invention will be apparent from the Definitions, Examples, Figures, and Claims. It should be understood that the aspects described herein are not limited to specific embodiments, methods, or configurations, and as such can, of course, vary. It is also to be understood that the terminology used herein is for the purpose of describing particular aspects only and, unless specifically defined herein, is not intended to be limiting.

BRIEF DESCRIPTION OF THE DRAWINGS

The accompanying drawings, which constitute a part of this specification, illustrate several embodiments of the invention and together with the description, provide non-limiting examples of the invention.

FIG. 1A: Schematic representation of ionizable lipids; FIG. 1B: General structure of rationally designed ionizable lipid; FIG. 1C: Synthesis of linkers with lipid tails; FIG. 1D: Synthesis of ionizable lipids using reductive amination.

FIG. 4A: Log luminescence of ionizable lipids screened in primary large and small airway ALI cultures FIG. 4B: Log luminescence of 117-17 tail variants screened in both small and large airway ALI cultures. FIG. 4C: Log luminescence of 19-Pyrazole tail variants screened in both small and large airway ALI cultures.

FIG. 5A: Analogs of 117-17; FIG. 5B: Analogs of 19-Pyrazole.

FIG. 6A: Comparison of luminescence of C12-200, 19-Pyrazole, and 117-17 nebulized delivery using a whole-body nebulization chamber and directly nebulized to the nose; FIG. 6B: Comparison of total luminescence after repeat dosing of inhaled formulations of C12-200, 19-Pyrazole, 117-17, or PBS; FIG. 6C: Time course of protein expression in nose as determined by luminescence of C12-200, 19-Pyrazole, and 117-17 nebulized delivery; FIG. 6D: Time course of protein expression in lung as determined by luminescence of C12-200, 19-Pyrazole, and 117-17 nebulized delivery, and verified delivery to lungs with 1 mouse from C12-200 group at 6 h (right); FIG. 6E: Whole-body images of mice showing time course of protein expression after nebulized delivery of C12-200, 19-Pyrazole, and 117-17.

FIG. 16A shows a Ai14 mice model. FIG. 16B shows functional delivery of Cre mRNA by IR-117-7C15-21 LNPs to different cell populations of the lung. FIGS. 16C-16D show representative whole-lung images (FIG. 16C) and percentage of lung endothelial cells that are positive for tdTomato (FIG. 16D) 48 hours after administration of C15-21 or C12-200/DOTAP SORT LNPs containing Cre mRNA. FIG. 16E shows whole lung images after functional delivery of luciferase mRNA to the lungs by IR-117-7-C15 and MD1. FIG. 16F shows quantification of luciferase expression in the lungs.

DEFINITIONS

Chemical Definitions

Figure 1A:
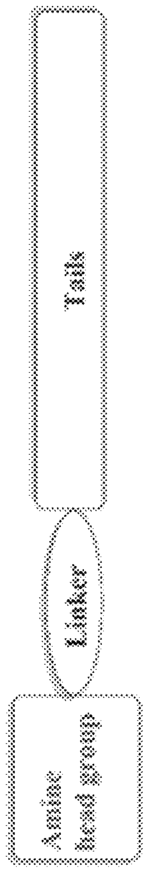
FIGS. 1A-1D show the synthesis of lipid compounds.

Definitions of specific functional groups and chemical terms are described in more detail below. The chemical elements are identified in accordance with the Periodic Table of the Elements, CAS version. Handbook of Chemistry and Physics, $75^{th}$ Ed., inside cover, and specific functional groups are generally defined as described therein. Additionally, general principles of organic chemistry, as well as specific functional moieties and reactivity, are described in Thomas Sorrell, *Organic Chemistry*. University Science Books. Sausalito, 1999; Michael B. Smith, *March's Advanced Organic Chemistry,* $7^{th}$ Edition. John Wiley & Sons. Inc., New York, 2013; Richard C. Larock, *Comprehensive Organic Transformations*, John Wiley & Sons. Inc., New York, 2018; and Carruthers, Some Modern Methods of Organic Synthesis, $3^{rd}$ Edition, Cambridge University Press. Cambridge, 1987.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example. Jacques et al., *Enantiomers, Racemates and Resolutions* (Wiley Interscience, New York, 1981); Wilen et al., Tetrahedron 33:2725 (1977); Eliel, E. L. *Stereochemistry of Carbon Compounds* (McGraw-Hill, N Y, 1962); and Wilen, S. H., *Tables of Resolving Agents and Optical Resolutions* p. 268 (E. L. Eliel, Ed., Univ. of Notre Dame Press, Notre Dame, Ind, 1972). The invention additionally encompasses compounds as individual isomers substantially free of other isomers, and alternatively, as mixtures of various isomers.

When a range of values is listed, it is intended to encompass each value and sub-range within the range. A range is inclusive of the values at the two ends of the range unless otherwise provided. For example "$C_{1-6}$ alkyl" encompasses. $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

Unless otherwise provided, formulae and structures depicted herein include compounds that do not include isotopically enriched atoms, and also include compounds that include isotopically enriched atoms. For example, compounds having the present structures except for the replacement of hydrogen by deuterium or tritium, replacement of $^{19}F$ with $^{18}F$, or the replacement of a carbon by a $^{13}C$- or $^{14}C$-enriched carbon are within the scope of the disclosure. Such compounds are useful, for example, as analytical tools or probes in biological assays.

The term "isotopes" refers to variants of a particular chemical element such that, while all isotopes of a given element share the same number of protons in each atom of the element, those isotopes differ in the number of neutrons.

The term "aliphatic" refers to alkyl, alkenyl, alkynyl, and carbocyclic groups. Likewise, the term "heteroaliphatic" refers to heteroalkyl, heteroalkenyl, heteroalkynyl, and heterocyclic groups.

The term "alkyl" refers to a radical of a straight-chain or branched saturated hydrocarbon group having from 1 to 20 carbon atoms ("$C_{1-20}$ alkyl"). In some embodiments, an alkyl group has 1 to 12 carbon atoms ("$C_{1-12}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, isobutyl), pentyl ($C_5$) (e.g., n-pentyl, 3-pentanyl, amyl, neopentyl, 3-methyl-2-butanyl, tert-amyl), and hexyl (CO) (e.g., n-hexyl). Additional examples of alkyl groups include n-heptyl ($C_7$), n-octyl ($C_8$), n-dodecyl ($C_{12}$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-12}$ alkyl (such as unsubstituted $C_{1-6}$ alkyl, e.g., $—CH_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu or s-Bu), unsubstituted isobutyl (i-Bu)). In certain embodiments, the alkyl group is a substituted $C_{1-12}$ alkyl (such as substituted $C_{1-6}$ alkyl, e.g., $—CH_2F$, $—CHF_2$, $—CF_3$, $—CH_2CH_2F$, $—CH_2CHF_2$, $—CH_2CF_3$, or benzyl (Bn)).

The term "heteroalkyl" refers to an alkyl group, which further includes at least one heteroatom (e.g., 1, 2, 3, or 4 heteroatoms) selected from oxygen, nitrogen, or sulfur within (e.g., inserted between adjacent carbon atoms of) and/or placed at one or more terminal position(s) of the parent chain. In certain embodiments, a heteroalkyl group refers to a saturated group having from 1 to 20 carbon atoms and 1 or more heteroatoms within the parent chain ("hetero$C_{1-20}$ alkyl"). In certain embodiments, a heteroalkyl group refers to a saturated group having from 1 to 12 carbon atoms and 1 or more heteroatoms within the parent chain ("hetero$C_{1-12}$ alkyl"). In some embodiments, a heteroalkyl group is a saturated group having 1 to 11 carbon atoms and 1 or more heteroatoms within the parent chain ("hetero$C_{1-11}$ alkyl"). In some embodiments, a heteroalkyl group is a saturated group having 1 to 10 carbon atoms and 1 or more heteroatoms within the parent chain ("hetero$C_{1-10}$ alkyl"). In some embodiments, a heteroalkyl group is a saturated group having 1 to 9 carbon atoms and 1 or more heteroatoms within the parent chain ("hetero$C_{1-9}$ alkyl"). In some embodiments, a heteroalkyl group is a saturated group having 1 to 8 carbon atoms and 1 or more heteroatoms within the parent chain ("hetero$C_{1-8}$ alkyl"). In some embodiments, a heteroalkyl group is a saturated group having 1 to 7 carbon atoms and 1 or more heteroatoms within the parent chain ("hetero$C_{1-7}$ alkyl"). In some embodiments, a heteroalkyl group is a saturated group having 1 to 6 carbon atoms and 1 or more heteroatoms within the parent chain ("hetero$C_{1-6}$ alkyl"). In some embodiments, a heteroalkyl group is a saturated group having 1 to 5 carbon atoms and 1 or 2 heteroatoms within the parent chain ("hetero$C_{1-5}$ alkyl"). In some embodiments, a heteroalkyl group is a saturated group having 1 to 4 carbon atoms and for 2 heteroatoms within the parent chain ("hetero$C_{1-4}$ alkyl"). In some embodiments, a heteroalkyl group is a saturated group having 1 to 3 carbon atoms and 1 heteroatom within the parent chain ("hetero$C_{1-3}$ alkyl"). In some embodiments, a heteroalkyl group is a saturated group having 1 to 2 carbon atoms and 1 heteroatom within the parent chain ("hetero$C_{1-2}$ alkyl"). In some embodiments, a heteroalkyl group is a saturated group having 1 carbon atom and 1 heteroatom ("hetero$C_1$ alkyl"). In some embodiments, a heteroalkyl group is a saturated group having 2 to 6 carbon atoms and 1 or 2 heteroatoms within the parent chain ("hetero$C_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted hetero$C_{1-12}$ alkyl. In certain embodiments, the heteroalkyl group is a substituted hetero$C_{1-12}$ alkyl.

The term "alkenyl" refers to a radical of a straight-chain or branched hydrocarbon group having from 1 to 20 carbon atoms and one or more carbon-carbon double bonds (e.g., 1, 2, 3, or 4 double bonds). In some embodiments, an alkenyl group has 1 to 20 carbon atoms ("$C_{1-20}$ alkenyl"). In some embodiments, an alkenyl group has 1 to 12 carbon atoms ("$C_{1-12}$ alkenyl"). In some embodiments, an alkenyl group has 1 to 11 carbon atoms ("$C_{1-11}$ alkenyl"). In some embodiments, an alkenyl group has 1 to 10 carbon atoms ("$C_{1-10}$ alkenyl"). In some embodiments, an alkenyl group has 1 to 9 carbon atoms ("$C_{1-9}$ alkenyl"). In some embodiments, an alkenyl group has 1 to 8 carbon atoms ("$C_{1-8}$ alkenyl"). In some embodiments, an alkenyl group has 1 to 7 carbon atoms ("$C_{1-7}$ alkenyl"). In some embodiments, an alkenyl group has 1 to 6 carbon atoms ("$C_{1-5}$ alkenyl"). In some embodiments, an alkenyl group has 1 to 5 carbon atoms ("$C_{1-5}$ alkenyl"). In some embodiments, an alkenyl group has 1 to 4 carbon atoms ("$C_{1-4}$ alkenyl"). In some embodiments, an alkenyl group has 1 to 3 carbon atoms ("$C_{1-3}$ alkenyl"). In some embodiments, an alkenyl group has 1 to 2 carbon atoms ("$C_{1-2}$ alkenyl"). In some embodiments, an alkenyl group has 1 carbon atom ("$C_1$ alkenyl"). The one or more carbon-carbon double bonds can be internal (such as in 2-butenyl) or terminal (such as in 1-butenyl). Examples of $C_{1-4}$ alkenyl groups include methylidenyl ($C_1$), ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{1-6}$ alkenyl groups include the aforementioned $C_{2-4}$ alkenyl groups as well as pentenyl (C), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted $C_{1-20}$ alkenyl. In certain embodiments, the alkenyl group is a substituted $C_{1-20}$ alkenyl. In an alkenyl group, a C═C double bond for which the stereochemistry is not specified (e.g., —CH═CHCH$_3$ or

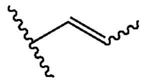

)

may be in the (E)- or (Z)-configuration.

The term "heteroalkenyl" refers to an alkenyl group, which further includes at least one heteroatom (e.g., 1, 2, 3, or 4 heteroatoms) selected from oxygen, nitrogen, or sulfur within (e.g., inserted between adjacent carbon atoms of) and/or placed at one or more terminal position(s) of the parent chain. In certain embodiments, a heteroalkenyl group refers to a group having from 1 to 20 carbon atoms, at least one double bond, and 1 or more heteroatoms within the parent chain ("hetero$C_{1-20}$ alkenyl"). In certain embodiments, a heteroalkenyl group refers to a group having from 1 to 12 carbon atoms, at least one double bond, and 1 or more heteroatoms within the parent chain ("hetero$C_{1-12}$ alkenyl"). In certain embodiments, a heteroalkenyl group refers to a group having from 1 to 11 carbon atoms, at least one double bond, and 1 or more heteroatoms within the parent chain ("hetero$C_{1-11}$ alkenyl"). In certain embodiments, a heteroalkenyl group refers to a group having from 1 to 10 carbon atoms, at least one double bond, and 1 or more heteroatoms within the parent chain ("hetero$C_{1-10}$ alkenyl"). In some embodiments, a heteroalkenyl group has 1 to 9 carbon atoms at least one double bond, and 1 or more heteroatoms within the parent chain ("hetero$C_{1-9}$ alkenyl"). In some embodiments, a heteroalkenyl group has 1 to 8 carbon atoms, at least one double bond, and 1 or more heteroatoms within the parent chain ("hetero$C_{1-8}$ alkenyl"). In some embodiments, a heteroalkenyl group has 1 to 7 carbon atoms, at least one double bond, and 1 or more heteroatoms within the parent chain ("hetero$C_{1-7}$ alkenyl"). In some embodiments, a heteroalkenyl group has 1 to 6 carbon atoms, at least one double bond, and 1 or more heteroatoms within the parent chain ("hetero$C_{1-6}$ alkenyl"). In some embodiments, a heteroalkenyl group has 1 to 5 carbon atoms, at least one double bond, and 1 or 2 heteroatoms within the parent chain ("hetero$C_{1-5}$ alkenyl"). In some embodiments, a heteroalkenyl group has 1 to 4 carbon atoms, at least one double bond, and 1 or 2 heteroatoms within the parent chain ("hetero$C_{1-4}$ alkenyl"). In some embodiments, a heteroalkenyl group has 1 to 3 carbon atoms, at least one double bond, and 1 heteroatom within the parent chain ("hetero$C_{1-3}$ alkenyl"). In some embodiments, a heteroalkenyl group has 1 to 2 carbon atoms, at least one double bond, and 1 heteroatom within the parent chain ("hetero$C_{1-2}$ alkenyl"). In some embodiments, a heteroalkenyl group has 1 to 6 carbon atoms, at least one double bond, and 1 or 2 heteroatoms within the parent chain ("hetero$C_{1-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted hetero$C_{1-20}$ alkenyl. In certain embodiments, the heteroalkenyl group is a substituted hetero$C_{1-20}$ alkenyl.

The term "alkynyl" refers to a radical of a straight-chain or branched hydrocarbon group having from 1 to 20 carbon atoms and one or more carbon-carbon triple bonds (e.g., 1, 2, 3, or 4 triple bonds) ("$C_{1-20}$ alkynyl"). In some embodiments, an alkynyl group has 1 to 10 carbon atoms ("$C_{1-10}$ alkynyl"). In some embodiments, an alkynyl group has 1 to 9 carbon atoms ("$C_{1-9}$ alkynyl"). In some embodiments, an alkynyl group has 1 to 8 carbon atoms ("$C_{1-8}$ alkynyl"). In some embodiments, an alkynyl group has 1 to 7 carbon atoms ("$C_{1-7}$ alkynyl"). In some embodiments, an alkynyl group has 1 to 6 carbon atoms ("$C_{1-6}$ alkynyl"). In some embodiments, an alkynyl group has 1 to 5 carbon atoms ("$C_{1-5}$ alkynyl"). In some embodiments, an alkynyl group has 1 to 4 carbon atoms ("$C_{1-4}$ alkynyl"). In some embodiments, an alkynyl group has 1 to 3 carbon atoms ("$C_{1-3}$ alkynyl"). In some embodiments, an alkynyl group has 1 to 2 carbon atoms ("$C_{1-2}$ alkynyl"). In some embodiments, an alkynyl group has 1 carbon atom ("$C_1$ alkynyl"). The one or more carbon-carbon triple bonds can be internal (such as in 2-butynyl) or terminal (such as in I-butynyl). Examples of $C_{1-4}$ alkynyl groups include, without limitation, methylidynyl ($C_1$), ethynyl ($C_2$), 1-propynyl ($C_3$), 2-propynyl ($C_3$), 1-butynyl ($C_4$), 2-butynyl ($C_4$), and the like. Examples of $C_{1-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted $C_{1-20}$ alkynyl. In certain embodiments, the alkynyl group is a substituted $C_{1-20}$ alkynyl.

The term "heteroalkynyl" refers to an alkynyl group, which further includes at least one heteroatom (e.g., 1, 2, 3, or 4 heteroatoms) selected from oxygen, nitrogen, or sulfur within (e.g., inserted between adjacent carbon atoms of) and/or placed at one or more terminal position(s) of the parent chain. In certain embodiments, a heteroalkynyl group refers to a group having from 1 to 20 carbon atoms, at least one triple bond, and 1 or more heteroatoms within the parent chain ("hetero$C_{1-20}$ alkynyl"). In certain embodiments, a heteroalkynyl group refers to a group having from 1 to 10 carbon atoms, at least one triple bond, and 1 or more heteroatoms within the parent chain ("hetero$C_{1-10}$ alkynyl"). In some embodiments, a heteroalkynyl group has 1 to 9 carbon atoms, at least one triple bond, and 1 or more heteroatoms within the parent chain ("hetero$C_{1-9}$ alkynyl"). In some embodiments, a heteroalkynyl group has 1 to 8 carbon atoms, at least one triple bond, and 1 or more heteroatoms within the parent chain ("hetero$C_{1-8}$ alkynyl"). In some embodiments, a heteroalkynyl group has 1 to 7 carbon atoms, at least one triple bond, and 1 or more heteroatoms within the parent chain ("hetero$C_{1-7}$ alkynyl"). In some embodiments, a heteroalkynyl group has 1 to 6 carbon atoms, at least one triple bond, and 1 or more heteroatoms within the parent chain ("hetero$C_{1-6}$ alkynyl"). In some embodiments, a heteroalkynyl group has 1 to 5 carbon atoms, at least one triple bond, and 1 or 2 heteroatoms within the parent chain ("hetero$C_{1-5}$ alkynyl"). In some embodiments, a heteroalkynyl group has 1 to 4 carbon atoms, at least one triple bond, and or 2 heteroatoms within the parent chain ("hetero$C_{1-4}$ alkynyl"). In some embodiments, a heteroalkynyl group has 1 to 3 carbon atoms, at least one triple bond, and 1 heteroatom within the parent chain ("hetero$C_{1-3}$ alkynyl"). In some embodiments, a heteroalkynyl group has 1 to 2 carbon atoms, at least one triple bond, and 1 heteroatom within the parent chain ("hetero$C_{1-2}$ alkynyl"). In some embodiments, a heteroalkynyl group has 1 to 6 carbon atoms, at least one triple bond, and 1 or 2 heteroatoms within the parent chain ("hetero$C_{1-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted hetero$C_{1-20}$ alkynyl. In certain embodiments, the heteroalkynyl group is a substituted hetero$C_{1-20}$ alkynyl.

The term "carbocyclyl" or "carbocyclic" refers to a radical of a non-aromatic cyclic hydrocarbon group having from 3 to 14 ring carbon atoms ("$C_{3-14}$ carbocyclyl") and zero heteroatoms in the non-aromatic ring system. In some embodiments, a carbocyclyl group has 3 to 14 ring carbon atoms ("$C_{3-14}$ carbocyclyl"). In some embodiments, a carbocyclyl group has 3 to 13 ring carbon atoms ("$C_{3-13}$ carbocyclyl"). In some embodiments, a carbocyclyl group has 3 to 12 ring carbon atoms ("$C_{3-12}$ carbocyclyl"). In some embodiments, a carbocyclyl group has 3 to 11 ring carbon atoms ("$C_{3-11}$ carbocyclyl"). In some embodiments, a carbocyclyl group has 3 to 10 ring carbon atoms ("$C_{3-10}$ carbocyclyl"). In some embodiments, a carbocyclyl group has 3 to 8 ring carbon atoms ("$C_{3-8}$ carbocyclyl"). In some embodiments, a carbocyclyl group has 3 to 7 ring carbon atoms ("$C_{3-7}$ carbocyclyl"). In some embodiments, a carbocyclyl group has 3 to 6 ring carbon atoms ("$C_{3-6}$ carbocyclyl"). In some embodiments, a carbocyclyl group has 4 to 6 ring carbon atoms ("$C_{4-6}$ carbocyclyl"). In some embodiments, a carbocyclyl group has 5 to 6 ring carbon atoms ("$C_{5-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include the aforementioned $C_{3-6}$ carbocyclyl groups as well as cycloheptyl ($C_7$), cycloheptenyl ($C_7$), cycloheptadienyl (C7), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. Exemplary $C_{3-8}$ carbocyclyl groups include the aforementioned $C_{3-10}$ carbocyclyl groups as well as cycloundecyl ($C_{11}$), spiro[5.5]undecanyl ($C_{11}$), cyclododecyl ($C_{12}$), cyclododecenyl ($C_{12}$), cyclotridecane ($C_{13}$), cyclotetradecane ($C_{14}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted $C_{3-14}$ carbocyclyl. In certain embodiments, the carbocyclyl group is a substituted $C_{3-14}$ carbocyclyl.

In some embodiments, "carbocyclyl" is a monocyclic, saturated carbocyclyl group having from 3 to 14 ring carbon atoms ("$C_{3-14}$ cycloalkyl"). In some embodiments, a cycloalkyl group has 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 4 to 6 ring carbon atoms ("$C_{4-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted C344 cycloalkyl. In certain embodiments, the cycloalkyl group is a substituted $C_{3-14}$ cycloalkyl. In certain embodiments, the carbocyclyl includes 0, 1, or 2 C═C double bonds in the carbocyclic ring system, as valency permits.

The term "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl. In certain embodiments, the heterocyclyl is substituted or unsubstituted, 3- to 7-membered, monocyclic heterocyclyl, wherein 1, 2, or 3 atoms in the heterocyclic ring system are independently oxygen, nitrogen, or sulfur, as valency permits.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include azirdinyl, oxiranyl, and thiiranyl. Exemplary 4-membered heterocyclyl groups containing 1 heteroatom include azetidinyl, oxetanyl, and thietanyl. Exemplary 5-membered heterocyclyl groups containing 1 heteroatom include tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include dioxolanyl, oxathiolanyl and dithiolanyl. Exemplary 5-membered heterocyclyl groups containing 3 heteroatoms include triazolinyl, oxadiazolinyl, and thiadiazolinyl. Exemplary 6-membered heterocyclyl groups containing 1 heteroatom include piperidinyl, tetrahydropyranyl, dihydropyridinyl, and thianyl, Exemplary 6-membered heterocyclyl groups containing 2 heteroatoms include piperazinyl, morpholinyl, dithianyl, and dioxanyl. Exemplary 6-membered heterocyclyl groups containing 3 heteroatoms include triazinyl. Exemplary 7-membered heterocyclyl groups containing 1 heteroatom include azepanyl, oxepanyl and thiepanyl. Exemplary 8-membered heterocyclyl groups containing 1 heteroatom include azocanyl, oxecanyl and thiocanyl. Exemplary bicyclic heterocyclyl groups include indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

The term "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

"Aralkyl" is a subset of "alkyl" and refers to an alkyl group substituted by an aryl group, wherein the point of attachment is on the alkyl moiety.

The term "heteroaryl" refers to a radical of a 5-14 membered monocyclic or polycyclic (e.g., bicyclic, tricyclic) 4n+2 aromatic ring system (e.g., having 6, 10, or 14 $\pi$ electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, e.g., either the ring bearing a heteroatom (e.g., 2-indolyl) or the ring that does not contain a heteroatom (e.g., 5-indolyl). In certain embodiments, the heteroaryl is substituted or unsubstituted, 5- or 6-membered, monocyclic heteroaryl, wherein 1, 2, 3, or 4 atoms in the heteroaryl ring system are independently oxygen, nitrogen, or sulfur. In certain embodiments, the heteroaryl is substituted or unsubstituted, 9- or 10-membered, bicyclic heteroaryl, wherein 1, 2, 3, or 4 atoms in the heteroaryl ring system are independently oxygen, nitrogen, or sulfur.

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include pyrrolyl, furanyl, and thiophenyl. Exemplary 5-membered heteroaryl groups containing 2 heteroatoms include imidazolyl, pyrazolyl, oxazolyl, isoxazolyl, thiazolyl, and isothiazolyl. Exemplary 5-membered heteroaryl groups containing 3 heteroatoms include triazolyl, oxadiazolyl, and thiadiazolyl. Exemplary 5-membered heteroaryl groups containing 4 heteroatoms include tetrazolyl. Exemplary 6-membered heteroaryl groups containing 1 heteroatom include pyridinyl. Exemplary 6-membered heteroaryl groups containing 2 heteroatoms include pyridazinyl, pyrimidinyl, and pyrazinyl. Exemplary 6-membered heteroaryl groups containing 3 or 4 heteroatoms include triazinyl and tetrazinyl, respectively. Exemplary 7-membered heteroaryl groups containing 1 heteroatom include azepinyl, oxepinyl, and thiepinyl. Exemplary 5,6-bicyclic heteroaryl groups include indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include naphthyridinyl, pteridinyl, quinolinyl, isoquinolinyl, cinnolinyl, quinoxalinyl, phthalazinyl, and quinazolinyl. Exemplary tricyclic heteroaryl groups include phenanthridinyl, dibenzofuranyl, carbazolyl, acridinyl, phenothiazinyl, phenoxazinyl, and phenazinyl.

"Heteroaralkyl" is a subset of "alkyl" and refers to an alkyl group substituted by a heteroaryl group, wherein the point of attachment is on the alkyl moiety.

The term "unsaturated bond" refers to a double or triple bond.

The term "unsaturated" or "partially unsaturated" refers to a moiety that includes at least one double or triple bond.

The term "saturated" or "fully saturated" refers to a moiety that does not contain a double or triple bond, e.g., the moiety only contains single bonds.

Affixing the suffix "-ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

A group is optionally substituted unless expressly provided otherwise. The term "optionally substituted" refers to being substituted or unsubstituted. In certain embodiments, alkyl, alkenyl, alkynyl, heteroalkyl, heteroalkenyl, heteroalkynyl, carbocyclyl, heterocyclyl, aryl, and heteroaryl groups are optionally substituted. "Optionally substituted" refers to a group which is substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl. "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, and includes any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety. The invention is not limited in any manner by the exemplary substituents described herein.

Exemplary carbon atom substituents include halogen, —CN, —$NO_2$, —$N_3$, —$SO_2H$, —$SO_3H$, —OH, —$OR^{aa}$, —$ON(R^{bb})_2$, —$N(R^{bb})_2$, —$N(R^{bb})_3^+X^-$, —$N(OR^{cc})R^{bb}$, —SH, —$SR^{aa}$, —$SSR^{cc}$, —C(═O)$R^{aa}$, —$CO_2H$, —CHO, —$C(OR^{cc})_2$, —$CO_2R^{aa}$, —OC(═O)$R^{aa}$, —$OCO_2R^{aa}$, —C(═O)$N(R^{bb})_2$, —OC(═O)$N(R^{bb})_2$, —$NR^{bb}$C(═O)$R^{aa}$, —$NR^{bb}CO_2R^{aa}$, —$NR^{bb}$C(═O)$N(R^{bb})_2$, —C(═$NR^{bb}$)$R^{aa}$, —C(═$NR^{bb}$)$OR^{aa}$, —OC(═$NR^{bb}$)$R^{aa}$, —OC(═$NR^{bb}$)$OR^{aa}$, —C(═$NR^{bb}$)$N(R^{bb})_2$, —OC(═$NR^{bb}$)$N(R^{bb})_2$, —$NR^{bb}$C(═$NR^{bb}$)$N(R^{bb})_2$, —C(═O)$NR^{bb}SO_2R^{aa}$, —$NR^{bb}SO_2R^{aa}$, —$SO_2N(R^{bb})_2$, —$SO_2R^{aa}$, —$SO_2OR^{aa}$, —$OSO_2R^{aa}$, —S(═O)$R^{aa}$, —OS(═O)$R^{aa}$, —$Si(R^{aa})_3$, —$OSi(R^{aa})_3$—C(═S)$N(R^{bb})_2$, —C(═O)$SR^{aa}$, —C(═S)$SR^{aa}$, —SC(═S)$SR^{aa}$, —SC(═O)$SR^{aa}$, —OC(═O)$SR^{aa}$, —SC(═O)$OR^{aa}$, —SC(═O)$R^{aa}$, —P(═O)$(R^{cc})_2$, —P(═O)$(OR^{cc})_2$, —OP(═O)$(R^{a})_2$, —OP(═O)$(OR^{aa})_2$, —P(═O)$(N(R^{bb})_2)_2$, —OP(═O)$(N(R^{bb})_2)_2$, —$NR^{bb}$P(═O)$(R^{aa})_2$, —$NR^{bb}$P(═O)$(OR^{aa})_2$, —$NR^{bb}$P(═O)$(N(R^{bb})_2)_2$, —$P(R^{cc})_2$, —$P(OR^{cc})_2$, —$P(R^{cc})_3^+X^-$, —$P(OR^{cc})_3^+X^-$, —$P(R^{cc})_4$, —$P(OR^{cc})_4$, —$OP(R^{cc})_2$, —$OP(R^{cc})_3^+X^-$, —$OP(OR^{cc})_2$, —$OP(OR^{cc})_3^+X^-$, —$OP(R^{cc})_4$, —$OP(OR^{cc})_4$, —$B(R^{aa})_2$, —$B(OR^{cc})_2$, —$BR^{aa}(OR^{cc})$, $C_{1-20}$ alkyl, $C_{1-20}$ perhaloalkyl, $C_{1-20}$ alkenyl, $C_{1-20}$ alkynyl, hetero$C_{1-20}$ alkyl, hetero$C_{1-20}$ alkenyl, hetero$C_{1-20}$ alkynyl, $C_{3-10}$ carbocyclyl, 3-14 membered heterocyclyl, $C_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups; wherein $X^-$ is a counterion;

or two geminal hydrogens on a carbon atom are replaced with the group ═O, ═S, ═$NN(R^{bb})_2$, ═$NNR^{bb}$C(═O)$R^{aa}$, ═$NNR^{bb}$C(═O)$OR^{aa}$, ═$NNR^{bb}$S(═O)$_2R^{aa}$, ═$NR^{bb}$, or ═$NOR^{cc}$;

wherein:

each instance of $R^{aa}$ is, independently, selected from $C_{1-20}$ alkyl, $C_{1-20}$ perhaloalkyl, $C_{1-30}$ alkenyl, $C_{1-20}$ alkynyl, hetero$C_{1-20}$ alkyl, hetero$C_{1-20}$ alkenyl, hetero$C_{1-20}$ alkynyl, $C_{3-10}$ carbocyclyl, 3-14 membered heterocyclyl, $C_{6-14}$ aryl, and 5-14 membered heteroaryl, or two $R^{aa}$ groups are joined to form a 3-14 membered heterocyclyl or 5-14 membered heteroaryl ring, wherein each of the alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{bb}$ is, independently, selected from hydrogen, —OH, —$OR^{aa}$, —$N(R^{cc})_2$, —CN, —C(═O)$R^{aa}$, —C(═O)$N(R^{cc})_2$, —$CO_2R^{aa}$, —$SO_2R$, —C(═$NR^{cc}$)$OR^{aa}$, —C(═$NR^{cc}$)$N(R^{cc})_2$, —$SO_2N(R^{cc})_2$, —$SO_2R^{cc}$, —$SO_2OR^{cc}$, —$SOR^{aa}$, —C(═S)$N(R^{cc})_2$, —C(═O)$SR^{cc}$, —C(═S)$SR^{cc}$, —P(═O)$(R^{aa})_2$, —P(═O)$(OR^{cc})_2$, —P(═O)$(N(R^{cc})_2)_2$, $C_{1-20}$ alkyl, $C_{1-20}$ perhaloalkyl, $C_{1-20}$ alkenyl, $C_{1-20}$ alkynyl, hetero$C_{1-20}$ alkyl, hetero$C_{1-20}$ alkenyl, hetero$C_{1-20}$ alkynyl. C3.10 carbocyclyl, 3-14 membered heterocyclyl, $C_{6-14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^1$ is, independently, selected from hydrogen. $C_{1-20}$ alkyl, $C_{1-20}$ perhaloalkyl, $C_{1-20}$ alkenyl, $C_{1-20}$ alkynyl, hetero$C_{1-20}$ alkyl, hetero$C_{1-20}$ alkenyl, hetero$C_{1-20}$ alkynyl, $C_{3-10}$ carbocyclyl, 3-14 membered heterocyclyl, $C_{6-14}$ aryl, and 5-14 membered heteroaryl, or two $R^1$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^d$ is, independently, selected from halogen, —CN, —$NO_2$, —$N_3$, —$SO_2H$, —$SO_3H$, —OH, —$OR^{ee}$, —$ON(R^{ff})_2$, —$N(R^{ff})_2$, —$N(R^{ff})_3^+X^-$, —$N(OR^{ee})R^{ff}$, —SH, —$SR^{ee}$, —$SSR^{ee}$, —C(═O)$R^{ee}$, —$CO_2H$, —$CO_2R^{ee}$, —OC(═O)$R^{ee}$, —$OCO_2R^{ee}$, —C(═O)$N(R^{ff})_2$, —OC(═O)$N(R^{ff})_2$, —$NR^{ff}$C(═O)$R^{ee}$, —$NR^{ff}CO_2R^{ee}$, —$NR^{ff}$C(═O)$N(R^{ff})_2$, —C(═$NR^{ff}$)$OR^{ee}$, —OC(═$NR^{ff}$)$R^{ee}$, —OC(═$NR^{ff}$)$OR^{ee}$, —C(═$NR^{ff}$)$N(R^{ff})_2$, —OC(═$NR^{ff}$)$N(R^{ff})_2$, —$NR^{ff}$C(═$NR^{ff}$)$N(R^{ff})_2$, —$NR^{ff}SO_2R^{ee}$, —$SO_2N(R^{ff})_2$, —$SO_2R^{ee}$, —$SO_2OR^{ee}$, —$OSO_2R^{ee}$, —S(═O)$R^{ee}$, —$Si(R^{ff})_3$, —$OSi(R^{ff})_3$, —C(═S)$N(R^{ff})_2$, —C(═O)$SR^{ee}$, —C(═S)$SR^{ee}$, —SC(═S)$SR^{ee}$, —P(═O)$(OR^{ee})_2$, —P(═O)$(R^{ee})_2$, —OP(═O)$(R')_2$, —OP(═O)$(OR^{ee})_2$, $C_{1-10}$ alkyl, $C_{1-10}$ perhaloalkyl, $C_{1-10}$ alkenyl, $C_{1-10}$ alkynyl, hetero$C_{1-10}$alkyl, hetero$C_{1-10}$alkenyl, hetero$C_{1-10}$alkynyl, $C_{3-10}$ carbocyclyl, 3-10 membered heterocyclyl, $C_{6-10}$ aryl, and 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups, or two geminal $R^{dd}$ substituents are joined to form ═O or ═S; wherein $X^-$ is a counterion;

each instance of $R^1$ is, independently, selected from $C_{1-10}$ alkyl, $C_{1-10}$ perhaloalkyl. $C_{1-10}$ alkenyl, $C_{1-10}$ alkynyl, hetero$C_{1-10}$ alkyl, hetero$C_{1-10}$ alkenyl, hetero$C_{1-10}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-10}$ alkyl, $C_{1-10}$ perhaloalkyl, $C_{1-10}$ alkenyl, $C_{1-10}$ alkynyl, hetero$C_{1-10}$ alkyl, hetero$C_{1-10}$ alkenyl, hetero$C_{1-10}$ alkynyl. C3.10 carbocyclyl, 3-10 membered heterocyclyl, $C_{6-10}$ aryl, and 5-10 membered heteroaryl, or two $R^{f}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups;

each instance of $R^{gg}$ is, independently, halogen, —CN, —$NO_2$, —$N_3$, —$SO_2H$, —$SO_3H$, —OH, —$OC_{1-6}$ alkyl, —$ON(C_{1-6}$ alkyl$)_2$, —$N(C_{1-6}$ alkyl$)_2$, —$N(C_{1-6}$ alkyl$)_3^+X^-$, —$NH(C_{1-6}$ alkyl$)_2^+X^-$, —$NH_2(C_{1-6}$ alkyl$)^+X^-$, —$NH_3^+X^-$, —$N(OC_{1-6}$ alkyl$)(C_{1-4}$, alkyl), —$N(OH)(C_{1-6}$ alkyl), —NH(OH), —SH, —$SC_{1-6}$ alkyl, —$SS(C_{1-6}$ alkyl), —C(=O)($C_{1-6}$ alkyl), —$CO_2H$, —$CO_2(C_{1-6}$ alkyl), —OC(=O)($C_{1-6}$ alkyl), —$OCO_2(C_{1-6}$ alkyl), —C(=O)$NH_2$, —C(=O)$N(C_{1-6}$ alkyl$)_2$, —OC(=O)NH($C_{1-6}$ alkyl), —NHC(=O)($C_{1-6}$ alkyl), —$N(C_{1-6}$ alkyl)C(=O)($C_{1-6}$ alkyl), —$NHCO_2(C_{1-6}$ alkyl), —NHC(=O)$N(C_{1-6}$ alkyl$)_2$, —NHC(=O)NH($C_{1-4}$ alkyl), —NHC(=O)$NH_2$, —C(=NH)O($C_{1-6}$ alkyl), —OC(=NH)($C_{1-6}$ alkyl), —OC(=NH)$OC_{1-6}$ alkyl, —C(=NH)$N(C_{1-6}$ alkyl$)_2$, —C(=NH)NH($C_{1-6}$ alkyl). —C(=NH)$NH_2$, —OC(=NH)$N(C_{1-6}$ alkyl$)_2$, —OC(NH)NH($C_{1-6}$ alkyl), —OC(NH)$NH_2$, —NHC(NH)$N(C_{1-6}$ alkyl$)_2$, —NHC(=NH)$NH_2$, —$NHSO_2(C_{1-6}$ alkyl), —$SO_2N(C_{1-6}$ alkyl$)_2$, —$SO_2NH(C_{1-6}$ alkyl), —$SO_2NH_2$, —$SO_2C_{1-6}$ alkyl, —$SO_2OC_{1-6}$ alkyl, —$OSO_2C_{1-6}$ alkyl, —$SOC_{1-6}$ alkyl, —$Si(C_{1-6}$ alkyl$)_3$, —$OSi(C_{1-6}$ alkyl$)_3$-C(=S)$N(C_{1-6}$ alkyl$)_2$, C(=S)NH($C_{1-6}$ alkyl), C(=S)$NH_2$, —C(=O)S($C_{1-6}$ alkyl), —C(=S)$SC_{1-6}$ alkyl, —SC(=S)$SC_{1-6}$ alkyl. —P(=O)($OC_{1-6}$ alkyl$)_2$, —P(=O)($C_{1-6}$ alkyl$)_2$, —OP(=O)($C_{1-6}$ alkyl$)_2$, —OP(=O)($OC_{1-6}$ alkyl$)_2$, $C_{1-10}$ alkyl, $C_{1-10}$ perhaloalkyl, $C_{1-10}$ alkenyl, $C_{1-10}$ alkynyl, hetero$C_{1-10}$ alkyl, hetero$C_{1-10}$ alkenyl, hetero$C_{1-10}$ alkynyl, $C_{3-10}$ carbocyclyl, $C_{6-10}$ aryl, 3-10 membered heterocyclyl, or 5-10 membered heteroaryl; or two geminal $R^{gg}$ substituents can be joined to form =O or =S; and each $X^-$ is a counterion.

In certain embodiments, each carbon atom substituent is independently halogen, substituted (e.g., substituted with one or more halogen) or unsubstituted $C_{1-4}$ alkyl, —$OR^{aa}$, —$SR^{aa}$, —$N(R^{bb})_2$, —CN, —SCN, —$NO_2$, —C(=O)$R^{aa}$, —$CO_2R^{aa}$, —C(=O)$N(R^{bb})_2$, —OC(=O)$R^{aa}$, —$OCO_2R^{aa}$, —OC(=O)$N(R^{bb})_2$, —$NR^{bb}$C(=O)$R^{aa}$, —$NR^{bb}CO_2R^{aa}$, or —$NR^{bb}$C(=O)$N(R^{bb})_2$. In certain embodiments, each carbon atom substituent is independently halogen, substituted (e.g., substituted with one or more halogen) or unsubstituted $C_{1-10}$ alkyl, —$OR^{aa}$, —$SR^{aa}$, —$N(R^{bb})_2$, —CN, —SCN, —$NO_2$, —C(=O)$R^{aa}$, —$CO_2R^{aa}$, —C(=O)$N(R^{bb})_2$, —OC(=O)$R^{aa}$, —$OCO_2R^{aa}$, —OC(=O)$N(R^{bb})_2$, —$NR^{bb}$C(=O)$R^{aa}$, —$NR^{bb}CO_2R^{aa}$, or —$NR^{bb}$C(=O)$N(R^{bb})_2$, wherein $R^{bb}$ is hydrogen, substituted (e.g., substituted with one or more halogen) or unsubstituted $C_{1-10}$ alkyl, an oxygen protecting group (e.g., silyl, TBDPS, TBDMS, TIPS, TES, TMS, MOM, THP, t-Bu, Bn, allyl, acetyl, pivaloyl, or benzoyl) when attached to an oxygen atom, or a sulfur protecting group (e.g., acetamidomethyl, t-Bu, 3-nitro-2-pyridine sulfenyl, 2-pyridine-sulfenyl, or triphenylmethyl) when attached to a sulfur atom; and each $R^{bb}$ is independently hydrogen, substituted (e.g., substituted with one or more halogen) or unsubstituted $C_{1-10}$ alkyl, or a nitrogen protecting group (e.g., Bn, Boc, Cbz, Fmoc, trifluoroacetyl, triphenylmethyl, acetyl, or Ts). In certain embodiments, each carbon atom substituent is independently halogen, substituted (e.g., substituted with one or more halogen) or unsubstituted $C_{1-6}$ alkyl, —$OR^{aa}$, —$SR^{aa}$, —$N(R^{bb})_2$, —CN, —SCN, or —$NO_2$. In certain embodiments, each carbon atom substituent is independently halogen, substituted (e.g., substituted with one or more halogen moieties) or unsubstituted $C_{1-10}$ alkyl, —$OR^{aa}$, —$SR^{aa}$, —$N(R^{bb})_2$, —CN, —SCN, or —$NO_2$, wherein $R^{aa}$ is hydrogen, substituted (e.g., substituted with one or more halogen) or unsubstituted $C_{1-10}$ alkyl, an oxygen protecting group (e.g., silyl, TBDPS. TBDMS, TIPS, TES, TMS, MOM, THP, t-Bu, Bn, allyl, acetyl, pivaloyl, or benzoyl) when attached to an oxygen atom, or a sulfur protecting group (e.g., acetamidomethyl, t-Bu, 3-nitro-2-pyridine sulfenyl, 2-pyridine-sulfenyl, or triphenylmethyl) when attached to a sulfur atom; and each $R^{bb}$ is independently hydrogen, substituted (e.g., substituted with one or more halogen) or unsubstituted $C_{1-10}$ alkyl, or a nitrogen protecting group (e.g., Bn, Boc, Cbz, Fmoc, trifluoroacetyl, triphenylmethyl, acetyl, or Ts).

The term "halo" or "halogen" refers to fluorine (fluoro, —F), chlorine (chloro, —Cl), bromine (bromo, —Br), or iodine (iodo, —I).

The term "hydroxyl" or "hydroxy" refers to the group —OH. The term "substituted hydroxyl" or "substituted hydroxyl," by extension, refers to a hydroxyl group wherein the oxygen atom directly attached to the parent molecule is substituted with a group other than hydrogen, and includes groups selected from —$OR^{aa}$, —$ON(R^{bb})_2$, —OC(=O)$SR^{aa}$, —OC(=O)$R^{aa}$, —$OCO_2R^{aa}$, —OC(=O)$N(R^{bb})_2$, —OC(=$NR^{bb}$)$R^{aa}$, —OC(=$NR^{bb}$)$OR^{aa}$, —OC(=$NR^{bb}$)$N(R^{bb})_2$, —OS(=O)$R^{aa}$, —$OSO_2R^{aa}$, —$OSi(R^{aa})_3$, —$OP(R^{cc})_2$, —$OP(R^{cc})_3^+X^-$, —$OP(OR^{cc})_2$, —$OP(OR^{cc})_3^+X^-$, —OP(=O)$(R^{aa})_2$, —OP(=O)$(OR^{cc})_2$, and —OP(=O)$(N(R^{bb}))_2$, wherein $X^-$, $R^{aa}$, $R^{bb}$, and $R^{cc}$ are as defined herein.

The term "amino" refers to the group —$NH_2$. The term "substituted amino," by extension, refers to a monosubstituted amino, a disubstituted amino, or a trisubstituted amino. In certain embodiments, the "substituted amino" is a monosubstituted amino or a disubstituted amino group.

The term "monosubstituted amino" refers to an amino group wherein the nitrogen atom directly attached to the parent molecule is substituted with one hydrogen and one group other than hydrogen, and includes groups selected from —$NH(R^{bb})$, —NHC(=O)$R^{aa}$, —$NHCO_2R^{aa}$, —NHC(=O)$N(R^{bb})_2$, —NHC(=$NR^{bb}$)$N(R^{bb})_2$, —$NHSO_2R^{aa}$, —NHP(=O)$(OR^{cc})_2$, and —NHP(=O)$(N(R^{bb})_2)_2$, wherein $R^{aa}$, $R^{bb}$ and $R^{cc}$ are as defined herein, and wherein $R^{bb}$ of the group —$NH(R^{bb})$ is not hydrogen.

The term "disubstituted amino" refers to an amino group wherein the nitrogen atom directly attached to the parent molecule is substituted with two groups other than hydrogen, and includes groups selected from —$N(R^{bb})_2$, —$NR^{bb}$C(=O)$R^{aa}$, —$NR^{bb}CO_2R^{aa}$, —$NR^{bb}$C(=O)$N(R^{bb})_2$, —$NR^{bb}$C(=NRb)$N(R^{bb})_2$, —$NR^{bb}SO_2R^{aa}$, —$NR^{bb}$P(=O)$(OR^{cc})_2$, and —$NR^{bb}$P(=O)$(N(R^{bb})_2)_2$, wherein $R^{aa}$, $R^{bb}$, and $R^{cc}$ are as defined herein, with the proviso that the nitrogen atom directly attached to the parent molecule is not substituted with hydrogen.

The term "trisubstituted amino" refers to an amino group wherein the nitrogen atom directly attached to the parent molecule is substituted with three groups, and includes groups selected from —N($R^{bb}$)$_3$ and —N($R^{bb}$)$_3^+X^-$, wherein $R^{bb}$ and $X^-$ are as defined herein.

The term "acyl" refers to a group having the general formula —C(=O)$R^{aa}$, —C(=O)O$R^{aa}$, —C(=O)—O—C(=O)$R^{aa}$, —C(=O)S$R^{aa}$, —C(=O)N($R^{bb}$)$_2$, —C(=S)$R^{aa}$, —C(=S)N($R^{bb}$)$_2$, and —C(=S)S($R^{aa}$), —C(=N$R^{bb}$)$R^{aa}$, —C(=N$R^{bb}$)O$R^{aa}$, —C(=N$R^{bb}$)S$R^{aa}$, and —C(=N$R^{bb}$)N($R^{bb}$)$_2$, wherein $R^{aa}$ and $R^{bb}$ are as defined herein. Exemplary acyl groups include aldehydes (—CHO), carboxylic acids (—$CO_2$H), ketones, acyl halides, esters, amides, imines, carbonates, carbamates, and ureas.

The term "carbonyl" refers to a group wherein the carbon directly attached to the parent molecule is $sp^2$ hybridized, and is substituted with an oxygen, nitrogen or sulfur atom, e.g., a group selected from ketones (—C(=O)$R^{aa}$), carboxylic acids (—$CO_2$H), aldehydes (—CHO), esters (—$CO_2R^{aa}$, —C(=O)S$R^{aa}$, —C(=S)S$R^{aa}$), amides (—C(=O)N($R^{bb}$)$_2$, —C(=O)N$R^{bb}$$SO_2R^{aa}$, —C(=S)N($R^{bb}$)$_2$), and imines (—C(=NRb)$R^{aa}$, —C(=N$R^{bb}$)O$R^{aa}$), —C(=N$R^{bb}$)N($R^{bb}$)$_2$), wherein $R^{aa}$ and $R^{bb}$ are as defined herein.

Nitrogen atoms can be substituted or unsubstituted as valency permits, and include primary, secondary, tertiary, and quaternary nitrogen atoms. Exemplary nitrogen atom substituents include hydrogen, —OH, —O$R^{aa}$, —N($R^{cc}$)$_2$, —CN, —C(=O)$R^{aa}$, —C(=O)N($R^{cc}$)$_2$, —$CO_2R^{aa}$, —$SO_2R^{aa}$, —C(=N$R^{bb}$)$R^{aa}$, —C(=N$R^{cc}$)O$R^{aa}$, —C(=N$R^{cc}$)N($R^{cc}$)$_2$, —$SO_2$N($R^{cc}$)$_2$, —$SO_2R^{cc}$, —$SO_2$O$R^{cc}$, —SO$R^{aa}$, —C(=S)N($R^{cc}$)$_2$, —C(=O)S$R^{cc}$, —C(=S)S$R^{cc}$, —P(=O)(O$R^{cc}$)$_2$, —P(=O)($R^{aa}$)$_2$, —P(=O)(N($R^{cc}$)$_2$)$_2$, $C_{1-20}$ alkyl, $C_{1-20}$ perhaloalkyl, $C_{1-20}$ alkenyl, $C_{1-20}$ alkynyl, hetero $C_{1-20}$ alkyl, hetero $C_{1-20}$ alkenyl, hetero $C_{1-20}$ alkynyl, $C_{3-10}$ carbocyclyl, 3-14 membered heterocyclyl, $C_{6-14}$ aryl, and 5-14 membered heteroaryl, or two $R^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined above.

In certain embodiments, each nitrogen atom substituent is independently substituted (e.g., substituted with one or more halogen) or unsubstituted $C_{1-6}$ alkyl, —C(=O)$R^{aa}$, —$CO_2R^{aa}$, —C(=O)N($R^{bb}$)$_2$, or a nitrogen protecting group. In certain embodiments, each nitrogen atom substituent is independently substituted (e.g., substituted with one or more halogen) or unsubstituted $C_{1-10}$ alkyl, —C(=O)$R^{aa}$, —$CO_2R^{aa}$, —C(=O)N($R^{bb}$)$_2$, or a nitrogen protecting group, wherein $R^{aa}$ is hydrogen, substituted (e.g., substituted with one or more halogen) or unsubstituted $C_{1-10}$ alkyl, or an oxygen protecting group when attached to an oxygen atom; and each $R^{bb}$ is independently hydrogen, substituted (e.g., substituted with one or more halogen) or unsubstituted $C_{1-10}$ alkyl, or a nitrogen protecting group. In certain embodiments, each nitrogen atom substituent is independently substituted (e.g., substituted with one or more halogen) or unsubstituted $C_{1-6}$ alkyl or a nitrogen protecting group.

In certain embodiments, the substituent present on the nitrogen atom is a nitrogen protecting group (also referred to herein as an "amino protecting group"). Nitrogen protecting groups include —OH, —O$R^{aa}$, —N($R^{cc}$)$_2$, —C(=O)$R^{aa}$, —C(=O)N($R^{cc}$)$_2$, —$CO_2R^{aa}$, —$SO_2R^{aa}$, —C(=N$R^{cc}$)$R^{aa}$, —C(=N$R^{cc}$)O$R^{aa}$, —C(=N$R^{cc}$)N($R^{cc}$)$_2$, —$SO_2$N($R^{cc}$)$_2$, —$SO_2R^{cc}$, —$SO_2$O$R^{cc}$, —SO$R^{aa}$, —C(=S)N($R^{cc}$)$_2$, —C(=O)S$R^{cc}$, —C(=S)S$R^{cc}$, $C_{1-10}$ alkyl (e.g., aralkyl, heteroaralkyl), $C_{1-20}$ alkenyl, $C_{1-20}$ alkynyl, hetero $C_{1-20}$ alkyl, hetero $C_{1-20}$ alkenyl, hetero $C_{1-20}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein. Nitrogen protecting groups are well known in the art and include those described in detail in *Protecting Groups in Organic Synthesis*, T. W. Greene and P. G. M. Wuts, 3rd edition. John Wiley & Sons, 1999, incorporated herein by reference.

For example, in certain embodiments, at least one nitrogen protecting group is an amide group (e.g., a moiety that include the nitrogen atom to which the nitrogen protecting groups (e.g., —C(=O)$R^{aa}$) is directly attached). In certain such embodiments, each nitrogen protecting group, together with the nitrogen atom to which the nitrogen protecting group is attached, is independently selected from the group consisting of formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivatives, benzamide, p-phenylbenzamide, o-nitophenylacetamide, o-nitrophenoxyacetamide, acetoacetamide, (N'-dithiobenzyloxyacylamino) acetamide, 3-(p-hydroxyphenyl)propanamide, 3-(o-nitrophenyl)propanamide, 2-methyl-2-(o-nitrophenoxy) propanamide, 2-methyl-2-(o-phenylazophenoxy) propanamide, 4-chlorobutanamide, 3-methyl-3-nitrobutanamide, o-nitrocinnamide. N-acetylmethionine derivatives, o-nitrobenzamide, and o-(benzoyloxymethyl) benzamide.

In certain embodiments, at least one nitrogen protecting group is a carbamate group (e.g., a moiety that include the nitrogen atom to which the nitrogen protecting groups (e.g., —C(=O)O$R^{aa}$) is directly attached). In certain such embodiments, each nitrogen protecting group, together with the nitrogen atom to which the nitrogen protecting group is attached, is independently selected from the group consisting of methyl carbamate, ethyl carbamate, 9-fluorenylmethyl carbamate (Fmoc), 9-(2-sulfo)fluorenylmethyl carbamate, 9-(2,7-dibromo)fluorenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphcnylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium) benzyl carbamate, and 2,4,6-trimethylbenzyl carbamate.

In certain embodiments, at least one nitrogen protecting group is a sulfonamide group (e.g., a moiety that include the nitrogen atom to which the nitrogen protecting groups (e.g., $—S(=O)_2R^{aa}$) is directly attached). In certain such embodiments, each nitrogen protecting group, together with the nitrogen atom to which the nitrogen protecting group is attached, is independently selected from the group consisting of p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pme), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

In certain embodiments, each nitrogen protecting group, together with the nitrogen atom to which the nitrogen protecting group is attached, is independently selected from the group consisting of phenothiazinyl-(10)-acyl derivatives, N'-p-toluenesulfonylaminoacyl derivatives, N'-phenylaminothioacyl derivatives. N-benzoylphenylalanyl derivatives. N-acetylmethionine derivatives, 4,5-diphenyl-3-oxazolin-2-one, N-phthalimide. N-dithiasuccinimide (Dts), N-2,3-diphenylmaleimide, N-2,5-dimethylpyrrole. N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone. N-methylamine. N-allylamine. N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine. N-5-dibenzosuberylamine. N-triphenylmethylamine (Tr). N-[(4-methoxyphenyl)diphenylmethyl]amine (MMTr), N-9-phenylfluorenylamine (PhF), N-2,7-dichloro-9-fluorenylmethyleneamine. N-ferrocenylmethylamino (Fcm). N-2-picolylamino N'-oxide, N-1,1-dimethylthiomethyleneamine. N-benzylideneamine, N-p-methoxybenzylideneamine, N-diphenylmethyleneamine, N-[(2-pyridyl)mesityl]methyleneamine. N—(N',N'-dimethylaminomethylene) amine. N-p-nitrobenzylidencamine. N-salicylideneamine, N-5-chlorosalicylideneamine, N-(5-chloro-2-hydroxyphenyl)phenylmethyleneamine, N-cyclohexylideneamine. N-(5,5-dimethyl-3-oxo-1-cyclohexenyl)amine. N-borane derivatives, N-diphenylborinic acid derivatives, N-[phenyl (pentaacylchromium- or tungsten)acyl]amine, N-copper chelate, N-zinc chelate, N-nitroamine. N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzcnesulfenamide (Nps), 2,4-dinitrobenzenesulfenamidc, pentachlorobenzenesulfenamide, 2-nitro-4-methoxy benzenesulfenamide, triphenylmethylsulfenamide, and 3-nitropyridinesulfenamide (Npys). In some embodiments, two instances of a nitrogen protecting group together with the nitrogen atoms to which the nitrogen protecting groups are attached are N,N'-isopropylidenediamine.

In certain embodiments, at least one nitrogen protecting group is Bn, Boc, Cbz, Fmoc, trifluoroacetyl, triphenylmethyl, acetyl, or Ts.

In certain embodiments, the molecular weight of a substituent is lower than 250, lower than 200, lower than 150, lower than 100, or lower than 50 g/mol. In certain embodiments, a substituent consists of carbon, hydrogen, fluorine, chlorine, bromine, iodine, oxygen, sulfur, nitrogen, and/or silicon atoms. In certain embodiments, a substituent consists of carbon, hydrogen, fluorine, chlorine, bromine, iodine, oxygen, sulfur, and/or nitrogen atoms. In certain embodiments, a substituent consists of carbon, hydrogen, fluorine, chlorine, bromine, and/or iodine atoms. In certain embodiments, a substituent consists of carbon, hydrogen, fluorine, and/or chlorine atoms. In certain embodiments, a substituent comprises 0, 1, 2, or 3 hydrogen bond donors. In certain embodiments, a substituent comprises 0, 1, 2, or 3 hydrogen bond acceptors.

Use of the phrase "at least one instance" refers to 1, 2, 3, 4, or more instances, but also encompasses a range, e.g., for example, from 1 to 4, from 1 to 3, from 1 to 2, from 2 to 4, from 2 to 3, or from 3 to 4 instances, inclusive.

The disclosure is not intended to be limited in any manner by the above exemplary listing of substituents. Additional terms may be defined in other sections of this disclosure.

Other Definitions

The following definitions are more general terms used throughout the present application.

As used herein, the term "salt" refers to any and all salts, and encompasses pharmaceutically acceptable salts. Salts include ionic compounds that result from the neutralization reaction of an acid and a base. A salt is composed of one or more cations (positively charged ions) and one or more anions (negative ions) so that the salt is electrically neutral (without a net charge). Salts of the compounds of this invention include those derived from inorganic and organic acids and bases. Examples of acid addition salts are salts of an amino group formed with inorganic acids, such as hydrochloric acid, hydrobromic acid, phosphoric acid, sulfuric acid, and perchloric acid, or with organic acids, such as acetic acid, oxalic acid, maleic acid, tartaric acid, citric acid, succinic acid, or malonic acid or by using other methods known in the art such as ion exchange. Other salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate, hippurate, and the like. Salts derived from appropriate bases include alkali metal, alkaline earth metal, ammonium and $N^+(C_{1-4}\ alkyl)_4$ salts. Representative alkali or alkaline earth metal salts include sodium, lithium, potassium, calcium, magnesium, and the like. Further salts include ammonium, quaternary ammonium, and amine cations formed using counterions such as halide, hydroxide, carboxylate, sulfate, phosphate, nitrate, lower alkyl sulfonate, and aryl sulfonate.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids, such as hydrochloric acid, hydrobromic acid, phosphoric acid, sulfuric acid, and perchloric acid or with organic acids, such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium, and $N^+(C_{1-4}\ alkyl)_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound, or a salt thereof, that are associated with a solvent, usually by a solvolysis reaction. This physical association may include hydrogen bonding. Conventional solvents include water, methanol, ethanol, acetic acid. DMSO, THF, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

The term "stoichiometric solvate" refers to a solvate, which comprises a compound (e.g., a compound disclosed herein) and a solvent, wherein the solvent molecules are an integral part of the crystal lattice, in which they interact strongly with the compound and each other. The removal of the solvent molecules will cause instability of the crystal network, which subsequently collapses into an amorphous phase or recrystallizes as a new crystalline form with reduced solvent content.

The term "non-stoichiometric solvate" refers to a solvate, which comprises a compound (e.g., a compound disclosed herein) and a solvent, wherein the solvent content may vary without major changes in the crystal structure. The amount of solvent in the crystal lattice only depends on the partial pressure of solvent in the surrounding atmosphere. In the fully solvated state, non-stoichiometric solvates may, but not necessarily have to, show an integer molar ratio of solvent to the compound. During drying of a non-stoichiometric solvate, a portion of the solvent may be removed without significantly disturbing the crystal network, and the resulting solvate can subsequently be resolvated to give the initial crystalline form. Unlike stoichiometric solvates, the desolvation and resolvation of non-stoichiometric solvates is not accompanied by a phase transition, and all solvation states represent the same crystal form.

The term "tautomers" or "tautomeric" refers to two or more interconvertible compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol, amide-to-imide, lactam-to-lactim, enamine-to-imine, and enamine-to-(a different enamine) tautomerizations.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

As used herein. "lipophilic" refers to the ability of a group to dissolve in fats, oils, lipids, and lipophilic non-polar solvents such as hexane or toluene. In general, a lipophilic group refers to an unsubstituted n-alkyl or unsubstituted n-alkenyl group having 6 to 50 carbon atoms, e.g., 6 to 40, 6 to 30, 6 to 20, 8 to 20, 8 to 19, 8 to 18, 8 to 17, 8 to 16, or 8 to 15 carbon atoms.

The terms "phosphorylethanolamine" and "phosphoethanolamine" are used interchangeably.

The term "sterol" refers to a subgroup of steroids also known as steroid alcohols, i.e., a steroid containing at least one hydroxyl group. Sterols are usually divided into two classes: (1) plant sterols also known as "phytosterols," and (2) animal sterols also known as "zoosterols." The term "sterol" includes, but is not limited to, cholesterol, sitosterol, campesterol, stigmasterol, brassicasterol (including dihydrobrassicasterol), desmosterol, chalinosterol, poriferasterol, clionasterol, ergosterol, coprosterol, codisterol, isofucosterol, fucosterol, clerosterol, nervisterol, lathosterol, stellasterol, spinasterol, chondrillasterol, peposterol, avenasterol, isoavenasterol, fecosterol, pollinastasterol, and all natural or synthesized forms and derivatives thereof, including isomers.

As used here, the term "PEG-lipid" refers to a PEGylated lipid.

An "amino acid" refers to natural and unnatural D/L alpha-amino acids, as well as natural and unnatural beta- and gamma-amino acids. A "peptide" refers to two amino acids joined by a peptide bond. A "polypeptide" refers to three or more amino acids joined by peptide bonds. An "amino acid side chain" refers to the group(s) pended to the alpha carbon (if an alpha amino acid), alpha and beta carbon (if a beta amino acid), or the alpha, beta, and gamma carbon (if a gamma amino acid). Exemplary amino acid side chains are depicted herein.

A "protein," "peptide," or "polypeptide" comprises a polymer of amino acid residues linked together by peptide bonds. The term, as used herein, refers to proteins, polypeptides, and peptides of any size, structure, or function. Typically, a protein will be at least three amino acids long. A protein may refer to an individual protein or a collection of proteins. Inventive proteins preferably contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in a protein may be modified, for example, by the addition of a chemical entity such as a carbohydrate group, a hydroxyl group, a phosphate group, a farnesyl group, an isofarnesyl group, a fatty acid group, a linker for conjugation or functionalization, or other modification. A protein may also be a single molecule or may be a multi-molecular complex. A protein may be a fragment of a naturally occurring protein or peptide. A protein may be naturally occurring, recombinant, synthetic, or any combination of these.

The term "apolipoprotein" refers to a protein that binds a lipid (e.g., triacylglycerol or cholesterol) to form a lipoprotein. Apolipoproteins also serve as enzyme cofactors, receptor ligands, and lipid transfer carriers that regulate the metabolism of lipoproteins and their uptake in tissues. Major types of apolipoproteins include integral and non-integral apolipoproteins. Exemplary apolipoproteins include apoA (e.g., apoA-I, apoA-II, apoA-IV, and apoA-V); apoB (e.g., apoB48 and apoB 100); apoC (e.g., apoC-I, apoC-II, apoC-III, and apoC-IV); apoD; apoE; apoH; and apoJ.

The term "gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" or "chimeric construct" refers to any gene or a construct, not a native gene, comprising regulatory and coding sequences that are not found together in nature. Accordingly, a chimeric gene or chimeric construct may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but which is introduced into the host organism by gene transfer. Foreign genes can comprise native genes inserted into a non-native organism, or chimeric genes. A "transgene" is a gene that has been introduced into the genome by a transformation procedure.

The terms "polynucleotide", "nucleotide sequence". "nucleic acid", "nucleic acid molecule", "nucleic acid sequence", and "oligonucleotide" refer to a series of nucleotide bases (also called "nucleotides") in DNA and RNA, and mean any chain of two or more nucleotides. The polynucleotides can be chimeric mixtures or derivatives or modified versions thereof, single-stranded or double-stranded. The oligonucleotide can be modified at the base moiety, sugar moiety, or phosphate backbone, for example, to improve stability of the molecule, its hybridization parameters, etc. The antisense oligonucleotide may comprise a modified base moiety which is selected from the group including, but not limited to, 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine. $N_6$-isopentenyladenine, 1-methylguanine, 1-methylinosine, 2,2-dimethylguanine, 2-methyladenine, 2-methylguanine, 3-methylcytosine, 5-methylcytosine. $N_6$-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-$N_6$-isopentenyladenine, wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid, 5-methyl-2-thiouracil, 3-(3-amino-3-N-2-carboxypropyl) uracil, a thio-guanine, and 2,6-diaminopurine. A nucleotide sequence typically carries genetic information, including the information used by cellular machinery to make proteins and enzymes. These terms include double- or single-stranded genomic and cDNA, RNA, any synthetic and genetically manipulated polynucleotide, and both sense and antisense polynucleotides. This includes single- and double-stranded molecules, i.e., DNA-DNA, DNA-RNA and RNA-RNA hybrids, as well as "protein nucleic acids" (PNAs) formed by conjugating bases to an amino acid backbone. This also includes nucleic acids containing carbohydrate or lipids. Exemplary DNAs include single-stranded DNA (ssDNA), double-stranded DNA (dsDNA), plasmid DNA (pDNA), genomic DNA (gDNA), complementary DNA (cDNA), antisense DNA, chloroplast DNA (ctDNA or cpDNA), microsatellite DNA, mitochondrial DNA (mtDNA or mDNA), kinetoplast DNA (kDNA), a provirus, a lysogen, repetitive DNA, satellite DNA, and viral DNA. Exemplary RNAs include single-stranded RNA (ssRNA), double-stranded RNA (dsRNA), small interfering RNA (siRNA), messenger RNA (mRNA), precursor messenger RNA (pre-mRNA), small hairpin RNA or short hairpin RNA (shRNA), microRNA (miRNA), guide RNA (gRNA), transfer RNA (tRNA), antisense RNA (asRNA), heterogeneous nuclear RNA (hnRNA), coding RNA, non-coding RNA (ncRNA), long non-coding RNA (long ncRNA or lncRNA), satellite RNA, viral satellite RNA, signal recognition particle RNA, small cytoplasmic RNA, small nuclear RNA (snRNA), ribosomal RNA (rRNA), Piwi-interacting RNA (piRNA), a polyinosinic acid, a ribozyme, a flexizyme, small nucleolar RNA (snoRNA), spliced leader RNA, viral RNA, and viral satellite RNA.

Polynucleotides described herein may be synthesized by standard methods known in the art, e.g., by use of an automated DNA synthesizer (such as those that are commercially available from Biosearch, Applied Biosystems, etc.). As examples, phosphorothioate oligonucleotides may be synthesized by the method of Stein et al., *Nucl. Acids Res.,* 16, 3209, (1988), methylphosphonate oligonucleotides can be prepared by use of controlled pore glass polymer supports (Sarin et al. *Proc. Natl. Acad. Sci. U.S.A.* 85, 7448-7451. (1988)). A number of methods have been developed for delivering antisense DNA or RNA to cells, e.g., antisense molecules can be injected directly into the tissue site, or modified antisense molecules, designed to target the desired cells (antisense linked to peptides or antibodies that specifically bind receptors or antigens expressed on the target cell surface) can be administered systemically. Alternatively, RNA molecules may be generated by in vitro and in vivo transcription of DNA sequences encoding the antisense RNA molecule. Such DNA sequences may be incorporated into a wide variety of vectors that incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines. However, it is often difficult to achieve intracellular concentrations of the antisense sufficient to suppress translation of endogenous mRNAs. Therefore a preferred approach utilizes a recombinant DNA construct in which the antisense oligonucleotide is placed under the control of a strong promoter. The use of such a construct to transfect target cells in the patient will result in the transcription of sufficient amounts of single stranded RNAs that will form complementary base pairs with the endogenous target gene transcripts and thereby prevent translation of the target gene mRNA. For example, a vector can be introduced in vivo such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human, cells. Such promoters can be inducible or constitutive. Such promoters include, but are not limited to: the SV40 early promoter region (Bernoist et al., *Nature,* 290, 304-310, (1981); Yamamoto et al., *Cell,* 22, 787-797, (1980); Wagner et al., *Proc. Natl. Acad. Sci. U.S.A.* 78, 1441-1445, (1981); Brinster et al., *Nature* 296, 39-42. (1982)). Any type of plasmid, cosmid, yeast artificial chromosome or viral vector can be used to prepare the recombinant DNA construct that can be introduced directly into the tissue site. Alternatively, viral vectors can be used which selectively infect the desired tissue, in which case administration may be accomplished by another route (e.g., systemically).

The polynucleotides may be flanked by natural regulatory (expression control) sequences, or may be associated with heterologous sequences, including promoters, internal ribosome entry sites (IRES) and other ribosome binding site sequences, enhancers, response elements, suppressors, signal sequences, polyadenylation sequences, introns, 5'- and 3'-non-coding regions, and the like. The nucleic acids may also be modified by many means known in the art. Non-limiting examples of such modifications include methylation. "caps", substitution of one or more of the naturally occurring nucleotides with an analog, and internucleotide modifications such as, for example, those with uncharged linkages (e.g., methyl phosphonates, phosphotriesters, phosphoroamidates, carbamates, etc.) and with charged linkages (e.g., phosphorothioates, phosphorodithioates, etc.). Polynucleotides may contain one or more additional covalently linked moieties, such as, for example, proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.), and alkylators. The polynucleotides may be derivatized by formation of a methyl or ethyl phosphotriester or an alkyl phosphoramidate linkage. Furthermore, the polynucleotides herein may also be modified with a label capable of providing a detectable signal, either directly or indirectly. Exemplary labels include radioisotopes, fluorescent molecules, biotin, and the like.

A "recombinant nucleic acid molecule" is a nucleic acid molecule that has undergone a molecular biological manipulation, i.e., non-naturally occurring nucleic acid molecule or genetically engineered nucleic acid molecule. Furthermore, the term "recombinant DNA molecule" refers to a nucleic acid sequence which is not naturally occurring, or can be made by the artificial combination of two otherwise separated segments of nucleic acid sequence. i.e., by ligating together pieces of DNA that are not normally continuous. By "recombinantly produced" is meant artificial combination often accomplished by either chemical synthesis means, or by the artificial manipulation of isolated segments of nucleic acids, e.g., by genetic engineering techniques using restriction enzymes, ligases, and similar recombinant techniques as described by, for example. Sambrook et al., Molecular Cloning, second edition. Cold Spring Harbor Laboratory, Plainview, N.Y.; (1989), or Ausubel et al., Current Protocols in Molecular Biology. Current Protocols (1989), and DNA Cloning: A Practical Approach. Volumes I and II (ed. D. N. Glover) IREL Press. Oxford. (1985); each of which is incorporated herein by reference.

Such manipulation may be done to replace a codon with a redundant codon encoding the same or a conservative amino acid, while typically introducing or removing a sequence recognition site. Alternatively, it may be performed to join together nucleic acid segments of desired functions to generate a single genetic entity comprising a desired combination of functions not found in nature. Restriction enzyme recognition sites are often the target of such artificial manipulations, but other site specific targets, e.g., promoters, DNA replication sites, regulation sequences, control sequences, open reading frames, or other useful features may be incorporated by design. Examples of recombinant nucleic acid molecule include recombinant vectors, such as cloning or expression vectors which contain DNA sequences encoding Ror family proteins or immunoglobulin proteins which are in a 5' to 3' (sense) orientation or in a 3' to 5' (antisense) orientation.

The term "pDNA," "plasmid DNA." or "plasmid" refers to a small DNA molecule that is physically separate from, and can replicate independently of, chromosomal DNA within a cell. Plasmids can be found in all three major domains: Archaea, Bacteria, and Eukarya. In nature, plasmids carry genes that may benefit survival of the subject (e.g., antibiotic resistance) and can frequently be transmitted from one bacterium to another (even of another species) via horizontal gene transfer. Artificial plasmids are widely used as vectors in molecular cloning, serving to drive the replication of recombinant DNA sequences within host subjects. Plasmid sizes may vary from 1 to over 1.000 kbp. Plasmids are considered replicons, capable of replicating autonomously within a suitable host.

"RNA transcript" refers to the product resulting from RNA polymerase-catalyzed transcription of a DNA sequence. When the RNA transcript is a complementary copy of the DNA sequence, it is referred to as the primary transcript or it may be an RNA sequence derived from post-transcriptional processing of the primary transcript and is referred to as the mature RNA. "Messenger RNA (mRNA)" refers to the RNA that is without introns and can be translated into polypeptides by the cell. "cRNA" refers to complementary RNA, transcribed from a recombinant cDNA template. "cDNA" refers to DNA that is complementary to and derived from an mRNA template. The cDNA can be single-stranded or converted to double-stranded form using, for example, the Klenow fragment of DNA polymerase I.

A sequence "complementary" to a portion of an RNA, refers to a sequence having sufficient complementarity to be able to hybridize with the RNA, forming a stable duplex; in the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

The terms "nucleic acid" or "nucleic acid sequence", "nucleic acid molecule". "nucleic acid fragment" or "polynucleotide" may be used interchangeably with "gene", "mRNA encoded by a gene" and "cDNA".

The term "mRNA" or "mRNA molecule" refers to messenger RNA, or the RNA that serves as a template for protein synthesis in a cell. The sequence of a strand of mRNA is based on the sequence of a complementary strand of DNA comprising a sequence coding for the protein to be synthesized.

The term "siRNA" or "siRNA molecule" refers to small inhibitory RNA duplexes that induce the RNA interference (RNAi) pathway, where the siRNA interferes with the expression of specific genes with a complementary nucleotide sequence, siRNA molecules can vary in length (e.g., between 18-30 or 20-25 basepairs) and contain varying degrees of complementarity to their target mRNA in the antisense strand. Some siRNA have unpaired overhanging bases on the 5' or 3' end of the sense strand and/or the antisense strand. The term siRNA includes duplexes of two separate strands, as well as single strands that can form hairpin structures comprising a duplex region.

The term "gene silencing" refers to an epigenetic process of gene regulation where a gene is "switched off" by a mechanism other than genetic modification. That is, a gene which would be expressed (i.e., "turned on") under normal circumstances is switched off by machinery in the cell. Gene silencing occurs when RNA is unable to make a protein during translation. Genes are regulated at either the transcriptional or post-transcriptional level. Transcriptional gene silencing is the result of histone modifications, creating an environment of heterochromatin around a gene that makes it inaccessible to transcriptional machinery (e.g., RNA polymerase and transcription factors). Post-transcriptional gene silencing is the result of mRNA of a particular gene being destroyed or blocked. The destruction of the mRNA prevents translation and thus the formation of a gene product (e.g., a protein). A common mechanism of post-transcriptional gene silencing is RNAi.

The term "particle" refers to a small object, fragment, or piece of a substance that may be a single element, inorganic material, organic material, or mixture thereof. Examples of particles include polymeric particles, single-emulsion particles, double-emulsion particles, coacervates, liposomes, microparticles, nanoparticles (e.g., lipid nanoparticles), macroscopic particles, pellets, crystals, aggregates, composites, pulverized, milled or otherwise disrupted matrices, and cross-linked protein or polysaccharide particles, each of which have an average characteristic dimension of about less than about 1 mm and at least 1 nm, where the characteristic dimension, or "critical dimension," of the particle is the smallest cross-sectional dimension of the particle. A particle may be composed of a single substance or multiple substances. In certain embodiments, the particle is not a viral particle. In other embodiments, the particle is not a liposome. In certain embodiments, the particle is not a micelle. In certain embodiments, the particle is substantially solid throughout. In certain embodiments, the particle is a nanoparticle. In certain embodiments, the particle is a microparticle.

The terms "composition" and "formulation" are used interchangeably.

A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. In certain embodiments, the non-human animal is a mammal (e.g., primate (e.g., cynomolgus monkey or rhesus monkey), commercially relevant mammal (e.g., cattle, pig, horse, sheep, goat, cat, or dog), or bird (e.g., commercially relevant bird, such as chicken, duck, goose, or turkey)). In certain embodiments, the non-human animal is a fish, reptile, or amphibian. The non-human animal may be a male or female at any stage of development. The non-human animal may be a transgenic animal or genetically engineered animal. The term "patient" refers to a human subject in need of treatment of a disease.

The term "administer." "administering," or "administration" refers to implanting, absorbing, ingesting, injecting, inhaling, or otherwise introducing a compound described herein, or a composition thereof, in or on a subject.

The terms "condition." "disease." and "disorder" are used interchangeably.

The terms "treatment." "treat," and "treating" refer to reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms and/or in light of exposure to a pathogen). Treatment may also be continued after symptoms have resolved, for example, to delay or prevent recurrence.

The term "prevent." "preventing," or "prevention" refers to a prophylactic treatment of a subject who is not and was not with a disease but is at risk of developing the disease or who was with a disease, is not with the disease, but is at risk of regression of the disease. In certain embodiments, the subject is at a higher risk of developing the disease or at a higher risk of regression of the disease than an average healthy member of a population.

An "effective amount" of a compound or agent described herein refers to an amount sufficient to elicit the desired biological response. An effective amount of a compound or agent described herein may vary depending on such factors as the desired biological endpoint, severity of side effects, disease, or disorder, the identity, pharmacokinetics, and pharmacodynamics of the particular compound or agent, the condition being treated, the mode, route, and desired or required frequency of administration, the species, age and health or general condition of the subject. In certain embodiments, an effective amount is a therapeutically effective amount. In certain embodiments, an effective amount is a prophylactic treatment. In certain embodiments, an effective amount is the amount of a compound or agent described herein in a single dose. In certain embodiments, an effective amount is the combined amounts of a compound or agent described herein in multiple doses. In certain embodiments, the desired dosage is delivered three times a day, two times a day, once a day, every other day, every third day, every week, every two weeks, every three weeks, or every four weeks. In certain embodiments, the desired dosage is delivered using multiple administrations (e.g., two, three, four, five, six, seven, eight, nine, ten, eleven, twelve, thirteen, fourteen, or more administrations).

In certain embodiments, an effective amount of a compound for administration one or more times a day to a 70 kg adult human comprises about 0.0001 mg to about 3000 mg, about 0.0001 mg to about 2000 mg, about 0.0001 mg to about $10)_0$ mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 100) mg, or about 100 mg to about 1000 mg, of a compound per unit dosage form.

In certain embodiments, the compounds of the invention may be administered orally or parenterally at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic effect.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

A "therapeutically effective amount" of a compound or agent described herein is an amount sufficient to provide a therapeutic benefit in the treatment of a condition or to delay or minimize one or more symptoms associated with the condition. A therapeutically effective amount of a compound or agent means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent. In certain embodiments, a therapeutically effective amount is an amount sufficient for delivering an agent to a subject or a cell. In certain embodiments, a therapeutically effective amount is an amount sufficient for delivering a polynucleotide to a subject or a cell. In certain embodiments, a therapeutically effective amount is an amount sufficient for delivering mRNA to a subject or a cell. In certain embodiments, a therapeutically effective amount is an amount sufficient for treating a disease, disorder, or condition. In certain embodiments, a therapeutically effective amount is an amount sufficient for delivering an agent to a subject or a cell and treating a disease, disorder, or condition. In certain embodiments, a therapeutically effective amount is an amount sufficient for delivering a polynucleotide to a subject or a cell and treating a disease, disorder, or condition. In certain embodiments, a therapeutically effective amount is an amount sufficient for delivering mRNA to a subject or a cell and treating a disease, disorder, or condition.

A "prophylactically effective amount" of a compound or agent described herein is an amount sufficient to prevent a condition, or one or more symptoms associated with the condition or prevent its recurrence. A prophylactically effective amount of a compound or agent means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent. In certain embodiments, a prophylactically effective amount is an amount sufficient for delivering an agent to a subject or a cell. In certain embodiments, a prophylactically effective amount is an amount sufficient for delivering a polynucleotide to a subject or a cell. In certain embodiments, a prophylactically effective amount is an amount sufficient for delivering mRNA to a subject or a cell. In certain embodiments, a prophylactically effective amount is an amount sufficient for preventing a disease, disorder, or condition. In certain embodiments, a prophylactically effective amount is an amount sufficient for delivering an agent to a subject or a cell and preventing a disease, disorder, or condition. In certain embodiments, a prophylactically effective amount is an amount sufficient for delivering a polynucleotide to a subject or a cell and preventing a disease, disorder, or condition. In certain embodiments, a prophylactically effective amount is an amount sufficient for delivering mRNA to a subject or a cell and preventing a disease, disorder, or condition.

The term "genetic disease" refers to a disease caused by one or more abnormalities in the genome of a subject, such as a disease that is present from birth of the subject. Genetic diseases may be heritable and may be passed down from the parents' genes. A genetic disease may also be caused by mutations or changes of the DNAs and/or RNAs of the subject. In such cases, the genetic disease will be heritable if it occurs in the germline. Exemplary genetic diseases include, but are not limited to, Aarskog-Scott syndrome. Aase syndrome, achondroplasia, acrodysostosis, addiction, adreno-leukodystrophy, albinism, ablepharon-macrostomia syndrome, alagille syndrome, alkaptonuria, alpha-1 antitrypsin deficiency. Alport's syndrome, Alzheimer's disease, asthma, autoimmune polyglandular syndrome, androgen insensitivity syndrome, Angelman syndrome, ataxia, ataxia telangiectasia, atherosclerosis, attention deficit hyperactivity disorder (ADHD), autism, baldness, Batten disease, Beckwith-Wiedemann syndrome, Best disease, bipolar disorder, brachydactyl), breast cancer, Burkitt lymphoma, chronic myeloid leukemia. Charcot-Marie-Tooth disease, Crohn's disease, cleft lip. Cockayne syndrome, Coffin Lowry syndrome, colon cancer, congenital adrenal hyperplasia. Cornelia de Lange syndrome. Costello syndrome. Cowden syndrome, craniofrontonasal dysplasia, Crigler-Najjar syndrome, Creutzfeldt-Jakob disease, cystic fibrosis, deafness, depression, diabetes, diastrophic dysplasia. DiGeorge syndrome, Down's syndrome, dyslexia. Duchenne muscular dystrophy. Dubowitz syndrome, ectodermal dysplasia Ellis-van Creveld syndrome. Ehlers-Danlos, epidermolysis bullosa, epilepsy, essential tremor, familial hypercholesterolemia, familial Mediterranean fever, fragile X syndrome, Friedreich's ataxia, Gaucher disease, glaucoma, glucose galactose malabsorption, glutaricaciduria, gyrate atrophy, Goldberg Shprintzen syndrome (velocardiofacial syndrome), Gorlin syndrome. Hailey-Hailey disease, hemihypertrophy, hemochromatosis, hemophilia, hereditary motor and sensory neuropathy (HMSN), hereditary non polyposis colorectal cancer (HNPCC). Huntington's disease, immunodeficiency with hyper-IgM, juvenile onset diabetes, Klinefelter's syndrome, Kabuki syndrome, Leigh's disease, long QT syndrome, lung cancer, malignant melanoma, manic depression, Marfan syndrome. Menkes syndrome, miscarriage, mucopolysaccharide disease, multiple endocrine neoplasia, multiple sclerosis, muscular dystrophy, myotrophic lateral sclerosis, myotonic dystrophy, neurofibromatosis. Niemann-Pick disease, Noonan syndrome, obesity, ovarian cancer, pancreatic cancer, Parkinson's disease, paroxysmal nocturnal hemoglobinuria, Pendred syndrome, peroneal muscular atrophy, phenylketonuria (PKU), polycystic kidney disease, Prader-Willi syndrome, primary biliary cirrhosis, prostate cancer, REAR syndrome. Refsum disease, retinitis pigmentosa, retinoblastoma. Rett syndrome. Sanfilippo syndrome, schizophrenia, severe combined immunodeficiency, sickle cell anemia, spina bifida, spinal muscular atrophy, spinocerebellar atrophy, sudden adult death syndrome, Tangier disease, Tay-Sachs disease, thrombocytopenia absent radius syndrome. Townes-Brocks syndrome, tuberous sclerosis. Turner syndrome. Usher syndrome, von Hippel-Lindau syndrome, Waardenburg syndrome, Weaver syndrome. Werner syndrome, Williams syndrome, Wilson's disease, xeroderma piginentosum, and Zellweger syndrome.

A "proliferative disease" refers to a disease that occurs due to abnormal growth or extension by the multiplication of cells (Walker, *Cambridge Dictionary of Biology*; Cambridge University Press: Cambridge, UK, 1990). A proliferative disease may be associated with: 1) the pathological proliferation of normally quiescent cells; 2) the pathological migration of cells from their normal location (e.g., metastasis of neoplastic cells); 3) the pathological expression of proteolytic enzymes such as the matrix metalloproteinases (e.g., collagenases, gelatinases, and elastases); or 4) the pathological angiogenesis as in proliferative retinopathy and tumor metastasis. Exemplary proliferative diseases include cancers (i.e., "malignant neoplasms"), benign neoplasms, angiogenesis, inflammatory diseases, and autoimmune diseases.

The term "angiogenesis" refers to the physiological process through which new blood vessels form from pre-existing vessels. Angiogenesis is distinct from vasculogenesis, which is the de novo formation of endothelial cells from mesoderm cell precursors. The first vessels in a developing embryo form through vasculogenesis, after which angiogenesis is responsible for most blood vessel growth during normal or abnormal development. Angiogenesis is a vital process in growth and development, as well as in wound healing and in the formation of granulation tissue. However, angiogenesis is also a fundamental step in the transition of tumors from a benign state to a malignant one, leading to the use of angiogenesis inhibitors in the treatment of cancer. Angiogenesis may be chemically stimulated by angiogenic proteins, such as growth factors (e.g., VEGF). "Pathological angiogenesis" refers to abnormal (e.g., excessive or insufficient) angiogenesis that amounts to and/or is associated with a disease.

The terms "neoplasm" and "tumor" are used herein interchangeably and refer to an abnormal mass of tissue wherein the growth of the mass surpasses and is not coordinated with the growth of a normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neoplasms." An exemplary pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites. The term "metastasis." "metastatic," or "metastasize" refers to the spread or migration of cancerous cells from a primary or original tumor to another organ or tissue and is typically identifiable by the presence of a "secondary tumor" or "secondary cell mass" of the tissue type of the primary or original tumor and not of that of the organ or tissue in which the secondary (metastatic) tumor is located. For example, a prostate cancer that has migrated to bone is said to be metastasized prostate cancer and includes cancerous prostate cancer cells growing in bone tissue.

The term "cancer" refers to a class of diseases characterized by the development of abnormal cells that proliferate uncontrollably and have the ability to infiltrate and destroy normal body tissues. See e.g., *Stedman's Medical Dictionary,* 25th ed.; Hensyl ed.; Williams & Wilkins: Philadelphia, 1990. Exemplary cancers include, but are not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; ocular cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML. T-cell CML), and chronic lymphocytic leukemia (CLL) (e.g., B-cell CLL. T-cell CLL)); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenström's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungoides. Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemia/lymphoma as described above; and multiple myeloma (MM)), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer, myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendoctrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

A "hematological disease" includes a disease which affects a hematopoietic cell or tissue. Hematological diseases include diseases associated with aberrant hematological content and/or function. Examples of hematological diseases include diseases resulting from bone marrow irradiation or chemotherapy treatments for cancer, diseases such as pernicious anemia, hemorrhagic anemia, hemolytic anemia, aplastic anemia, sickle cell anemia, sideroblastic anemia, anemia associated with chronic infections such as malaria, trypanosomiasis, HTV, hepatitis virus or other viruses, myelophthisic anemias caused by marrow deficiencies, renal failure resulting from anemia, anemia, polycythemia, infectious mononucleosis (EVI), acute non-lymphocytic leukemia (ANLL), acute myeloid leukemia (AML), acute promyelocytic leukemia (APL), acute myelomonocytic leukemia (AMMoL), polycythemia vera, lymphoma, acute lymphocytic leukemia (ALL), chronic lymphocytic leukemia, Wilm's tumor, Ewing's sarcoma, retinoblastoma, hemophilia, disorders associated with an increased risk of thrombosis, herpes, thalassemia, antibody-mediated disorders such as transfusion reactions and erythroblastosis, mechanical trauma to red blood cells such as micro-angiopathic hemolytic anemias, thrombotic thrombocytopenic purpura and disseminated intravascular coagulation, infections by parasites such as *Plasmodium*, chemical injuries from, e.g., lead poisoning, and hypersplenism.

The term "neurological disease" refers to any disease of the nervous system, including diseases that involve the central nervous system (brain, brainstem and cerebellum), the peripheral nervous system (including cranial nerves), and the autonomic nervous system (parts of which are located in both central and peripheral nervous system). Neurodegenerative diseases refer to a type of neurological disease marked by the loss of nerve cells, including, but not limited to. Alzheimer's disease, Parkinson's disease, amyotrophic lateral sclerosis, tauopathies (including frontotemporal dementia), and Huntington's disease. Examples of neurological diseases include, but are not limited to, headache, stupor and coma, dementia, seizure, sleep disorders, trauma, infections, neoplasms, neuro-ophthalmology, movement disorders, demyelinating diseases, spinal cord disorders, and disorders of peripheral nerves, muscle and neuromuscular junctions. Addiction and mental illness, include, but are not limited to, bipolar disorder and schizophrenia, are also included in the definition of neurological diseases. Further examples of neurological diseases include acquired epileptiform aphasia; acute disseminated encephalomyelitis; adrenoleukodystrophy; agenesis of the corpus callosum; agnosia; Aicardi syndrome; Alexander disease; Alpers' disease; alternating hemiplegia; Alzheimer's disease; amyotrophic lateral sclerosis; anencephaly; Angelman syndrome; angiomatosis; anoxia; aphasia; apraxia; arachnoid cysts; arachnoiditis; Arnold-Chiari malformation; arteriovenous malformation; Asperger syndrome; ataxia telangiectasia; attention deficit hyperactivity disorder; autism; autonomic dysfunction; back pain; Batten disease; Behcet's disease; Bell's palsy; benign essential blepharospasm; benign focal: amyotrophy; benign intracranial hypertension; Binswanger's disease; blepharospasm; Bloch Sulzberger syndrome; brachial plexus injury; brain abscess; brain injury; brain tumors (including glioblastoma multiforme); spinal tumor; Brown-Sequard syndrome; Canavan disease; carpal tunnel syndrome (CTS); causalgia; central pain syndrome; central pontine myelinolysis; cephalic disorder; cerebral aneurysm; cerebral arteriosclerosis; cerebral atrophy; cerebral gigantism; cerebral palsy; Charcot-Marie-Tooth disease; chemotherapy-induced neuropathy and neuropathic pain; Chiari malformation; chorea; chronic inflammatory demyclinating polyneuropathy (CIDP); chronic pain; chronic regional pain syndrome; Coffin Lowry syndrome; coma, including persistent vegetative state; congenital facial diplegia; corticobasal degeneration; cranial arteritis; craniosynostosis; Creutzfeldt-Jakob disease; cumulative trauma disorders; Cushing's syndrome; cytomegalic inclusion body disease (CIBD); cytomegalovirus infection; dancing eyes-dancing feet syndrome; Dandy-Walker syndrome; Dawson disease; De Morsier's syndrome; Dejerine-Klumpke palsy; dementia; dermatomyositis; diabetic neuropathy; diffuse sclerosis; dysautonomia; dysgraphia; dyslexia; dystonias; early infantile epileptic encephalopathy; empty sella syndrome; encephalitis; encephaloceles; encephalotrigeminal angiomatosis; epilepsy; Erb's palsy; essential tremor; Fabry's disease; Fahr's syndrome; fainting; familial spastic paralysis; febrile seizures; Fisher syndrome; Friedreich's ataxia; frontotemporal dementia and other "tauopathies"; Gaucher's disease; Gerstmann's syndrome; giant cell arteritis; giant cell inclusion disease; globoid cell leukodystrophy; Guillain-Barre syndrome; HTLV-1 associated myelopathy; Hallervorden-Spatz disease; head injury; headache; hemifacial spasm; hereditary spastic paraplegia; heredopathia atactica polyneuritiformis; herpes zoster oticus; herpes zoster; Hirayama syndrome; HIV-associated dementia and neuropathy (see also neurological manifestations of AIDS); holoprosencephaly; Huntington's disease and other polyglutamine repeat diseases; hydranencephaly; hydrocephalus; hypercortisolism; hypoxia; immune-mediated encephalomyelitis; inclusion body myositis; incontinentia pigmenti; infantile; phytanic acid storage disease; Infantile Refsum disease; infantile spasms; inflammatory myopathy; intracranial cyst; intracranial hypertension; Joubert syndrome; Kearns-Sayre syndrome; Kennedy disease; Kinsbourne syndrome; Klippel Feil syndrome; Krabbe disease; Kugelberg-Welander disease; kuru; Lafora disease; Lambert-Eaton myasthenic syndrome; Landau-Kleffner syndrome; lateral medullary (Wallenberg) syndrome; learning disabilities; Leigh's disease; Lennox-Gastaut syndrome; Lesch-Nyhan syndrome; leukodystrophy; Lewy body dementia; lissencephaly; locked-in syndrome; Lou Gehrig's disease (aka motor neuron disease or amyotrophic lateral sclerosis); lumbar disc disease; lyme disease-neurological sequelae; Machado-Joseph disease; macrencephaly; megalencephaly; Melkersson-Rosenthal syndrome; Menieres disease; meningitis; Menkes disease; metachromatic leukodystrophy; microcephaly; migraine; Miller Fisher syndrome; mini-strokes; mitochondrial myopathies; Mobius syndrome; monomelic amyotrophy; motor neurone disease; moyamoya disease; mucopolysaccharidoses; multi-infarct dementia; multifocal motor neuropathy; multiple sclerosis and other demyelinating disorders; multiple system atrophy with postural hypotension; muscular dystrophy; myasthenia gravis; myelinoclastic diffuse sclerosis; myoclonic encephalopathy of infants; myoclonus; myopathy; myotonia congenital; narcolepsy; neurofibromatosis; neuroleptic malignant syndrome; neurological manifestations of AIDS; neurological sequelae of lupus; neuromyotonia; neuronal ceroid lipofuscinosis; neuronal migration disorders; Niemann-Pick disease; O'Sullivan-McLeod syndrome; occipital neuralgia; occult spinal dysraphism sequence; Ohtahara syndrome; olivopontocerebellar atrophy; opsoclonus myoclonus; optic neuritis; orthostatic hypotension; overuse syndrome; paresthesia; Parkinson's disease; paramyotonia congenita; paraneoplastic diseases; paroxysmal attacks; Parry Romberg syndrome; Pelizaeus-Merzbacher disease; periodic paralyses; peripheral neuropathy; painful neuropathy and neuropathic pain; persistent vegetative state; pervasive developmental disorders; photic sneeze reflex; phytanic acid storage disease; Pick's disease; pinched nerve; pituitary tumors; polymyositis; porencephaly; Post-Polio syndrome; postherpetic neuralgia (PHN); postinfectious encephalomyelitis; postural hypotension; Prader-Willi syndrome; primary lateral sclerosis; prion diseases; progressive; hemifacial atrophy; progressive multifocal leukoencephalopathy; progressive sclerosing poliodystrophy; progressive supranuclear palsy; pseudotumor cerebri; Ramsay-Hunt syndrome (Type I and Type II); Rasmussen's Encephalitis; reflex sympathetic dystrophy syndrome; Refsum disease; repetitive motion disorders; repetitive stress injuries; restless legs syndrome; retrovirus-associated myelopathy; Rett syndrome; Reye's syndrome; Saint Vitus Dance; Sandhoff disease; Schilder's disease; schizencephaly; septo-optic dysplasia; shaken baby syndrome; shingles; Shy-Drager syndrome; Sjogren's syndrome; sleep apnea; Soto's syndrome; spasticity; spina bifida; spinal cord injury; spinal cord tumors: spinal muscular atrophy; stiff-person syndrome; stroke; Sturge-Weber syndrome; subacute sclerosing panencephalitis; subarachnoid hemorrhage; subcortical arteriosclerotic encephalopathy; sydenham chorea; syncope; syringomyelia; tardive dyskinesia; Tay-Sachs disease; temporal arteritis; tethered spinal cord syndrome; Thomsen disease; thoracic outlet syndrome; tic douloureux; Todd's paralysis; Tourette syndrome; transient ischemic attack: transmissible spongiform encephalopathies; transverse myelitis; traumatic brain injury; tremor; trigeminal neuralgia; tropical spastic paraparesis; tuberous sclerosis; vascular dementia (multi-infarct dementia); vasculitis including temporal arteritis; Von Hippel-Lindau Disease (VFHL); Wallenberg's syndrome; Werdnig-Hoffman disease; West syndrome; whiplash; Williams syndrome; Wilson's disease; and Zellweger syndrome.

The term "liver disease" or "hepatic disease" refers to damage to or a disease of the liver. Non-limiting examples of liver disease include intrahepatic cholestasis (e.g., alagille syndrome, biliary liver cirrhosis), fatty liver (e.g., alcoholic fatty liver. Reye's syndrome), hepatic vein thrombosis, hepatolenticular degeneration (i.e., Wilson's disease), hepatomegaly, liver abscess (e.g., amebic liver abscess), liver cirrhosis (e.g., alcoholic, biliary, and experimental liver cirrhosis), alcoholic liver diseases (e.g., fatty liver, hepatitis, cirrhosis), parasitic liver disease (e.g., hepatic echinococcosis, fascioliasis, amebic liver abscess), jaundice (e.g., hemolytic, hepatocellular, cholestatic jaundice), cholestasis, portal hypertension, liver enlargement, ascites, hepatitis (e.g., alcoholic hepatitis, animal hepatitis, chronic hepatitis (e.g., autoimmune, hepatitis B, hepatitis C, hepatitis D, drug induced chronic hepatitis), toxic hepatitis, viral human hepatitis (e.g., hepatitis A, hepatitis B, hepatitis C, hepatitis D, hepatitis E), granulomatous hepatitis, secondary biliary cirrhosis, hepatic encephalopathy, varices, primary biliary cirrhosis, primary sclerosing cholangitis, hepatocellular adenoma, hemangiomas, bile stones, liver failure (e.g., hepatic encephalopathy, acute liver failure), angiomyolipoma, calcified liver metastases, cystic liver metastases, fibrolamellar hepatocarcinoma, hepatic adenoma, hepatoma, hepatic cysts (e.g., Simple cysts, Polycystic liver disease, hepatobiliary cystadenoma, choledochal cyst), mesenchymal tumors (mesenchymal hamartoma, infantile hemangioendothelioma, hemangioma, peliosis hepatis, lipomas, inflammatory pseudotumor), epithelial tumors (e.g., bile duct hamartoma, bile duct adenoma), focal nodular hyperplasia, nodular regenerative hyperplasia, hepatoblastoma, hepatocellular carcinoma, cholangiocarcinoma, cystadenocarcinoma, tumors of blood vessels, angiosarcoma, Karposi's sarcoma, hemangioendothelioma, embryonal sarcoma, fibrosarcoma, leiomyosarcoma, rhabdomyosarcoma, carcinosarcoma, teratoma, carcinoid, squamous carcinoma, primary lymphoma, peliosis hepatis, erythrohepatic porphyria, hepatic porphyria (e.g., acute intermittent porphyria, porphyria cutanea tarda), and Zellweger syndrome.

The term "spleen disease" refers to a disease of the spleen. Example of spleen diseases include, but are not limited to, splenomegaly, spleen cancer, asplenia, spleen trauma, idiopathic purpura, Felty's syndrome. Hodgkin's disease, and immune-mediated destruction of the spleen.

The term "lung disease" or "pulmonary disease" refers to a disease of the lung. Examples of lung diseases include, but are not limited to, bronchiectasis, bronchitis, bronchopulmonary dysplasia, interstitial lung disease, occupational lung disease, emphysema, cystic fibrosis, acute respiratory distress syndrome (ARDS), severe acute respiratory syndrome (SARS), asthma (e.g., intermittent asthma, mild persistent asthma, moderate persistent asthma, severe persistent asthma), chronic bronchitis, chronic obstructive pulmonary disease (COPD), emphysema, interstitial lung disease, sarcoidosis, asbestosis, aspergilloma, aspergillosis, pneumonia (e.g., lobar pneumonia, multilobar pneumonia, bronchial pneumonia, interstitial pneumonia), pulmonary fibrosis, pulmonary tuberculosis, rheumatoid lung disease, pulmonary embolism, and lung cancer (e.g., non-small-cell lung carcinoma (e.g., adenocarcinoma, squamous-cell lung carcinoma, large-cell lung carcinoma), small-cell lung carcinoma).

A "painful condition" includes, but is not limited to, neuropathic pain (e.g., peripheral neuropathic pain), central pain, deafferentiation pain, chronic pain (e.g., chronic nociceptive pain, and other forms of chronic pain such as post-operative pain, e.g., pain arising after hip, knee, or other replacement surgery), pre-operative pain, stimulus of nociceptive receptors (nociceptive pain), acute pain (e.g., phantom and transient acute pain), noninflammatory pain, inflammatory pain, pain associated with cancer, wound pain, burn pain, postoperative pain, pain associated with medical procedures, pain resulting from pruritus, painful bladder syndrome, pain associated with premenstrual dysphoric disorder and/or premenstrual syndrome, pain associated with chronic fatigue syndrome, pain associated with pre-term labor, pain associated with withdrawal symptoms from drug addiction, joint pain, arthritic pain (e.g., pain associated with crystalline arthritis, osteoarthritis, psoriatic arthritis, gouty arthritis, reactive arthritis, rheumatoid arthritis or Reiter's arthritis), lumbosacral pain, musculo-skeletal pain, headache, migraine, muscle ache, lower back pain, neck pain, toothache, dental/maxillofacial pain, visceral pain and the like. One or more of the painful conditions contemplated herein can comprise mixtures of various types of pain provided above and herein (e.g., nociceptive pain, inflammatory pain, neuropathic pain, etc.). In some embodiments, a particular pain can dominate. In other embodiments, the painful condition comprises two or more types of pains without one dominating. A skilled clinician can determine the dosage to achieve a therapeutically effective amount for a particular subject based on the painful condition.

In certain embodiments, the painful condition is neuropathic pain. The term "neuropathic pain" refers to pain resulting from injury to a nerve. Neuropathic pain is distinguished from nociceptive pain, which is the pain caused by acute tissue injury involving small cutaneous nerves or small nerves in muscle or connective tissue. Neuropathic pain typically is long-lasting or chronic and often develops days or months following an initial acute tissue injury. Neuropathic pain can involve persistent, spontaneous pain as well as allodynia, which is a painful response to a stimulus that normally is not painful. Neuropathic pain also can be characterized by hyperalgesia, in which there is an accentuated response to a painful stimulus that usually is trivial, such as a pin prick. Neuropathic pain conditions can develop following neuronal injury and the resulting pain may persist for months or years, even after the original injury has healed. Neuronal injury may occur in the peripheral nerves, dorsal roots, spinal cord or certain regions in the brain. Neuropathic pain conditions include, but are not limited to, diabetic neuropathy (e.g., peripheral diabetic neuropathy); sciatica; non-specific lower back pain; multiple sclerosis pain; carpal tunnel syndrome, fibromyalgia; HIV-related neuropathy; neuralgia (e.g., post-herpetic neuralgia, trigeminal neuralgia); pain resulting from physical trauma (e.g., amputation; surgery, invasive medical procedures, toxins, burns, infection), pain resulting from cancer or chemotherapy (e.g., chemotherapy-induced pain such as chemotherapy-induced peripheral neuropathy), and pain resulting from an inflammatory condition (e.g., a chronic inflammatory condition). Neuropathic pain can result from a peripheral nerve disorder such as neuroma; nerve compression; nerve crush, nerve stretch or incomplete nerve transsection; mononeuropathy or polyneuropathy. Neuropathic pain can also result from a disorder such as dorsal root ganglion compression; inflammation of the spinal cord; contusion, tumor or hemisection of the spinal cord; tumors of the brainstem, thalamus or cortex; or trauma to the brainstem, thalamus or cortex.

The symptoms of neuropathic pain are heterogeneous and are often described as spontaneous shooting and lancinating pain, or ongoing, burning pain. In addition, there is pain associated with normally non-painful sensations such as "pins and needles" (paraesthesias and dysesthesias), increased sensitivity to touch (hyperesthesia), painful sensation following innocuous stimulation (dynamic, static or thermal allodynia), increased sensitivity to noxious stimuli (thermal, cold, mechanical hyperalgesia), continuing pain sensation after removal of the stimulation (hyperpathia) or an absence of or deficit in selective sensory pathways (hypoalgesia).

In certain embodiments, the painful condition is non-inflammatory pain. The types of non-inflammatory pain include, without limitation, peripheral neuropathic pain (e.g., pain caused by a lesion or dysfunction in the peripheral nervous system), central pain (e.g., pain caused by a lesion or dysfunction of the central nervous system), deafferentation pain (e.g., pain due to loss of sensory input to the central nervous system), chronic nociceptive pain (e.g., certain types of cancer pain), noxious stimulus of nociceptive receptors (e.g., pain felt in response to tissue damage or impending tissue damage), phantom pain (e.g., pain felt in a part of the body that no longer exists, such as a limb that has been amputated), pain felt by psychiatric subjects (e.g., pain where no physical cause may exist), and wandering pain (e.g., wherein the pain repeatedly changes location in the body).

In certain embodiments, the painful condition is inflammatory pain. In certain embodiments, the painful condition (e.g., inflammatory pain) is associated with an inflammatory condition and/or an immune disorder.

The term "psychiatric disorder" refers to a disease of the mind and includes diseases and disorders listed in the Diagnostic and Statistical Manual of Mental Disorders—Fourth Edition (DSM-IV), published by the American Psychiatric Association, Washington D. C. (1994). Psychiatric disorders include, but are not limited to, anxiety disorders (e.g., acute stress disorder agoraphobia, generalized anxiety disorder, obsessive-compulsive disorder, panic disorder, posttraumatic stress disorder, separation anxiety disorder, social phobia, and specific phobia), childhood disorders, (e.g., attention-deficit/hyperactivity disorder, conduct disorder, and oppositional defiant disorder), eating disorders (e.g., anorexia nervosa and bulimia nervosa), mood disorders (e.g., depression, bipolar disorder, cyclothymic disorder, dysthymic disorder, and major depressive disorder), personality disorders (e.g., antisocial personality disorder, avoidant personality disorder, borderline personality disorder, dependent personality disorder, histrionic personality disorder, narcissistic personality disorder, obsessive-compulsive personality disorder, paranoid personality disorder, schizoid personality disorder, and schizotypal personality disorder), psychotic disorders (e.g., brief psychotic disorder, delusional disorder, schizoaffective disorder, schizophreniform disorder, schizophrenia, and shared psychotic disorder), substance-related disorders (e.g., alcohol dependence, amphetamine dependence, cannabis dependence, cocaine dependence, hallucinogen dependence, inhalant dependence, nicotine dependence, opioid dependence, phencyclidine dependence, and sedative dependence), adjustment disorder, autism, delirium, dementia, multi-infarct dementia, learning and memory disorders (e.g., amnesia and age-related memory loss), and Tourette's disorder.

The term "musculoskeletal disease" or "MSD" refers to an injury and/or pain in a subject's joints, ligaments, muscles, nerves, tendons, and structures that support limbs, neck, and back. In certain embodiments, an MSD is a degenerative disease. In certain embodiments, an MSD includes an inflammatory condition. Body parts of a subject that may be associated with MSDs include upper and lower back, neck, shoulders, and extremities (arms, legs, feet, and hands). In certain embodiments, an MSD is a bone disease, such as achondroplasia, acromegaly, bone callus, bone demineralization, bone fracture, bone marrow disease, bone marrow neoplasm, dyskeratosis congenita, leukemia (e.g., hairy cell leukemia, lymphocytic leukemia, myeloid leukemia, Philadelphia chromosome-positive leukemia, plasma cell leukemia, stem cell leukemia), systemic mastocytosis, myelodysplastic syndromes, paroxysmal nocturnal hemoglobinuria, myeloid sarcoma, myeloproliferative disorders, multiple myeloma, polycythemia vera, pearson marrow-pancreas syndrome, bone neoplasm, bone marrow neoplasm, Ewing sarcoma, osteochondroma, osteoclastoma, osteosarcoma, brachydactyly, Camurati-Engelmann syndrome, Craniosynostosis, Crouzon craniofacial dysostosis, dwarfism, achondroplasia, bloom syndrome, Cockayne syndrome, Ellis-van Creveld syndrome, Seckel syndrome, spondyloepiphyseal dysplasia, spondyloepiphyseal dysplasia congenita, Werner syndrome, hyperostosis, osteophyte, Klippel-Trenaunay-Weber syndrome, Marfan syndrome, McCune-Albright syndrome, osteitis, osteoarthritis, osteochondritis, osteochondrodysplasia, Kashin-Beck disease, Leri-Weill dyschondrosteosis, osteochondrosis, osteodystrophy, osteogenesis imperfecta, osteolysis, Gorham-Stout syndrome, osteomalacia, osteomyelitis, osteonecrosis, osteopenia, osteopetrosis, osteoporosis, osteosclerosis, otospondylomegaepiphyseal dysplasia, pachydermoperiostosis, Paget disease of bone, Polydactyly, Meckel syndrome, rickets, Rothmund-Thomson syndrome, Sotos syndrome, spondyloepiphyseal dysplasia, spondyloepiphyseal dysplasia congenita, syndactyly, Apert syndrome, syndactyly type II, or Werner syndrome. In certain embodiments, an MSD is a cartilage disease, such as cartilage neoplasm, osteochondritis, osteochondrodysplasia, Kashin-Beck disease, or Leri-Weill dyschondrosteosis. In certain embodiments, an MSD is hernia, such as intervertebral disk hernia. In certain embodiments, an MSD is a joint disease, such as arthralgia, arthritis (e.g., gout (e.g., Kelley-Seegmiller syndrome, Lesch-Nyhan syndrome), Lyme disease, osteoarthritis, psoriatic arthritis, reactive arthritis, rheumatic fever, rheumatoid arthritis, Felty syndrome, synovitis, Blau syndrome, nail-patella syndrome, spondyloarthropathy, reactive arthritis, Stickler syndrome, synovial membrane disease, synovitis, or Blau syndrome. In certain embodiments, an MSD is Langer-Giedion syndrome. In certain embodiments, an MSD is a muscle disease, such as Barth syndrome, mitochondrial encephalomyopathy, MELAS syndrome, MERRF syndrome, MNGIE syndrome, mitochondrial myopathy, Keams-Sayre syndrome, myalgia, fibromyalgia, polymyalgia rheumatica, myoma, myositis, dermatomyositis, neuromuscular disease, Kearns-Sayre syndrome, muscular dystrophy, myasthenia, congenital myasthenic syndrome, Lambert-Eaton myasthenic syndrome, myasthenia gravis, myotonia, myotonia congenita, spinal muscular atrophy, tetany, ophthalmoplegia, or rhabdomyolysis. In certain embodiments, an MSD is *Proteus* syndrome. In certain embodiments, an MSD is a rheumatic diseases, such as arthritis (e.g., gout (e.g., Kelley-Seegmiller syndrome, Lesch-Nyhan lyme disease)), osteoarthritis, psoriatic arthritis, reactive arthritis, rheumatic fever, rheumatoid arthritis, Felty syndrome, synovitis, Blau syndrome, gout (e.g., Kelley-Seegmiller syndrome, Lesch-Nyhan syndrome), polymyalgia rheumatica, rheumatic fever, rheumatic heart disease, or Sjogren syndrome. In certain embodiments, an MSD is Schwartz-Jampel syndrome. In certain embodiments, an MSD is a skeleton disease, such as Leri-Weill dyschondrosteosis, skeleton malformations, Melnick-Needles syndrome, pachydermoperiostosis, Rieger syndrome, spinal column disease, intervertebral disk hernia, scoliosis, spina bifida, spondylitis, ankylosing spondylitis, spondyloarthropathy, reactive arthritis, spondyloepiphyseal dysplasia, spondyloepiphyseal dysplasia congenita, or spondylosis.

The term "metabolic disorder" refers to any disorder that involves an alteration in the normal metabolism of carbohydrates, lipids, proteins, nucleic acids, or a combination thereof. A metabolic disorder is associated with either a deficiency or excess in a metabolic pathway resulting in an imbalance in metabolism of nucleic acids, proteins, lipids, and/or carbohydrates. Factors affecting metabolism include, and are not limited to, the endocrine (hormonal) control system (e.g., the insulin pathway, the enteroendocrine hormones including GLP-1, PYY or the like), the neural control system (e.g., GLP-1 in the brain), or the like. Examples of metabolic disorders include, but are not limited to, diabetes (e.g., Type I diabetes, Type II diabetes, gestational diabetes), hyperglycemia, hyperinsulinemia, insulin resistance, and obesity.

The terms "inflammatory disease" and "inflammatory condition" are used interchangeably herein, and refer to a disease or condition caused by, resulting from, or resulting in inflammation. Inflammatory diseases and conditions include those diseases, disorders or conditions that are characterized by signs of pain (dolor, from the generation of noxious substances and the stimulation of nerves), heat (calor, from vasodilatation), redness (rubor, from vasodilatation and increased blood flow), swelling (tumor, from excessive inflow or restricted outflow of fluid), and/or loss of function (functio laesa, which can be partial or complete, temporary or permanent. Inflammation takes on many forms and includes, but is not limited to, acute, adhesive, atrophic, catarrhal, chronic, cirrhotic, diffuse, disseminated, exudative, fibrinous, fibrosing, focal, granulomatous, hyperplastic, hypertrophic, interstitial, metastatic, necrotic, obliterative, parenchymatous, plastic, productive, proliferous, pseudomembranous, purulent, sclerosing, seroplastic, serous, simple, specific, subacute, suppurative, toxic, traumatic, and/or ulcerative inflammation. The term "inflammatory disease" may also refer to a dysregulated inflammatory reaction that causes an exaggerated response by macrophages, granulocytes, and/or T-lymphocytes leading to abnormal tissue damage and/or cell death. An inflammatory disease can be either an acute or chronic inflammatory condition and can result from infections or non-infectious causes. Inflammatory diseases include, without limitation, atherosclerosis, arteriosclerosis, autoimmune disorders, multiple sclerosis, systemic lupus erythematosus, polymyalgia rheumatica (PMR), gouty arthritis, degenerative arthritis, tendonitis, bursitis, psoriasis, cystic fibrosis, arthrosteitis, rheumatoid arthritis, inflammatory arthritis, Sjogren's syndrome, giant cell arteritis, progressive systemic sclerosis (scleroderma), ankylosing spondylitis, polymyositis, dermatomyositis, pemphigus, pemphigoid, diabetes (e.g., Type I), myasthenia gravis, Hashimoto's thyroiditis, Graves' disease, Goodpasture's disease, mixed connective tissue disease, sclerosing cholangitis, inflammatory bowel disease, Crohn's disease, ulcerative colitis, pernicious anemia, inflammatory dermatoses, usual interstitial pneumonitis (UIP), asbestosis, silicosis, bronchiectasis, berylliosis, talcosis, pneumoconiosis, sarcoidosis, desquamative interstitial pneumonia, lymphoid interstitial pneumonia, giant cell interstitial pneumonia, cellular interstitial pneumonia, extrinsic allergic alveolitis, Wegener's granulomatosis and related forms of angiitis (temporal arteritis and polyarteritis nodosa), inflammatory dermatoses, hepatitis, delayed-type hypersensitivity reactions (e.g., poison ivy dermatitis), pneumonia, respiratory tract inflammation, Adult Respiratory Distress Syndrome (ARDS), encephalitis, immediate hypersensitivity reactions, asthma, hayfever, allergies, acute anaphylaxis, rheumatic fever, glomerulonephritis, pyclonephritis, cellulitis, cystitis, chronic cholecystitis, ischemia (ischemic injury), reperfusion injury, allograft rejection, host-versus-graft rejection, appendicitis, arteritis, blepharitis, bronchiolitis, bronchitis, cervicitis, cholangitis, chorioamnionitis, conjunctivitis, dacryoadenitis, dermatomyositis, endocarditis, endometritis, enteritis, enterocolitis, epicondylitis, epididymitis, fasciitis, fibrositis, gastritis, gastroenteritis, gingivitis, ileitis, iritis, laryngitis, myelitis, myocarditis, nephritis, omphalitis, oophoritis, orchitis, osteitis, otitis, pancreatitis, parotitis, pericarditis, pharyngitis, pleuritis, phlebitis, pneumonitis, proctitis, prostatitis, rhinitis, salpingitis, sinusitis, stomatitis, synovitis, testitis, tonsillitis, urethritis, urocystitis, uveitis, vaginitis, vasculitis, vulvitis, vulvovaginitis, angitis, chronic bronchitis, osteomyelitis, optic neuritis, temporal arteritis, transverse myelitis, necrotizing fasciitis, and necrotizing enterocolitis. An ocular inflammatory disease includes, but is not limited to, post-surgical inflammation.

Additional exemplary inflammatory conditions include, but are not limited to, inflammation associated with acne, anemia (e.g., aplastic anemia, haemolytic autoimmune anaemia), asthma, arteritis (e.g., polyarteritis, temporal arteritis, periarteritis nodosa, Takayasu's arteritis), arthritis (e.g., crystalline arthritis, osteoarthritis, psoriatic arthritis, gouty arthritis, reactive arthritis, rheumatoid arthritis and Reiter's arthritis), ankylosing spondylitis, amylosis, amyotrophic lateral sclerosis, autoimmune diseases, allergies or allergic reactions, atherosclerosis, bronchitis, bursitis, chronic prostatitis, conjunctivitis, Chagas disease, chronic obstructive pulmonary disease, cermatomyositis, diverticulitis, diabetes (e.g., type I diabetes mellitus, Type II diabetes mellitus), a skin condition (e.g., psoriasis, eczema, burns, dermatitis, pruritus (itch)), endometriosis, Guillain-Barre syndrome, infection, ischaemic heart disease, Kawasaki disease, glomerulonephritis, gingivitis, hypersensitivity, headaches (e.g., migraine headaches, tension headaches), ileus (e.g., postoperative ileus and ileus during sepsis), idiopathic thrombocytopenic purpura, interstitial cystitis (painful bladder syndrome), gastrointestinal disorder (e.g., selected from peptic ulcers, regional enteritis, diverticulitis, gastrointestinal bleeding, eosinophilic gastrointestinal disorders (e.g., eosinophilic esophagitis, eosinophilic gastritis, eosinophilic gastroenteritis, eosinophilic colitis), gastritis, diarrhea, gastroesophageal reflux disease (GORD, or its synonym GERD), inflammatory bowel disease (IBD) (e.g., Crohn's disease, ulcerative colitis, collagenous colitis, lymphocytic colitis, ischaemic colitis, diversion colitis, Behcet's syndrome, indeterminate colitis) and inflammatory bowel syndrome (IBS)), lupus, multiple sclerosis, morphea, myeasthenia gravis, myocardial ischemia, nephrotic syndrome, pemphigus vulgaris, pernicious aneaemia, peptic ulcers, polymyositis, primary biliary cirrhosis, neuroinflammation associated with brain disorders (e.g., Parkinson's disease, Huntington's disease, and Alzheimer's disease), prostatitis, chronic inflammation associated with cranial radiation injury, pelvic inflammatory disease, reperfusion injury, regional enteritis, rheumatic fever, systemic lupus erythematosus, schleroderma, scierodoma, sarcoidosis, spondyloarthopathies, Sjogren's syndrome, thyroiditis, transplantation rejection, tendonitis, trauma or injury (e.g., frostbite, chemical irritants, toxins, scarring, burns, physical injury), vasculitis, vitiligo and Wegener's granulomatosis. In certain embodiments, the inflammatory disorder is selected from arthritis (e.g., rheumatoid arthritis), inflammatory bowel disease, inflammatory bowel syndrome, asthma, psoriasis, endometriosis, interstitial cystitis and prostatistis. In certain embodiments, the inflammatory condition is an acute inflammatory condition (e.g., for example, inflammation resulting from infection). In certain embodiments, the inflammatory condition is a chronic inflammatory condition (e.g., conditions resulting from asthma, arthritis and inflammatory bowel disease). The compounds may also be useful in treating inflammation associated with trauma and non-inflammatory myalgia. The compounds disclosed herein may also be useful in treating inflammation associated with cancer.

An "autoimmune disease" refers to a disease arising from an inappropriate immune response of the body of a subject against substances and tissues normally present in the body. In other words, the immune system mistakes some part of the body as a pathogen and attacks its own cells. This may be restricted to certain organs (e.g., in autoimmune thyroiditis) or involve a particular tissue in different places (e.g., Goodpasture's disease which may affect the basement membrane in both the lung and kidney). The treatment of autoimmune diseases is typically with immunosuppression, e.g., medications which decrease the immune response. Exemplary autoimmune diseases include, but are not limited to, glomerulonephritis, Goodpasture's syndrome, necrotizing vasculitis, lymphadenitis, peri-arteritis nodosa, systemic lupus erythematosis, rheumatoid arthritis, psoriatic arthritis, systemic lupus erythematosis, psoriasis, ulcerative colitis, systemic sclerosis, dermatomyositis/polymyositis, anti-phospholipid antibody syndrome, scleroderma, pemphigus vulgaris, ANCA-associated vasculitis (e.g., Wegener's granulomatosis, microscopic polyangiitis), uveitis, Sjogren's syndrome. Crohn's disease, Reiter's syndrome, ankylosing spondylitis, Lyme disease, Guillain-Barré syndrome, Hashimoto's thyroiditis, and cardiomyopathy.

In certain embodiments, the inflammatory disorder and/or the immune disorder is a gastrointestinal disorder. In some embodiments, the gastrointestinal disorder is selected from gastrointestinal disorder (e.g., selected from peptic ulcers, regional enteritis, diverticulitis, gastrointestinal bleeding, eosinophilic gastrointestinal disorders (e.g., eosinophilic esophagitis, eosinophilic gastritis, eosinophilic gastroenteritis, eosinophilic colitis), gastritis, diarrhea, gastroesophageal reflux disease (GORD, or its synonym GERD), inflammatory bowel disease (IBD) (e.g., Crohn's disease, ulcerative colitis, collagenous colitis, lymphocytic colitis, ischaemic colitis, diversion colitis. Behcet's syndrome, indeterminate colitis) and inflammatory bowel syndrome (IBS)). In certain embodiments, the gastrointestinal disorder is inflammatory bowel disease (IBD). In certain embodiments, the inflammatory condition and/or immune disorder is a skin condition. In some embodiments, the skin condition is pruritus (itch), psoriasis, eczema, burns or dermatitis. In certain embodiments, the skin condition is psoriasis. In certain embodiments, the skin condition is pruritis.

Other than in the examples, or where otherwise indicated, all numbers expressing quantities of ingredients or reaction conditions used herein should be understood as modified in all instances by the term "about." "About" and "approximately" shall generally mean an acceptable degree of error for the quantity measured given the nature or precision of the measurements. Exemplary degrees of error are within 20 percent (%), typically, within 10%, or more typically, within 5%, 4%, 3%, 2%, or 1% of a given value or range of values.

Unless otherwise required by context, singular terms shall include pluralities, and plural terms shall include the singular.

DETAILED DESCRIPTION OF CERTAIN EMBODIMENTS

Provided herein are compounds (e.g., compounds of Formula (I)), and pharmaceutically acceptable salts, solvates, tautomers, stereoisomers, and isotopically labeled derivatives thereof, and compositions and kits thereof. The compounds provided herein can form particles and may therefore be used to deliver agents (e.g., polynucleotides) to a subject, target tissue, or cell. Also provided herein are methods of delivery and methods of treating a disease, disorder, or condition, comprising administering to the subject a composition comprising a compound provided herein (e.g., a compound of Formula (I)), or a pharmaceutically acceptable salt, solvate, tautomer, stereoisomer, or isotopically labeled derivative thereof. Methods of synthesis of a compound provided herein (e.g., a compound of Formula (I)), or a pharmaceutically acceptable salt, solvate, tautomer, stereoisomer, or isotopically labeled derivative thereof, are also provided.

Compounds

Provided herein is a compound of Formula (I):

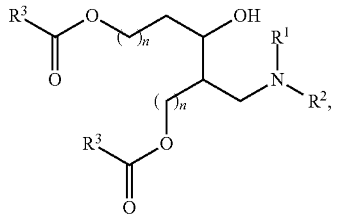

(I)

or a pharmaceutically acceptable salt, solvate, tautomer, stereoisomer, or isotopically labeled derivative thereof, wherein:

$R^1$ is —H, optionally substituted alkyl, optionally substituted alkenyl, optionally substituted alkynyl, optionally substituted heteroalkyl, optionally substituted heteroalkenyl, optionally substituted heteroalkynyl, optionally substituted aryl, optionally substituted heteroaryl, optionally substituted carbocyclyl, optionally substituted heterocyclyl, or a nitrogen protecting group;

$R^2$ is —H, optionally substituted alkyl, optionally substituted alkenyl, optionally substituted alkynyl, optionally substituted heteroalkyl, optionally substituted heteroalkenyl, optionally substituted heteroalkynyl, optionally substituted aryl, optionally substituted heteroaryl, optionally substituted carbocyclyl, optionally substituted heterocyclyl, or a nitrogen protecting group; or $R^1$ and $R^2$ are joined together with the intervening atoms to form an optionally substituted heterocyclyl;

each $R^3$ independently is optionally substituted $C_6$-$C_{25}$ aliphatic; and each n independently is 0-15, inclusive.

As defined herein, $R^1$ is —H, optionally substituted alkyl, optionally substituted alkenyl, optionally substituted alkynyl, optionally substituted heteroalkyl, optionally substituted heteroalkenyl, optionally substituted heteroalkynyl, optionally substituted aryl, optionally substituted heteroaryl, optionally substituted carbocyclyl, optionally substituted heterocyclyl, or a nitrogen protecting group; or $R^1$ and $R^2$ are joined together with the intervening atoms to form an optionally substituted heterocyclyl.

In some embodiments, $R^1$ is —H, optionally substituted alkyl, optionally substituted alkenyl, optionally substituted alkynyl, optionally substituted heteroalkyl, optionally substituted heteroalkenyl, optionally substituted heteroalkynyl, optionally substituted aryl, optionally substituted heteroaryl, optionally substituted carbocyclyl, optionally substituted heterocyclyl, or a nitrogen protecting group. In certain embodiments, $R^1$ is —H, optionally substituted $C_1$-$C_{20}$ alkyl, optionally substituted $C_1$-$C_{20}$ alkenyl, optionally substituted $C_1$-$C_{20}$ alkynyl, optionally substituted $C_1$-$C_{20}$ heteroalkyl, optionally substituted $C_1$-$C_{20}$ heteroalkenyl, optionally substituted $C_1$-$C_{20}$ heteroalkynyl, optionally substituted $C_6$-$C_{14}$ aryl, optionally substituted 5- to 14-membered heteroaryl, optionally substituted $C_3$-$C_{14}$ carbocyclyl, optionally substituted 3- to 14-membered heterocyclyl, or a nitrogen protecting group. In certain embodiments, $R^1$ is —H, optionally substituted $C_1$-$C_{10}$ alkyl, optionally substituted $C_1$-$C_{10}$ alkenyl, optionally substituted $C_1$-$C_{10}$ alkynyl, optionally substituted $C_1$-$C_{10}$ heteroalkyl, optionally substituted $C_1$-$C_{10}$ heteroalkenyl, optionally substituted $C_1$-$C_{10}$ heteroalkynyl, optionally substituted $C_6$-$C_{14}$ aryl, optionally substituted 5- to 14-membered heteroaryl, optionally substituted $C_3$-$C_{14}$ carbocyclyl, optionally substituted 3- to 14-membered heterocyclyl, or a nitrogen protecting group.

In certain embodiments, $R^1$ is —H, optionally substituted alkyl, optionally substituted alkenyl, optionally substituted alkynyl, optionally substituted heteroalkyl, optionally substituted heteroalkenyl, optionally substituted heteroalkynyl, or a nitrogen protecting group. In some embodiments, $R^1$ is —H, optionally substituted $C_1$-$C_{10}$ alkyl, optionally substituted $C_1$-$C_{10}$ alkenyl, optionally substituted $C_1$-$C_{10}$ alkynyl, optionally substituted $C_1$-$C_{10}$ heteroalkyl, optionally substituted $C_1$-$C_{10}$ heteroalkenyl, optionally substituted $C_1$-$C_{10}$ heteroalkynyl, or a nitrogen protecting group. In certain embodiments, $R^1$ is —H, optionally substituted $C_1$-$C_{10}$ alkyl, optionally substituted $C_1$-$C_{10}$ heteroalkyl, or a nitrogen protecting group.

In some embodiments, $R^1$ is —H or a nitrogen protecting group. In certain embodiments, $R^1$ is —H. In some embodiments, $R^1$ is a nitrogen protecting group. In certain embodiments, the nitrogen protecting group is Bn. Boc. Cbz, Fmoc, trifluoroacetyl, triphenylmethyl, acetyl, or Ts.

In certain embodiments, $R^1$ is optionally substituted $C_1$-$C_{10}$ alkyl or optionally substituted $C_1$-$C_{10}$ heteroalkyl. In some embodiments, $R^1$ is optionally substituted $C_1$-$C_{10}$ alkyl. In certain embodiments, $R^1$ is unsubstituted $C_1$-$C_{10}$ alkyl. In some embodiments, $R^1$ is substituted $C_1$-$C_{10}$ alkyl. In certain embodiments, $R^1$ is optionally substituted $C_1$-$C_6$ alkyl. In some embodiments, $R^1$ is unsubstituted $C_1$-$C_6$ alkyl. In certain embodiments, $R^1$ is substituted $C_1$-$C_6$ alkyl. In some embodiments, $R^1$ is methyl, ethyl, propyl, butyl, pentyl, or hexyl. In certain embodiments, $R^1$ is methyl, ethyl, propyl, or butyl. In some embodiments, $R^1$ is methyl, ethyl, or propyl. In certain embodiments, $R^1$ is propyl. In some embodiments, $R^1$ is -Et. In certain embodiments, $R^1$ is -Me.

In some embodiments, $R^1$ is optionally substituted $C_1$-$C_{10}$ heteroalkyl. In certain embodiments, $R^1$ is unsubstituted $C_1$-$C_{10}$ heteroalkyl. In some embodiments, $R^1$ is substituted $C_1$-$C_{10}$ heteroalkyl. In certain embodiments, $R^1$ is optionally substituted $C_1$-$C_6$ heteroalkyl. In some embodiments, $R^1$ is unsubstituted $C_1$-$C_6$ heteroalkyl. In certain embodiments, $R^1$ is substituted $C_1$-$C_6$ heteroalkyl. In some embodiments, $R^1$ is optionally substituted heteroalkyl comprising one or more nitrogen atoms. In some embodiments, $R^1$ is optionally substituted $C_1$-$C_{10}$ heteroalkyl comprising one or more nitrogen atoms. In some embodiments, $R^1$ is optionally substituted $C_1$-$C_6$ heteroalkyl comprising one or more nitrogen atoms. In certain embodiments, $R^1$ is

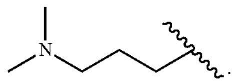

In certain embodiments, $R^1$ is optionally substituted aryl. In some embodiments, $R^1$ is optionally substituted $C_6$-$C_{14}$ aryl. In some embodiments, $R^1$ is substituted $C_6$-$C_{14}$ aryl. In some embodiments, $R^1$ is unsubstituted $C_6$-$C_{14}$ aryl. In certain embodiments, $R^1$ is optionally substituted $C_6$-$C_{10}$ aryl. In certain embodiments, $R^1$ is substituted $C_6$-$C_{10}$ aryl. In certain embodiments, $R^1$ is unsubstituted $C_6$-$C_{10}$ aryl. In some embodiments, $R^1$ is optionally substituted phenyl or optionally substituted naphthyl. In certain embodiments, $R^1$ is optionally substituted phenyl. In some embodiments, $R^1$ is optionally substituted naphthyl.

In certain embodiments, $R^1$ is optionally substituted heteroaryl. In some embodiments, $R^1$ is optionally substituted 5- to 14-membered heteroaryl. In some embodiments, $R^1$ is substituted 5- to 14-membered heteroaryl. In some embodiments, $R^1$ is unsubstituted 5- to 14-membered heteroaryl. In some embodiments, $R^1$ is optionally substituted 5- to 10-membered heteroaryl. In some embodiments, $R^1$ is substituted 5- to 10-membered heteroaryl. In some embodiments, $R^1$ is unsubstituted 5- to 10-membered heteroaryl.

In some embodiments, $R^1$ is optionally substituted carbocyclyl. In some embodiments, $R^1$ is optionally substituted $C_3$-$C_{14}$ carbocyclyl. In some embodiments, $R^1$ is substituted $C_3$-$C_{14}$ carbocyclyl. In some embodiments, $R^1$ is unsubstituted $C_3$-$C_{14}$ carbocyclyl. In some embodiments, $R^1$ is optionally substituted $C_3$-$C_8$ carbocyclyl. In some embodiments, $R^1$ is substituted $C_3$-$C_8$ carbocyclyl. In some embodiments, $R^1$ is unsubstituted $C_3$-$C_8$ carbocyclyl. In some embodiments, $R^1$ is $C_3$-$C_8$ carbocyclyl substituted with optionally substituted alkyl, optionally substituted heteroalkyl, optionally substituted cycloalkyl, optionally substituted heterocyclyl, optionally substituted heteroaryl, or optionally substituted aryl.

In some embodiments, $R^1$ is optionally substituted heterocyclyl. In some embodiments, $R^1$ is optionally substituted 3- to 14-membered heterocyclyl. In some embodiments, $R^1$ is substituted 3- to 14-membered heterocyclyl. In some embodiments, $R^1$ is unsubstituted 3- to 14-membered heterocyclyl. In some embodiments, $R^1$ is optionally substituted 3- to 8-membered heterocyclyl. In some embodiments, $R^1$ is substituted 3- to 8-membered heterocyclyl. In some embodiments, $R^1$ is unsubstituted 3- to 8-membered heterocyclyl. In some embodiments, $R^1$ is 3- to 8-membered heterocyclyl substituted with optionally substituted alkyl, optionally substituted heteroalkyl, optionally substituted cycloalkyl, optionally substituted heterocyclyl, optionally substituted heteroaryl, or optionally substituted aryl.

As defined herein, $R^2$ is —H, optionally substituted alkyl, optionally substituted alkenyl, optionally substituted alkynyl, optionally substituted heteroalkyl, optionally substituted heteroalkenyl, optionally substituted heteroalkynyl, optionally substituted aryl, optionally substituted heteroaryl, optionally substituted carbocyclyl, optionally substituted heterocyclyl, or a nitrogen protecting group; or $R^1$ and $R^2$ are joined together with the intervening atoms to form an optionally substituted heterocyclyl.

In some embodiments, $R^2$ is —H, optionally substituted alkyl, optionally substituted alkenyl, optionally substituted alkynyl, optionally substituted heteroalkyl, optionally substituted heteroalkenyl, optionally substituted heteroalkynyl, optionally substituted aryl, optionally substituted heteroaryl, optionally substituted carbocyclyl, optionally substituted heterocyclyl, or a nitrogen protecting group. In certain embodiments, $R^2$ is —H, optionally substituted $C_1$-$C_{20}$ alkyl, optionally substituted $C_1$-$C_{20}$ alkenyl, optionally substituted $C_1$-$C_{20}$ alkynyl, optionally substituted $C_1$-$C_{20}$ heteroalkyl, optionally substituted $C_1$-$C_{20}$ heteroalkenyl, optionally substituted $C_1$-$C_{20}$ heteroalkynyl, optionally substituted $C_6$-$C_{14}$ aryl, optionally substituted 5- to 14-membered heteroaryl, optionally substituted $C_3$-$C_{14}$ carbocyclyl, optionally substituted 3- to 14-membered heterocyclyl, or a nitrogen protecting group. In certain embodiments, $R^2$ is —H, optionally substituted $C_1$-$C_{10}$ alkyl, optionally substituted $C_1$-$C_{10}$ alkenyl, optionally substituted $C_1$-$C_{10}$ alkynyl, optionally substituted $C_1$-$C_{10}$ heteroalkyl, optionally substituted $C_1$-$C_{10}$ heteroalkenyl, optionally substituted $C_1$-$C_{10}$ heteroalkynyl, optionally substituted $C_6$-$C_{14}$ aryl, optionally substituted 5- to 14-membered heteroaryl, optionally substituted $C_3$-$C_{14}$ carbocyclyl, optionally substituted 3- to 14-membered heterocyclyl, or a nitrogen protecting group.

In some embodiments, $R^2$ is —H, optionally substituted optionally substituted alkyl, optionally substituted alkenyl, optionally substituted alkynyl, optionally substituted heteroalkyl, optionally substituted heteroalkenyl, optionally substituted heteroalkynyl, optionally substituted carbocyclyl, optionally substituted heterocyclyl, or a nitrogen protecting group. In certain embodiments, $R^2$ is —H, optionally substituted alkyl, optionally substituted heteroalkyl, optionally substituted carbocyclyl, optionally substituted heterocyclyl, or a nitrogen protecting group. In some embodiments, $R^2$ is —H, optionally substituted $C_1$-$C_{20}$ alkyl, optionally substituted $C_1$-$C_{20}$ heteroalkyl, optionally substituted $C_3$-$C_{14}$ carbocyclyl, optionally substituted 3- to 14-membered heterocyclyl, or a nitrogen protecting group. In certain embodiments, $R^2$ is —H, optionally substituted $C_1$-$C_{10}$ alkyl, optionally substituted $C_1$-$C_{10}$ heteroalkyl, optionally substituted $C_3$-$C_{14}$ carbocyclyl, optionally substituted 3- to 14-membered heterocyclyl, or a nitrogen protecting group.

In some embodiments, $R^2$ is optionally substituted optionally substituted alkyl, optionally substituted alkenyl, optionally substituted alkynyl, optionally substituted heteroalkyl, optionally substituted heteroalkenyl, optionally substituted heteroalkynyl, optionally substituted carbocyclyl, optionally substituted heterocyclyl, or a nitrogen protecting group. In certain embodiments, $R^2$ is optionally substituted alkyl, optionally substituted heteroalkyl, optionally substituted carbocyclyl, optionally substituted heterocyclyl, or a nitrogen protecting group. In some embodiments, $R^2$ is optionally substituted $C_1$-$C_{20}$ alkyl, optionally substituted $C_1$-$C_{20}$ heteroalkyl, optionally substituted $C_3$-$C_{14}$ carbocyclyl, optionally substituted 3- to 14-membered heterocyclyl, or a nitrogen protecting group. In certain embodiments, $R^2$ is optionally substituted $C_1$-$C_{10}$ alkyl, optionally substituted $C_1$-$C_{10}$ heteroalkyl, optionally substituted $C_3$-$C_{14}$ carbocyclyl, optionally substituted 3- to 14-membered heterocyclyl, or a nitrogen protecting group.

In some embodiments, $R^2$ is —H or a nitrogen protecting group. In certain embodiments, $R^2$ is —H. In some embodiments, $R^2$ is not —H. In certain embodiments, $R^2$ is a nitrogen protecting group. In certain embodiments, the nitrogen protecting group is Bn, Boc, Cbz, Fmoc, trifluoroacetyl, triphenylmethyl, acetyl, or Ts.

In certain embodiments, $R^2$ is optionally substituted $C_1$-$C_{10}$ alkyl or optionally substituted $C_1$-$C_{10}$ heteroalkyl. In some embodiments, $R^2$ is optionally substituted $C_1$-$C_{10}$ alkyl. In certain embodiments, $R^2$ is unsubstituted $C_1$-$C_{10}$ alkyl. In some embodiments, $R^2$ is substituted $C_1$-$C_{10}$ alkyl.

In certain embodiments, $R^2$ is optionally substituted $C_1$-$C_6$ alkyl. In some embodiments, $R^2$ is unsubstituted $C_1$-$C_6$ alkyl. In certain embodiments, $R^2$ is substituted $C_1$-$C_6$ alkyl. In some embodiments, $R^2$ is methyl, ethyl, propyl, butyl, pentyl, or hexyl. In certain embodiments, $R^2$ is methyl, ethyl, propyl, or butyl. In some embodiments, $R^2$ is methyl, ethyl, or propyl. In certain embodiments, $R^2$ is propyl. In some embodiments, $R^2$ is -Et. In certain embodiments, $R^2$ is -Me.

In some embodiments, $R^2$ is optionally substituted $C_1$-$C_{10}$ heteroalkyl. In certain embodiments, $R^2$ is unsubstituted $C_1$-$C_{10}$ heteroalkyl. In some embodiments, $R^2$ is substituted $C_1$-$C_{10}$ heteroalkyl. In certain embodiments, $R^2$ is optionally substituted $C_1$-$C_6$ heteroalkyl. In some embodiments, $R^2$ is unsubstituted $C_1$-$C_6$ heteroalkyl. In certain embodiments, $R^2$ is substituted $C_1$-$C_6$ heteroalkyl. In some embodiments, $R^2$ is optionally substituted heteroalkyl comprising one or more nitrogen atoms. In some embodiments, $R^2$ is optionally substituted $C_1$-$C_{10}$ heteroalkyl comprising one or more nitrogen atoms. In some embodiments, $R^2$ is optionally substituted $C_1$-$C_6$ heteroalkyl comprising one or more nitrogen atoms. In certain embodiments, $R^2$ is

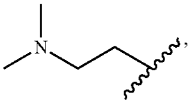, 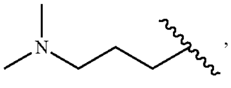,

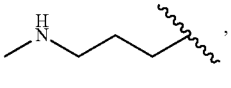, 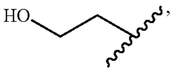,

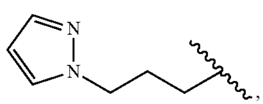, 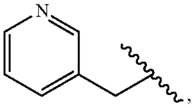,

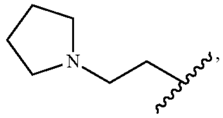, 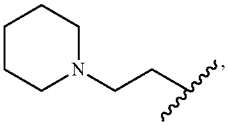,

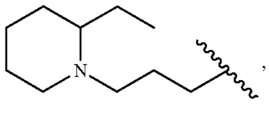, 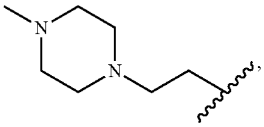,

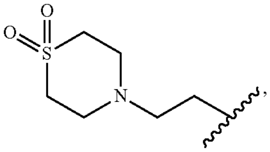, 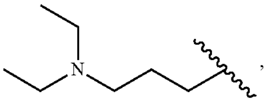,

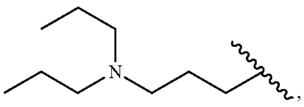,

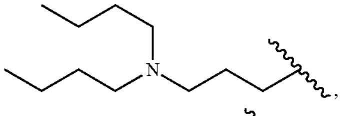,

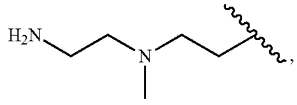,

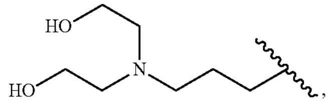, 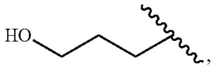,

-continued

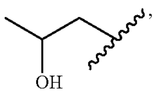, 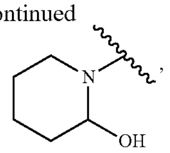, or

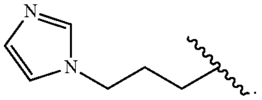.

In certain embodiments, $R^2$ is optionally substituted heteroalkyl comprising one or more N atoms substituted with

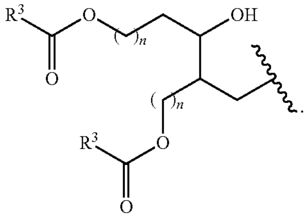.

In some embodiments, $R^2$ is

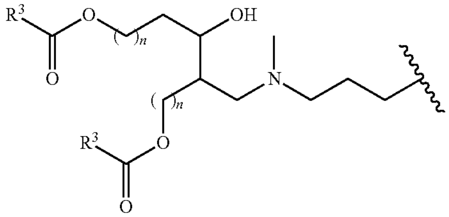 or

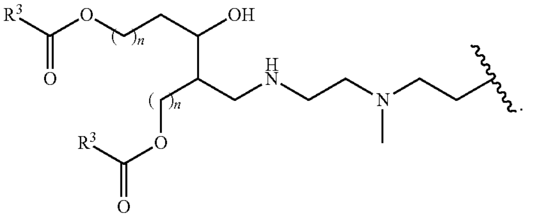.

In certain embodiments, $R^2$ is optionally substituted aryl. In some embodiments, $R^2$ is optionally substituted $C_6$-$C_{14}$ aryl. In some embodiments, $R^2$ is substituted $C_6$-$C_{14}$ aryl. In some embodiments, $R^2$ is unsubstituted $C_6$-$C_{14}$ aryl. In certain embodiments, $R^2$ is optionally substituted $C_6$-$C_{10}$ aryl. In certain embodiments, $R^2$ is substituted $C_6$-$C_{10}$ aryl. In certain embodiments, $R^2$ is unsubstituted $C_6$-$C_{10}$ aryl. In some embodiments, $R^2$ is optionally substituted phenyl or optionally substituted naphthyl. In certain embodiments, $R^2$ is optionally substituted phenyl. In some embodiments, $R^2$ is optionally substituted naphthyl.

In certain embodiments, $R^2$ is optionally substituted heteroaryl. In some embodiments, $R^2$ is optionally substituted 5- to 14-membered heteroaryl. In some embodiments, $R^2$ is substituted 5- to 14-membered heteroaryl. In some embodiments, $R^2$ is unsubstituted 5- to 14-membered heteroaryl. In some embodiments, $R^2$ is optionally substituted 5- to 10-membered heteroaryl. In some embodiments, $R^2$ is substituted 5- to 10-membered heteroaryl. In some embodiments, $R^2$ is unsubstituted 5- to 10-membered heteroaryl.

In some embodiments, $R^2$ is optionally substituted carbocyclyl. In some embodiments, $R^2$ is optionally substituted $C_3$-$C_{14}$ carbocyclyl. In some embodiments, $R^2$ is substituted $C_3$-$C_{14}$ carbocyclyl. In some embodiments, $R^2$ is unsubstituted $C_3$-$C_{14}$ carbocyclyl. In some embodiments, $R^2$ is optionally substituted $C_3$-$C_8$ carbocyclyl. In some embodiments, $R^2$ is substituted $C_3$-$C_8$ carbocyclyl. In some embodiments, $R^2$ is unsubstituted $C_3$-$C_8$ carbocyclyl. In some embodiments, $R^2$ is $C_3$-$C_8$ carbocyclyl substituted with optionally substituted alkyl, optionally substituted heteroalkyl, optionally substituted cycloalkyl, optionally substituted heterocyclyl, optionally substituted heteroaryl, or optionally substituted aryl.

In some embodiments, $R^2$ is optionally substituted heterocyclyl. In some embodiments, $R^2$ is optionally substituted 3- to 14-membered heterocyclyl. In some embodiments, $R^2$ is substituted 3- to 14-membered heterocyclyl. In some embodiments, $R^2$ is unsubstituted 3- to 14-membered heterocyclyl. In some embodiments, $R^2$ is optionally substituted 3- to 8-membered heterocyclyl. In some embodiments, $R^2$ is substituted 3- to 8-membered heterocyclyl. In some embodiments, $R^2$ is unsubstituted 3- to 8-membered heterocyclyl. In some embodiments, $R^2$ is 3- to 8-membered heterocyclyl substituted with optionally substituted alkyl, optionally substituted heteroalkyl, optionally substituted cycloalkyl, optionally substituted heterocyclyl, optionally substituted heteroaryl, or optionally substituted aryl.

In certain embodiments, $R^1$ and $R^2$ are joined together with the intervening atoms to form an optionally substituted heterocyclyl. In some embodiments, $R^1$ and $R^2$ are joined together with the intervening atoms to form a substituted heterocyclyl. In certain embodiments, $R^1$ and $R^2$ are joined together with the intervening atoms to form an unsubstituted heterocyclyl.

In some embodiments, $R^1$ and $R^2$ are joined together with the intervening atoms to form an optionally substituted heterocyclyl comprising one or two nitrogen atoms. In certain embodiments, $R^1$ and $R^2$ are joined together with the intervening atoms to form an optionally substituted heterocyclyl comprising one nitrogen atoms. In some embodiments, $R^1$ and $R^2$ are joined together with the intervening atoms to form an optionally substituted heterocyclyl comprising two nitrogen atoms. In certain embodiments, $R^1$ and $R^2$ are joined together with the intervening atoms to form an optionally substituted heterocyclyl comprising two or more nitrogen atoms.

In some embodiments, —$NR^1R^2$ is

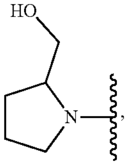, 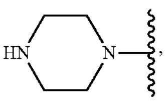, 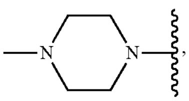,

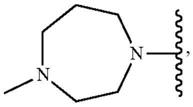, 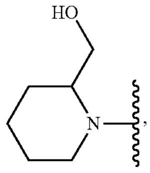, or

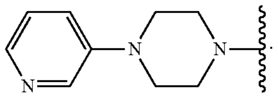.

In certain embodiments, $R^1$ and $R^2$ are joined together with the intervening atoms to form an optionally substituted heterocyclyl comprising two or more N atoms substituted with

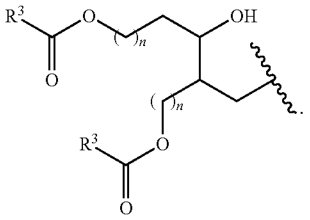

In some embodiments, $R^1$ and $R^2$ are joined together with the intervening atoms to form an optionally substituted heterocyclyl comprising two N atoms substituted with

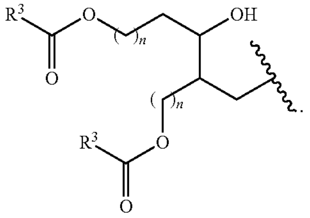

As defined herein, each $R^3$ independently is optionally substituted $C_6$-$C_{25}$ aliphatic. In some embodiments, $R^3$ is optionally substituted $C_6$-$C_{25}$ alkyl, optionally substituted $C_6$-$C_{25}$ alkenyl, or optionally substituted $C_6$-$C_{25}$ alkynyl. In certain embodiments, $R^3$ is optionally substituted $C_6$-$C_{25}$ alkyl or optionally substituted $C_6$-$C_{25}$ alkenyl. In some embodiments, $R^3$ is optionally substituted $C_6$-$C_{25}$ alkyl or optionally substituted $C_6$-$C_{25}$ alkynyl. In certain embodiments, $R^3$ is optionally substituted $C_6$-$C_{25}$ alkenyl or optionally substituted $C_6$-$C_{25}$ alkynyl. In some embodiments, $R^3$ is substituted $C_6$-$C_{25}$ alkyl, substituted $C_6$-$C_{25}$ alkenyl, or substituted $C_6$-$C_{25}$ alkynyl. In certain embodiments, $R^3$ is substituted $C_6$-$C_{25}$ alkyl or substituted $C_6$-$C_{25}$ alkenyl. In some embodiments, $R^3$ is substituted $C_6$-$C_{25}$ alkyl or substituted $C_6$-$C_{25}$ alkynyl. In certain embodiments, $R^3$ is substituted $C_6$-$C_{25}$ alkenyl or substituted $C_6$-$C_{25}$ alkynyl. In some embodiments, $R^3$ is unsubstituted $C_6$-$C_{25}$ alkyl, unsubstituted $C_6$-$C_{25}$ alkenyl, or unsubstituted $C_6$-$C_{25}$ alkynyl. In certain embodiments, $R^3$ is unsubstituted $C_6$-$C_{25}$ alkyl or unsubstituted $C_6$-$C_{25}$ alkenyl. In some embodiments, $R^3$ is unsubstituted $C_6$-$C_{25}$ alkyl or unsubstituted $C_6$-$C_{25}$ alkynyl. In certain embodiments, $R^3$ is unsubstituted $C_6$-$C_{25}$ alkenyl or unsubstituted $C_6$-$C_{25}$ alkynyl. In each of the foregoing embodiments, the aliphatic, alkyl, alkenyl, or alkynyl group may have 6-12 carbon atoms, 12-18 carbon atoms, or 18-25 carbon atoms.

In some embodiments, $R^3$ is optionally substituted $C_6$-$C_{25}$ alkyl. In certain embodiments, $R^3$ is substituted $C_6$-$C_{25}$ alkyl. In some embodiments, $R^3$ is unsubstituted $C_6$-$C_{25}$ alkyl. In certain embodiments $R^3$ is

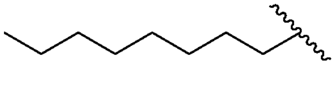,

-continued

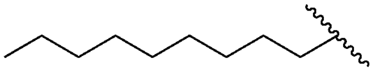,

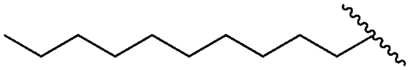,

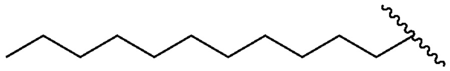,

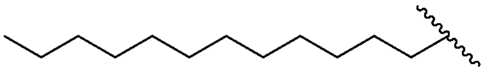,

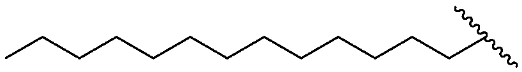,

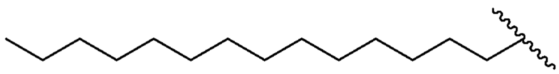,

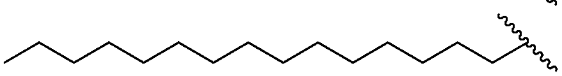,

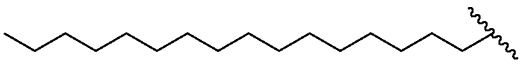, or

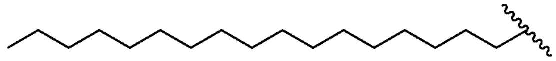.

In certain embodiments, $R^3$ is optionally substituted $C_6$-$C_{25}$ alkenyl. In some embodiments, $R^3$ is substituted $C_6$-$C_{25}$ alkenyl. In certain embodiments, $R^3$ is unsubstituted $C_6$-$C_2$, alkenyl. In some embodiments, $R^3$ comprises one or more double bonds. In certain embodiments, $R^3$ comprises two or more double bonds. In some embodiments, $R^3$ comprises three or more double bonds. In certain embodiments, $R^3$ comprises one, two, or three double bonds. In some embodiments, $R^3$ comprises one double bond. In certain embodiments, $R^3$ comprises two double bonds. In some embodiments, $R^3$ comprises three double bonds. In certain embodiments, $R^3$ is

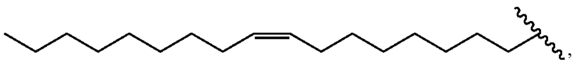,

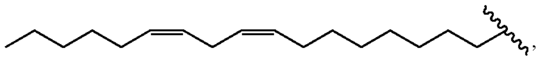, or

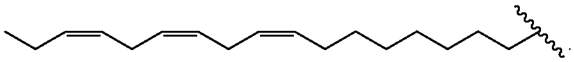.

In some embodiments, $R^3$ is optionally substituted $C_6$-$C_{25}$ alkynyl. In some embodiments, $R^3$ is substituted $C_6$-$C_{25}$ alkynyl. In certain embodiments, $R^3$ is unsubstituted $C_6$-$C_{25}$alkynyl. In some embodiments, $R^3$ comprises one or more triple bonds. In certain embodiments, $R^3$ comprises two or more triple bonds. In some embodiments, $R^3$ comprises three or more triple bonds. In certain embodiments, $R^3$ comprises one, two, or three triple bonds. In some embodiments, $R^3$ comprises one triple bond. In certain embodiments, $R^3$ comprises two triple bonds. In some embodiments, $R^3$ comprises three triple bonds.

As defined herein, each n independently is 0-15, inclusive. In some embodiments, each n is independently 1-10, inclusive. In certain embodiments, each n is independently 1-8, inclusive. In some embodiments, each n is independently 1-6, inclusive. In certain embodiments, each n is different. In certain embodiments, each n is different, and n is 1-10, inclusive. In certain embodiments, each n is different, and n is 1-8, inclusive. In some embodiments, each n is different, and n is 1-6, inclusive. In some embodiments, n is 1. In certain embodiments, n is 2. In some embodiments, n is 3. In certain embodiments, n is 4. In some embodiments, n is 5. In certain embodiments, n is 6. In some embodiments, n is 7. In certain embodiments, n is 8. In some embodiments, n is 9. In certain embodiments, n is 10. In some embodiments, n is 11. In certain embodiments, n is 12. In some embodiments, n is 13. In certain embodiments, n is 14. In some embodiments, n is 15. In some embodiments, each n is the same. In certain embodiments, each n is the same, and n is 1-10, inclusive. In certain embodiments, each n is the same, and n is 1-8, inclusive. In some embodiments, each n is the same, and n is 1-6, inclusive. In some embodiments, each n is 1. In certain embodiments, each n is 2. In some embodiments, each n is 3. In certain embodiments, each n is 4. In some embodiments, each n is 5. In certain embodiments, each n is 6. In some embodiments, each n is 7. In certain embodiments, each n is 8. In some embodiments, each n is 9. In certain embodiments, each n is 10. In some embodiments, each n is 11. In certain embodiments, each n is 12. In some embodiments, each n is 13. In certain embodiments, each n is 14. In some embodiments, each n is 15.

In certain embodiments, the compound of Formula (I) is

1

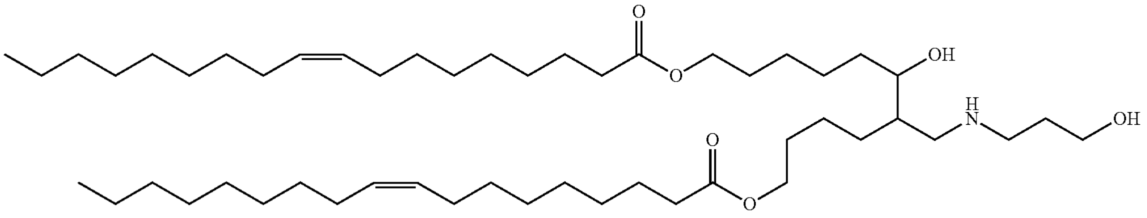

2

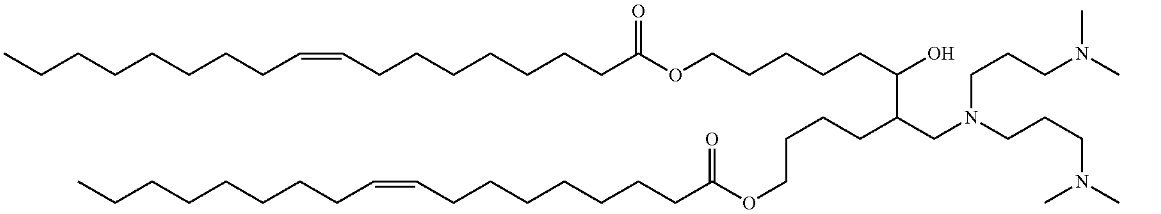

3

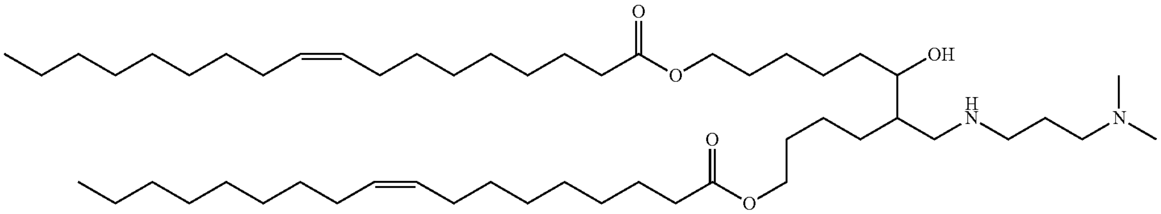

4

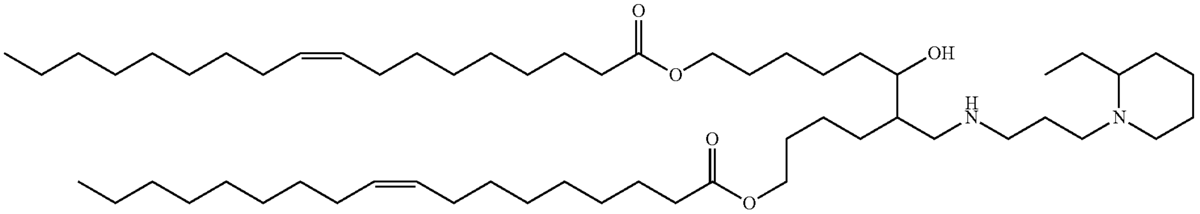

5

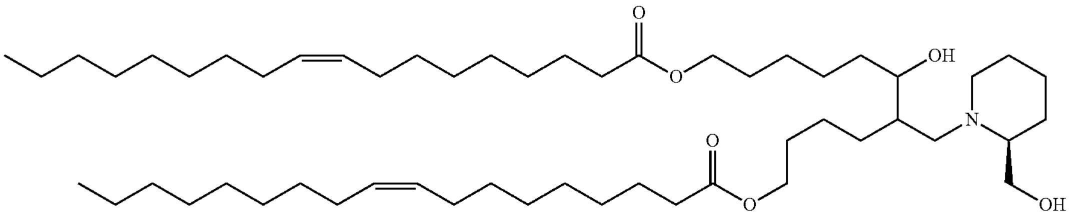

-continued
6
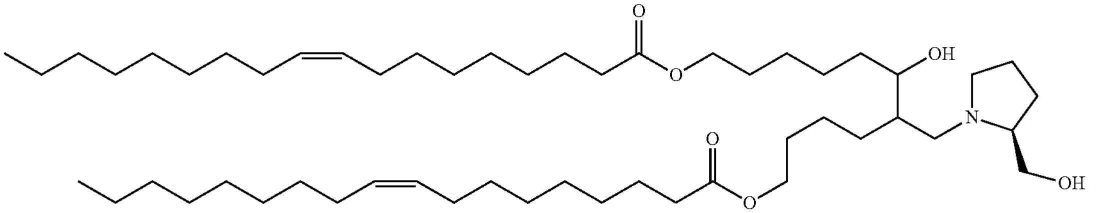
7
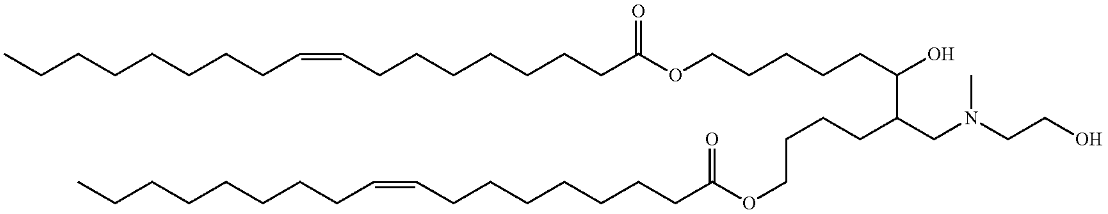
8
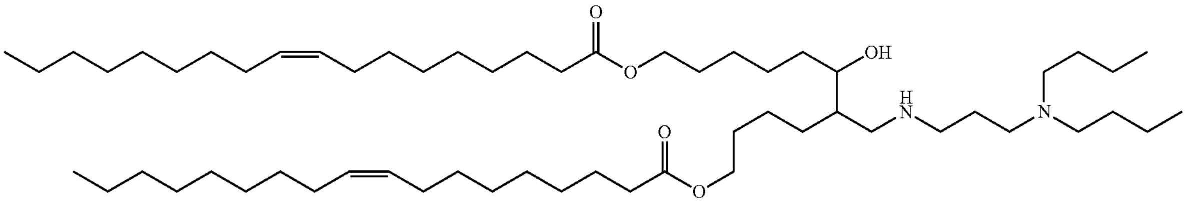
9
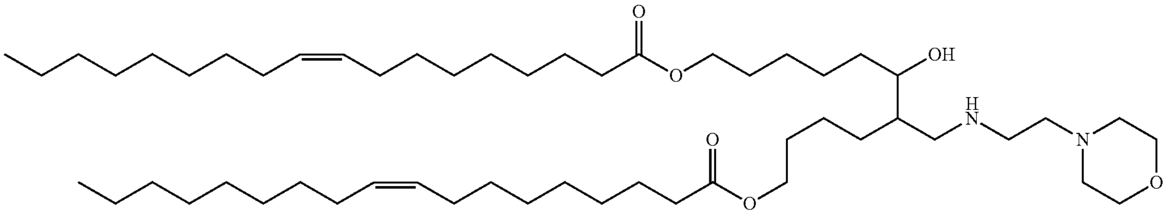
10
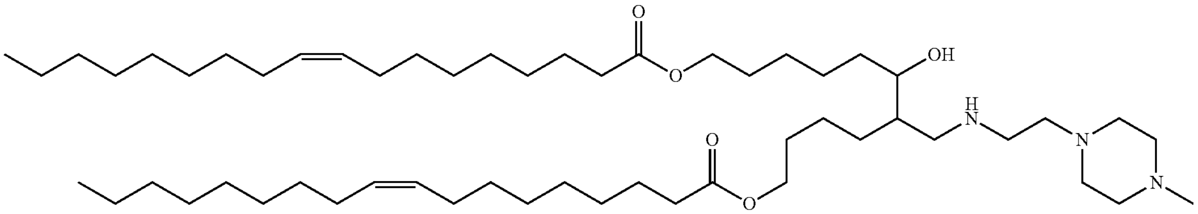
11
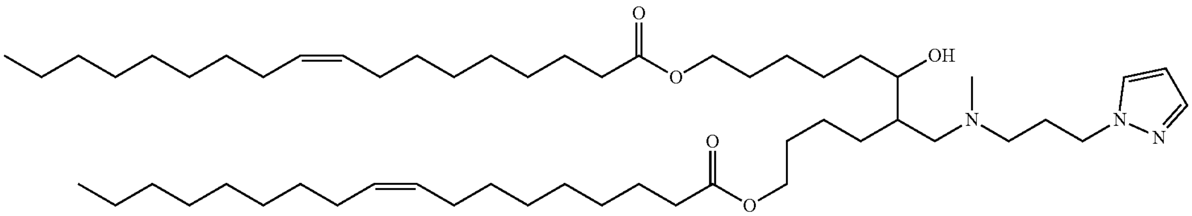
12
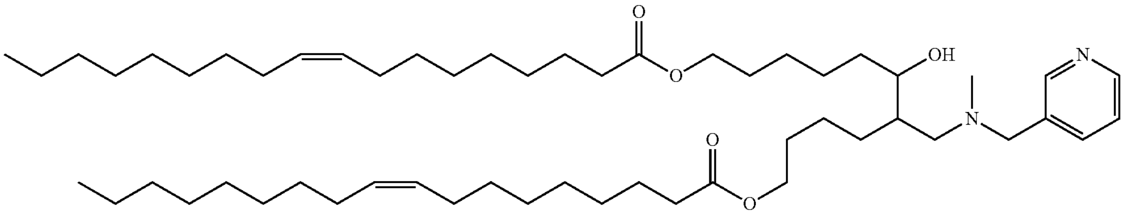

-continued
13
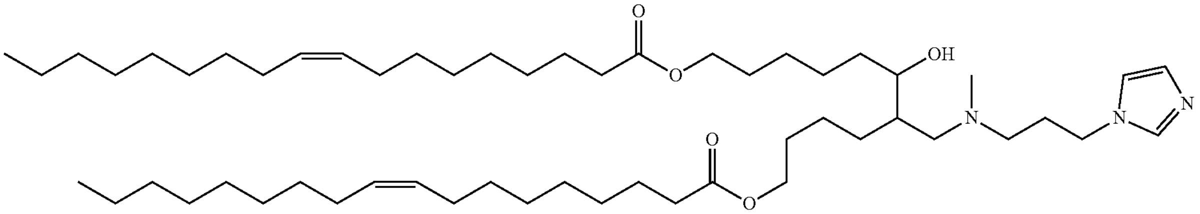
14
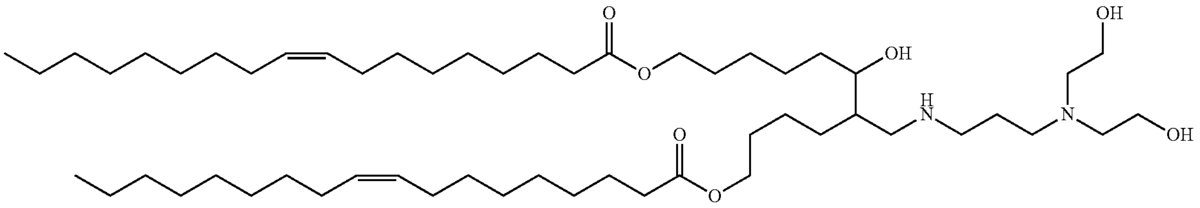
15
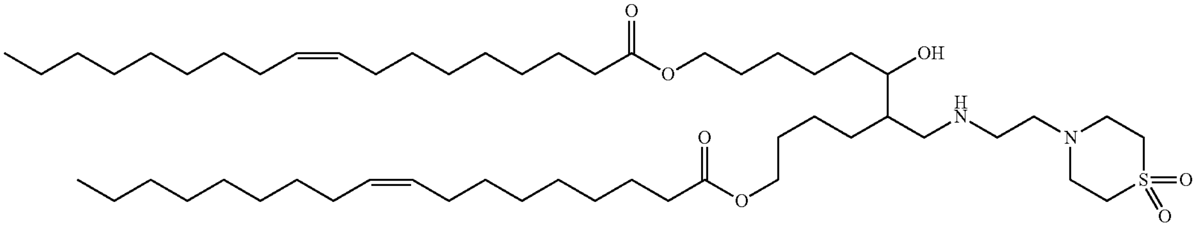
16
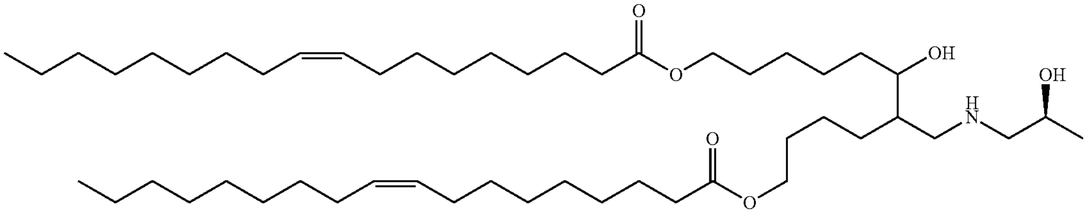
17
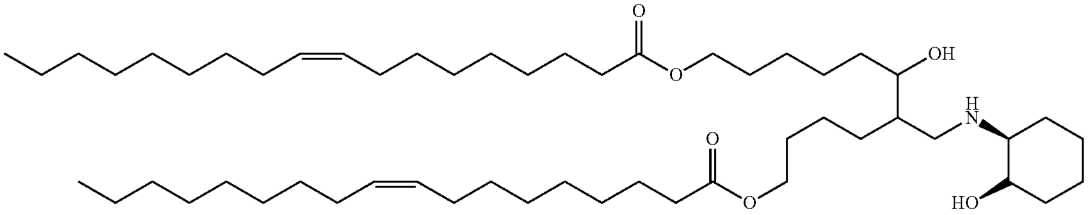
18
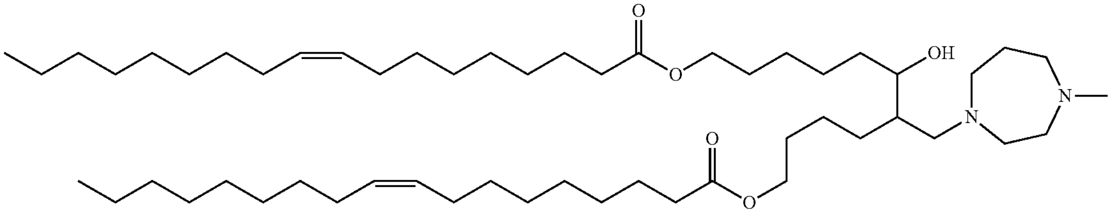
19
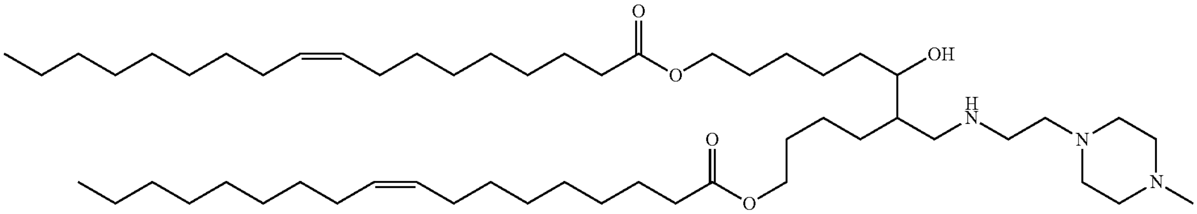

-continued
20
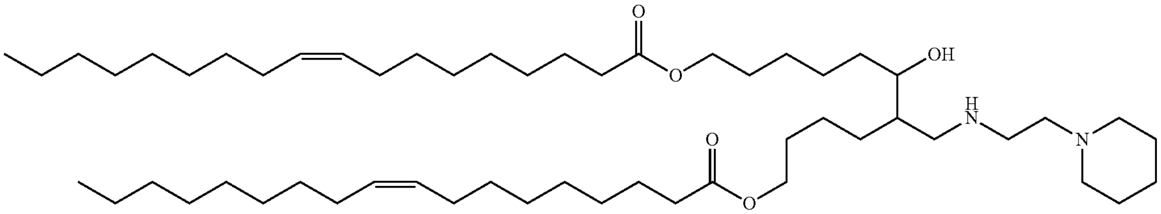
21
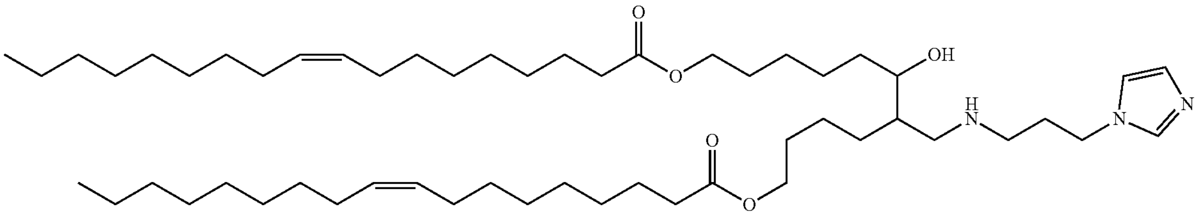
22
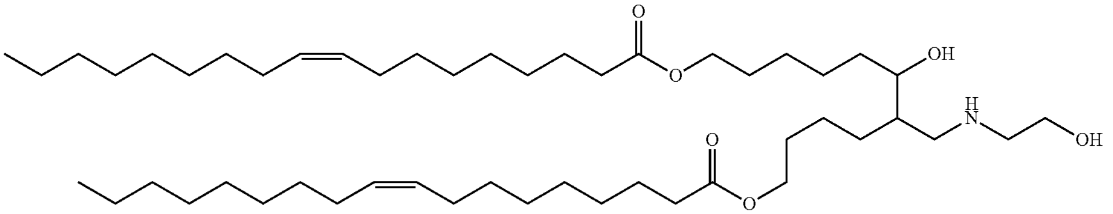
23
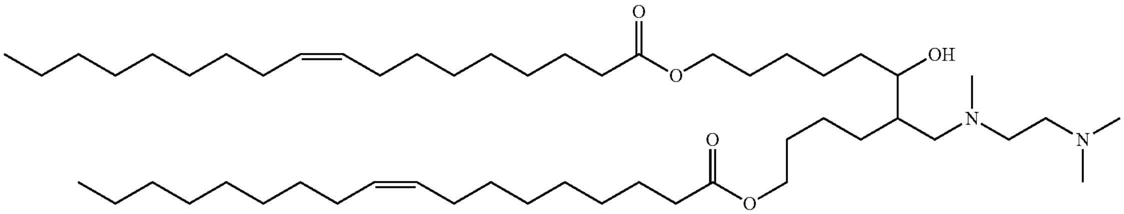
24
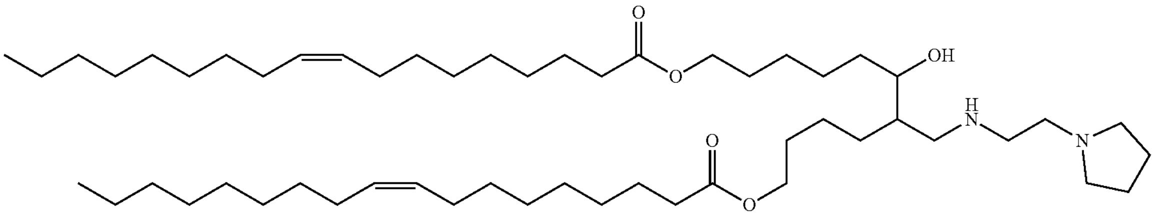
25
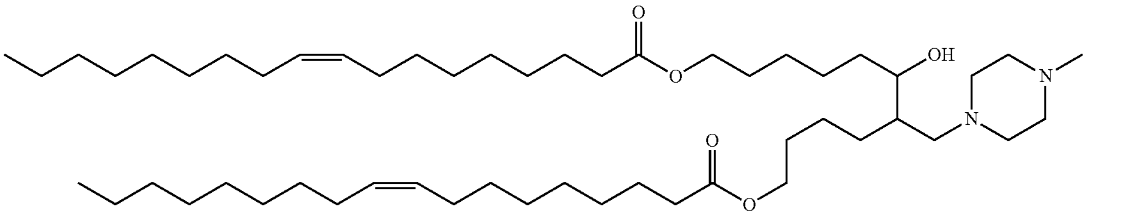
26
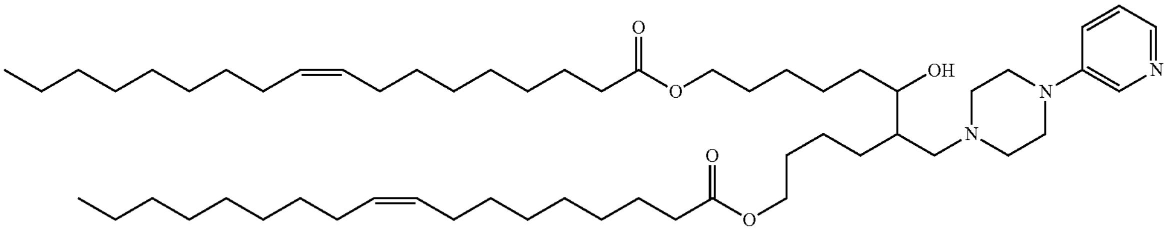

-continued
27
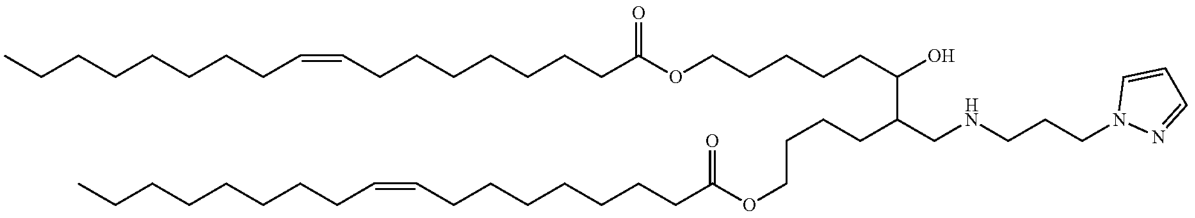
28
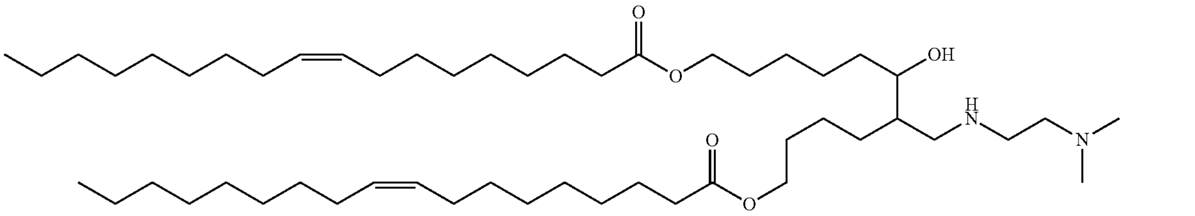
29
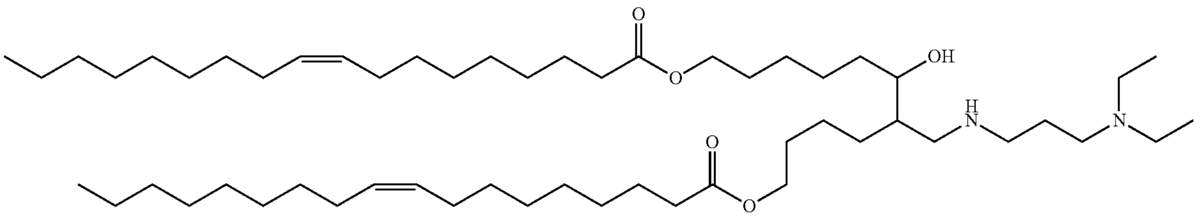
30
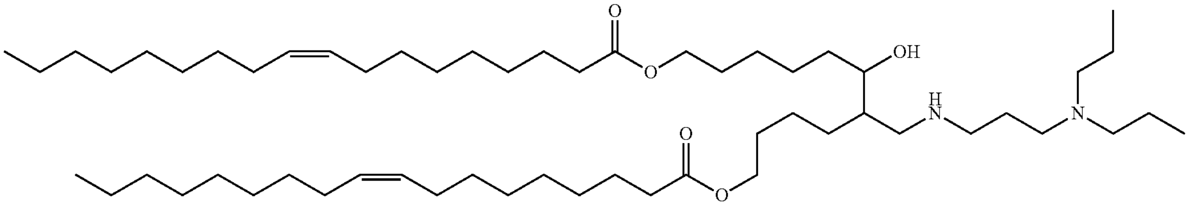
31
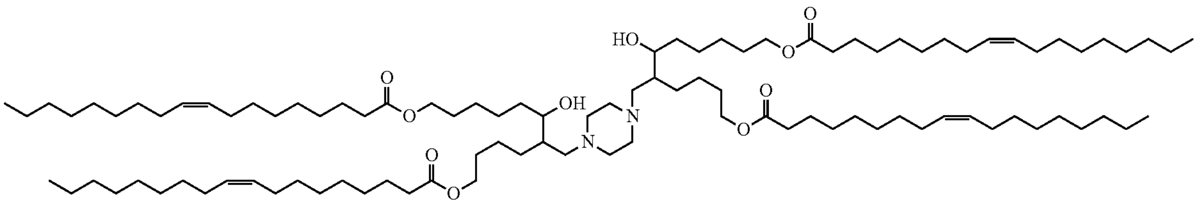
32
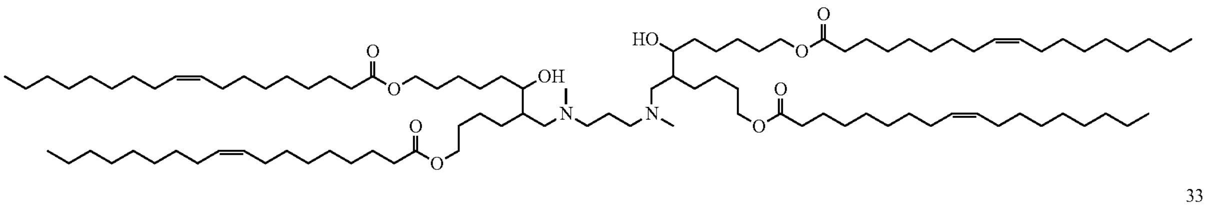
33
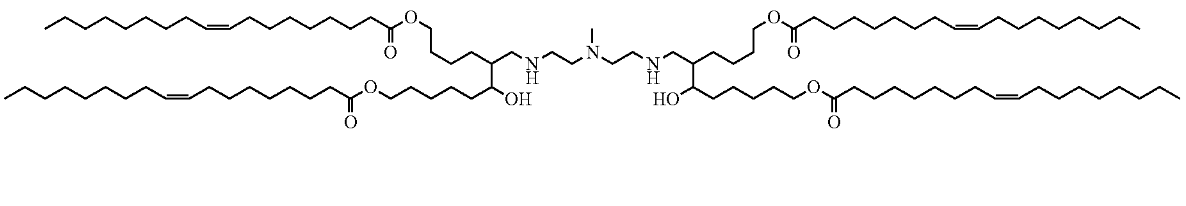

-continued
34
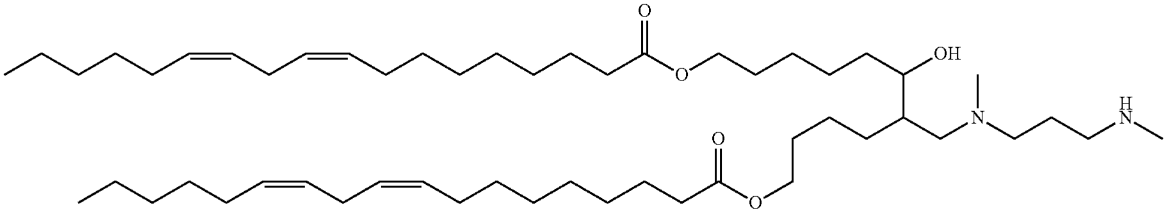
35
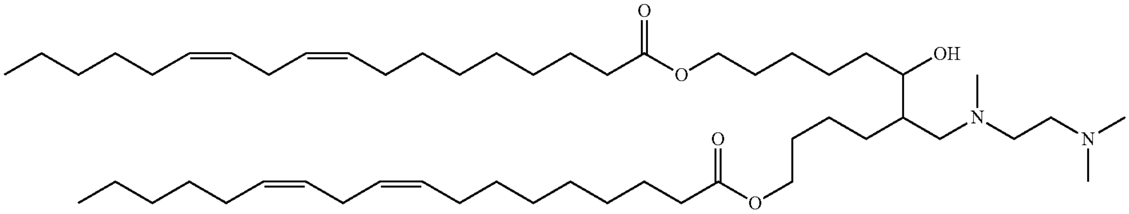
36
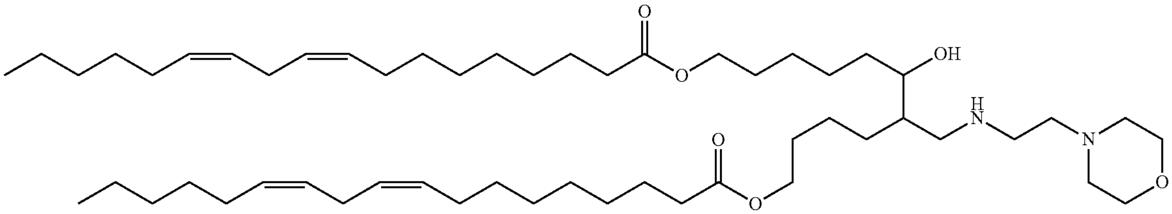
37
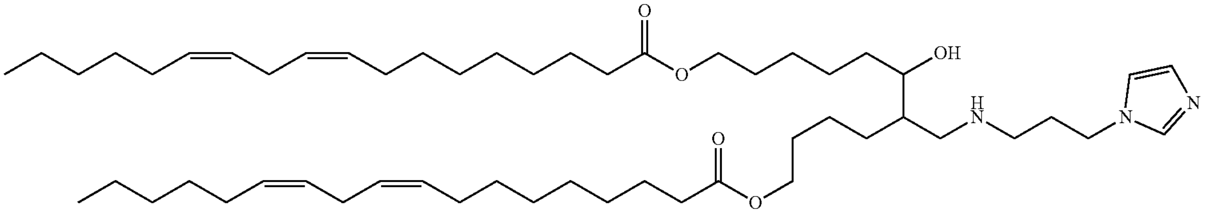
38
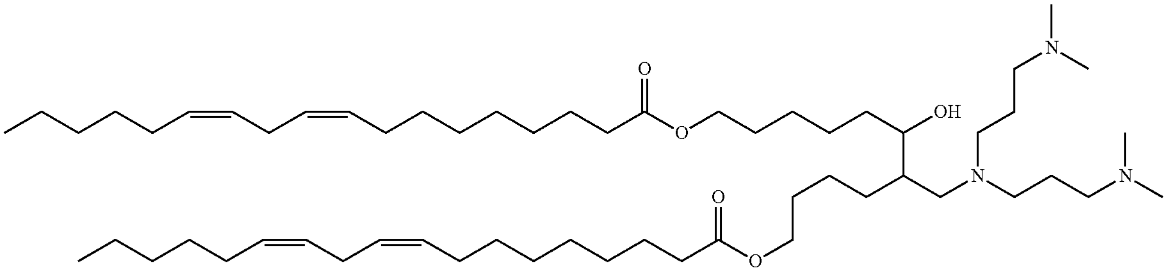
39
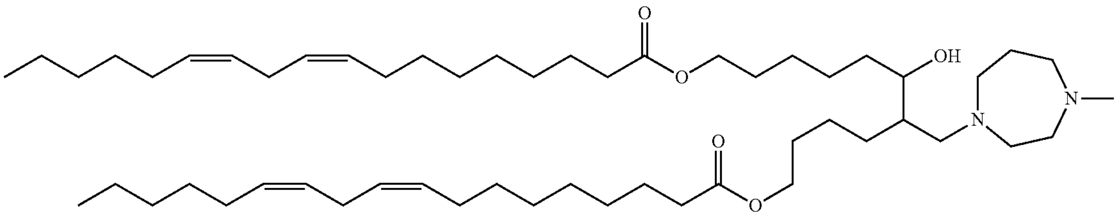

-continued
40
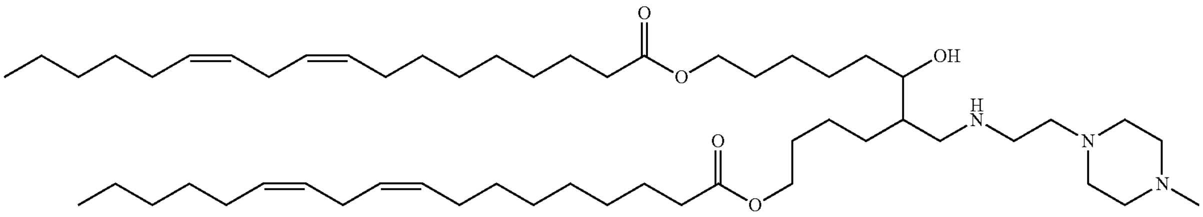
41
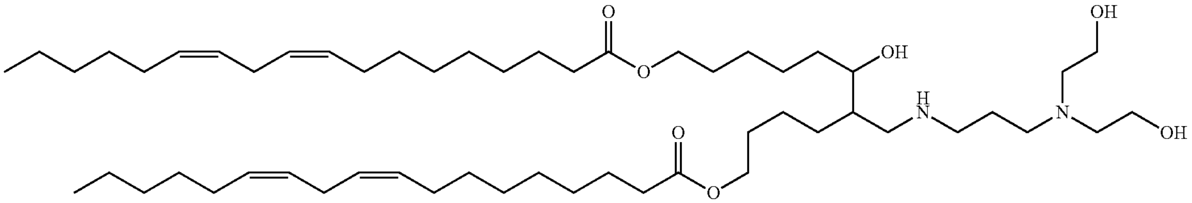
42
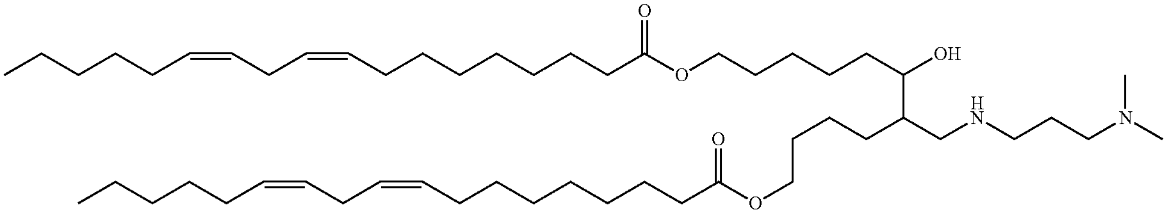
43
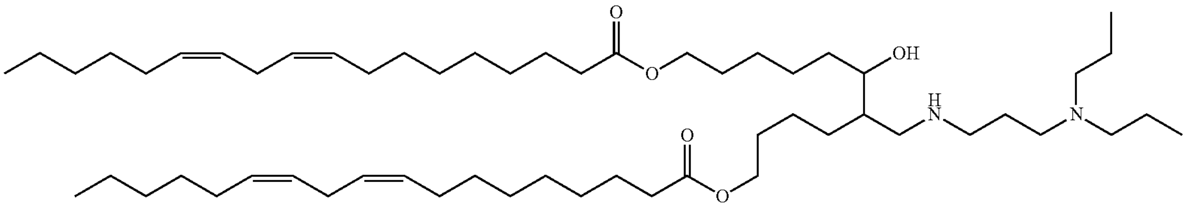
44
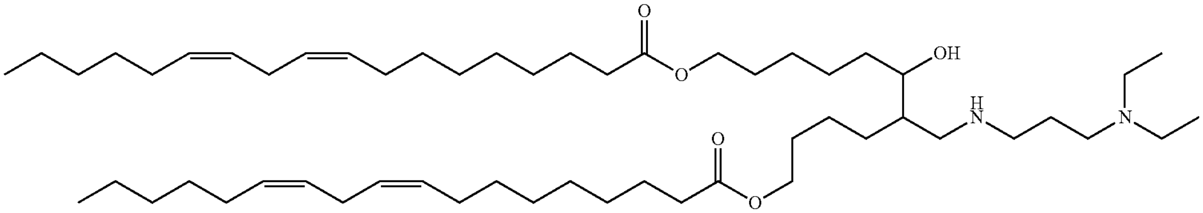
45
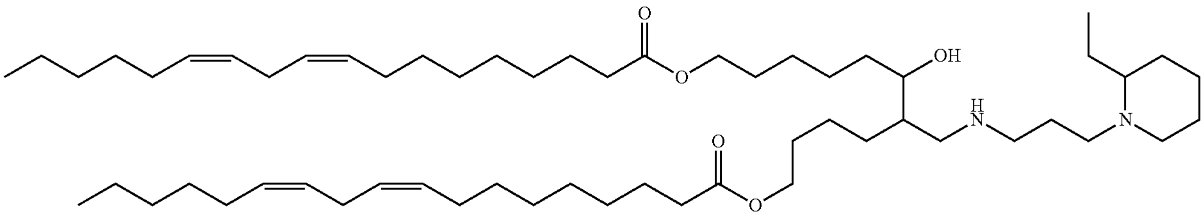
46
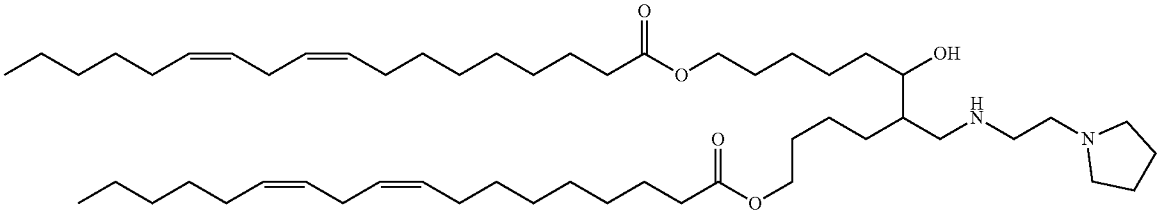

-continued
47
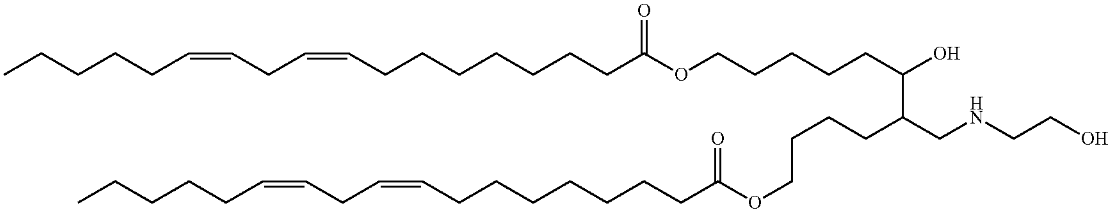
48
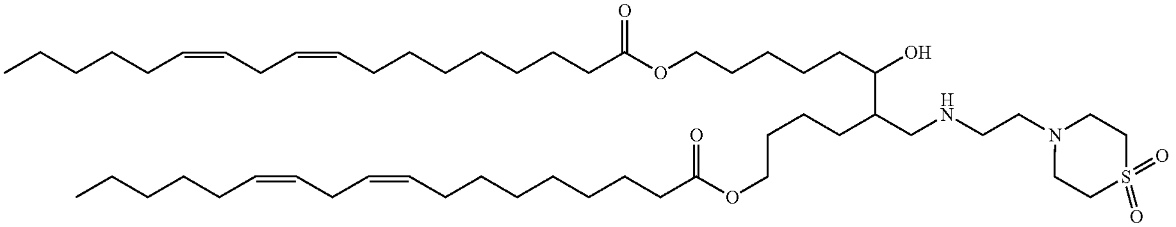
49
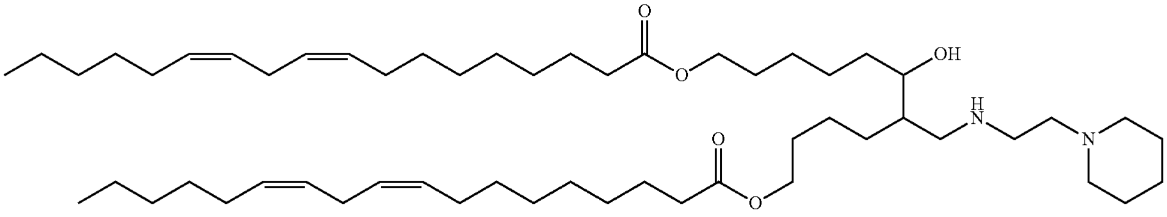
50
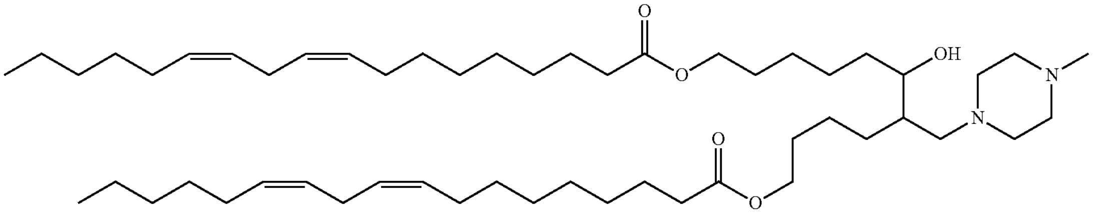
51
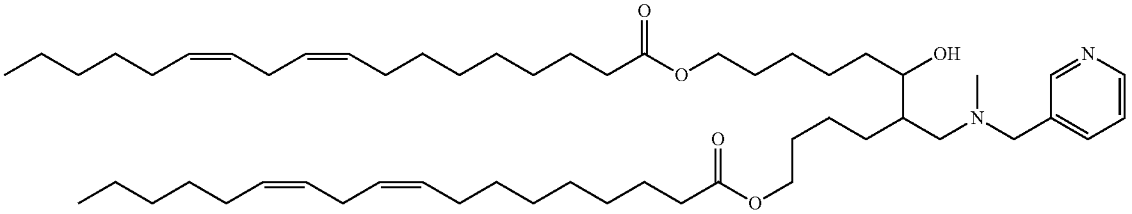
52
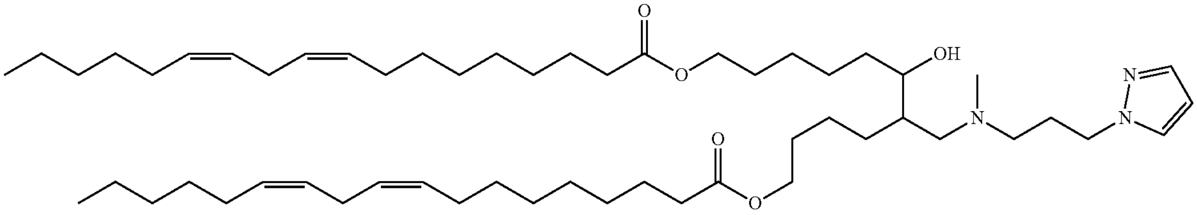
53
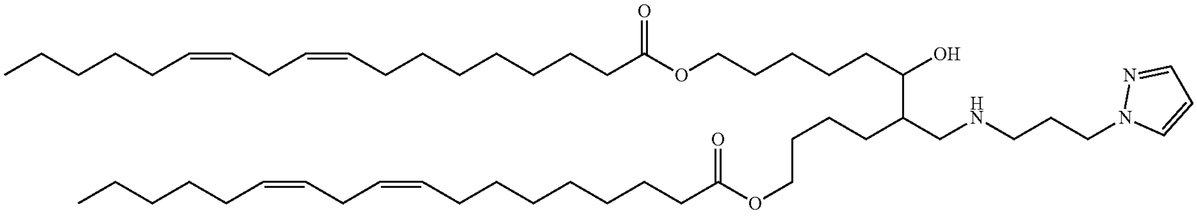

-continued
54
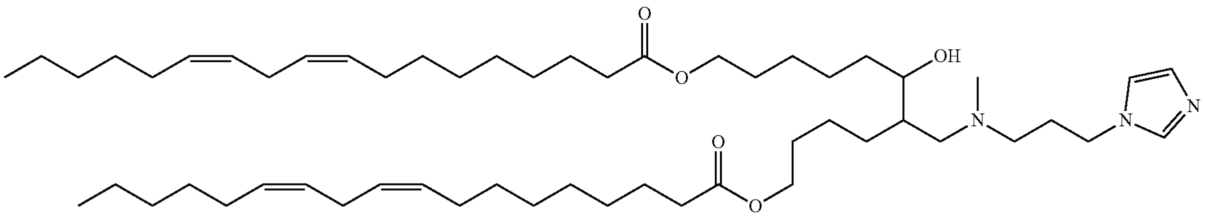
55
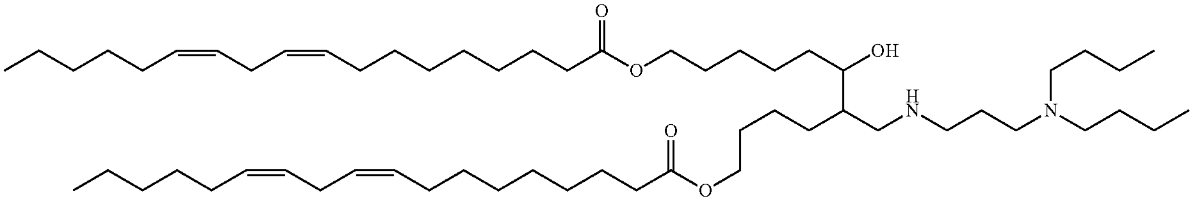
56
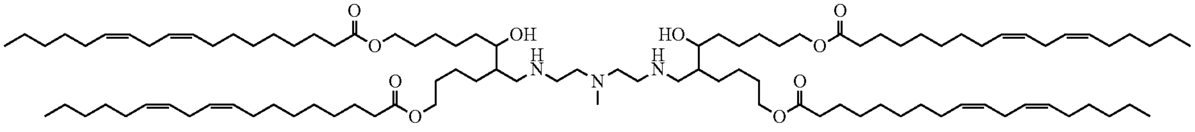
62
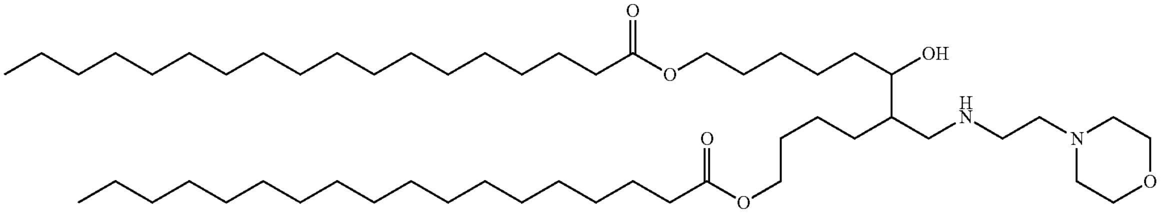
63
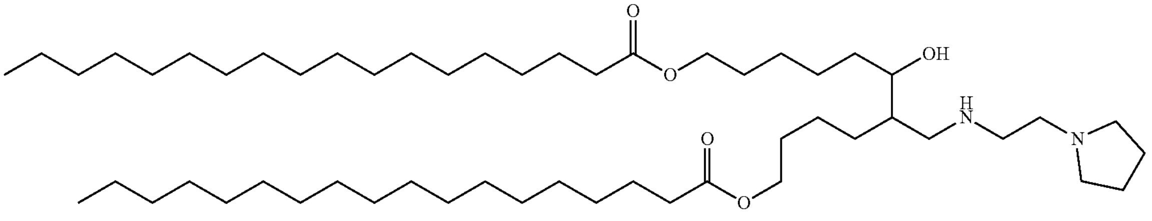
64
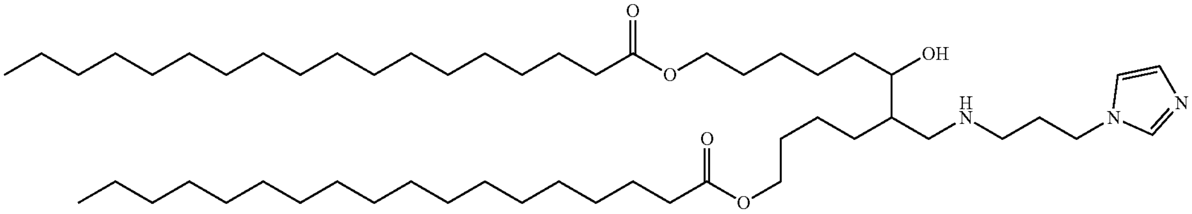
65
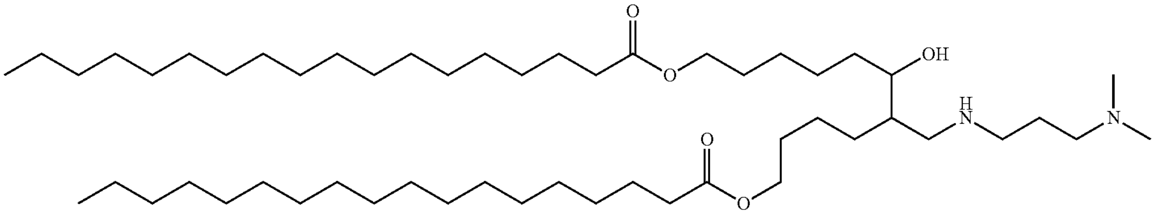

-continued
66
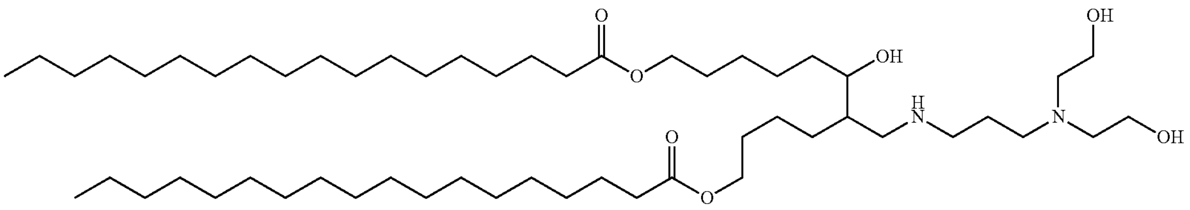
67
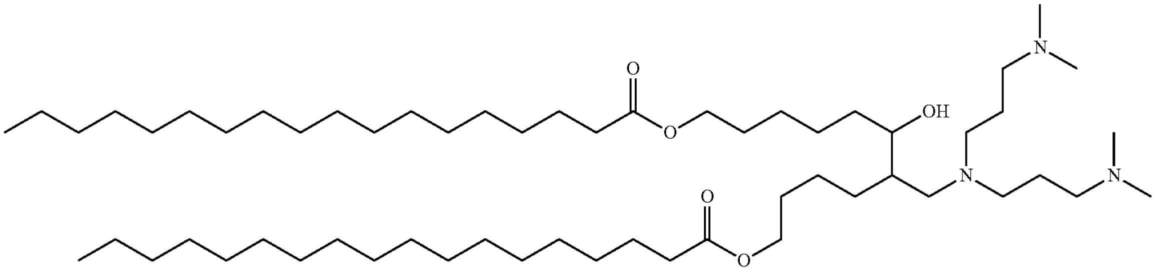
68
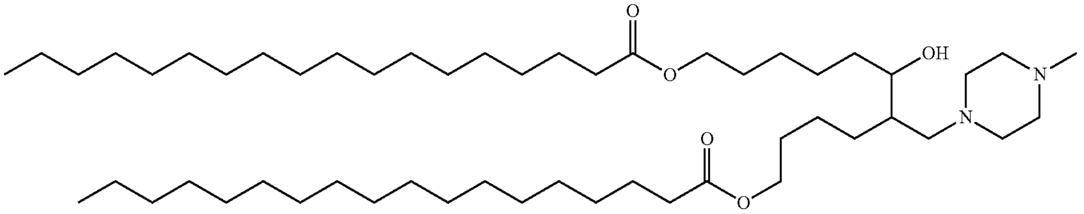
69
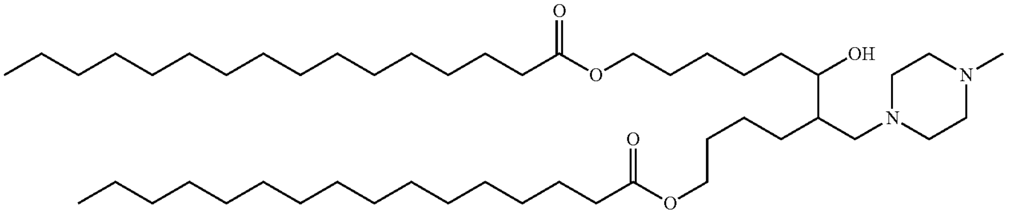
70
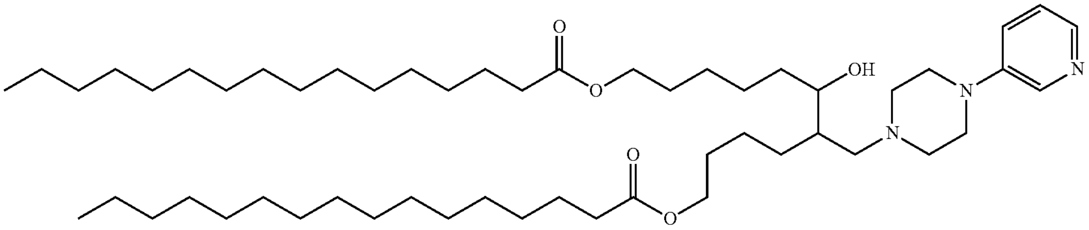
71
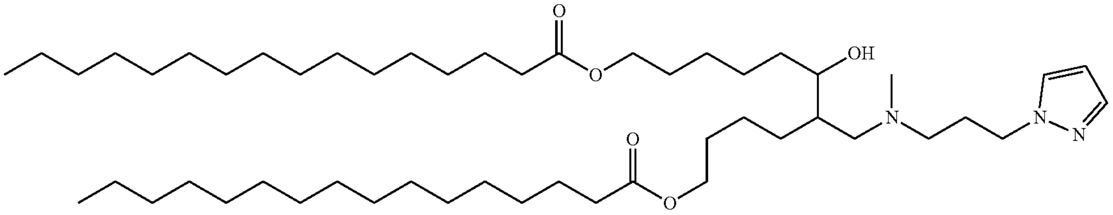
72
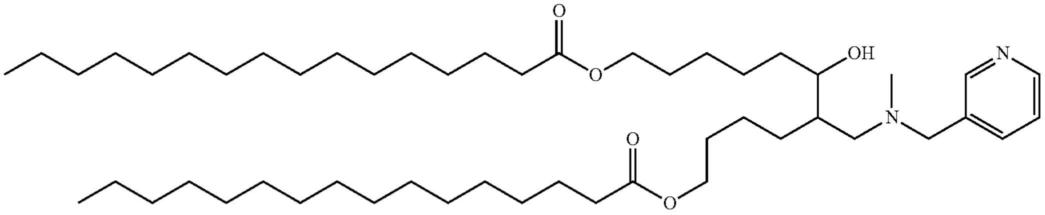

-continued
73
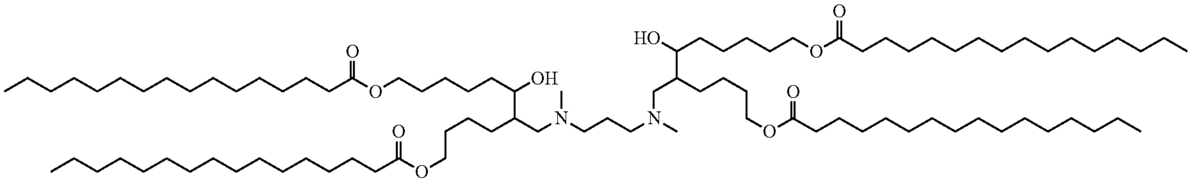
74
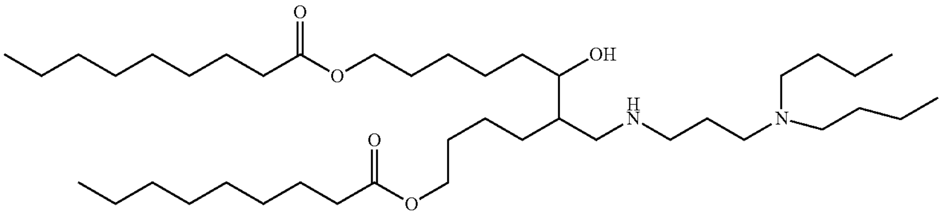
117-17-$C_9$
75
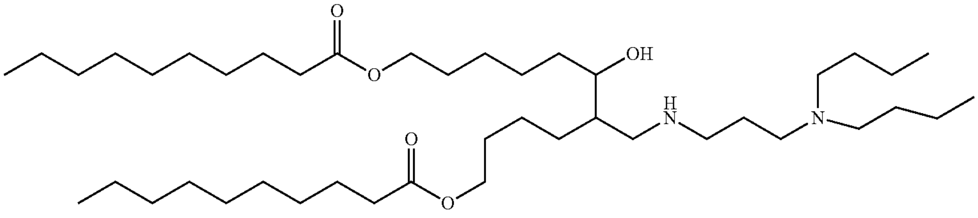
117-17-$C_{10}$
76
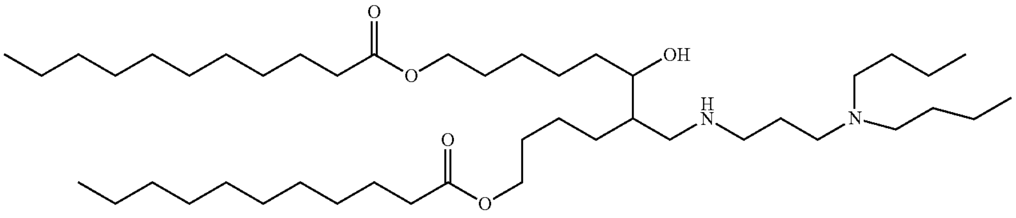
117-17-$C_{11}$
77
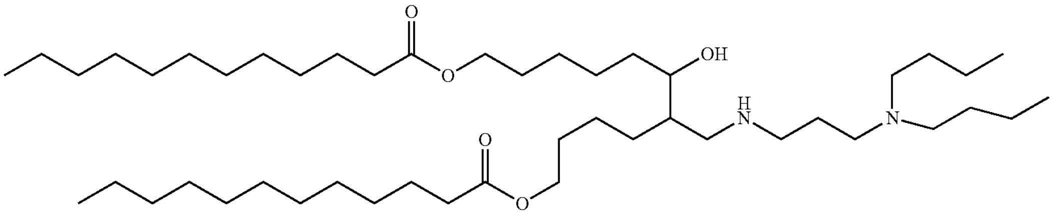
117-17-$C_{12}$
78
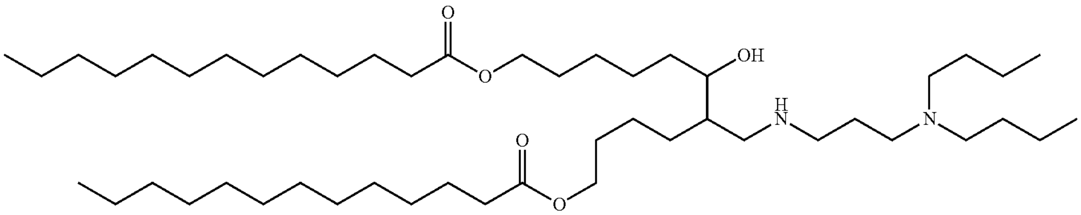
117-17-$C_{13}$ -continued
79
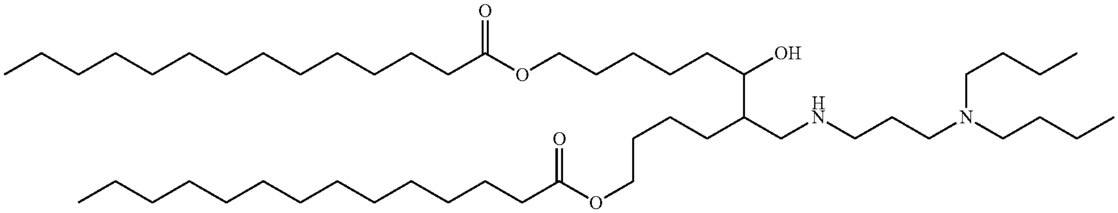
117-17-$C_{14}$
80
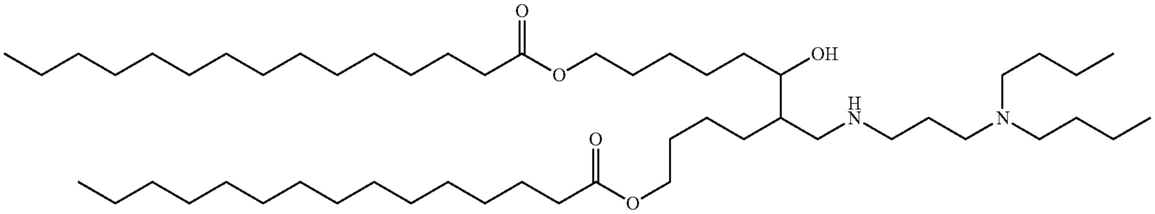
117-17-$C_{15}$
81
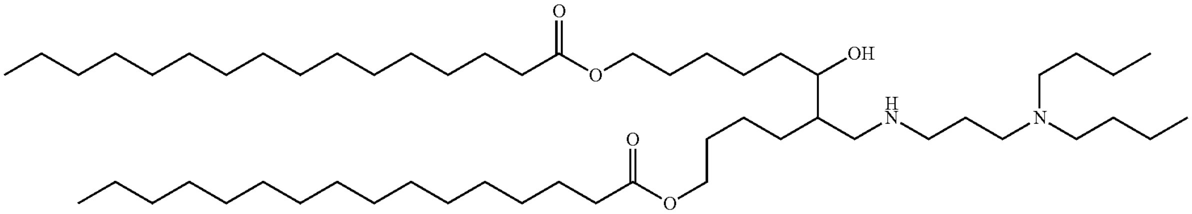
117-17-$C_{16}$
82
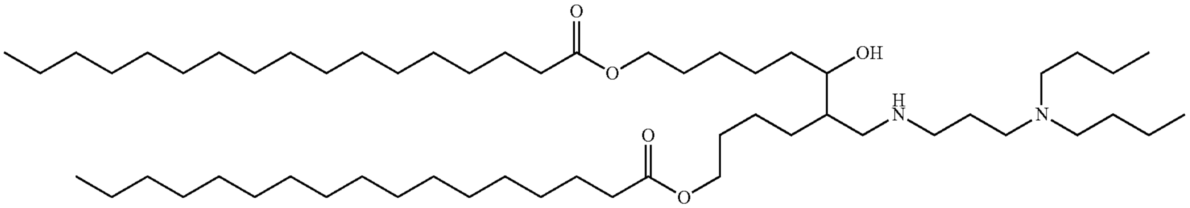
117-17-$C_{17}$
83
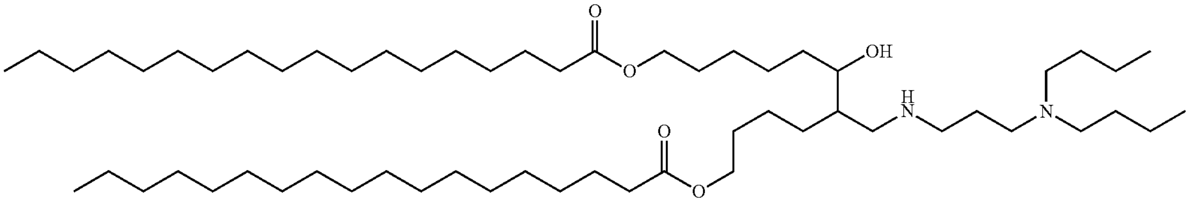
117-17-$C_{18}$
84
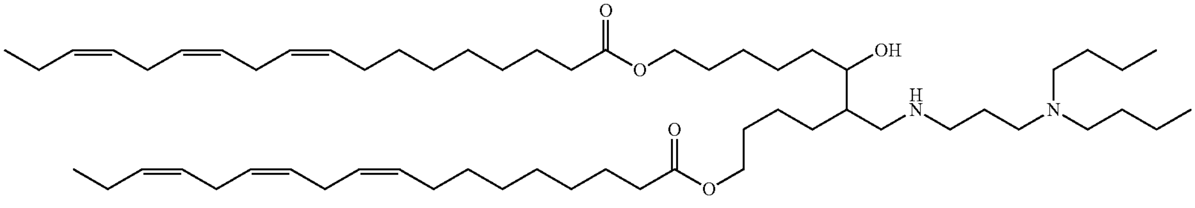
117-17-Linolenic -continued
85
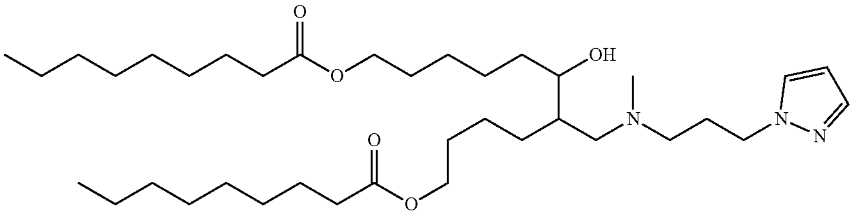
19-Pyrazole-$C_9$
86
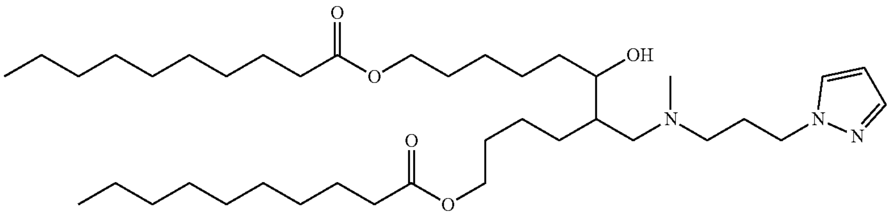
19-Pyrazole-$C_{10}$
87
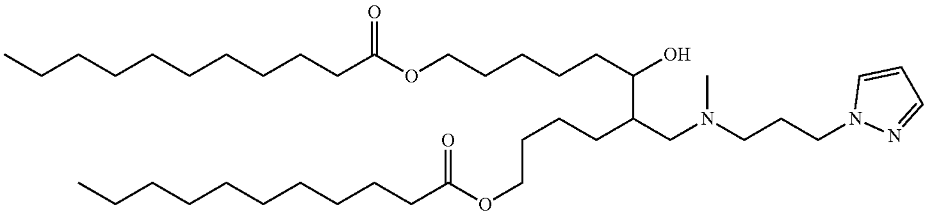
19-Pyrazole-$C_{11}$
88
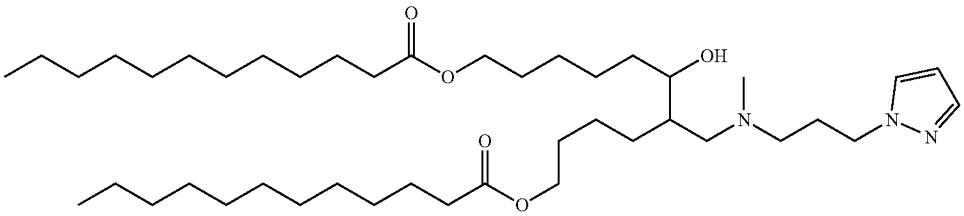
19-Pyrazole-$C_{12}$
89
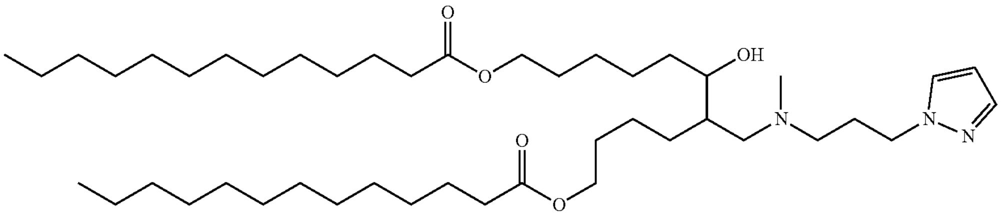
19-Pyrazole-$C_{13}$
90
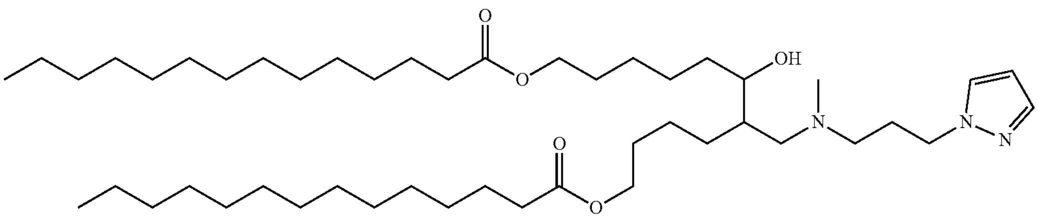
19-Pyrazole-$C_{14}$ -continued
91
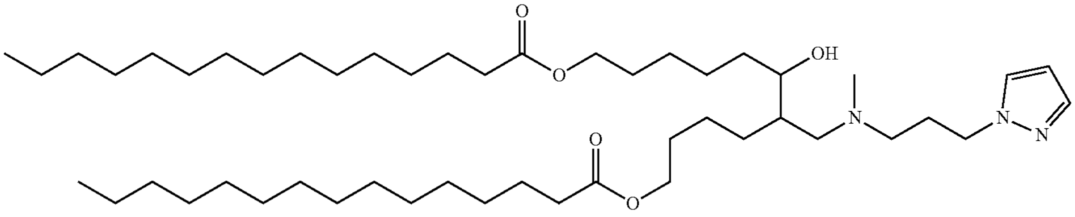
19-Pyrazole-$C_{15}$
92
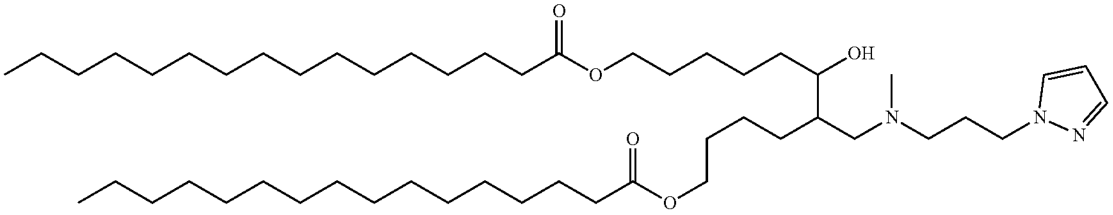
19-Pyrazole-$C_{16}$
93
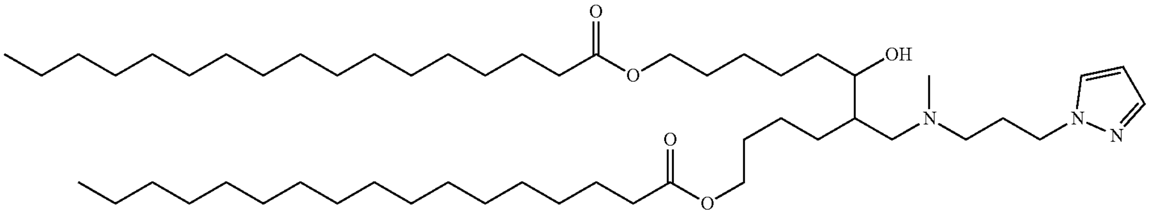
19-Pyrazole-$C_{17}$
94
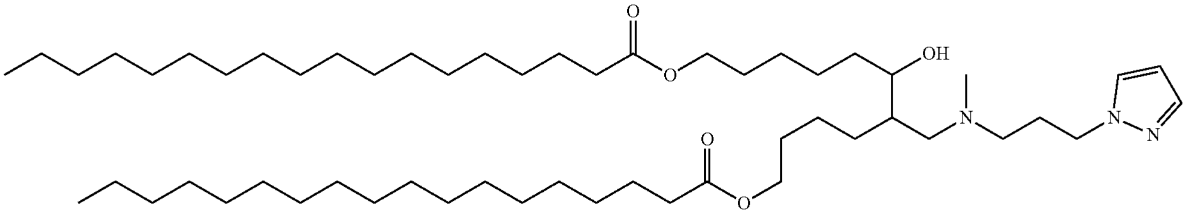
19-Pyrazole-$C_{18}$
95
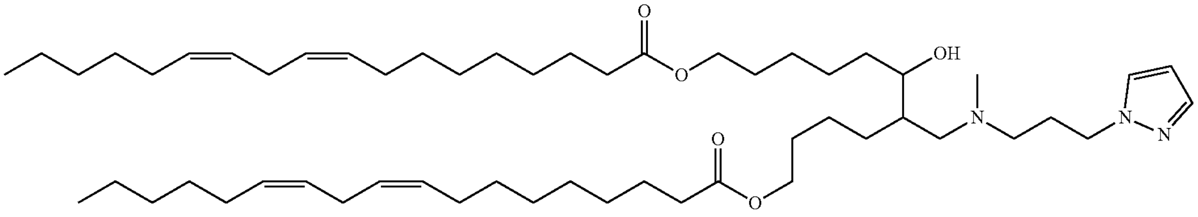
19-Pyrazole-linoleic
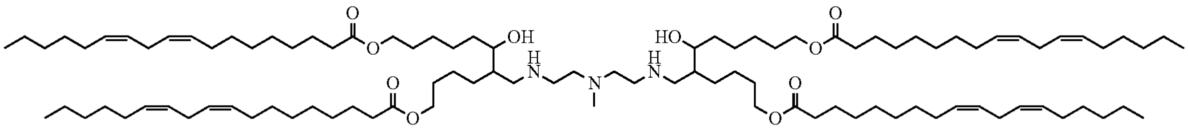
117-7

-continued
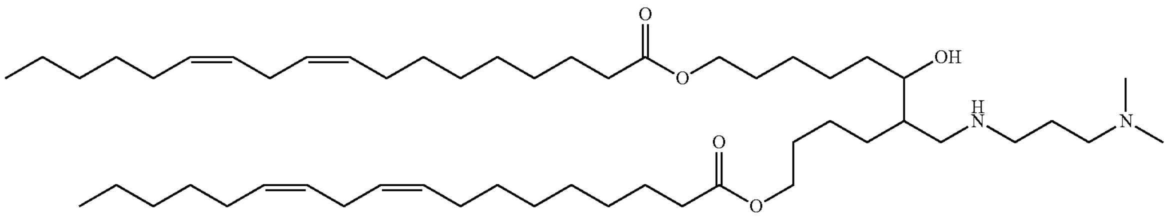
117-8
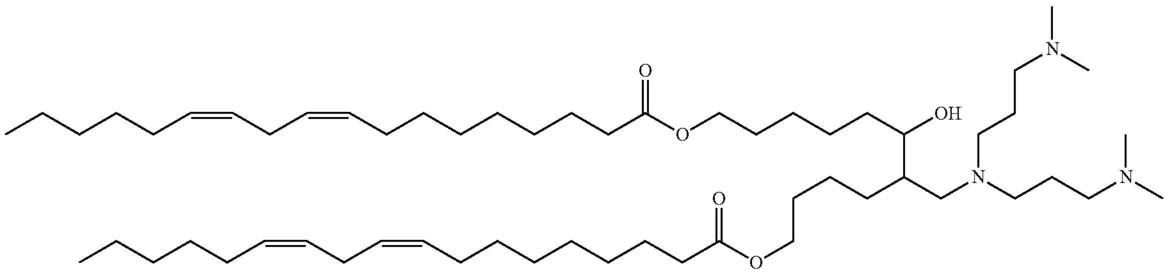
117-9
96
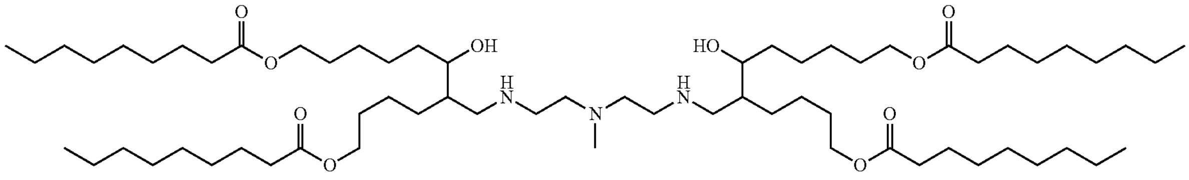
117-7-$C_9$
97
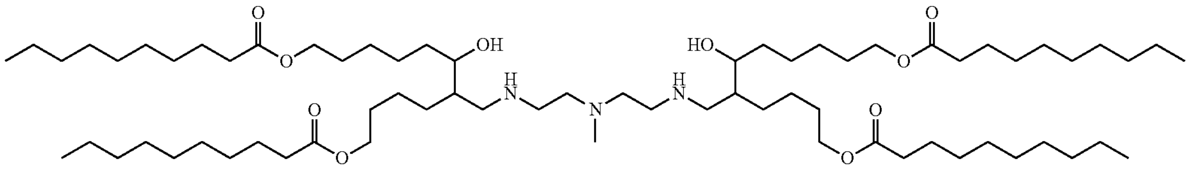
117-7-$C_{10}$
98
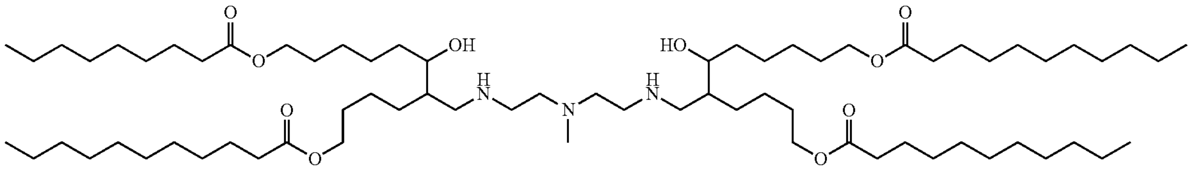
117-7-$C_{11}$
99
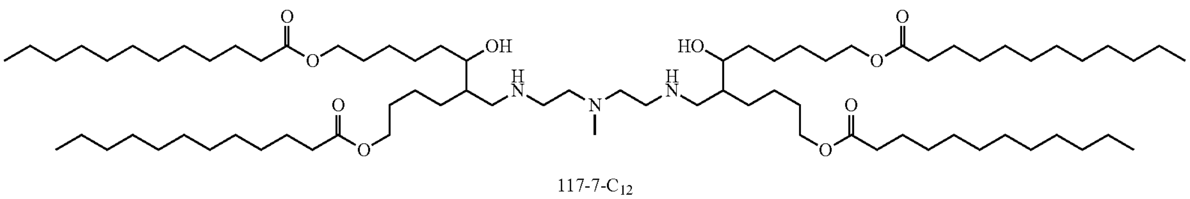
117-7-$C_{12}$ -continued
100
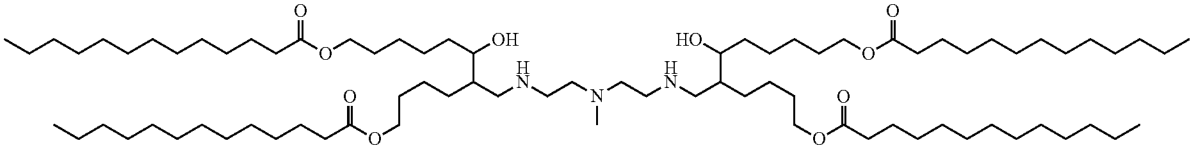
117-7-$C_{13}$
101
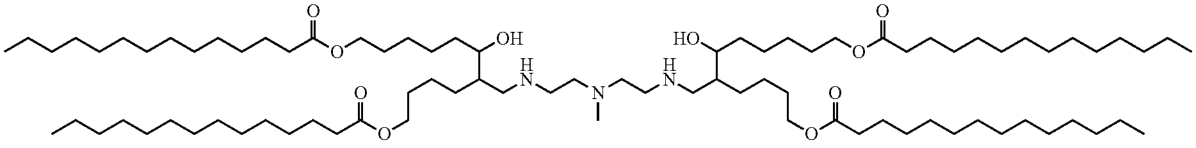
117-7-$C_{14}$
102
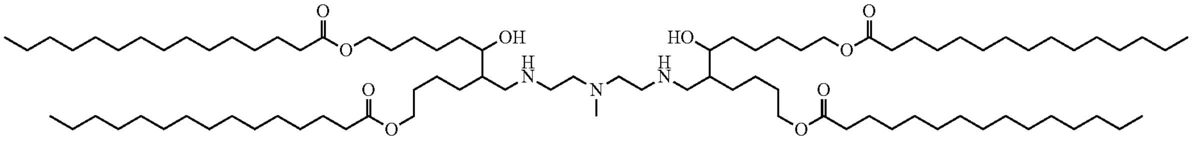
117-7-$C_{15}$
103
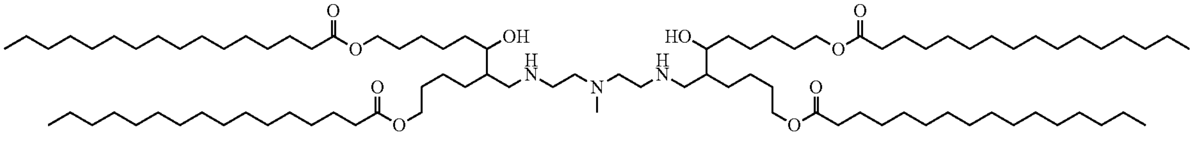
117-7-$C_{16}$
104
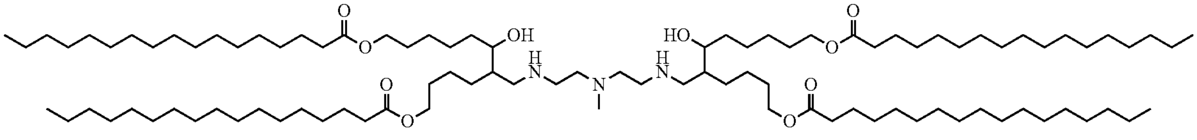
117-7-$C_{17}$
105
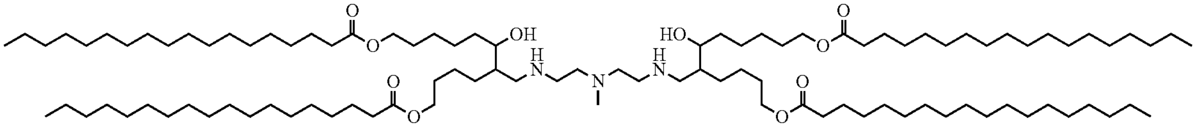
117-7-$C_{18}$
106
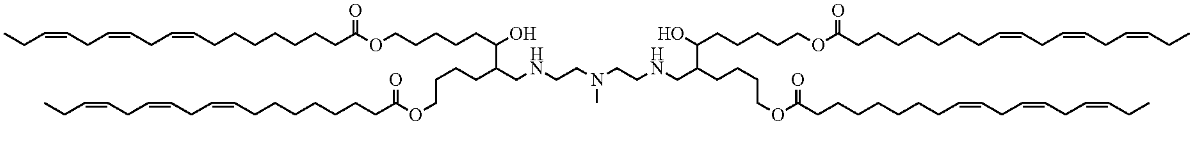
117-7-Linolenic or a pharmaceutically acceptable salt, solvate, tautomer, stereoisomer, or isotopically labeled derivative thereof.
In some embodiments, the compound is
11 (19-Pyrazole)
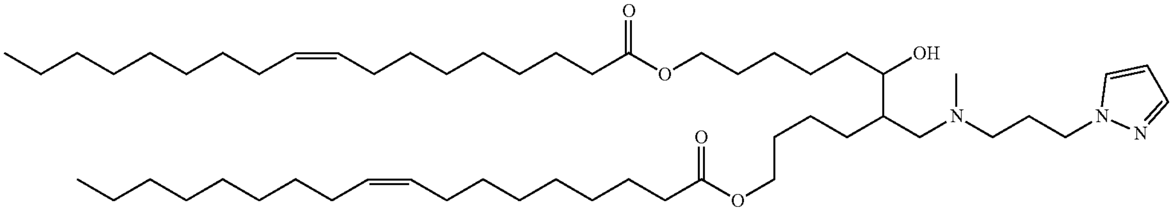
or
55 (117-17)
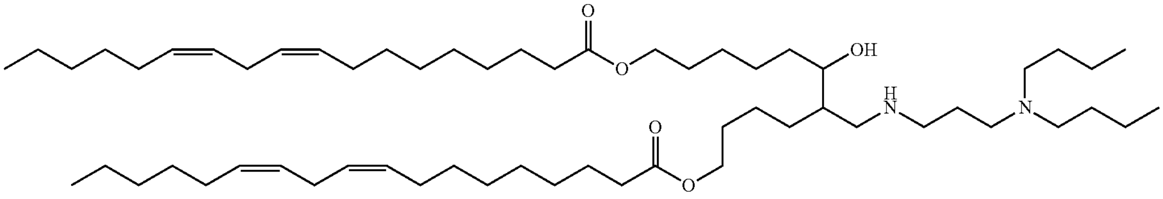
,
or a pharmaceutically acceptable salt, solvate, tautomer, stereoisomer, or isotopically labeled derivative thereof.
In some embodiments, the compound is
117-7
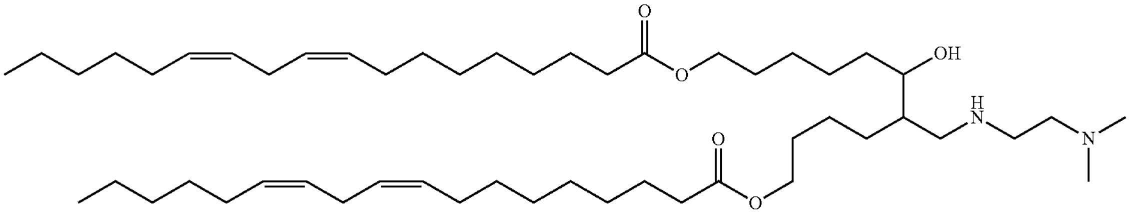
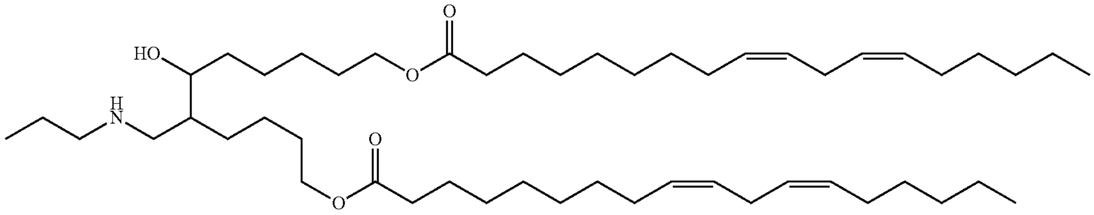
or
104
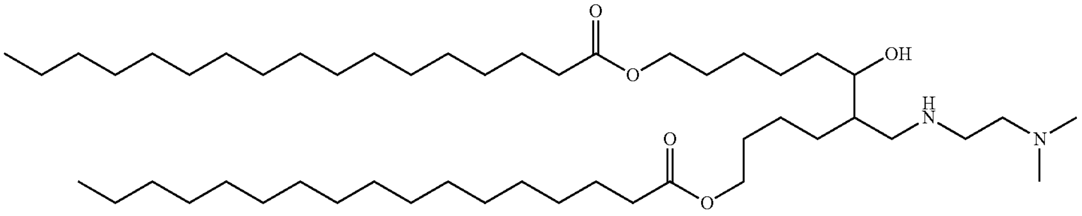
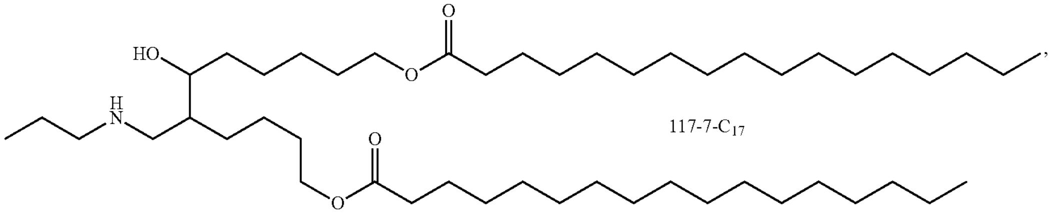
,
117-7-$C_{17}$ or a pharmaceutically acceptable salt, solvate, tautomer, stereoisomer, or isotopically labeled derivative thereof.

Compositions and Administration

The present disclosure provides compositions (e.g., pharmaceutical compositions) comprising a compound provided herein (e.g., a compound of Formula (I)), or a pharmaceutically acceptable salt, solvate, tautomer, stereoisomer, or isotopically labeled derivative thereof, and an agent.

In certain embodiments, the compound provided herein is provided in an effective amount in the pharmaceutical composition. In certain embodiments, the effective amount is an amount effective for delivering an agent to a subject or cell. In certain embodiments, the effective amount is an amount effective for delivering a polynucleotide to a subject or cell. In certain embodiments, the effective amount is an amount effective for delivering mRNA to a subject or cell.

In certain embodiments, the composition further comprises one or more of a PEG-lipid, sterol, phospholipid, helper lipid, or stabilizing excipient. In certain embodiments, the composition comprises a PEG-lipid, sterol, and phospholipid. In certain embodiments, the composition comprises a PEG-lipid, sterol, phospholipid, and helper lipid. In certain embodiments, the composition comprises a PEG-lipid, sterol, phospholipid, and stabilizing excipient. In certain embodiments, the composition comprises a PEG-lipid, sterol, phospholipid, helper lipid, and stabilizing excipient. In certain embodiments, the composition comprises a PEG-lipid. In some embodiments, the composition comprises a sterol. In certain embodiments, the composition comprises a phospholipid. In some embodiments, the composition comprises a helper lipid. In some embodiments, the composition comprises a stabilizing excipient. In certain embodiments, the composition comprises one or more of a PEG-lipid, sterol, phospholipid, helper lipid, or stabilizing excipient and is formulated as a particle. In some embodiments, the composition comprises one or more of a PEG-lipid, sterol, phospholipid, helper lipid, or stabilizing excipient and is formulated as a nanoparticle or microparticle. In certain embodiments, the composition comprises one or more of a PEG-lipid, sterol, phospholipid, helper lipid, or stabilizing excipient and is formulated as a lipid nanoparticle.

In some embodiments, the composition comprises approximately 30-70% of a compound of Formula (I) by mass. In certain embodiments, the composition comprises approximately 40-60% of a compound of Formula (I) by mass. In some embodiments, the composition comprises approximately 45-55% of a compound of Formula (I) by mass. In some embodiments, the composition comprises approximately 50% of a compound of Formula (I) by mass.

In some embodiments, the composition comprises approximately 15-35% of a helper lipid by mass. In some embodiments, the composition comprises approximately 20-30% of a helper lipid by mass. In some embodiments, the composition comprises approximately 25% of a helper lipid by mass.

In some embodiments, the composition comprises approximately 5-25% of a sterol by mass. In some embodiments, the composition comprises approximately 10-20% of a sterol by mass. In some embodiments, the composition comprises approximately 17% of a sterol by mass.

In some embodiments, the composition comprises approximately 0-20% of a PEG-lipid by mass. In some embodiments, the composition comprises approximately 5-15% of a PEG-lipid by mass. In some embodiments, the composition comprises approximately 8.5% of a PEG-lipid by mass.

In some embodiments, the composition comprises approximately 50% of a compound of Formula (I), approximately 25% of a charged lipid, approximately 17% of a sterol, and approximately 8% of a PEG-lipid by mass. In some embodiments, the composition comprises approximately 50% of a compound of Formula (I), approximately 24.6% of a charged lipid, approximately 16.8% of a sterol, and approximately 8.5% of a PEG-lipid by mass.

In some embodiments, the composition comprises a 10:1 weight ratio of a compound of Formula (I):agent. In some embodiments, the composition comprises a 10:1 weight ratio of a compound of Formula (I):polynucleotide. In some embodiments, the composition comprises a 10:1 weight ratio of a compound of Formula (I):mRNA.

In some embodiments, the composition comprises approximately 10-50 mol % of a compound of Formula (I). In certain embodiments, the composition comprises approximately 20-40 mol % of a compound of Formula (I). In some embodiments, the composition comprises approximately 35 mol % of a compound of Formula (I).

In some embodiments, the composition comprises approximately 5-35 mol % of a helper lipid. In some embodiments, the composition comprises approximately 10-20 mol % of a helper lipid. In some embodiments, the composition comprises approximately 16 mol % of a helper lipid.

In some embodiments, the composition comprises approximately 30-60 mol % of a sterol. In some embodiments, the composition comprises approximately 40-50 mol % of a sterol. In some embodiments, the composition comprises approximately 46 mol % of a sterol.

In some embodiments, the composition comprises approximately 0-10 mol % of a PEG-lipid. In some embodiments, the composition comprises approximately 0-5 mol % of a PEG-lipid. In some embodiments, the composition comprises approximately 2.5 mol % of a PEG-lipid.

In some embodiments, the composition comprises between approximately 0.1% and 5% of a stabilizing excipient (w/v). In come embodiments, the composition comprises between approximately 1% and 3% of a stabilizing excipient (w/v). In some embodiments, the composition comprises approximately 2% of a stabilizing excipient (w/v).

In certain embodiments, the composition further comprises a buffer. In certain embodiments, the composition comprises a buffer and a stabilizing excipient.

In certain embodiments, the composition is formulated for aerosolization or nebulization. In certain embodiments, the composition is an aerosol. Aerosols may comprise solid particles, semi-solid particles, liquid particles (i.e., droplets), or mixtures thereof. Compounds used in the form of solid or semi-solid particles may be encapsulated or complexed in order to achieve favorable or advantageous properties such as size, weight, solubility, and dispersibility. The size of aerosol particles can be controlled by a device used to produce such particles. Particle (e.g., droplet) size and distribution and deposition in the respiratory tract will result from the device used and the inhalation pattern of the subject. See, e.g., Laube B L, et al. *Eur. Respir. J.* 2011, 37, 1308-1311. In certain embodiments, the aerosol is produced by nebulization. In certain embodiments, the aerosol is produced by a nebulizer.

In certain embodiments, the composition is a pharmaceutical composition. In some embodiments, the composition further comprises a pharmaceutically acceptable excipient.

Pharmaceutical compositions described herein can be prepared by any method known in the art of pharmaceutics. In general, such preparatory methods include bringing a compound, agent, or particle described herein (i.e., the "active ingredient") into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as one-half or one-third of such a dosage.

Relative amounts of the active ingredient, the pharmaceutically acceptable excipient, and/or any additional ingredients in a pharmaceutical composition described herein will vary, depending upon the identity, size, and/or condition of the subject treated and further depending upon the route by which the composition is to be administered. The composition may comprise between 0.1% and 100% (w/w) active ingredient.

Pharmaceutically acceptable excipients used in the manufacture of provided pharmaceutical compositions include inert diluents such as calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates described herein are mixed with solubilizing agents such as Cremophor®, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form may be accomplished by dissolving or suspending the drug in an oil vehicle.

Compositions for rectal or vaginal administration are typically suppositories which can be prepared by mixing the conjugates described herein with suitable non-irritating excipients or carriers such as cocoa butter, polyethylene glycol, or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid. (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (II) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polyethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of encapsulating agents which can be used include polymeric substances and waxes.

Dosage forms for topical and/or transdermal administration of a compound, agent, or particle described herein may include ointments, pastes, creams, lotions, gels, powders, solutions, sprays, inhalants, and/or patches. Generally, the active ingredient is admixed under sterile conditions with a pharmaceutically acceptable carrier or excipient and/or any needed preservatives and/or buffers as can be required. Additionally, the present disclosure contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices. Intradermal compositions can be administered by devices which limit the effective penetration length of a needle into the skin. Alternatively or additionally, conventional syringes can be used in the classical mantoux method of intradermal administration. Jet injection devices which deliver liquid formulations to the dermis via a liquid jet injector and/or via a needle which pierces the stratum corneum and produces a jet which reaches the dermis are suitable. Ballistic powder/particle delivery devices which use compressed gas to accelerate the compound, agent, or particle in powder form through the outer layers of the skin to the dermis are suitable.

Formulations suitable for topical administration include, but are not limited to, liquid and/or semi-liquid preparations such as liniments, lotions, oil-in-water and/or water-in-oil emulsions such as creams, ointments, and/or pastes, and/or solutions and/or suspensions. Topically administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition described herein can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers, or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions described herein formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition described herein. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) to as much as 100% (w/w) of the active ingredient, and may comprise one or more of the additional ingredients described herein. A pharmaceutical composition described herein can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition described herein can be prepared, packaged, and/or sold in a formulation for ophthalmic administration. Such formulations may, for example, be in the form of eye drops including, for example, a 0.1-1.0% (w/w) solution and/or suspension of the active ingredient in an aqueous or oily liquid carrier or excipient. Such drops may further comprise buffering agents, salts, and/or one or more other of the additional ingredients described herein. Other ophthalmically-administrable formulations which are useful include those which comprise the active ingredient in microcrystalline form and/or in a liposomal preparation. Ear drops and/or eye drops are also contemplated as being within the scope of this disclosure.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds, agents, or particles provided herein are typically formulated in dosage unit form for ease of administration and uniformity of dosage. It will be understood, however, that the total daily usage of the compositions described herein will be decided by a physician within the scope of sound medical judgment. The specific therapeutically effective dose level for any particular subject or organism will depend upon a variety of factors including the disease being treated and the severity of the disorder, the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, buccal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration).

The exact amount of a compound, agent, or particle required to achieve an effective amount will vary from subject to subject, depending, for example, on species, age, and general condition of a subject, severity of the side effects or disorder, identity of the particular compound, agent or particle, mode of administration, and the like. An effective amount may be included in a single dose (e.g., single oral dose) or multiple doses (e.g., multiple oral doses). In certain embodiments, when multiple doses are administered to a subject or applied to a tissue or cell, any two doses of the multiple doses include different or substantially the same amounts of a compound, agent, or particle described herein. In certain embodiments, when multiple doses are administered to a subject or applied to a tissue or cell, the frequency of administering the multiple doses to the subject or applying the multiple doses to the tissue or cell is three doses a day, two doses a day, one dose a day, one dose every other day, one dose every third day, one dose every week, one dose every two weeks, one dose every three weeks, or one dose every four weeks. In certain embodiments, the frequency of administering the multiple doses to the subject or applying the multiple doses to the tissue or cell is one dose per day. In certain embodiments, the frequency of administering the multiple doses to the subject or applying the multiple doses to the tissue or cell is two doses per day. In certain embodiments, the frequency of administering the multiple doses to the subject or applying the multiple doses to the tissue or cell is three doses per day. In certain embodiments, when multiple doses are administered to a subject or applied to a tissue or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, tissue, or cell. In certain embodiments, the duration between the first dose and last dose of the multiple doses is three months, six months, or one year. In certain embodiments, the duration between the first dose and last dose of the multiple doses is the lifetime of the subject, tissue, or cell. In certain embodiments, a dose (e.g., a single dose, or any dose of multiple doses) described herein includes independently between 0.1 μg and 1 μg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of a compound, agent, or particle described herein. In certain embodiments, a dose described herein includes independently between 1 mg and 3 mg, inclusive, of a compound, agent, or particle described herein. In certain embodiments, a dose described herein includes independently between 3 mg and 10 mg, inclusive, of a compound, agent, or particle described herein. In certain embodiments, a dose described herein includes independently between 10 mg and 30 mg, inclusive, of a compound, agent, or particle described herein. In certain embodiments, a dose described herein includes independently between 30 mg and 100 mg, inclusive, of a compound, agent, or particle described herein.

Dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

A compound or composition, as described herein, can be administered in combination with one or more additional pharmaceutical agents (e.g., therapeutically and/or prophylactically active agents). The compounds or compositions can be administered in combination with additional pharmaceutical agents that treat a disease in a subject in need thereof, prevent a disease in a subject in need thereof, or reduce the risk to develop a disease in a subject in need thereof, improve bioavailability, improve safety, reduce drug resistance, reduce and/or modify metabolism, inhibit excretion, and/or modify distribution in a subject or cell. It will also be appreciated that the therapy employed may achieve a desired effect for the same disorder, and/or it may achieve different effects. In certain embodiments, a pharmaceutical composition described herein including a compound described herein and an additional pharmaceutical agent shows a synergistic effect that is absent in a pharmaceutical composition including one of the compound and the additional pharmaceutical agent, but not both. In some embodiments, the additional pharmaceutical agent achieves a desired effect for the same disorder. In some embodiments, the additional pharmaceutical agent achieves different effects.

The compound or composition can be administered concurrently with, prior to, or subsequent to one or more additional pharmaceutical agents, which may be useful as, e.g., combination therapies. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, polynucleotides, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful for treating and/or preventing a disease (e.g., lung disease or liver disease). Each additional pharmaceutical agent may be administered at a dose and/or on a time schedule determined for that pharmaceutical agent. The additional pharmaceutical agents may also be administered together with each other and/or with the compound or composition described herein in a single dose or composition or administered separately in different doses or compositions. The particular combination to employ in a regimen will take into account compatibility of the compound described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

Additional pharmaceutical agents include, but are not limited to, anti-proliferative agents, anti-cancer agents, anti-angiogenesis agents, steroidal or non-steroidal anti-inflammatory agents, immunosuppressants, anti-bacterial agents, anti-viral agents, cardiovascular agents, cholesterol-lowering agents, anti-diabetic agents, anti-allergic agents, contraceptive agents, pain-relieving agents, anesthetics, anti-coagulants, inhibitors of an enzyme, steroidal agents, steroidal or antihistamine, antigens, vaccines, antibodies, decongestant, sedatives, opioids, analgesics, anti-pyretics, hormones, and prostaglandins.

PEG-Lipid

In some embodiments, the PEG-lipid is a PEG-phospholipid or PEG-glyceride lipid. In certain embodiments, the PEG-lipid is a PEG-phospholipid. In certain embodiments, the PEG-phospholipid is a PEG-phosphoethanolamine. In some embodiments, the PEG-phospholipid is a PEG-phosphatidylcholine. In certain embodiments, the PEG-lipid is 1,2-dimyristoyl-sn-glycero-3-phosphoethanolamine-N-[methoxy(polyethylene glycol)-2000] ($C_{14}$PEG2000).

In certain embodiments, the PEG component has a molecular weight of about 350, about 550, about 750, about 1000, about 2000, about 3000, or about 5000. In some embodiments, the PEG component has a molecular weight of about 750, about 1000, about 2000, about 3000, or about 5000. In certain embodiments, the PEG component has a molecular weight of about 1000, about 2000, or about 3000. In some embodiments, the PEG component has a molecular weight of about 2000.

In certain embodiments, the PEG-lipid is stearoyl-substituted ($C_{18}$). In some embodiments, the PEG-phospholipid is palmitoyl-substituted ($C_{16}$). In certain embodiments, the PEG-phospholipid is myristoyl-substituted ($C_{14}$).

In certain embodiments, the PEG-lipid is selected from the group consisting of 1,2-distearoyl-sn-glycero-3-phosphoethanolamine-N-[methoxy(polyethylene glycol)-50(00] ($C_{18}$PEG5000), 1,2-dipalmitoyl-sn-glycero-3-phosphoethanolamine-N-[methoxy(polyethylene glycol)-5000] ($C_{16}$PEG5000), 1,2-dimyristoyl-sn-glycero-3-phosphoethanolamine-N-[methoxy(polyethylene glycol)-5000] ($C_{14}$PEG5000), 1,2-distearoyl-sn-glycero-3-phosphoethanolamine-N-[methoxy(polyethylene glycol)-3000] ($C_{18}$PEG3000), 1,2-dipalmitoyl-sn-glycero-3-phosphoethanolamine-N-[methoxy(polyethylene glycol)-3000] ($C_{16}$PEG3000), 1,2-dimyristoyl-sn-glycero-3-phosphoethanolamine-N-[methoxy(polyethylene glycol)-3000] ($C_{14}$PEG3000), 1,2-distearoyl-sn-glycero-3-phosphoethanolamine-N-[methoxy(polyethylene glycol)-2000] ($C_{18}$PEG2000), 1,2-dipalmitoyl-sn-glycero-3-phosphoethanolamine-N-[methoxy(polyethylene glycol)-2000] ($C_{16}$PEG2000), 1,2-dimyristoyl-sn-glycero-3-phosphoethanolamine-N-[methoxy(polyethylene glycol)-2000] ($C_{14}$PEG2000), 1,2-distearoyl-sn-glycero-3-phosphoethanolamine-N-[methoxy(polyethylene glycol)-1000] ($C_{18}$PEG1000), 1,2-dipalmitoyl-sn-glycero-3-phosphoethanolamine-N-[methoxy(polyethylene glycol)-1000] ($C_{16}$PEG1000), 1,2-dimyristoyl-sn-glycero-3-phosphoethanolamine-N-[methoxy(polyethylene glycol)-1000] ($C_{14}$PEG1000), 1,2-distearoyl-sn-glycero-3-phosphoethanolamine-N-[methoxy(polyethylene glycol)-750] ($C_{18}$PEG750), 1,2-dipalmitoyl-sn-glycero-3-phosphoethanolamine-N-[methoxy(polyethylene glycol)-750] ($C_{16}$PEG750), and 1,2-dimyristoyl-sn-glycero-3-phosphoethanolamine-N-[methoxy(polyethylene glycol)-750] ($C_{14}$PEG750). In some embodiments, the PEG-lipid is selected from the group consisting of 1,2-distearoyl-sn-glycero-3-phosphoethanolamine-N-[methoxy(polyethylene glycol)-2000]($C_{18}$PEG2000), 1,2-dipalmitoyl-sn-glycero-3-phosphoethanolamine-N-[methoxy(polyethylene glycol)-2000] ($C_{16}$PEG2000), and 1,2-dimyristoyl-sn-glycero-3-phosphoethanolamine-N-[methoxy(polyethylene glycol)-2000] ($C_{14}$PEG2000). In certain embodiments, the PEG-lipid is selected from the group consisting of 1,2-dimyristoyl-sn-glycero-3-phosphoethanolamine-N-[methoxy(polyethylene glycol)-5000] ($C_{14}$PEG5000), 1,2-dimyristoyl-sn-glycero-3-phosphoethanolamine-N-[methoxy(polyethylene glycol)-3000] ($C_{14}$PEG3000), 1,2-dimyristoyl-sn-glycero-3-phosphoethanolamine-N-[methoxy(polyethylene glycol)-2000] ($C_{14}$PEG2000), 1,2-dimyristoyl-sn-glycero-3-phosphoethanolamine-N-[methoxy(polyethylene glycol)-1000]($C_{14}$PEG1000), and 1,2-dimyristoyl-sn-glycero-3-phosphoethanolamine-N-[methoxy(polyethylene glycol)-750] ($C_{14}$PEG750). In certain embodiments, the PEG-phospholipid is 1,2-dimyristoyl-sn-glycero-3-phosphoethanolamine-N-[methoxy (polyethylene glycol)-2000] ($C_{14}$PEG2000).

In some embodiments, the PEG-lipid is a PEG-glyceride lipid. In certain embodiments, the PEG-lipid is 1,2-distearoyl-rac-glycero-3-methoxypolyethylene glycol or 1,2-dimyristoyl-rac-glycero-3-methoxypolyethylene glycol. In certain embodiments, the PEG-lipid is 1,2-distearoyl-rac-glycero-3-methoxypolyethylene glycol-2000 (DSG-PEG2000) or 1,2-dimyristoyl-rac-glycero-3-methoxypolyethylene glycol-2000 (DMG-PEG2000). In some embodiments, the PEG-lipid is 1,2-distearoyl-rac-glycero-3-methoxypolyethylene glycol-2000 (DSG-PEG2000). In certain embodiments, the PEG-lipid is 1,2-dimyristoyl-rac-glycero-3-methoxypolyethylene glycol-2000 (DMG-PEG2000).

Sterol

In certain embodiments, the sterol is cholesterol, sitosterol, campesterol, stigmasterol, brassicasterol (including dihydrobrassicasterol), desmosterol, chalinosterol, poriferasterol, clionasterol, ergosterol, coprosterol, codisterol, isofucosterol, fucosterol, clerosterol, nervisterol, lathosterol, stellasterol, spinasterol, chondrillasterol, peposterol, avenasterol, isoavenasterol, fecosterol, pollinastasterol, or a derivative thereof. In some embodiments, the sterol is cholesterol, or a derivative thereof. In certain embodiments, the sterol is cholesterol.

Helper Lipid

In some embodiments, the helper lipid is a fixed cationic lipid or salt thereof. In some embodiments, the fixed cationic lipid is 1,2-dioleoyl-3-trimethylammonium propane (DOTAP), 1,2-di-O-octadecenyl-3-trimethylammonium propane (DOTMA), 1,2-stearoyl-3-trimethylammonium-propane (18:0 TAP), 1,2-dipalmitoyl-3-trimethylammonium-propane (16:0 TAP), 1,2-dimyristoyl-3-trimethylammonium-propane (14:0 TAP), dimethyldioctadecylammonium (18:0 DDAB), 1,2-dimyristoleoyl-sn-glycero-3-ethylphosphocholine (14:1 EPC), 1-palmitoyl-2-oleoyl-sn-glycero-3-ethylphosphocholine (16:0-18:1 EPC), 1,2-dioleoyl-sn-glycero-3-ethylphosphocholine (18:1 EPC), 1,2-distearoyl-sn-glycero-3-ethylphosphocholine (18:0 EPC), 1,2-dipalmitoyl-sn-glycero-3-ethylphosphocholine (16:0 EPC), 1,2-dimyristoyl-sn-glycero-3-ethylphosphocholine (14:0 EPC), 1,2-dilauroyl-sn-glycero-3-ethylphosphocholine (12:0 EPC). O,O'-ditetradecanoyl-N-(α-trimethylammonio-acetyl)diethanolamine (DC-6-14), or N-(2-hydroxyethyl)-N,N-dimethyl-2,3-bis(oleoyloxy)propan-1-aminium. In some embodiments, the fixed cationic lipid is 1,2-dioleoyl-3-trimethylammonium propane (DOTAP).

In some embodiments, the helper lipid is a salt of a fixed cationic ligand. In certain embodiments, the salt of a fixed cationic lipid is a chloride salt, bromide salt, methyl sulfate salt, or triflate salt. In some embodiments, the salt of a fixed cationic ligand is a chloride salt.

In some embodiments, the helper lipid is an ionizable lipid. In certain embodiments, the ionizable lipid is 1,2-distearoyl-3-dimethylammonium-propane (18:0 DAP), 1,2-dipalmitoyl-3-dimethylammonium-propane (16:0 DAP), 1,2-dimyristoyl-3-dimethylammonium-propane (14:0 DAP), 1,2-dioleoyl-3-dimethylammonium-propane (DODAP or 18:1 DAP), or 1,2-dioleyloxy-3-dimethylaminopropane (DODMA).

In some embodiments, the helper lipid is a phospholipid. In certain embodiments, the helper lipid is not a phospholipid.

Phospholipid

In certain embodiments, the phospholipid is a phosphoethanolamine or phosphatidylcholine. In some embodiments, the phospholipid is 1,2-distearoyl-sn-glycero-3-phosphorylethanolamine (DSPE), 1,2-distearoyl-sn-glycero-3-phosphocholine (DSPC), or 1,2-dioleoyl-sn-glycero-3-phosphoethanolamine (DOPE). In some embodiments, the phospholipid is a phosphoethanolamine. In certain embodiments, the phospholipid is 1,2-distearoyl-sn-glycero-3-phosphorylethanolamine (DSPE) or phospholipid is 1,2-dioleoyl-sn-glycero-3-phosphoethanolamine (DOPE). In certain embodiments, the phospholipid is 1,2-distearoyl-sn-glycero-3-phosphorylethanolamine (DSPE). In certain embodiments, the phospholipid is 1,2-dioleoyl-sn-glycero-3-phosphoethanolamine (DOPE). In some embodiments, the phospholipid is a phosphatidylcholine. In some embodiments, the phospholipid is 1,2-distearoyl-sn-glycero-3-phosphocholine (DSPC).

Stabilizing Excipient

In certain embodiments, the stabilizing excipient is a disaccharide lyoprotectant (e.g., trehalose, sucrose). In some embodiments, the stabilizing excipient is trehalose. In some embodiments, the stabilizing excipient is sucrose.

In certain embodiments, the stabilizing excipient is an inert hydrophilic polymeric excipient (e.g., a polysaccharide (e.g., Dextran. Ficoll), linear PEG (e.g., PEG6K, PEG20k), branched PEG (e.g., bPEG20K)). In certain embodiments, the stabilizing excipient is a polysaccharide (e.g., Dextran, Ficoll). In certain embodiments, the stabilizing excipient is Dextran. In certain embodiments, the stabilizing excipient is Ficoll. In certain embodiments, the stabilizing excipient is linear PEG (e.g., PEG6K, PEG20k). In certain embodiments, the stabilizing excipient is PEG6K. In certain embodiments, the stabilizing excipient is PEG20k. In certain embodiments, the stabilizing excipient is branched PEG (e.g., bPEG20K). In certain embodiments, the stabilizing excipient is bPEG20K. In some embodiments, the stabilizing excipient is between approximately 0.1% and 5% bPEG20K (w/v). In come embodiments, the stabilizing excipient is between approximately 1% and 3% bPEG20K (w/v). In some embodiments, the stabilizing excipient is approximately 2% bPEG20K (w/v).

Buffer

In certain embodiments, the composition further comprises a buffer. In certain embodiments, the buffer comprises citrate buffer. In certain embodiments, the buffer comprises 10 mM citrate buffer. In certain embodiments, the buffer comprises 0.9% saline. In certain embodiments, the buffer comprises 0.9% saline at pH 7.0. In certain embodiments, the buffer comprises sodium acetate (NaAc). In certain embodiments, the buffer comprises 100 mM sodium acetate (NaAc). In certain embodiments, the buffer comprises 100 mM sodium acetate (NaAc) at pH 5.2.

In certain embodiments, the buffer reduces LNP aggregation during nebulization. In certain embodiments, the buffer attenuates the increase in LNP size following nebulization. In certain embodiments, the buffer comprises sodium acetate (NaAc) and reduces LNP aggregation during nebulization. In certain embodiments, the buffer comprises sodium acetate (NaAc) and attenuates the increase in LNP size following nebulization.

In some embodiments, the composition comprises a stabilizing excipient and further comprises a buffer. In some embodiments, the stabilizing excipient is branched PEG (e.g., bPEG20K) and the buffer comprises sodium acetate. In some embodiments, the stabilizing excipient is bPEG20K and the buffer comprises sodium acetate.

Agents

In certain embodiments, the composition further comprises an agent. In some embodiments, the agent is an organic molecule, inorganic molecule, protein, peptide, polynucleotide, targeting agent, an isotopically labeled chemical compound, vaccine, an immunological agent, or an agent useful in bioprocessing.

In some embodiments, the agent and the compound, or the pharmaceutically acceptable salt, solvate, tautomer, stereoisomer, or isotopically labeled derivative thereof, are not covalently attached.

Agents that are delivered by the systems (e.g., compositions) described herein may be therapeutic, prophylactic, diagnostic, cosmetic, or nutraceutical agents. Any chemical compound to be administered to a subject may be delivered using the complexes, picoparticles, nanoparticles (e.g., lipid nanoparticles), microparticles, micelles, or liposomes, described herein. In some embodiments, the agent is an organic molecule, inorganic molecule, protein, peptide, polynucleotide, targeting agent, an isotopically labeled chemical compound, vaccine, an immunological agent, or an agent useful in bioprocessing (e.g., intracellular manufacturing of proteins, such as a cell's bioprocessing of a commercially useful chemical or fuel). For example, intracellular delivery of an agent may be useful in bioprocessing by maintaining the cell's health and/or growth, e.g., in the manufacturing of proteins. Any chemical compound to be administered to a subject or contacted with a cell may be delivered to the subject or cell using the compositions. In certain embodiments, the vaccine is a nasal vaccine.

Exemplary agents that may be included in a composition described herein include, but are not limited to, small molecules, organometallic compounds, polynucleotides, proteins, peptides, carbohydrates, monosaccharides, oligosaccharides, polysaccharides, nucleoproteins, mucoproteins, lipoproteins, small molecules linked to proteins, glycoproteins, steroids, nucleotides, oligonucleotides, polynucleotides, nucleosides, antisense oligonucleotides, lipids, hormones, vitamins, cells, metals, targeting agents, isotopically labeled chemical compounds, drugs (e.g., compounds approved for human or veterinary use by the U.S. Food and Drug Administration as provided in the Code of Federal Regulations), vaccines, immunological agents, agents useful in bioprocessing, and mixtures thereof. The targeting agents are described in more detail herein. In certain embodiments, the agents are nutraceutical agents. In certain embodiments, the agents are pharmaceutical agents (e.g., a therapeutic or prophylactic agent). In certain embodiments, the agent is an antibiotic agent (e.g., an anti-bacterial, anti-viral, or anti-fungal agent), anesthetic, steroidal agent, anti-proliferative agent, anti-inflammatory agent, anti-angiogenesis agent, anti-neoplastic agent, anti-cancer agent, anti-diabetic agent, antigen, vaccine, antibody, decongestant, antihypertensive, sedative, birth control agent, progestational agent, anti-cholinergic, analgesic, immunosuppressant, anti-depressant, anti-psychotic, p-adrenergic blocking agent, diuretic, cardiovascular active agent, vasoactive agent, non-steroidal, nutritional agent, anti-allergic agent, or pain-relieving agent. Vaccines may comprise isolated proteins or peptides, inactivated organisms and viruses, dead organisms and viruses, genetically altered organisms or viruses, polynucleotides (e.g., mRNA), and cell extracts. Therapeutic and prophylactic agents may be combined with interleukins, interferon, cytokines, and adjuvants such as cholera toxin, alum, and Freund's adjuvant, etc.

In certain embodiments, an agent to be delivered or used in a composition described herein is a polynucleotide. In certain embodiments, the agent is plasmid DNA (pDNA). In certain embodiments, the agent is single-stranded DNA (ssDNA), double-stranded DNA (dsDNA), genomic DNA (gDNA), complementary DNA (cDNA), antisense DNA, chloroplast DNA (ctDNA or cpDNA), microsatellite DNA, mitochondrial DNA (mtDNA or mDNA), kinetoplast DNA (kDNA), provirus, lysogen, repetitive DNA, satellite DNA, or viral DNA. In certain embodiments, the agent is RNA. In certain embodiments, the agent is small interfering RNA (siRNA). In certain embodiments, the agent is messenger RNA (mRNA). In certain embodiments, the agent is single-stranded RNA (ssRNA), double-stranded RNA (dsRNA), small interfering RNA (siRNA), precursor messenger RNA (pre-mRNA), small hairpin RNA or short hairpin RNA (shRNA), microRNA (miRNA), guide RNA (gRNA), transfer RNA (tRNA), antisense RNA (asRNA), heterogeneous nuclear RNA (hnRNA), coding RNA, non-coding RNA (ncRNA), long non-coding RNA (long ncRNA or lncRNA), satellite RNA, viral satellite RNA, signal recognition particle RNA, small cytoplasmic RNA, small nuclear RNA (snRNA), ribosomal RNA (rRNA), Piwi-interacting RNA (piRNA), polyinosinic acid, ribozyme, flexizyme, small nucleolar RNA (snoRNA), spliced leader RNA, viral RNA, or viral satellite RNA. In certain embodiments, the agent is an RNA that carries out RNA interference (RNAi). The phenomenon of RNAi is discussed in greater detail, for example, in the following references: Elbashir et al., 2001, *Genes Dev.,* 15:188; Fire et al, 1998, *Nature,* 391:806; Tabara et al., 1999. *Cell,* 99:123; Hammond et al., *Nature,* 2000, 404:293; Zamore et al., 2000. *Cell,* 101:25; Chakraborty, 2007, *Curr. Drug Targets,* 8:469; and Morris and Rossi, 2006, *Gene Ther.,* 13:553. In certain embodiments, upon delivery of an RNA into a subject, tissue, or cell, the RNA is able to interfere with the expression of a specific gene in the subject, tissue, or cell. In certain embodiments, the agent is a pDNA, siRNA, mRNA, or a combination thereof.

In certain embodiments, the polynucleotide may be provided as an antisense agent or RNAi. See, e.g., Fire et al., *Nature* 391:806-811, 1998. Antisense therapy is meant to include, e.g., administration or in situ provision of single- or double-stranded polynucleotides, or derivatives thereof, which specifically hybridize, e.g., bind, under cellular conditions, with cellular mRNA and/or genomic DNA, or mutants thereof, so as to inhibit the expression of the encoded protein, e.g., by inhibiting transcription and/or translation. See, e.g., Crooke, "Molecular mechanisms of action of antisense drugs," *Biochim. Biophys. Acta* 1489(1): 31-44, 1999; Crooke, "Evaluating the mechanism of action of anti-proliferative antisense drugs." *Antisense Nucleic Acid Drug Dev.* 10(2):123-126, discussion 127, 20100; *Methods in Enzymology* volumes 313-314, 1999. The binding may be by conventional base pair complementarity, or, for example, in the case of binding to DNA duplexes, through specific interactions in the major groove of the double helix (i.e., triple helix formation). See, e.g., Chan et al., *J. Mol. Med.* 75(4):267-282, 1997.

In some embodiments, pDNA, siRNA, dsRNA, shRNA, miRNA, mRNA, tRNA, asRNA, and/or RNAi can be designed and/or predicted using one or more of a large number of available algorithms. To give but a few examples, the following resources can be utilized to design and/or predict polynucleotides: algorithms found at Alnylum Online; Dharmacon Online; OligoEngine Online; Molecula Online; Ambion Online; BioPredsi Online; RNAi Web Online; Chang Bioscience Online; Invitrogen Online; LentiWeb Online GenScript Online; Protocol Online; Reynolds et al., 2004, *Nat. Biotechnol.,* 22:326; Naito et al., 2006, *Nucleic Acids Res.,* 34:W448; Li et al., 2007. *RNA.* 13:1765; Yiu et al., 2005, *Bioinformatics.* 21:144; and Jia et al., 2006, *BMC Bioinformatics.* 7: 271.

The polynucleotide included in a composition may be of any size or sequence, and they may be single- or double-stranded. In certain embodiments, the polynucleotide includes at least about 30, at least about 100, at least about 300, at least about 1,000, at least about 3,000, or at least about 10,000 base pairs. In certain embodiments, the polynucleotide includes less than about 10,000, less than about 3,000, less than about 1,000, less than about 300, less than about 100, or less than about 30 base pairs. Combinations of the above ranges (e.g., at least about 100 and less than about 1,000) are also within the scope of the invention. The polynucleotide may be provided by any means known in the art. In certain embodiments, the polynucleotide is engineered using recombinant techniques. See, e.g., Ausubel et al., *Current Protocols in Molecular Biology* (John Wiley & Sons. Inc., New York, 1999); *Molecular Cloning: A Laboratory Manual.* 2nd Ed., ed. by Sambrook. Fritsch, and Maniatis (Cold Spring Harbor Laboratory Press: 1989). The polynucleotide may also be obtained from natural sources and purified from contaminating components found normally in nature. The polynucleotide may also be chemically synthesized in a laboratory. In certain embodiments, the polynucleotide is synthesized using standard solid phase chemistry. The polynucleotide may be isolated and/or purified. In certain embodiments, the polynucleotide is substantially free of impurities. In certain embodiments, the polynucleotide is at least about 50%, at least about 60%, at least about 70%, at least about 80%, at least about 90%, at least about 95%, or at least about 99% free of impurities.

The polynucleotide may be modified by physical, chemical, and/or biological means. The modifications include methylation, phosphorylation, and end-capping, etc. In certain embodiments, the modifications lead to increased stability of the polynucleotide.

Wherever a polynucleotide is employed in the composition, a derivative of the polynucleotide may also be used. These derivatives include products resulted from modifications of the polynucleotide in the base moieties, sugar moieties, and/or phosphate moieties of the polynucleotide. Modified base moieties include, but are not limited to, 2-aminoadenosine, 2-thiothymidine, inosine, pyrrolo-pyrimidine, 3-methyl adenosine, 5-methylcytidine. C5-bromouridine, C5-fluorouridine. C5-iodouridine. C5-propynyl-uridine. C5-propynyl-cytidine, C5-methylcytidine, 7-deazaadenosine, 7-deazaguanosine, 8-oxoadenosine, 8-oxoguanosine, O(6)-methylguanine, and 2-thiocytidine. Modified sugar moieties include, but are not limited to, 2'-fluororibose, ribose, 2'-deoxyribose, 3'-azido-2',3'-dideoxyribose, 2',3'-dideoxyribose, arabinose (the 2'-epimer of ribose), acyclic sugars, and hexoses. The nucleosides may be strung together by linkages other than the phosphodiester linkage found in naturally occurring DNA and RNA. Modified linkages include, but are not limited to, phosphorothioate and 5'-N-phosphoramidite linkages. Combinations of the various modifications may be used in a single polynucleotide. These modified polynucleotides may be provided by any means known in the art; however, as will be appreciated by those of skill in the art, the modified polynucleotides may be prepared using synthetic chemistry in vitro.

The polynucleotide described herein may be in any form, such as a circular plasmid, a linearized plasmid, a cosmid, a viral genome, a modified viral genome, and an artificial chromosome.

The polynucleotide described herein may be of any sequence. In certain embodiments, the polynucleotide encodes a protein or peptide. The encoded protein may be an enzyme, structural protein, receptor, soluble receptor, ion channel, active (e.g., pharmaceutically active) protein, cytokine, interleukin, antibody, antibody fragment, antigen, coagulation factor, albumin, growth factor, hormone, and insulin, etc. The polynucleotide may also comprise regulatory regions to control the expression of a gene. These regulatory regions may include, but are not limited to, promoters, enhancer elements, repressor elements, TATA boxes, ribosomal binding sites, and stop sites for transcription, etc. In certain embodiments, the polynucleotide is not intended to encode a protein. For example, the polynucleotide may be used to fix an error in the genome of the cell being transfected.

In certain embodiments, the polynucleotide described herein comprises a sequence encoding an antigenic peptide or protein. A composition containing the polynucleotide can be delivered to a subject to induce an immunologic response sufficient to decrease the chance of a subsequent infection and/or lessen the symptoms associated with such an infection. The polynucleotide of these vaccines may be combined with interleukins, interferon, cytokines, and/or adjuvants described herein.

The antigenic protein or peptides encoded by the polynucleotide may be derived from bacterial organisms, such as *Streptococccus pneumoniae. Haemophilus influenzae, Staphylococcus aureus, Streptococcus pyrogenes. Corvnebacterium diphtheriae, Listeria nonocytogenes, Bacillus anthracis, Clostridium tetani. Clostridiunm botulinum, Clostridium perfringens, Neisseria meningitidis, Neisseria gonorrhoeae, Streptococcus mutans, Pseudomonas aeruginosa, Salmonella typhi, Haemophilus parainfluenzae, Bordetella pertussis. Francisella tularensis, Yersinia pestis. Vibrio cholerae, Legionella pneumophila, Mycobacterium tuberculosis, Mycobacterium leprae, Treponema pallidum, Leptospirosis interrogans, Borrelia burgdorferi*, and *Camphylobacter jejuni*; from viruses, such as smallpox virus, influenza A virus, influenza B virus, respiratory syncytial virus, parainfluenza virus, measles virus. HIV virus, varicella-zoster virus, herpes simplex 1 virus, herpes simplex 2 virus, cytomegalovirus, Epstein-Barr virus, rotavirus, rhinovirus, adenovirus, papillomavirus, poliovirus, mumps virus, rabies virus, rubella virus, coxsackieviruses, equine encephalitis virus, Japanese encephalitis virus, yellow fever virus. Rift Valley fever virus, hepatitis A virus, hepatitis B virus, hepatitis C virus, hepatitis D virus, and hepatitis E virus; and from fungal, protozoan, or parasitic organisms, such as *Cryptococcus neoformans. Histoplasma capsulatum. Candida albicans, Candida tropicalis, Nocardia asteroides, Rickettsia ricketsii, Rickettsia typhi, Mycoplasma pneumoniae, Chlamydial psittaci. Chlamydial trachomatis, Plasmodium falciparum, Trypanosona brucei, Entamoeba histolytica, Toxoplasma gondii, Trichomonas vaginalis*, and *Schistosoma mansoni.*

In certain embodiments, the agent is erythropoietin (EPO), e.g., recombinant human erythropoietin (rhEPO). Erythropoietin is an essential hormone for red blood cell production, and may be used in treating hematological diseases, e.g., anemia, such as anemia resulting from chronic kidney disease, chemotherapy induced anemia in patients with cancer, inflammatory bowel disease (Crohn's disease and ulcerative colitis) and myelodysplasia from the treatment of cancer (chemotherapy and radiation). Recombinant human erythropoietins available for use include EPOGEN/PROCRIT (Epoetin alfa, rINN) and ARANESP (Darbepoetin alfa, rINN).

An agent described herein may be non-covalently (e.g., complexed or encapsulated) attached to a compound as described herein, or included in a composition described herein. In certain embodiments, upon delivery of the agent into a cell, the agent is able to interfere with the expression of a specific gene in the cell.

In certain embodiments, the agent in a composition that is delivered to a subject in need thereof may be a mixture of two or more agents that may be useful as, e.g., combination therapies. The compositions including the two or more agents can be administered to achieve a synergistic effect. In certain embodiments, the compositions including the two or more agents can be administered to improve the activity and/or bioavailability, reduce and/or modify the metabolism, inhibit the excretion, and/or modify the distribution within the body of a subject, of each one of the two or more agents. It will also be appreciated that the therapy employed may achieve a desired effect for the same disorder, and/or it may achieve different effects.

The compositions (e.g., pharmaceutical compositions) can be administered concurrently with, prior to, or subsequent to the one or more agents (e.g., pharmaceutical agents). The two or more agents may be useful for treating and/or preventing a same disease or different diseases described herein. Each one of the agents may be administered at a dose and/or on a time schedule determined for that agent. The agents may also be administered together with each other and/or with the composition described herein in a single dose or administered separately in different doses. The particular combination to employ in a regimen will take into account compatibility of the agents and/or the desired therapeutic and/or prophylactic effect to be achieved. In general, it is expected that the agents utilized in combination be utilized at levels that do not exceed the levels at which they are utilized individually. In some embodiments, the levels utilized in combination will be lower than those utilized individually.

Targeting Agents

Since it is often desirable to target a particular cell, collection of cells, or tissue, compounds provided herein, and the complexes, liposomes, micelles, and particles (e.g., microparticles and nanoparticles) thereof, may be modified to include targeting moieties. For example, a compound provided herein may include a targeting moiety. A variety of agents or regions that target particular cells are known in the art. See, e.g., Cotten et al., *Methods Enzym.* 217:618, 1993. The targeting agent may be included throughout a particle of a compound provided herein or may be only on the surface of the particle. The targeting agent may be a protein, peptide, carbohydrate, glycoprotein, lipid, small molecule, or polynucleotide, etc. The targeting agent may be used to target specific cells or tissues or may be used to promote endocytosis or phagocytosis of the particle. Examples of targeting agents include, but are not limited to, antibodies, fragments of antibodies, proteins, peptides, carbohydrates, receptor ligands, sialic acid, and aptamers, etc. If the targeting agent is included throughout a particle, the targeting agent may be included in the mixture that is used to form the particle. If the targeting agent is only on the surface of a particle, the targeting agent may be associated with (e.g., by covalent or non-covalent (e.g., electrostatic, hydrophobic, hydrogen bonding, van der Waals, π-π stacking) interactions) the formed particle using standard chemical techniques.

Particles

In some embodiments, a composition including a compound provided herein and an agent is in the form of a particle. In certain embodiments, the compound provided herein and agent form a complex, and the complex is in the form of a particle. In certain embodiments, the compound provided herein encapsulates the agent and is in the form of a particle. In certain embodiments, the compound provided herein is mixed with the agent, and the mixture is in the form of a particle. In some embodiments, the particle encapsulates the agent.

In certain embodiments, a complex of a compound provided herein and an agent in a composition of is in the form of a particle. In some embodiments, the particle is a nanoparticle or a microparticle. In certain embodiments, the particle is a microparticle (i.e., particle having a characteristic dimension of less than about 1 millimeter and at least about 1 micrometer, where the characteristic dimension of the particle is the smallest cross-sectional dimension of the particle). In certain embodiments, the particle is a nanoparticle (i.e., a particle having a characteristic dimension of less than about 1 micrometer and at least about 1 nanometer, where the characteristic dimension of the particle is the smallest cross-sectional dimension of the particle). In certain embodiments, the average diameter of the particle is at least about 10 nm, at least about 30 nm, at least about 100 nm, at least about 300 nm, at least about 1 μm, at least about 3 μm, at least about 10 μm, at least about 30 μm, at least about 100 μm, at least about 300 μm, or at least about 1 mm. In certain embodiments, the average diameter of the particle is less than about 1 mm, less than about 300 μm, less than about 100 μm, less than about 30 μm less than about 10 μm, less than about 3 μm, less than about 1 μm, less than about 300 nm, less than about 100 nm, less than about 30 nm, or less than about 10 nm. Combinations of the above ranges (e.g., at least about 100 nm and less than about 1 μm) are also within the scope of the present invention.

The particles described herein may include additional materials such as polymers (e.g., synthetic polymers (e.g., PEG, PLGA) and natural polymers (e.g., phospholipids)). In certain embodiments, the additional materials are approved by a regulatory agency, such as the U.S. FDA, for human and veterinary use.

The particles may be prepared using any method known in the art, such as precipitation, milling, spray drying, single and double emulsion solvent evaporation, solvent extraction, phase separation, and simple and complex coacervation. In certain embodiments, methods of preparing the particles are the double emulsion process and spray drying. The conditions used in preparing the particles may be altered to yield particles of a desired size or property (e.g., hydrophobicity, hydrophilicity, external morphology, "stickiness", shape, polydispersity, etc.). The method of preparing the particle and the conditions (e.g., solvent, temperature, concentration, and air flow rate, etc.) used may also depend on the agent being complexed, encapsulated, or mixed, and/or the composition of the matrix.

Methods developed for making particles for delivery of agents that are included in the particles are described in the literature. See, e.g., Doubrow, M., Ed., "Microcapsules and Nanoparticles in Medicine and Pharmacy," CRC Press. Boca Raton, 1992; Mathiowitz and Langer, *J. Controlled Release* 5:13-22, 1987; Mathiowitz et al., *Reactive Polymers* 6:275-283, 1987; Mathiowitz et al., *J. Appl. Polymer Sci.* 35:755-774, 1988.

If the particles prepared by any of the above methods have a size range outside of the desired range, the particles can be sized, for example, using a sieve. The particles may also be coated. In certain embodiments, the particles are coated with a targeting agent. In certain embodiments, the particles are coated with a surface-altering agent. In some embodiments, the particles are coated to achieve desirable surface properties (e.g., a particular charge).

In certain embodiments, the polydispersity index (PDI, determined by dynamic light scattering) of the particles described herein (e.g., particles included in a composition described herein) is between 0.01 and 0.9, between 0.1 and 0.9, between 0.1 and 0.7, between 0.1 and 0.5, between 0.01 and 0.4, between 0.03 and 0.4, between 0.1 and 0.4, between 0.01 and 0.3, between 0.03 and 0.3, or between 0.1 and 0.3.

Micelles and Liposomes

A composition including one or more compounds provided herein and an agent may be in the form of a micelle, liposome, or lipoplex. In certain embodiments, the compound provided herein is in the form of a micelle or liposome. In certain embodiments, the agent is in the form of a micelle or liposome. In certain embodiments, the compound provided herein and agent form a complex, and the complex is in the form of a micelle or liposome. In certain embodiments, the compound provided herein encapsulates the agent and is in the form of a micelle or liposome. In certain embodiments, the compound provided herein is mixed with the agent, and the mixture is in the form of a micelle or liposome. Micelles and liposomes are particularly useful in delivering an agent, such as a hydrophobic agent. When the micelle or liposome is complexed with (e.g., encapsulates or covers) a polynucleotide, the resulting complex may be referred to as a "lipoplex." Many techniques for preparing micelles and liposomes are known in the art, and any such method may be used herein to make micelles and liposomes.

In certain embodiments, liposomes are formed through spontaneous assembly. In some embodiments, liposomes are formed when thin lipid films or lipid cakes are hydrated and stacks of lipid crystalline bilayers become fluid and swell. The hydrated lipid sheets detach during agitation and self-close to form large, multilamellar vesicles (LMV). This prevents interaction of water with the hydrocarbon core of the bilayers at the edges. Once these liposomes have formed, reducing the size of the liposomes can be modified through input of sonic energy (sonication) or mechanical energy (extrusion). See, e.g., Walde, P. "Preparation of Vesicles (Liposomes)" In *Encylopedia of Nanoscience and Nanotechnology*; Nalwa, H. S. Ed. American Scientific Publishers: Los Angeles, 2004; Vol. 9. pp. 43-79; Szoka et al., "Comparative Properties and Methods of Preparation of Lipid Vesicles (Liposomes)" *Ann. Rev. Biophys. Bioeng.* 9:467-508, 1980; each of which is incorporated herein by reference. The preparation of liposomes may involve preparing a compound provided herein for hydration, hydrating the compound with agitation, and sizing the vesicles to achieve a homogenous distribution of liposomes. A compound provided herein may be first dissolved in an organic solvent in a container to result in a homogeneous mixture. The organic solvent is then removed to form a polymer-derived film. This polymer-derived film is thoroughly dried to remove residual organic solvent by placing the container on a vacuum pump for a period of time. Hydration of the polymer-derived film is accomplished by adding an aqueous medium and agitating the mixture. Disruption of LMV suspensions using sonic energy typically produces small unilamellar vesicles (SUV) with diameters in the range of 15-50 nm. Lipid extrusion is a technique in which a lipid/polymer suspension is forced through a polycarbonate filter with a defined pore size to yield particles having a diameter near the pore size of the filter used. Extrusion through filters with 100 nm pores typically yields large, unilamellar polymer-derived vesicles (LUV) with a mean diameter of 120-140 nm. In certain embodiments, the amount of a compound provided herein in the liposome ranges from about 30 mol % to about 80 mol %, from about 40 mol % to about 70 mol %, or from about 60 mol % to about 70 mol %. In certain embodiments, the compound provided herein employed further complexes an agent, such as a polynucleotide. In such embodiments, the application of the liposome is the delivery of the polynucleotide.

The following scientific papers described other methods for preparing liposomes and micelles: Narang et al., "Cationic Lipids with Increased DNA Binding Affinity for Nonviral Gene Transfer in Dividing and Nondividing Cells," *Bioconjugate Chem.* 16:156-68, 2005; Hofland et al., "Formation of stable cationic lipid/DNA complexes for gene transfer," *Proc. Natl. Acad. Sci. USA* 93:7305-7309, July 1996; Byk et al., "Synthesis. Activity, and Structure-Activity Relationship Studies of Novel Cationic Lipids for DNA Transfer," *J. Med. Chem.* 41(2):224-235, 1998; Wu et al., "Cationic Lipid Polymerization as a Novel Approach for Constructing New DNA Delivery Agents," *Bioconjugate Chem,* 12:251-57, 2001; Lukyanov el al., "Micelles from lipid derivatives of water-soluble polymers as delivery systems for poorly soluble drugs," *Advanced Drug Delivery Reviews* 56:1273-1289, 2004; Tranchant et al., "Physicochemical optimisation of plasmid delivery by cationic lipids." *J. Gene Med.* 6:S24-S35, 2004; van Balen et al., "Liposome/Water Lipophilicity: Methods, Information Content. and Pharmaceutical Applications," *Medicinal Research Rev.* 24(3):299-324, 2004.

Kits

Also encompassed by the disclosure are kits (e.g., pharmaceutical packs). The kits provided may comprise a composition or compound described herein and a container (e.g., a vial, ampule, bottle, syringe, and/or dispenser package, or other suitable container). In some embodiments, provided kits may optionally further include a second container comprising a pharmaceutical excipient for dilution or suspension of a composition or compound described herein. In some embodiments, the composition or compound described herein provided in the first container and the second container are combined to form one unit dosage form.

Thus, in one aspect, provided are kits including a first container comprising a compound or composition described herein. In certain embodiments, the kits are useful for treating a disease (e.g., genetic disease, proliferative disease, hematological disease, neurological disease, liver disease, spleen disease, lung disease, painful condition, psychiatric disorder, musculoskeletal disease, a metabolic disorder, inflammatory disease, or autoimmune disease) in a subject in need thereof. In certain embodiments, the kits are useful for preventing a disease (e.g., genetic disease, proliferative disease, hematological disease, neurological disease, liver disease, spleen disease, lung disease, painful condition, psychiatric disorder, musculoskeletal disease, a metabolic disorder, inflammatory disease, or autoimmune disease) in a subject in need thereof. In certain embodiments, the kits are useful for reducing the risk of developing a disease (e.g., genetic disease, proliferative disease, hematological disease, neurological disease, liver disease, spleen disease, lung disease, painful condition, psychiatric disorder, musculoskeletal disease, a metabolic disorder, inflammatory disease, or autoimmune disease) in a subject in need thereof. In certain embodiments, the kits are useful for delivering an agent to a subject or cell. In certain embodiments, the kits are useful for delivering a polynucleotide to a subject or cell. In certain embodiments, the kits are useful for delivering mRNA to a subject or cell.

In certain embodiments, a kit described herein further includes instructions for using the kit. A kit described herein may also include information as required by a regulatory agency such as the U.S. Food and Drug Administration (FDA). In certain embodiments, the information included in the kits is prescribing information. In certain embodiments, the kits and instructions provide for treating a disease (e.g., genetic disease, proliferative disease, hematological disease, neurological disease, liver disease, spleen disease, lung disease, painful condition, psychiatric disorder, musculoskeletal disease, a metabolic disorder, inflammatory disease, or autoimmune disease) in a subject in need thereof. In certain embodiments, the kits and instructions provide for preventing a disease (e.g., genetic disease, proliferative disease, hematological disease, neurological disease, liver disease, spleen disease, lung disease, painful condition, psychiatric disorder, musculoskeletal disease, a metabolic disorder, inflammatory disease, or autoimmune disease) in a subject in need thereof. In certain embodiments, the kits and instructions provide for reducing the risk of developing a disease (e.g., genetic disease, proliferative disease, hematological disease, neurological disease, liver disease, spleen disease, lung disease, painful condition, psychiatric disorder, musculoskeletal disease, a metabolic disorder, inflammatory disease, or autoimmune disease) in a subject in need thereof. In certain embodiments, the kits and instructions provide for delivering an agent to a subject or cell. In certain embodiments, the kits and instructions provide for delivering a polynucleotide to a subject or cell. In certain embodiments, the kits and instructions provide for delivering mRNA to a subject or cell. A kit described herein may include one or more additional pharmaceutical agents described herein as a separate composition.

Methods of Treatment and Uses

Also provided herein are methods for treating and/or preventing a disease, disorder, or condition in a subject, comprising administering to the subject a composition provided herein, e.g., a composition comprising an agent and a compound of Formula (I), or a pharmaceutically acceptable salt, solvate, tautomer, stereoisomer, or isotopically labeled derivative thereof.

In certain embodiments, the disease, disorder, or condition is a genetic disease, proliferative disease, hematological disease, neurological disease, liver disease, spleen disease, lung disease, painful condition, psychiatric disorder, musculoskeletal disease, a metabolic disorder, inflammatory disease, or autoimmune disease. In some embodiments, the disease, disorder, or condition is a genetic disease. In some embodiments, the disease, disorder, or condition is a proliferative disease. In some embodiments, the disease, disorder, or condition is a hematological disease. In some embodiments, the disease, disorder, or condition is a neurological disease. In some embodiments, the disease, disorder, or condition is a liver disease. In some embodiments, the disease, disorder, or condition is a spleen disease. In some embodiments, the disease, disorder, or condition is a lung disease. In some embodiments, the disease, disorder, or condition is a painful condition. In some embodiments, the disease, disorder, or condition is a psychiatric disorder. In some embodiments, the disease, disorder, or condition is a musculoskeletal disease. In some embodiments, the disease, disorder, or condition is a metabolic disorder. In some embodiments, the disease, disorder, or condition is an inflammatory disease. In some embodiments, the disease, disorder, or condition is an autoimmune disease.

In some embodiments, the lung disease is cystic fibrosis, sepsis, or lung cancer. In some embodiments, the lung disease is cystic fibrosis. In some embodiments, the lung disease is sepsis. In some embodiments, the lung disease is lung cancer.

In certain embodiments, the subject is an animal. The animal may be of either sex and may be at any stage of development. In certain embodiments, the subject described herein is a human. In certain embodiments, the subject is a non-human animal. In certain embodiments, the subject is a mammal. In certain embodiments, the subject is a non-human mammal. In certain embodiments, the subject is a domesticated animal, such as a dog, cat, cow, pig, horse, sheep, or goat. In certain embodiments, the subject is a companion animal, such as a dog or cat. In certain embodiments, the subject is a livestock animal, such as a cow, pig, horse, sheep, or goat. In certain embodiments, the subject is a zoo animal. In another embodiment, the subject is a research animal, such as a rodent (e.g., mouse, rat), dog, pig, or non-human primate. In certain embodiments, the animal is a genetically engineered animal. In certain embodiments, the animal is a transgenic animal (e.g., transgenic mice and transgenic pigs). In certain embodiments, the subject is a fish or reptile.

In some embodiments, the agent is any agent provided herein. In certain embodiments, the agent is a polynucleotide. In some embodiments, the agent is mRNA.

In some embodiments, the composition is administered by any method provided herein. In certain embodiments, the composition is administered by nebulized administration or IV administration. In some embodiments, the composition is administered by nebulized administration. In certain embodiments, the composition is administered by IV administration.

In certain embodiments, the administration comprises inducing increased expression of a protein. In certain embodiments, the administration comprises inducing increased expression of a protein in the nose and/or lungs. In certain embodiments, the administration comprises inducing increased expression of a protein in the nose. In certain embodiments, the administration comprises inducing increased expression of a protein in the lungs. In certain embodiments, the increased expression of the protein lasts for at least 1 hour. In certain embodiments, the increased expression of the protein lasts for at least 4 hours. In certain embodiments, the increased expression of the protein lasts for at least 12 hours. In certain embodiments, the increased expression of the protein lasts for at least 24 hours. In certain embodiments, the increased expression of the protein lasts for at least 48 hours. In certain embodiments, the increased expression of the protein lasts for at least 72 hours. In certain embodiments, the increased expression of the protein lasts for at least 96 hours.

In certain embodiments, the composition is administered to the subject more than once. In certain embodiments, the composition is administered to the subject at least once daily. In certain embodiments, the composition is administered to the subject at least once every 2 days. In certain embodiments, the composition is administered to the subject at least once every 3 days. In certain embodiments, the composition is administered to the subject at least once every 5 days. In certain embodiments, the composition is administered to the subject at least once every 7 days.

Additional Methods and Uses

Also provided herein are methods of delivering an agent (e.g., a polynucleotide), comprising administering a composition comprising a polynucleotide and a compound provided herein (e.g., a compound of Formula (I) or (II)), or a pharmaceutically acceptable salt, solvate, tautomer, stereoisomer, or isotopically labeled derivative thereof. In certain embodiments, the method is for delivering an agent to a subject, cell, collection of cells, or tissue. In some embodiments, the method is for delivering an agent to a subject or cell. In certain embodiments, the method is for delivering an agent to a subject. In some embodiments, the method is for delivering an agent to a cell.

In some embodiments, the agent is any agent provided herein. In certain embodiments, the agent is a polynucleotide. In some embodiments, the agent is mRNA.

In some embodiments, the agent is delivered to a subject. In some embodiments, the agent is delivered to the lung or nasal epithelium of the subject. In certain embodiments, the agent is delivered to the lung of the subject. In certain embodiments, the agent is delivered to the lung epithelium of the subject. In certain embodiments, the agent is delivered to the lung endothelium of the subject. In some embodiments, the agent is delivered to the nasal epithelium of the subject. In certain embodiments, the polynucleotide is delivered to a subject. In some embodiments, the polynucleotide is delivered to the lung or nasal epithelium of the subject. In certain embodiments, the polynucleotide is delivered to the lung of the subject. In certain embodiments, the polynucleotide is delivered to the lung epithelium of the subject. In some embodiments, the lung epithelium of the subject comprises club cells. In some embodiments, the polynucleotide is delivered to club cells in the lung epithelium of the subject. In certain embodiments, the polynucleotide is delivered to the lung endothelium of the subject. In some embodiments, the polynucleotide is delivered to the nasal epithelium of the subject. In certain embodiments, the mRNA is delivered to a subject. In some embodiments, the mRNA is delivered to the lung or nasal epithelium of the subject. In certain embodiments, the mRNA is delivered to the lung of the subject. In certain embodiments, the mRNA is delivered to the lung epithelium of the subject. In some embodiments, the mRNA is delivered to club cells in the lung epithelium of the subject. In certain embodiments, the mRNA is delivered to the lung endothelium of the subject. In some embodiments, the mRNA is delivered to the nasal epithelium of the subject. In some embodiments, the composition is nebulized or aerosolized before the agent is delivered to the subject. In some embodiments, the composition is nebulized before the agent is delivered to the subject. In some embodiments, the composition is aerosolized before the agent is delivered to the subject.

In certain embodiments, the agent is delivered to a cell. In some embodiments, the agent is delivered to a lung cell or nasal epithelial cell. In certain embodiments, the agent is delivered to a lung cell. In some embodiments, the agent is delivered to a nasal epithelial cell. In certain embodiments, the polynucleotide is delivered to a cell. In some embodiments, the polynucleotide is delivered to a lung cell or nasal epithelial cell. In certain embodiments, the polynucleotide is delivered to a lung cell. In some embodiments, the polynucleotide is delivered to a nasal epithelial cell. In certain embodiments, the mRNA is delivered to a cell. In some embodiments, the mRNA is delivered to a lung cell or nasal epithelial cell. In certain embodiments, the mRNA is delivered to a lung cell. In some embodiments, the mRNA is delivered to a nasal epithelial cell. In certain embodiments, the agent is delivered to a club cell. In certain embodiments, the polynucleotide is delivered to a club cell. In certain embodiments, the mRNA is delivered to a club cell. In some embodiments, the composition is nebulized or aerosolized before the agent is delivered to the cell. In some embodiments, the composition is nebulized before the agent is delivered to the cell. In some embodiments, the composition is aerosolized before the agent is delivered to the cell.

In some embodiments, the lung cell is an endothelium cell. In certain embodiments, the lung cell is a lung epithelial cell. In some embodiments, the cell is an A549 cell. In certain embodiments, the lung cell is a human bronchial epithelial cell. In some embodiments, the lung cell is a pulmonary endothelial cell. In some embodiments, the lung cell is a club cell.

In some embodiments, the cell is in vivo, e.g., in an organism. In certain embodiments, the cell is in vitro, e.g., in cell culture. In some embodiments, the cell culture is an air-liquid interface (ALI) culture. In some embodiments, the composition is nebulized before the agent is delivered to the ALI culture. In some embodiments, the cell is ex vivo, meaning the cell is removed from an organism prior to the delivery.

In some embodiments, the composition is administered by any method provided herein. In certain embodiments, the composition is administered by nebulized administration, aerosolized administration, or IV administration. In some embodiments, the composition is administered by nebulized administration. In some embodiments, the composition is administered by aerosolized administration. In some embodiments, when the composition is administered by nebulized administration, there is microscale heterogeneity in transfection. In some embodiments, microscale heterogeneity is due to differences in transfectability and/or particle deposition. In some embodiments, when the composition is administered by nebulized administration, there is at least one stretch of airway with near-complete transfection. In certain embodiments, the composition is administered by IV administration.

In some embodiments, the composition is administered by a device for delivering to a subject via inhalation or exhalation (e.g., oral or nasal) an aerosol as described herein, i.e., an aerosolized form of a pharmaceutical composition as described herein. In certain embodiments, the device is a nebulizer (e.g., jet or ultrasonic), atomizer, vaporizer, or electrospray. In certain embodiments, the device is propellant-driven, breath-actuated, or pump-actuated. In certain embodiments, the device comprises a metering valve. In certain embodiments, the device is configured to control or regulate aerosol droplet or particle size. In certain embodiments, the device is configured to produce the aerosol for a duration in the range of 5 seconds to 30 minutes. In certain embodiments, the device is configured to control or regulate aerosol velocity.

In certain embodiments, the device is configured to deliver an amount of the composition in the range of 0.1-130 mg, e.g., 0.1-1 mg, 1-5 mg, 5-10 mg, 10-20 mg, 10-50 mg, 25-75 mg, 50-75 mg, 75-100 mg, 75-130 mg, or 100-130 mg. In certain embodiments, a dose of compound in the range of 1-130 mg, e.g., 1-5 mg, 5-10 mg, 10-20 mg, 10-50 mg, 25-75 mg, 50-75 mg, 75-100 mg, 75-130 mg, or 100-130 mg. In certain embodiments, the device is configured to deliver the composition to the respiratory tract with an efficiency (i.e., percent agent delivered) of at least 1%, at least 5%, at least 10%, at least 20%, at least 30%, at least 40%, at least 50%, at least 60%, at least 70%, at least 80%, at least 90%, or at least 99%.

In certain embodiments, the device is a metered-dose inhaler. See, e.g., Newman S P. "Principles of metered-dose inhaler design." *Respir Care.* 2005 September; 50(9):1177-88; Roche N. Dekhuijezen R. "The evolution of pressurized metered-dose inhalers from early to modern devices." *J Aerosol Med Pulm Drug Deliv.* 2016; 29(4):311.

In certain embodiments, the device comprises a non-pressurized reservoir containing the composition. In certain embodiments, the device a pressurized reservoir containing the composition. See, e.g., Cogan P S, Sucher B J. "Appropriate use of pressurized metered-dose inhalers for asthma." *US Pharm.* 2015; 40(7), 36-41; Vehring R. Ballesteros D L.

Joshi V. Noga B, Dwivedi S K. “Co-suspensions of microcrystals and engineered microparticles for uniform and efficient delivery of respiratory therapeutics from pressurized metered dose inhalers.” *Langmuir* 2012 28(42), 15015-15023.

In certain embodiments, the device is a breath-actuated inhaler. In certain embodiments, the device is dry powder inhaler. See, e.g., Islam N, Gladki E. “Dry powder inhalers (DPIs)-a review of device reliability and innovation.” *Int J Pharm.* 2008; Daniher D I, Zhu J. “Dry powder platform for pulmonary drug delivery.” *Parliculogy.* 2008 August Dry powder inhalers may be breath-actuated, may deliver particles having a mean mass aerodynamic diameter (MMAD) of less than 5 microns, and may produce inspiratory flow rates of 30-60 L/min. Other soft mist inhalers such as AERx and Medspray have been in development based on extrusion of liquids through arrays of nozzles (Dayton et al., *Respiratory Drug Delivery* 2006, Davis Healthcare International Publishing. River Grove, IL, USA. pp. 429-432). In certain embodiments, the device is a soft mist inhaler. See, e.g., Dalby R N. Eicher J, Zierenberg B. “Development of Respimat Soft Mist inhaler and its clinical utility in respiratory disorder.” *Med Devices.* 2011 August. In certain embodiments, the device is a Respimat® Soft Mist inhaler. In certain embodiments, the device is an Aerogen® Ultra/Aerogen® Solo nebulizer. The device is manufactured by Aerogen Ltd. Aerogen® Ultra is an accessory specific to the Aerogen® Solo nebulizer. This device facilitates intermittent and continuous nebulization and optional supply of supplemental oxygen to pediatric (29 days or older) and adult patients in hospital use environments via mouthpiece or aerosol face mask. The Aerogen® Ultra is a single patient use device. In certain embodiments, the device is used intermittently for a maximum of 20 treatments, which is based upon a typical usage profile of four 3 ml doses per day over 5 days, with an average treatment time of 9 minutes. In other embodiments, the device is used continuously for a maximum of 3 hours. In other embodiments the device uses a volume of approximately 0.5 mL that can be delivered in about 1 minute. In certain embodiments, the device is a PARI LC Sprint, used in conjunction with a compressor. The PARI LC Sprint is manufactured by PARI Respiratory Equipment. Inc. In certain embodiments, the device is a soft mist inhaler manufactured by Medspray (Enschede, Twente, Netherlands). Such devices include the following: ADI/Colistair (puff size 50 μL, capacity 1 mL); PFSI (puff size 30 μL, capacity 90 μL); Ecomyst90 (puff size 25 μL, capacity 5 or 10 mL); and Pulmospray, Pulmospray ICU devices (patient breaths in through mouth and out through nose).

The present disclosure contemplates specific combinations of the compositions and devices disclosed herein.

In another aspect, the disclosure provides a method of preparing a compound of Formula (I), the method comprising reacting a compound of Formula (II):

(II)

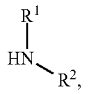

or a salt, solvate, tautomer, stereoisomer, or isotopically labeled derivative thereof, with a compound of Formula (III):

(III)

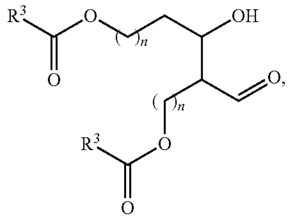

or a salt, solvate, tautomer, stereoisomer, or isotopically labeled derivative thereof, wherein:

$R^1$ is —H, optionally substituted alkyl, optionally substituted alkenyl, optionally substituted alkynyl, optionally substituted heteroalkyl, optionally substituted heteroalkenyl, optionally substituted heteroalkynyl, optionally substituted aryl, optionally substituted heteroaryl, optionally substituted carbocyclyl, optionally substituted heterocyclyl, or a nitrogen protecting group;

$R^2$ is —H, optionally substituted alkyl, optionally substituted alkenyl, optionally substituted alkynyl, optionally substituted heteroalkyl, optionally substituted heteroalkenyl, optionally substituted heteroalkynyl, optionally substituted aryl, optionally substituted heteroaryl, optionally substituted carbocyclyl, optionally substituted heterocyclyl, or a nitrogen protecting group; or $R^1$ and $R^2$ are joined together with the intervening atoms to form an optionally substituted heterocyclyl;

each $R^3$ independently is optionally substituted $C_6$-$C_{25}$ aliphatic; and each n independently is 0-15, inclusive.

In some embodiments, the compound of Formula (III), or a salt, solvate, tautomer, stereoisomer, or isotopically labeled derivative thereof, is prepared by reacting one or more compounds of Formula (IV):

(IV)

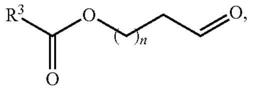

or a salt, solvate, tautomer, stereoisomer, or isotopically labeled derivative thereof, with a base or acid catalyst, wherein:

each $R^3$ independently is optionally substituted $C_6$-$C_{25}$ aliphatic; and each n independently is 0-15, inclusive.

In some embodiments, the one or more compounds of Formula (IV) comprise at least two equivalents of the same compound. In certain embodiments, the compound of Formula (III) is prepared via Aldol dimerization of a compound of Formula (IV).

In some embodiments, the base is titanium (IV) butoxide and/or potassium tert-butoxide. In some embodiments, the base is titanium (IV) butoxide and potassium tert-butoxide.

In some embodiments, the base is titanium (IV) butoxide. In some embodiments, the base is potassium tert-butoxide.

Figure 2:
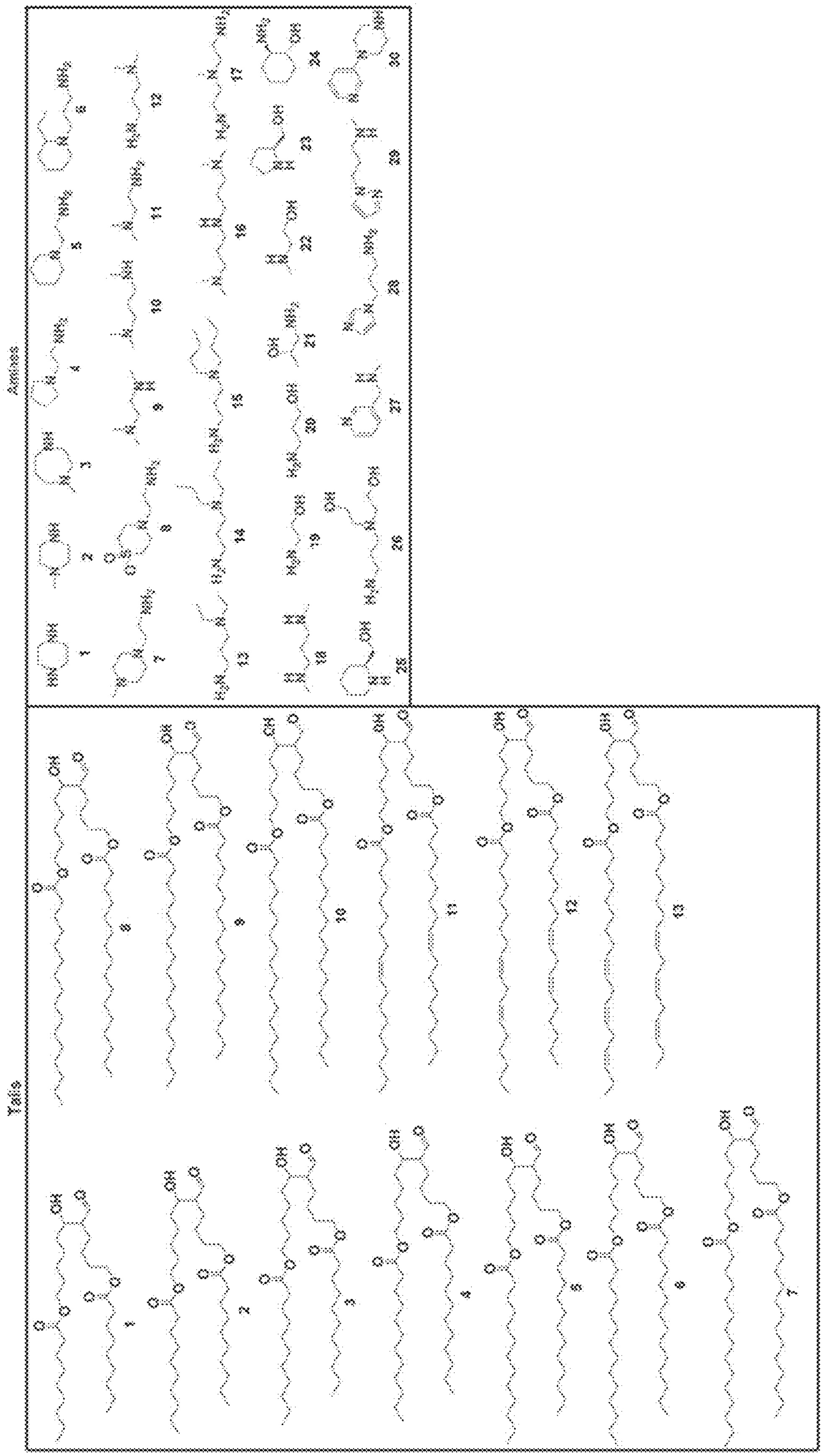
FIG. 2 shows the structures of amines and linkers with lipid tails used for ionizable lipid synthesis.
Figure 3A:
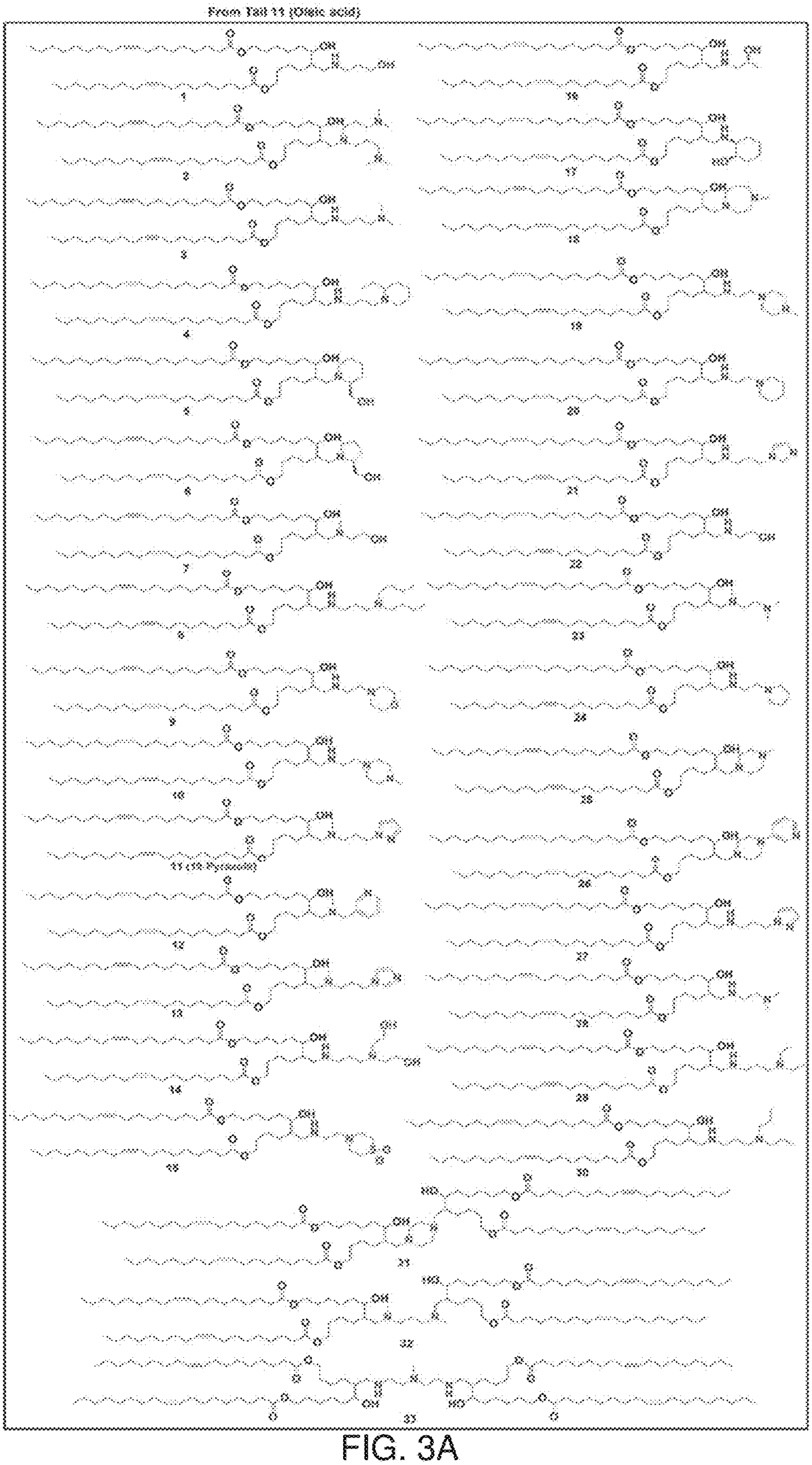
FIGS. 3A-3D show structures of the first series of ionizable lipids that were synthesized and screened for efficacy for delivery of mRNA to the lungs.
Figure 3B:
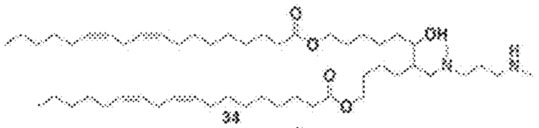
Figure 3B:
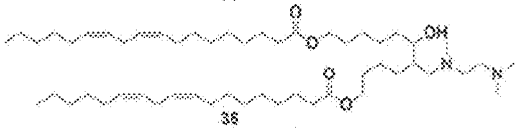
Figure 3B:
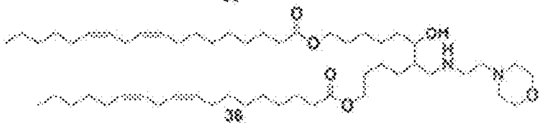
Figure 3B:
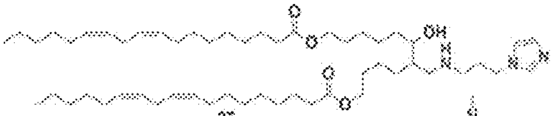
Figure 3B:
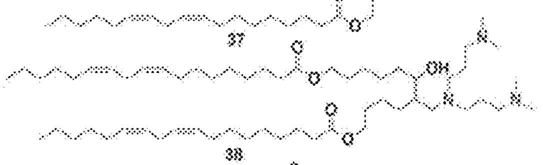
Figure 3B:
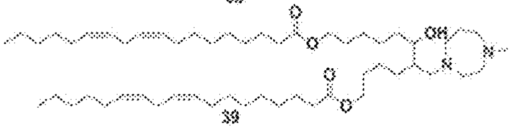
Figure 3B:
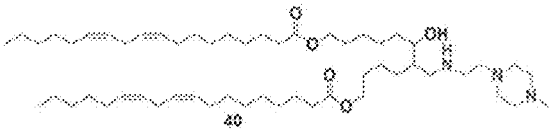
Figure 3B:
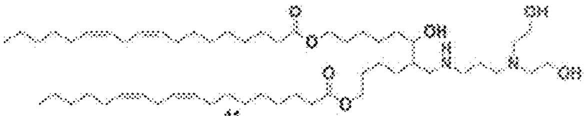
Figure 3B:
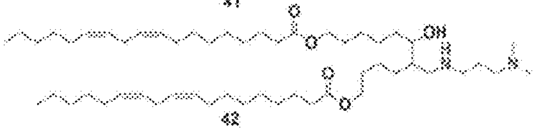
Figure 3B:
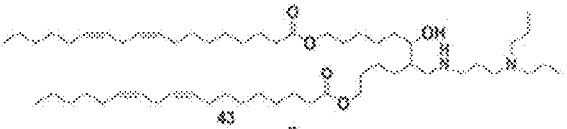
Figure 3B:
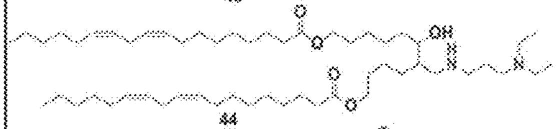
Figure 3B:
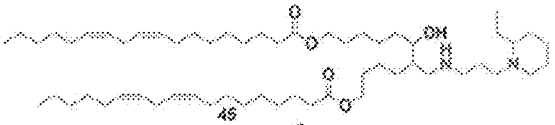
Figure 3B:
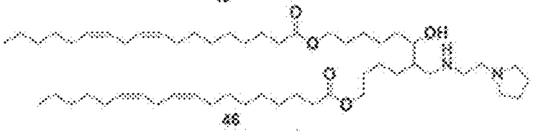
Figure 3B:
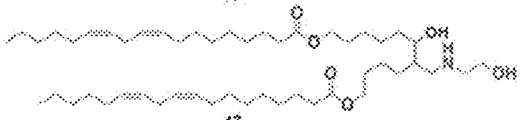
Figure 3B:
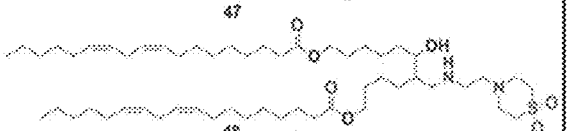
Figure 3B:
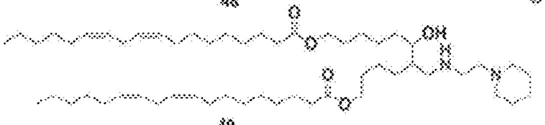
Figure 3B:
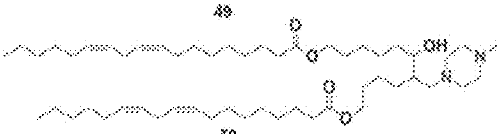
Figure 3B:
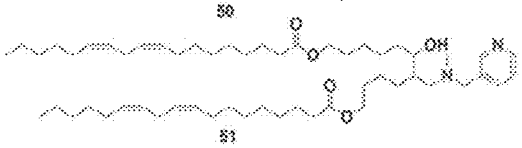
Figure 3B:
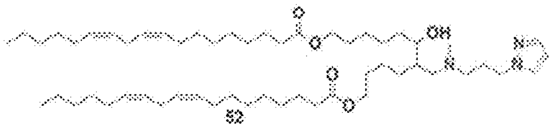
Figure 3B:
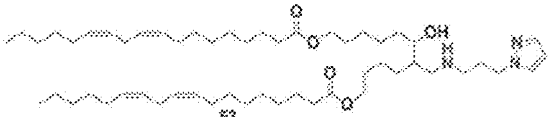
Figure 3B:
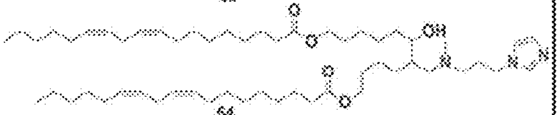
Figure 3B:
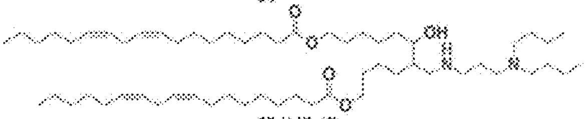
Figure 3B:
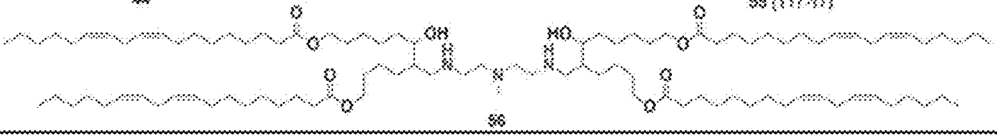
Figure 3C:
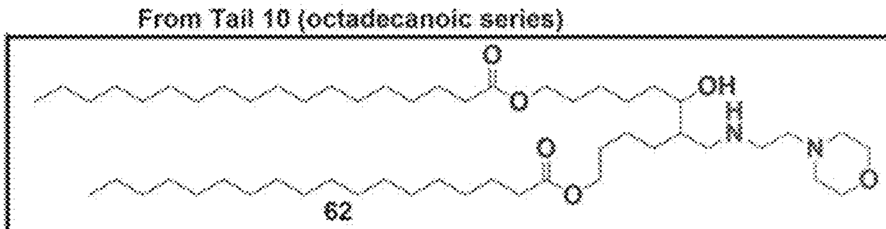
Figure 3C:
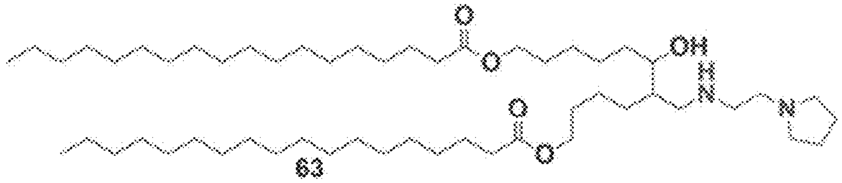
Figure 3C:
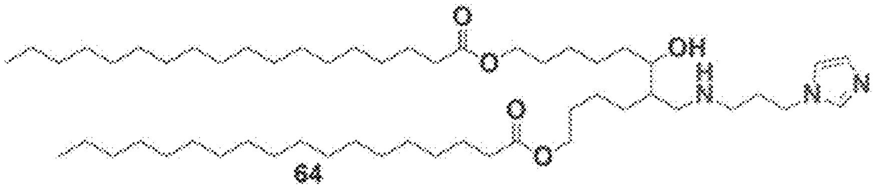
Figure 3C:
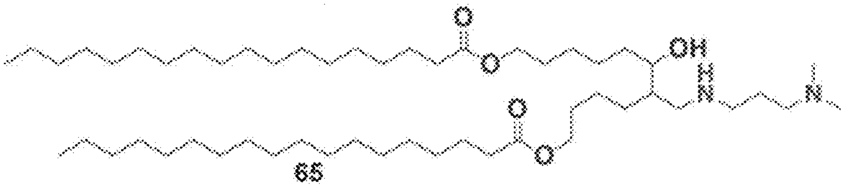
Figure 3C:
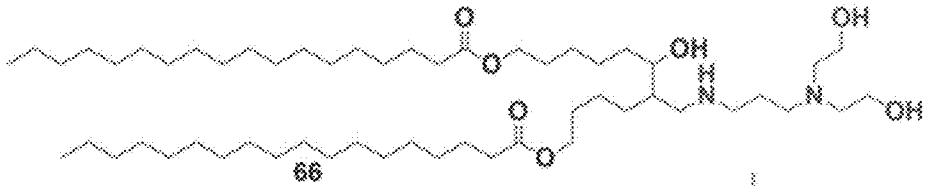
Figure 3C:
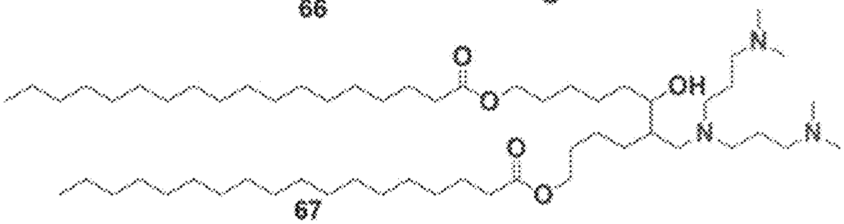
Figure 3C:
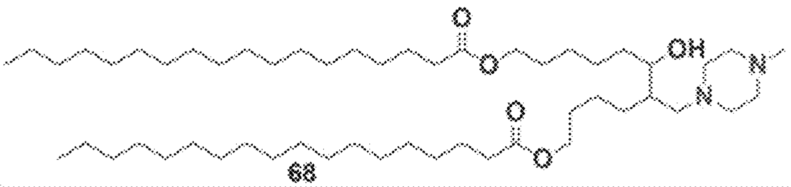
Figure 3D:
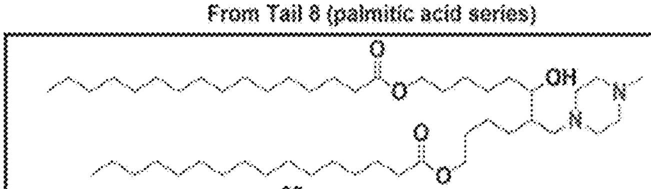
Figure 3D:
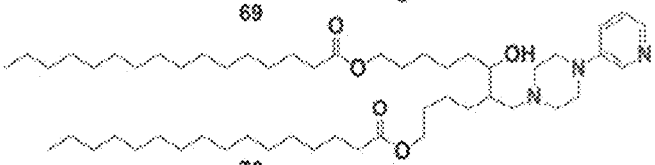
Figure 3D:
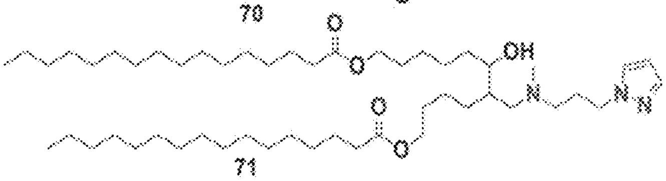
Figure 3D:
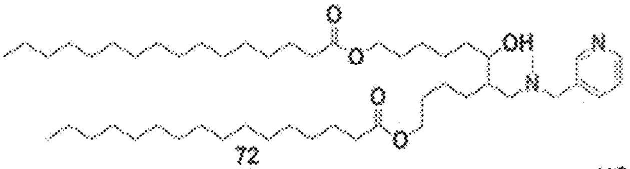
Figure 3D:
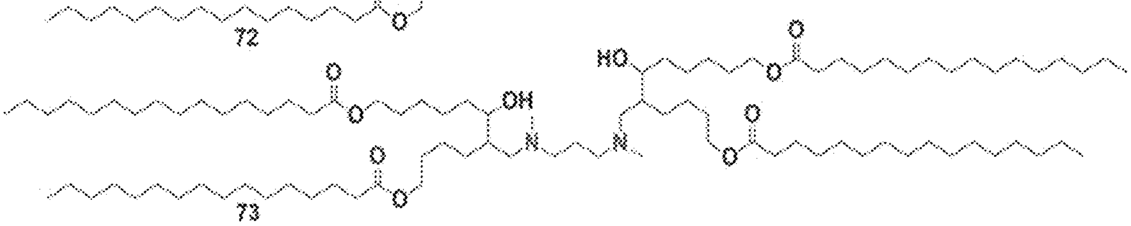

In some embodiments, the compound of Formula (II) is an amine provided in FIG. 2.

As defined herein. $R^1$ is —H, optionally substituted alkyl, optionally substituted alkenyl, optionally substituted alkynyl, optionally substituted heteroalkyl, optionally substituted heteroalkenyl, optionally substituted heteroalkynyl, optionally substituted aryl, optionally substituted heteroaryl, optionally substituted carbocyclyl, optionally substituted heterocyclyl, or a nitrogen protecting group; or $R^1$ and $R^2$ are joined together with the intervening atoms to form an optionally substituted heterocyclyl.

In some embodiments, $R^1$ is —H, optionally substituted alkyl, optionally substituted alkenyl, optionally substituted alkynyl, optionally substituted heteroalkyl, optionally substituted heteroalkenyl, optionally substituted heteroalkynyl, optionally substituted aryl, optionally substituted heteroaryl, optionally substituted carbocyclyl, optionally substituted heterocyclyl, or a nitrogen protecting group. In certain embodiments, $R^1$ is —H, optionally substituted $C_1$-$C_{20}$ alkyl, optionally substituted $C_1$-$C_{20}$ alkenyl, optionally substituted $C_1$-$C_{20}$ alkynyl, optionally substituted $C_1$-$C_{20}$ heteroalkyl, optionally substituted $C_1$-$C_{20}$ heteroalkenyl, optionally substituted $C_1$-$C_{20}$ heteroalkynyl, optionally substituted $C_6$-$C_{14}$ aryl, optionally substituted 5- to 14-membered heteroaryl, optionally substituted $C_3$-$C_{14}$ carbocyclyl, optionally substituted 3- to 14-membered heterocyclyl, or a nitrogen protecting group. In certain embodiments, $R^1$ is —H, optionally substituted $C_1$-$C_{10}$ alkyl, optionally substituted $C_1$-$C_{10}$ alkenyl, optionally substituted $C_1$-$C_{10}$ alkynyl, optionally substituted $C_1$-$C_{10}$ heteroalkyl, optionally substituted $C_1$-$C_{10}$ heteroalkenyl, optionally substituted $C_1$-$C_{10}$ heteroalkynyl, optionally substituted $C_6$-$C_{14}$ aryl, optionally substituted 5- to 14-membered heteroaryl, optionally substituted $C_3$-$C_{14}$ carbocyclyl, optionally substituted 3- to 14-membered heterocyclyl, or a nitrogen protecting group.

In certain embodiments, $R^1$ is —H, optionally substituted alkyl, optionally substituted alkenyl, optionally substituted alkynyl, optionally substituted heteroalkyl, optionally substituted heteroalkenyl, optionally substituted heteroalkynyl, or a nitrogen protecting group. In some embodiments, $R^1$ is —H, optionally substituted $C_1$-$C_{10}$ alkyl, optionally substituted $C_1$-$C_{10}$ alkenyl, optionally substituted $C_1$-$C_{10}$ alkynyl, optionally substituted $C_1$-$C_{10}$ heteroalkyl, optionally substituted $C_1$-$C_{10}$ heteroalkenyl, optionally substituted $C_1$-$C_{10}$ heteroalkynyl, or a nitrogen protecting group. In certain embodiments, $R^1$ is —H, optionally substituted $C_1$-$C_{10}$ alkyl, optionally substituted $C_1$-$C_{10}$ heteroalkyl, or a nitrogen protecting group.

In some embodiments, $R^1$ is —H or a nitrogen protecting group. In certain embodiments, $R^1$ is —H. In some embodiments, $R^1$ is a nitrogen protecting group. In certain embodiments, the nitrogen protecting group is Bn, Boc, Cbz, Fmoc, trifluoroacetyl, triphenylmethyl, acetyl, or Ts.

In certain embodiments, $R^1$ is optionally substituted $C_1$-$C_{10}$ alkyl or optionally substituted $C_1$-$C_{10}$ heteroalkyl. In some embodiments, $R^1$ is optionally substituted $C_1$-$C_{10}$ alkyl. In certain embodiments, $R^1$ is unsubstituted $C_1$-$C_{10}$ alkyl. In some embodiments, $R^1$ is substituted $C_1$-$C_{10}$ alkyl. In certain embodiments, $R^1$ is optionally substituted $C_1$-$C_6$ alkyl. In some embodiments, $R^1$ is unsubstituted $C_1$-$C_6$ alkyl. In certain embodiments, $R^1$ is substituted $C_1$-$C_6$ alkyl. In some embodiments, $R^1$ is methyl, ethyl, propyl, butyl, pentyl, or hexyl. In certain embodiments, $R^1$ is methyl, ethyl, propyl, or butyl. In some embodiments, $R^1$ is methyl, ethyl, or propyl. In certain embodiments, $R^1$ is propyl. In some embodiments, $R^1$ is -Et. In certain embodiments, $R^1$ is -Me.

In some embodiments, $R^1$ is optionally substituted $C_1$-$C_{10}$ heteroalkyl. In certain embodiments, $R^1$ is unsubstituted $C_1$-$C_{10}$ heteroalkyl. In some embodiments, $R^1$ is substituted $C_1$-$C_{10}$ heteroalkyl. In certain embodiments, $R^1$ is optionally substituted $C_1$-$C_6$ heteroalkyl. In some embodiments, $R^1$ is unsubstituted $C_1$-$C_6$ heteroalkyl. In certain embodiments, $R^1$ is substituted $C_1$-$C_6$ heteroalkyl. In some embodiments, $R^1$ is optionally substituted heteroalkyl comprising one or more nitrogen atoms. In some embodiments, $R^1$ is optionally substituted $C_1$-$C_{10}$ heteroalkyl comprising one or more nitrogen atoms. In some embodiments, $R^1$ is optionally substituted $C_1$-$C_6$ heteroalkyl comprising one or more nitrogen atoms. In certain embodiments, $R^1$ is

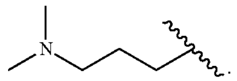 [SMILES: *CCCN(C)C]

In certain embodiments, $R^1$ is optionally substituted aryl. In some embodiments, $R^1$ is optionally substituted $C_6$-$C_{14}$ aryl. In some embodiments, $R^1$ is substituted $C_6$-$C_{14}$ aryl. In some embodiments, $R^1$ is unsubstituted $C_6$-$C_{14}$ aryl. In certain embodiments, $R^1$ is optionally substituted $C_6$-$C_{10}$ aryl. In certain embodiments, $R^1$ is substituted $C_6$-$C_{10}$ aryl. In certain embodiments, $R^1$ is unsubstituted $C_6$-$C_{10}$ aryl. In some embodiments, $R^1$ is optionally substituted phenyl or optionally substituted naphthyl. In certain embodiments, $R^1$ is optionally substituted phenyl. In some embodiments, $R^1$ is optionally substituted naphthyl.

In certain embodiments, $R^1$ is optionally substituted heteroaryl. In some embodiments, $R^1$ is optionally substituted 5- to 14-membered heteroaryl. In some embodiments, $R^1$ is substituted 5- to 14-membered heteroaryl. In some embodiments, $R^1$ is unsubstituted 5- to 14-membered heteroaryl. In some embodiments, $R^1$ is optionally substituted 5- to 10-membered heteroaryl. In some embodiments, $R^1$ is substituted 5- to 10-membered heteroaryl. In some embodiments, $R^1$ is unsubstituted 5- to 10-membered heteroaryl.

In some embodiments, $R^1$ is optionally substituted carbocyclyl. In some embodiments, $R^1$ is optionally substituted $C_3$-$C_{14}$ carbocyclyl. In some embodiments, $R^1$ is substituted $C_3$-$C_{14}$ carbocyclyl. In some embodiments, $R^1$ is unsubstituted $C_3$-$C_{14}$ carbocyclyl. In some embodiments, $R^1$ is optionally substituted $C_3$-$C_8$ carbocyclyl. In some embodiments, $R^1$ is substituted $C_3$-$C_8$ carbocyclyl. In some embodiments, $R^1$ is unsubstituted $C_3$-$C_8$ carbocyclyl. In some embodiments, $R^1$ is $C_3$-$C_8$ carbocyclyl substituted with optionally substituted alkyl, optionally substituted heteroalkyl, optionally substituted cycloalkyl, optionally substituted heterocyclyl, optionally substituted heteroaryl, or optionally substituted aryl.

In some embodiments, $R^1$ is optionally substituted heterocyclyl. In some embodiments, $R^1$ is optionally substituted 3- to 14-membered heterocyclyl. In some embodiments, $R^1$ is substituted 3- to 14-membered heterocyclyl. In some embodiments, $R^1$ is unsubstituted 3- to 14-membered heterocyclyl. In some embodiments, $R^1$ is optionally substituted 3- to 8-membered heterocyclyl. In some embodiments, $R^1$ is substituted 3- to 8-membered heterocyclyl. In some embodiments, $R^1$ is unsubstituted 3- to 8-membered heterocyclyl. In some embodiments, $R^1$ is 3- to 8-membered heterocyclyl substituted with optionally substituted alkyl, optionally substituted heteroalkyl, optionally substituted cycloalkyl, optionally substituted heterocyclyl, optionally substituted heteroaryl, or optionally substituted aryl.

As defined herein, $R^2$ is —H, optionally substituted alkyl, optionally substituted alkenyl, optionally substituted alkynyl, optionally substituted heteroalkyl, optionally substituted heteroalkenyl, optionally substituted heteroalkynyl, optionally substituted aryl, optionally substituted heteroaryl, optionally substituted carbocyclyl, optionally substituted heterocyclyl, or a nitrogen protecting group; or $R^1$ and $R^2$ are joined together with the intervening atoms to form an optionally substituted heterocyclyl.

In some embodiments, $R^2$ is —H, optionally substituted alkyl, optionally substituted alkenyl, optionally substituted alkynyl, optionally substituted heteroalkyl, optionally substituted heteroalkenyl, optionally substituted heteroalkynyl, optionally substituted aryl, optionally substituted heteroaryl, optionally substituted carbocyclyl, optionally substituted heterocyclyl, or a nitrogen protecting group. In certain embodiments, $R^2$ is —H, optionally substituted $C_1$-$C_{20}$ alkyl, optionally substituted $C_1$-$C_{20}$ alkenyl, optionally substituted $C_1$-$C_{20}$ alkynyl, optionally substituted $C_1$-$C_{20}$ heteroalkyl, optionally substituted $C_1$-$C_{20}$ heteroalkenyl, optionally substituted $C_1$-$C_{20}$ heteroalkynyl, optionally substituted $C_6$-$C_{14}$ aryl, optionally substituted 5- to 14-membered heteroaryl, optionally substituted $C_3$-$C_{14}$ carbocyclyl, optionally substituted 3- to 14-membered heterocyclyl, or a nitrogen protecting group. In certain embodiments, $R^2$ is —H, optionally substituted $C_1$-$C_{10}$ alkyl, optionally substituted $C_1$-$C_{10}$ alkenyl, optionally substituted $C_1$-$C_{10}$ alkynyl, optionally substituted $C_1$-$C_{10}$ heteroalkyl, optionally substituted $C_1$-$C_{10}$ heteroalkenyl, optionally substituted $C_1$-$C_{10}$ heteroalkynyl, optionally substituted $C_6$-$C_{14}$ aryl, optionally substituted 5- to 14-membered heteroaryl, optionally substituted $C_3$-$C_{14}$ carbocyclyl, optionally substituted 3- to 14-membered heterocyclyl, or a nitrogen protecting group.

In some embodiments, $R^2$ is —H, optionally substituted optionally substituted alkyl, optionally substituted alkenyl, optionally substituted alkynyl, optionally substituted heteroalkyl, optionally substituted heteroalkenyl, optionally substituted heteroalkynyl, optionally substituted carbocyclyl, optionally substituted heterocyclyl, or a nitrogen protecting group. In certain embodiments, $R^2$ is —H, optionally substituted alkyl, optionally substituted heteroalkyl, optionally substituted carbocyclyl, optionally substituted heterocyclyl, or a nitrogen protecting group. In some embodiments, $R^2$ is —H, optionally substituted $C_1$-$C_{20}$ alkyl, optionally substituted $C_1$-$C_{20}$ heteroalkyl, optionally substituted $C_3$-$C_{14}$ carbocyclyl, optionally substituted 3- to 14-membered heterocyclyl, or a nitrogen protecting group. In certain embodiments, $R^2$ is —H, optionally substituted $C_1$-$C_{10}$ alkyl, optionally substituted $C_1$-$C_{10}$ heteroalkyl, optionally substituted $C_3$-$C_{14}$ carbocyclyl, optionally substituted 3- to 14-membered heterocyclyl, or a nitrogen protecting group.

In some embodiments, $R^2$ is optionally substituted optionally substituted alkyl, optionally substituted alkenyl, optionally substituted alkynyl, optionally substituted heteroalkyl, optionally substituted heteroalkenyl, optionally substituted heteroalkynyl, optionally substituted carbocyclyl, optionally substituted heterocyclyl, or a nitrogen protecting group. In certain embodiments, $R^2$ is optionally substituted alkyl, optionally substituted heteroalkyl, optionally substituted carbocyclyl, optionally substituted heterocyclyl, or a nitrogen protecting group. In some embodiments, $R^2$ is optionally substituted $C_1$-$C_{20}$ alkyl, optionally substituted $C_1$-$C_{20}$ heteroalkyl, optionally substituted $C_3$-$C_{14}$ carbocyclyl, optionally substituted 3- to 14-membered heterocyclyl, or a nitrogen protecting group. In certain embodiments, $R^2$ is optionally substituted $C_1$-$C_{10}$ alkyl, optionally substituted $C_1$-$C_{10}$ heteroalkyl, optionally substituted $C_3$-$C_{14}$ carbocyclyl, optionally substituted 3- to 14-membered heterocyclyl, or a nitrogen protecting group.

In some embodiments, $R^2$ is —H or a nitrogen protecting group. In certain embodiments, $R^2$ is —H. In some embodiments, $R^2$ is not —H. In certain embodiments, $R^2$ is a nitrogen protecting group. In certain embodiments, the nitrogen protecting group is Bn, Boc, Cbz, Fmoc, trifluoroacetyl, triphenylmethyl, acetyl, or Ts.

In certain embodiments, $R^2$ is optionally substituted $C_1$-$C_{10}$ alkyl or optionally substituted $C_1$-$C_{10}$ heteroalkyl. In some embodiments, $R^2$ is optionally substituted $C_1$-$C_{10}$ alkyl. In certain embodiments, $R^2$ is unsubstituted $C_1$-$C_{10}$ alkyl. In some embodiments, $R^2$ is substituted $C_1$-$C_{10}$ alkyl. In certain embodiments, $R^2$ is optionally substituted $C_1$-$C_6$ alkyl. In some embodiments, $R^2$ is unsubstituted $C_1$-$C_6$ alkyl. In certain embodiments, $R^2$ is substituted $C_1$-$C_6$ alkyl. In some embodiments, $R^2$ is methyl, ethyl, propyl, butyl, pentyl, or hexyl. In certain embodiments, $R^2$ is methyl, ethyl, propyl, or butyl. In some embodiments, $R^2$ is methyl, ethyl, or propyl. In certain embodiments, $R^2$ is propyl. In some embodiments, $R^2$ is -Et. In certain embodiments, $R^2$ is -Me.

In some embodiments, $R^2$ is optionally substituted $C_1$-$C_{10}$ heteroalkyl. In certain embodiments, $R^2$ is unsubstituted $C_1$-$C_{10}$ heteroalkyl. In some embodiments, $R^2$ is substituted $C_1$-$C_{10}$ heteroalkyl. In certain embodiments, $R^2$ is optionally substituted $C_1$-$C_6$ heteroalkyl. In some embodiments, $R^2$ is unsubstituted $C_1$-$C_6$ heteroalkyl. In certain embodiments, $R^2$ is substituted $C_1$-$C_6$ heteroalkyl. In some embodiments, $R^2$ is optionally substituted heteroalkyl comprising one or more nitrogen atoms. In some embodiments, $R^2$ is optionally substituted $C_1$-$C_{10}$ heteroalkyl comprising one or more nitrogen atoms. In some embodiments, $R^2$ is optionally substituted $C_1$-$C_6$ heteroalkyl comprising one or more nitrogen atoms. In certain embodiments, $R^2$ is

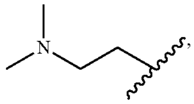,
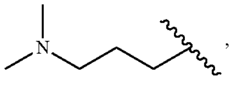,
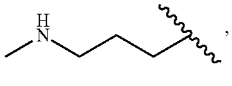,
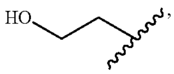,
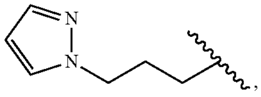,
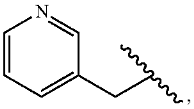,
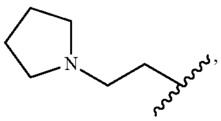,
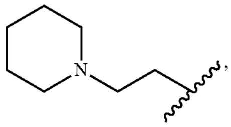,
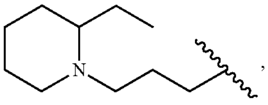,
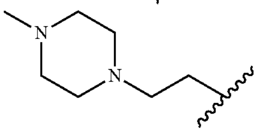,
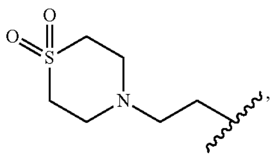,
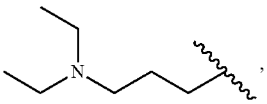,
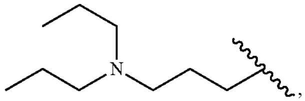,
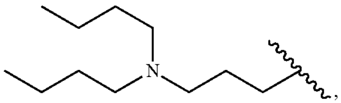, -continued

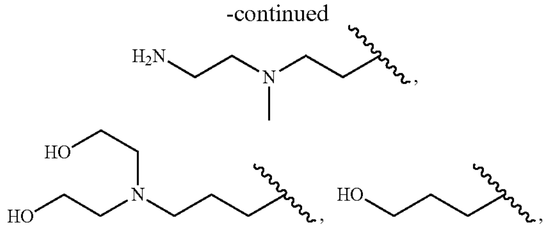

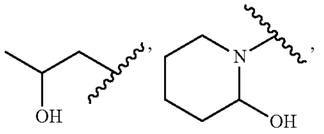

or

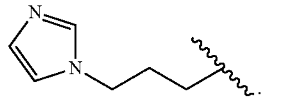

In certain embodiments, $R^2$ is optionally substituted heteroalkyl comprising one or more N atoms substituted with

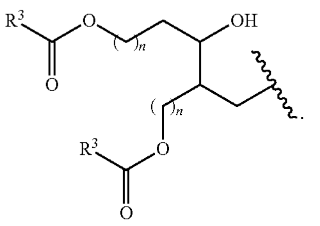

In some embodiments, $R^2$ is

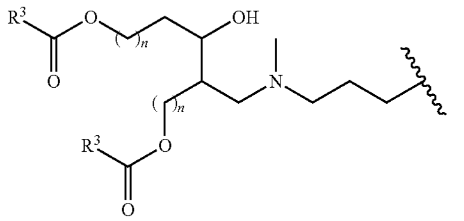

or

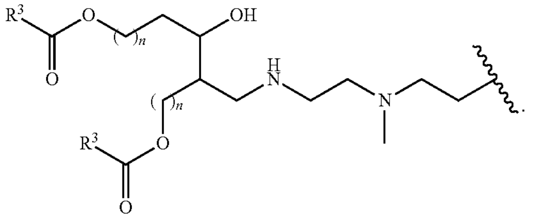

In certain embodiments, $R^2$ is optionally substituted aryl. In some embodiments, $R^2$ is optionally substituted $C_6$-$C_{14}$ aryl. In some embodiments, $R^2$ is substituted $C_6$-$C_{14}$ aryl. In some embodiments, $R^2$ is unsubstituted $C_6$-$C_{14}$ aryl. In certain embodiments, $R^2$ is optionally substituted $C_6$-$C_{10}$ aryl. In certain embodiments, $R^2$ is substituted $C_6$-$C_{10}$ aryl. In certain embodiments, $R^2$ is unsubstituted $C_6$-$C_{10}$ aryl. In some embodiments, $R^2$ is optionally substituted phenyl or optionally substituted naphthyl. In certain embodiments, $R^2$ is optionally substituted phenyl. In some embodiments, $R^2$ is optionally substituted naphthyl.

In certain embodiments, $R^2$ is optionally substituted heteroaryl. In some embodiments, $R^2$ is optionally substituted 5- to 14-membered heteroaryl. In some embodiments, $R^2$ is substituted 5- to 14-membered heteroaryl. In some embodiments, $R^2$ is unsubstituted 5- to 14-membered heteroaryl. In some embodiments, $R^2$ is optionally substituted 5- to 10-membered heteroaryl. In some embodiments, $R^2$ is substituted 5- to 10-membered heteroaryl. In some embodiments, $R^2$ is unsubstituted 5- to 10-membered heteroaryl.

In some embodiments, $R^2$ is optionally substituted carbocyclyl. In some embodiments, $R^2$ is optionally substituted $C_3$-$C_{14}$ carbocyclyl. In some embodiments, $R^2$ is substituted $C_3$-$C_{14}$ carbocyclyl. In some embodiments, $R^2$ is unsubstituted $C_3$-$C_{14}$ carbocyclyl. In some embodiments, $R^2$ is optionally substituted $C_3$-$C_8$ carbocyclyl. In some embodiments, $R^2$ is substituted $C_3$-$C_8$ carbocyclyl. In some embodiments, $R^2$ is unsubstituted $C_3$-$C_8$ carbocyclyl. In some embodiments, $R^2$ is $C_3$-$C_8$ carbocyclyl substituted with optionally substituted alkyl, optionally substituted heteroalkyl, optionally substituted cycloalkyl, optionally substituted heterocyclyl, optionally substituted heteroaryl, or optionally substituted aryl.

In some embodiments, $R^2$ is optionally substituted heterocyclyl. In some embodiments. $R^2$ is optionally substituted 3- to 14-membered heterocyclyl. In some embodiments, $R^2$ is substituted 3- to 14-membered heterocyclyl. In some embodiments, $R^2$ is unsubstituted 3- to 14-membered heterocyclyl. In some embodiments, $R^2$ is optionally substituted 3- to 8-membered heterocyclyl. In some embodiments, $R^2$ is substituted 3- to 8-membered heterocyclyl. In some embodiments, $R^2$ is unsubstituted 3- to 8-membered heterocyclyl. In some embodiments, $R^2$ is 3- to 8-membered heterocyclyl substituted with optionally substituted alkyl, optionally substituted heteroalkyl, optionally substituted cycloalkyl, optionally substituted heterocyclyl, optionally substituted heteroaryl, or optionally substituted aryl.

In certain embodiments, $R^1$ and $R^2$ are joined together with the intervening atoms to form an optionally substituted heterocyclyl. In some embodiments, $R^1$ and $R^2$ are joined together with the intervening atoms to form a substituted heterocyclyl. In certain embodiments, $R^1$ and $R^2$ are joined together with the intervening atoms to form an unsubstituted heterocyclyl.

In some embodiments, $R^1$ and $R^2$ are joined together with the intervening atoms to form an optionally substituted heterocyclyl comprising one or two nitrogen atoms. In certain embodiments, $R^1$ and $R^2$ are joined together with the intervening atoms to form an optionally substituted heterocyclyl comprising one nitrogen atoms. In some embodiments, $R^1$ and $R^2$ are joined together with the intervening atoms to form an optionally substituted heterocyclyl comprising two nitrogen atoms. In certain embodiments, $R^1$ and $R^2$ are joined together with the intervening atoms to form an optionally substituted heterocyclyl comprising two or more nitrogen atoms.

In some embodiments, —$NR^1R^2$ is

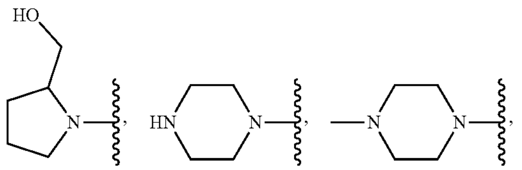

-continued

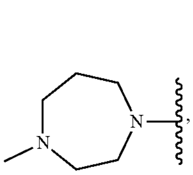, 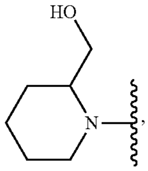, or

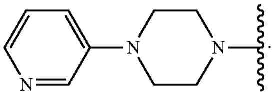.

In certain embodiments, $R^1$ and $R^2$ are joined together with the intervening atoms to form an optionally substituted heterocyclyl comprising two or more N atoms substituted with

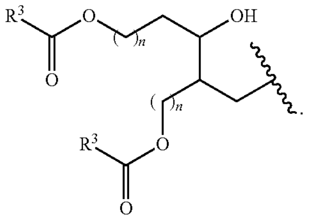.

In some embodiments, $R^1$ and $R^2$ are joined together with the intervening atoms to form an optionally substituted heterocyclyl comprising two N atoms substituted with

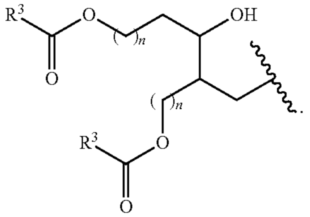.

As defined herein, each $R^3$ independently is optionally substituted $C_6$-$C_{25}$ aliphatic. In some embodiments, $R^3$ is optionally substituted $C_6$-$C_{25}$ alkyl, optionally substituted $C_6$-$C_{25}$ alkenyl, or optionally substituted $C_6$-$C_{25}$ alkynyl. In certain embodiments, $R^3$ is optionally substituted $C_6$-$C_{25}$ alkyl or optionally substituted $C_6$-$C_{25}$ alkenyl. In some embodiments, $R^3$ is optionally substituted $C_6$-$C_{25}$ alkyl or optionally substituted $C_6$-$C_{25}$ alkynyl. In certain embodiments, $R^3$ is optionally substituted $C_6$-$C_{25}$ alkenyl or optionally substituted $C_6$-$C_{25}$ alkynyl. In some embodiments, $R^3$ is substituted $C_6$-$C_{25}$ alkyl, substituted $C_6$-$C_{25}$ alkenyl, or substituted $C_6$-$C_{25}$ alkynyl. In certain embodiments, $R^3$ is substituted $C_6$-$C_{25}$ alkyl or substituted $C_6$-$C_{25}$ alkenyl. In some embodiments, $R^3$ is substituted $C_6$-$C_{25}$ alkyl or substituted $C_6$-$C_{25}$ alkynyl. In certain embodiments, $R^3$ is substituted $C_6$-$C_{25}$ alkenyl or substituted $C_6$-$C_{25}$ alkynyl. In some embodiments, $R^3$ is unsubstituted $C_6$-$C_{25}$ alkyl, unsubstituted $C_6$-$C_{25}$ alkenyl, or unsubstituted $C_6$-$C_{25}$ alkynyl. In certain embodiments, $R^3$ is unsubstituted $C_6$-$C_{25}$ alkyl or unsubstituted $C_6$-$C_{25}$ alkenyl. In some embodiments, $R^3$ is unsubstituted $C_6$-$C_{25}$ alkyl or unsubstituted $C_6$-$C_{25}$ alkynyl. In certain embodiments, $R^3$ is unsubstituted $C_6$-$C_{25}$ alkenyl or unsubstituted $C_6$-$C_{25}$ alkynyl. In each of the foregoing embodiments, the aliphatic, alkyl, alkenyl, or alkynyl group may have 6-12 carbon atoms, 12-18 carbon atoms, or 18-25 carbon atoms.

In some embodiments, $R^3$ is optionally substituted $C_6$-$C_{25}$ alkyl. In certain embodiments, $R^3$ is substituted $C_6$-$C_{25}$ alkyl. In some embodiments, $R^3$ is unsubstituted $C_6$-$C_{25}$ alkyl. In certain embodiments, $R^3$ is

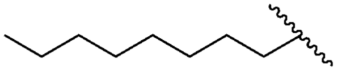,

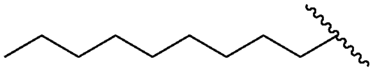,

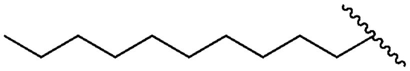,

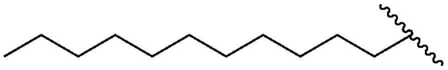,

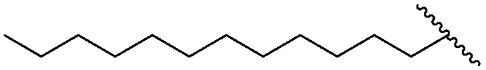,

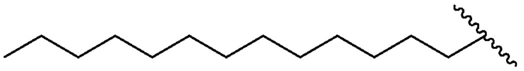,

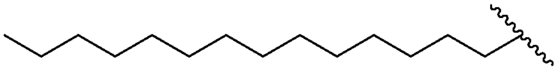,

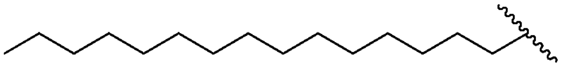,

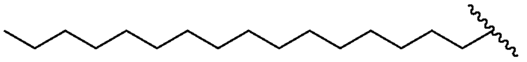, or

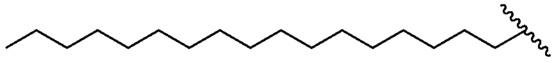.

In certain embodiments, $R^3$ is optionally substituted $C_6$-$C_{25}$ alkenyl. In some embodiments, $R^3$ is substituted $C_6$-$C_{25}$ alkenyl. In certain embodiments, $R^3$ is unsubstituted $C_6$-$C_2$, alkenyl. In some embodiments, $R^3$ comprises one or more double bonds. In certain embodiments, $R^3$ comprises two or more double bonds. In some embodiments, $R^3$ comprises three or more double bonds. In certain embodiments, $R^3$ comprises one, two, or three double bonds. In some embodiments, $R^3$ comprises one double bond. In certain embodiments, $R^3$ comprises two double bonds. In some embodiments, $R^3$ comprises three double bonds. In certain embodiments, $R^3$ is

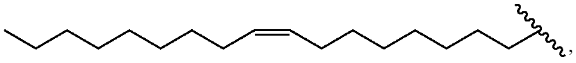,

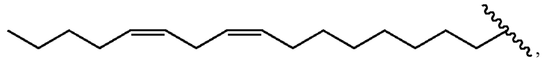, or

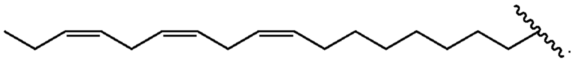.

In some embodiments, $R^3$ is optionally substituted $C_6$-$C_{25}$ alkynyl. In some embodiments, $R^3$ is substituted $C_6$-$C_{25}$ alkynyl. In certain embodiments, $R^3$ is unsubstituted $C_6$-$C_{25}$alkynyl. In some embodiments, $R^3$ comprises one or more triple bonds. In certain embodiments, $R^3$ comprises two or more triple bonds. In some embodiments, $R^3$ comprises three or more triple bonds. In certain embodiments, $R^3$ comprises one, two, or three triple bonds. In some embodiments, $R^3$ comprises one triple bond. In certain embodiments, $R^3$ comprises two triple bonds. In some embodiments, $R^3$ comprises three triple bonds.

As defined herein, each n independently is 0-15, inclusive. In some embodiments, each n is independently 1-10, inclusive. In certain embodiments, each n is independently 1-8, inclusive. In some embodiments, each n is independently 1-6, inclusive. In certain embodiments, each n is different. In certain embodiments, each n is different, and n is 1-10, inclusive. In certain embodiments, each n is different, and n is 1-8, inclusive. In some embodiments, each n is different, and n is 1-6, inclusive. In some embodiments, n is 1. In certain embodiments, n is 2. In some embodiments, n is 3. In certain embodiments, n is 4. In some embodiments, n is 5. In certain embodiments, n is 6. In some embodiments, n is 7. In certain embodiments, n is 8. In some embodiments, n is 9. In certain embodiments, n is 10. In some embodiments, n is 11. In certain embodiments, n is 12. In some embodiments, n is 13. In certain embodiments, n is 14. In some embodiments, n is 15. In some embodiments, each n is the same. In certain embodiments, each n is the same, and n is 1-10, inclusive. In certain embodiments, each n is the same, and n is 1-8, inclusive. In some embodiments, each n is the same, and n is 1-6, inclusive. In some embodiments, each n is 1. In certain embodiments, each n is 2. In some embodiments, each n is 3. In certain embodiments, each n is 4. In some embodiments, each n is 5. In certain embodiments, each n is 6. In some embodiments, each n is 7. In certain embodiments, each n is 8. In some embodiments, each n is 9. In certain embodiments, each n is 10. In some embodiments, each n is 11. In certain embodiments, each n is 12. In some embodiments, each n is 13. In certain embodiments, each n is 14. In some embodiments, each n is 15.

In some embodiments, the compound of Formula (III) is a linker compound with lipid tail provided in FIG. 2.

EXAMPLES

In order that the present disclosure may be more fully understood, the following examples are set forth. The synthetic and biological examples described in this application are offered to illustrate the compounds, compositions, and methods provided herein and are not to be construed in any way as limiting in their scope.

In vivo delivery of messenger RNA is a rapidly expanding field with the promise to treat and prevent a wide variety of genetic, infectious, or other diseases.[1-17] Notably, intramuscularly delivered lipid nanoparticle (LNP)-based mRNA vaccines have showed excellent efficacy against the SARS-CoV-2 virus driving the COVID19 pandemic.[13,14] Numerous other therapies including vaccines against cancer[6,18-20] and non-SARS-CoV-2 infectious diseases,[21-27] protein replacement therapy,[28] and gene editing[15] are in various stages of clinical trials or preclinical investigation.

The respiratory epithelium is a target for mRNA delivery for a range of these applications. Protein replacement therapy and/or gene editing could treat single-gene disorders such as cystic fibrosis (CF),[29,29,30] primary ciliary dyskinesia (PCD),[31,32] or alpha-1 antitrypsin deficiency (AATD),[33] mRNA-based delivery of cytokines or other inflammatory mediators is also a promising strategy for treating asthma,[34,35] For vaccines, in addition to inducing systemic immunity, mucosal vaccination induces a localized mucosal immune response that is particularly promising for vaccines against respiratory infections.[34-36] While nasal spray-based vaccines may provide some benefits of pulmonary vaccination, antigen delivery to the deep lung may further enhance mucosal or even systemic immunity.[46,47]

The two primary approaches to lung mRNA delivery are intravenous (IV) and topical delivery of nanoparticles (NPs).[48-51] IV lung targeting formulations typically preferentially deliver cargo to the endothelium rather than the epithelium[48,49]. However, the epithelium is the therapeutically relevant cellular target for the treatment of many diseases, including CF. PCD, and asthma.[52] Topical delivery of mRNA to the epithelium of the lung has been reported with both nebulized hyperbranched poly(beta amino ester) (hPBAE) based nanoparticless[53] and lipid nanoparticles (LNPs).[54] While polymer-based delivery systems are promising for inhaled delivery of mRNA, LNPs remain the more clinically advanced method of delivery.[17] However, a recent clinical trial for CF gene therapy using nebulized mRNA LNPs did not show notable efficacy, suggesting that further improvements are necessary for this delivery modality.[55]

The difficulty of LNP-based nebulized mRNA delivery is related to several nebulization- and lung-specific barriers. First, nebulization itself induces powerful shear forces that can disrupt nanoparticle structure and induce aggregation.[54] Second, transfecting the lung can be difficult, in particular because access to bronchial epithelial cells involves penetration of a mucus layer that is a steric and chemical barrier to diffusion.[56-59] This barrier is particularly difficult to penetrate in muco-obstructive lung diseases such as asthma and CF.[56-58] Furthermore, the lung epithelium itself is a challenging target because NP uptake is more efficient on the basolateral side of polarized lung epithelial cells, but the basolateral side can be rendered inaccessible to apically delivered LNPs by tight junctions.[52-60] Lastly, there is a NP challenge of endosomal escape and mRNA release from the nanoformulation.[1]

These factors are addressed by first optimizing the LNP formulation. An mRNA-LNP contains 5 components: an ionizable lipid (the component with the most chemical diversity), cholesterol, a helper lipid, a PEG-lipid, and mRNA.[1,3,61] To improve nebulized delivery, screened a range of component ratios, or formulations, were screened to identify one with maximal stability to nebulization. This stability to nebulization was further enhanced by rational design of buffer conditions and excipients.

To avoid toxicity due to accumulation of ionizable lipids in target organs, incorporation of biodegradable ester bonds into the structures of ionizable lipids have been explored, and shown to be successful at mitigating toxicity in target organs. The studies provided herein focused on creating a library of biodegradable ionizable lipids for mRNA encapsulation into LNPs and delivery to the lungs. Lipids were identified that were particularly effective for nebulized delivery of mRNA to the lung and nasal epithelium. A subset of lipids were effective at delivering mRNA to the lung endothelium upon IV administration. These lipids will be useful for the delivery of therapeutic mRNA in the form of LNPs to treat diseases affecting the lungs such as cystic fibrosis, sepsis, and lung cancer.

To date lung mRNA delivery has not generally been focused on developing lipids for apical delivery to the lung epithelium in particular. Instead, lipids have been adapted from IV or intramuscular use[54] or from DNA delivery formulations.[62] Herein an in vitro mRNA delivery assay was developed based on primary airway cell air-liquid interface (ALI) cultures to screen for lung delivery. While in vitro evaluation of novel lipids for RNA delivery can be a poor predictor of in vivo delivery, screens using primary cells perform better than immortalized cells.[63,64] It was hypothesized that primary fully differentiated, air-liquid interface (ALI) cultures would provide an improved in vitro cellular model for in vivo lung delivery, as they retain key qualities of the lung: mucus secretion. mRNA delivery was therefore screened in ALI cultures, showing that the top performing formulation did indeed perform excellently in vivo.

Two candidates, IR-117-17 and IR-19-Py, when formulated using the nebulization optimized formulation and delivered with nebulization optimized buffer and excipient, significantly outperform state-of-the-art mRNA delivery formulations to the lung and nose respectively. Nebulized IR-117-17 LNPs had a 300-fold improvement in lung mRNA delivery over the top previously described LNP,[54] and a twofold improvement over a previously identified top polymeric NP (PNP).[53]

Example 1: Formulation Optimization of LNPs for Nebulized Delivery Using DOE

Figure 17A:
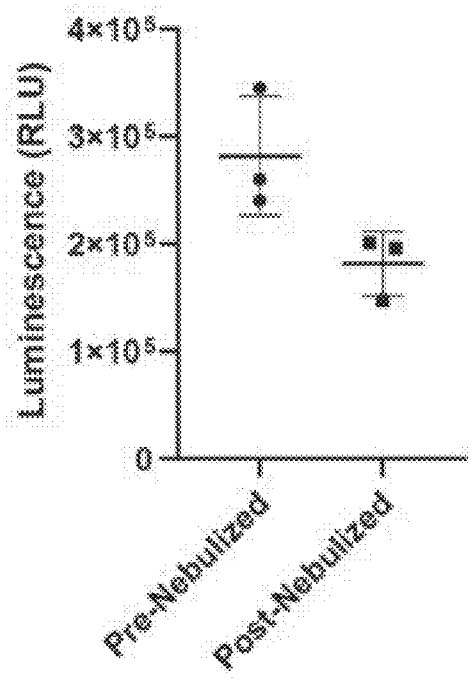
FIGS. 17A-17C show comparison of C12-200 LNP: transfection efficiency in A549 cells (Average±SD, well replicates shown) (FIG. 17A), mRNA encapsulation efficiency (Average±SD, n=3 repeated measurements) (FIG. 17B), and size as measured by DLS, before and after nebulization (FIG. 17C).
Figure 17B:
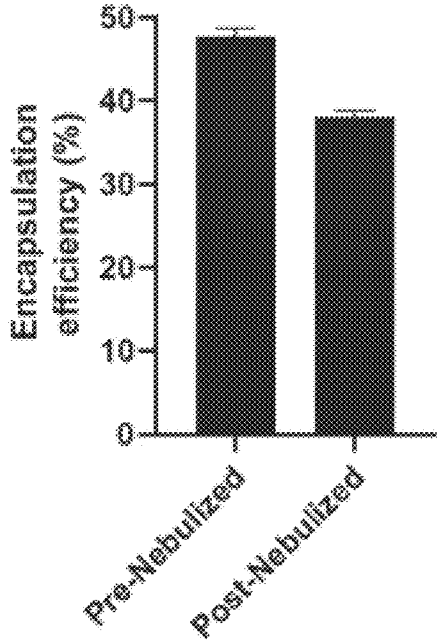
Figure 17C:
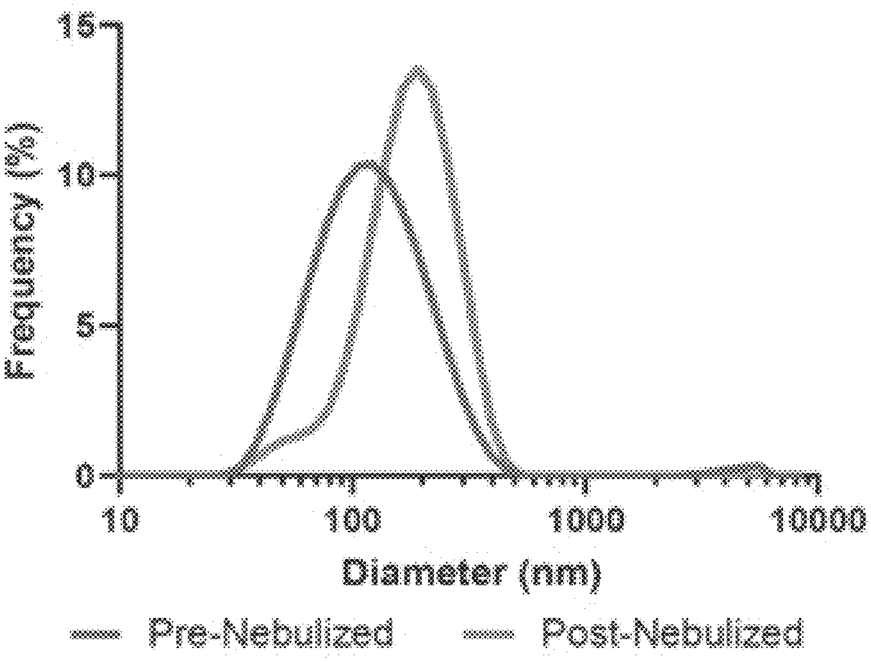

Given the vast chemical space available for LNP formulations and the material-intensive nature of nebulization experiments, a design-of-experiment (DOE) approach[68,69] was used to optimize LNPs for stability to the harsh conditions of nebulization. Initial experiments with a liver-optimized C12-200 based LNP formulation[68] showed that LNPs collected after nebulization using an Aeroneb vibrating mesh nebulizer had reduced in vitro transfection ability in A549 cells, loss of mRNA encapsulation, and increased size (FIGS. 17A-17C). Using these three measurements as readouts for LNP structural disruption post nebulization, formulations with maximal post nebulization stability were screened for.

Figure 18:
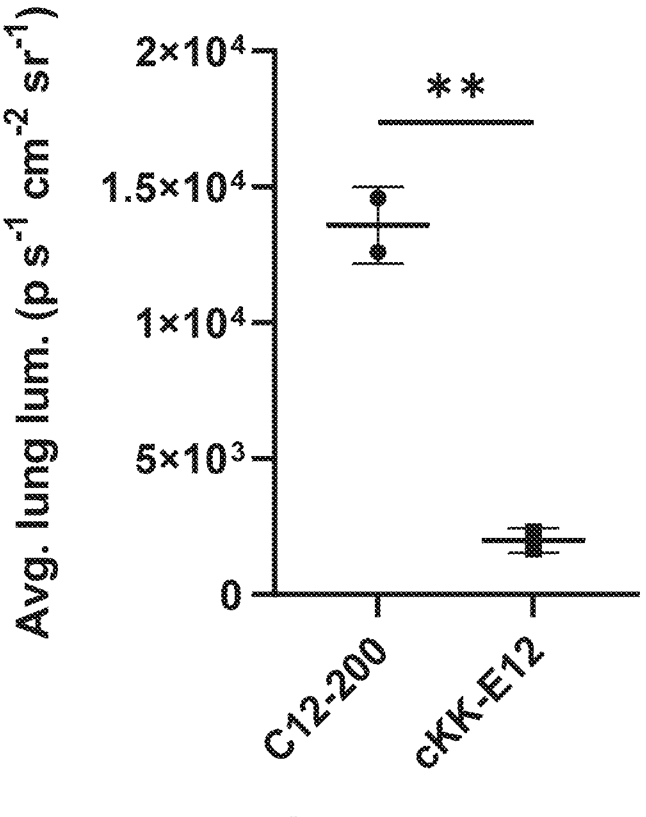
FIG. 18 shows a Comparison of bioluminescence in lung 6 h after nebulized administration of liver-targeting C12-200 LNP formulation and lung-targeting cKK-E12 LNP formulation delivering 0.5 mg FFL mRNA.[10,89] Two-tailed Student's t-test. Average±SD. **p=0.0081, biological replicates shown.

To identify a starting LNP delivery baseline, an in vivo pilot experiment was performed comparing two LNP formulations previously developed for systemic delivery of mRNA via i.v. administration. As previously described for delivery of PNPs, 0.5 mg of firefly luciferase (FFL) mRNA was delivered to mice via nebulization to a whole-body exposure chamber, and luminescence was measured in excised lungs 6 h after delivery.[53] It was found that the C12-200 based liver-targeting formulation resulted in a higher lung luminescence than the cKK-E12 based lung-targeting formulation (FIG. 18)[70] and the C12-200 based formulation was therefore selected as the central formulation for screening. This result also showed that LNPs developed for lung-specific i.v. administration are not necessarily superior for nebulized delivery of mRNA to the lung epithelium.

Figure 10A:
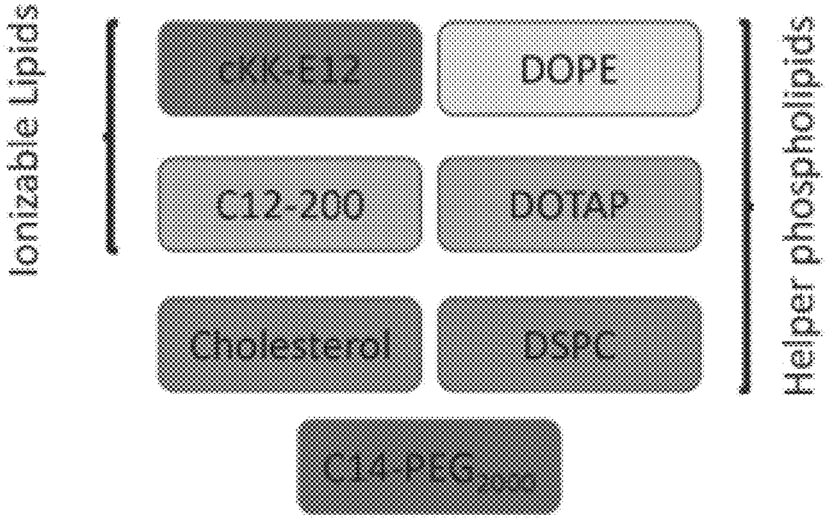
FIG. 10A shows the molar ratios of the ionizable lipid, helper phospholipid, and cholesterol were varied along with the identity of the ionizable lipid and phospholipid. FIG. OB shows the molar ratios of the resultant 19 LNP formulations with T1-1 representing the original formulation previously developed in our lab around which the formulation design is centered.
Figure 10B:
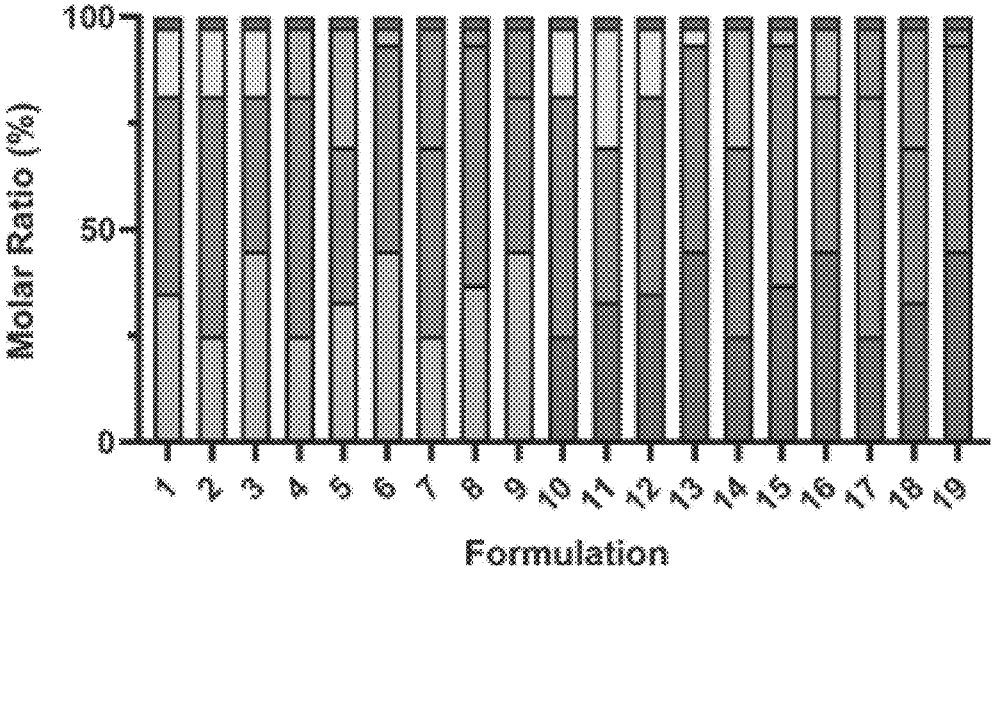
FIG. 10C shows in vitro transfection efficiencies of formulations before and after nebulization in A549 cells, 50 ng of FFL mRNA was delivered for pre-nebulized formulations and volume-matched doses of post-nebulized formulations. Average±SD, n=3.
FIG. 10D shows encapsulation efficiency of FFL mRNA before and after nebulization. Average±SEM, n=3 technical replicates.
FIG. 10E shows lung luminescence 6 h after nebulized delivery of 0.5 mg FFL mRNA to mice demonstrating T1-5 significantly increasing luminescent signal compared to the original T1-5 formulation. Representative images of lungs imaged by IVIS are shown. $*p<0.05$, $p<0.015$, $**p<0.0001$, one-way ANOVA, average±SD, biological replicates shown.

For the mixture-constrained DOE screen, the molar ratios of the ionizable lipid, helper phospholipid, and cholesterol were varied, while also varying the identity of the ionizable lipid and helper phospholipid (FIG. 10A), cKK-E12 was included as a second ionizable lipid in the screen given that the ionizable lipid identity has been shown to significantly impact LNP transfection efficiencies. Additionally, helper phospholipids DSPC and DOTAP were included to test the effect of saturated alkyl chains and positive charge respectively on LNP stability during nebulization. In total, 19 formulations were prepared, including the initial liver-targeting C12-200 formulation (T1-1), encapsulating FFL mRNA via microfluidic mixing for evaluation (FIG. 10B).

Figure 10C:
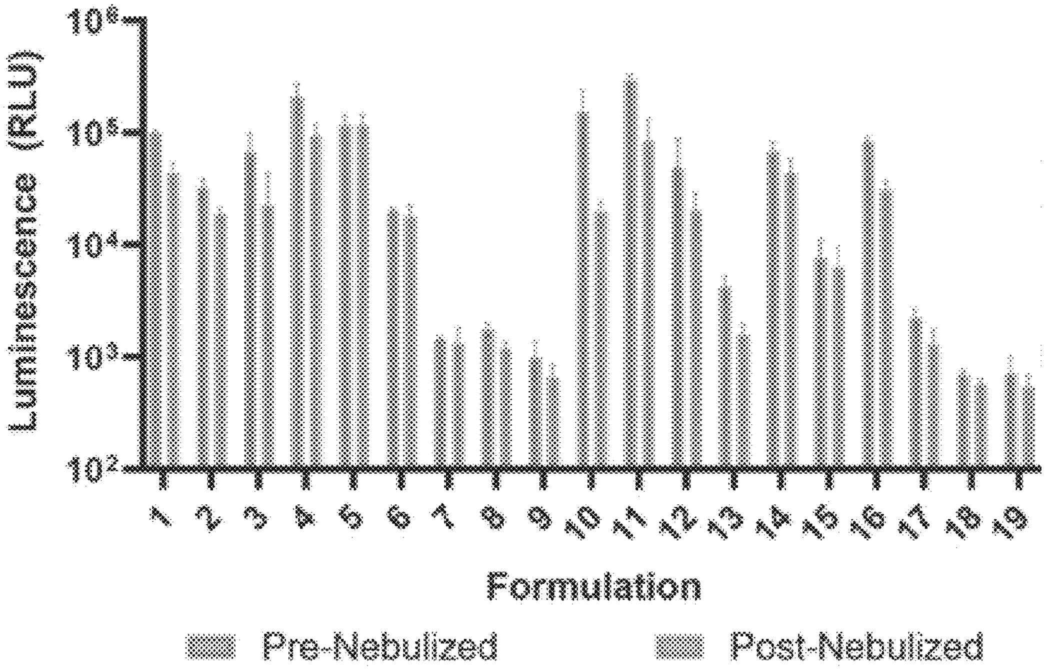
Figure 10D:
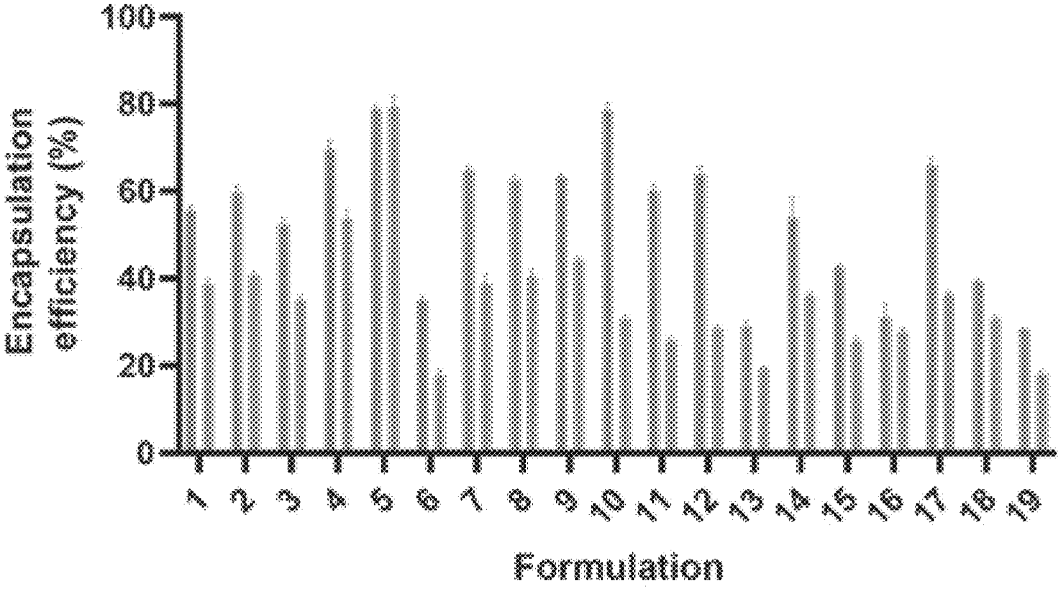
Figure 19:
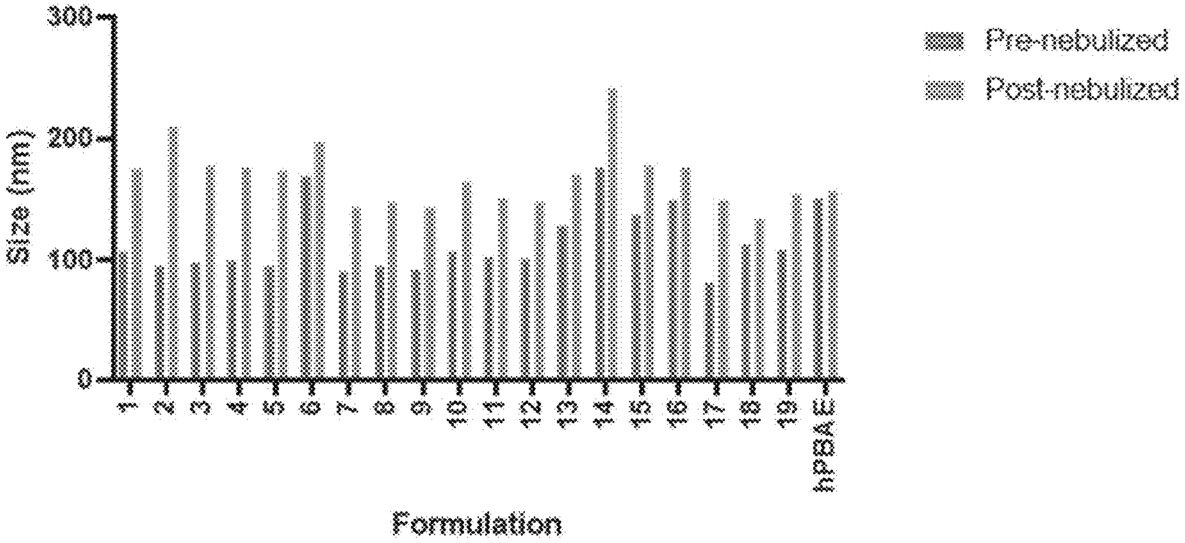
FIG. 19 shows DLS measurements of nanoparticle size before and after nebulization for all 19 formulations in this screen and polymeric hPBAE nanoparticles.
Figure 20:
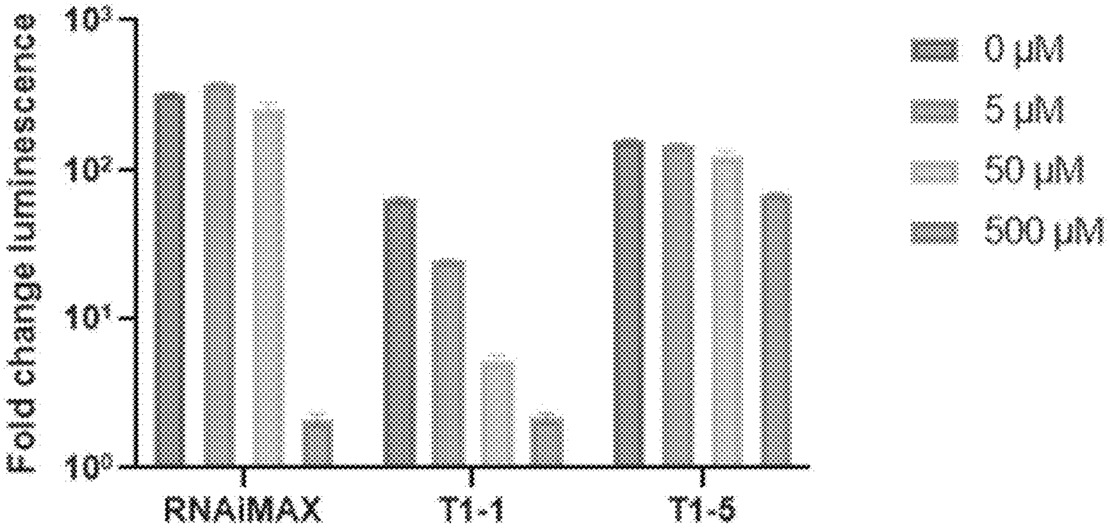
FIG. 20 shows in vitro transfection efficiency in A549 cells transfected in the presence of increasing concentrations of pulmonary surfactant POPG. Luminescence values were normalized to PBS treated samples with corresponding concentrations of POPG. Average±SD, n=3.

The formulations were then evaluated for in vitro transfection ability, encapsulation efficiency, and size before and after nebulization (FIGS. 10C-10D, 19). Of the 19, one formulation (T1-5) was identified with high transfection efficiency in A549 cells both before and after nebulization and no loss in encapsulation efficiency due to nebulization (FIG. 10C). Like the other formulations, T1-5 showed a substantial post-nebulization size increase (FIG. 19), but was nevertheless considered a promising formulation. It was also tested whether POPG, a primary component of pulmonary surfactant that has been reported to destabilize liposomes, inhibited transfection. POPG inhibited both commercial lipofection reagent RNAiMAX and the original formulation T1-1 in a concentration dependent manner, but formulation T1-5 showed minimal loss in transfection efficiency even at concentrations similar to the physiologically highest levels found in alveolar spaces[71] (FIG. 20).

Figure 10E:
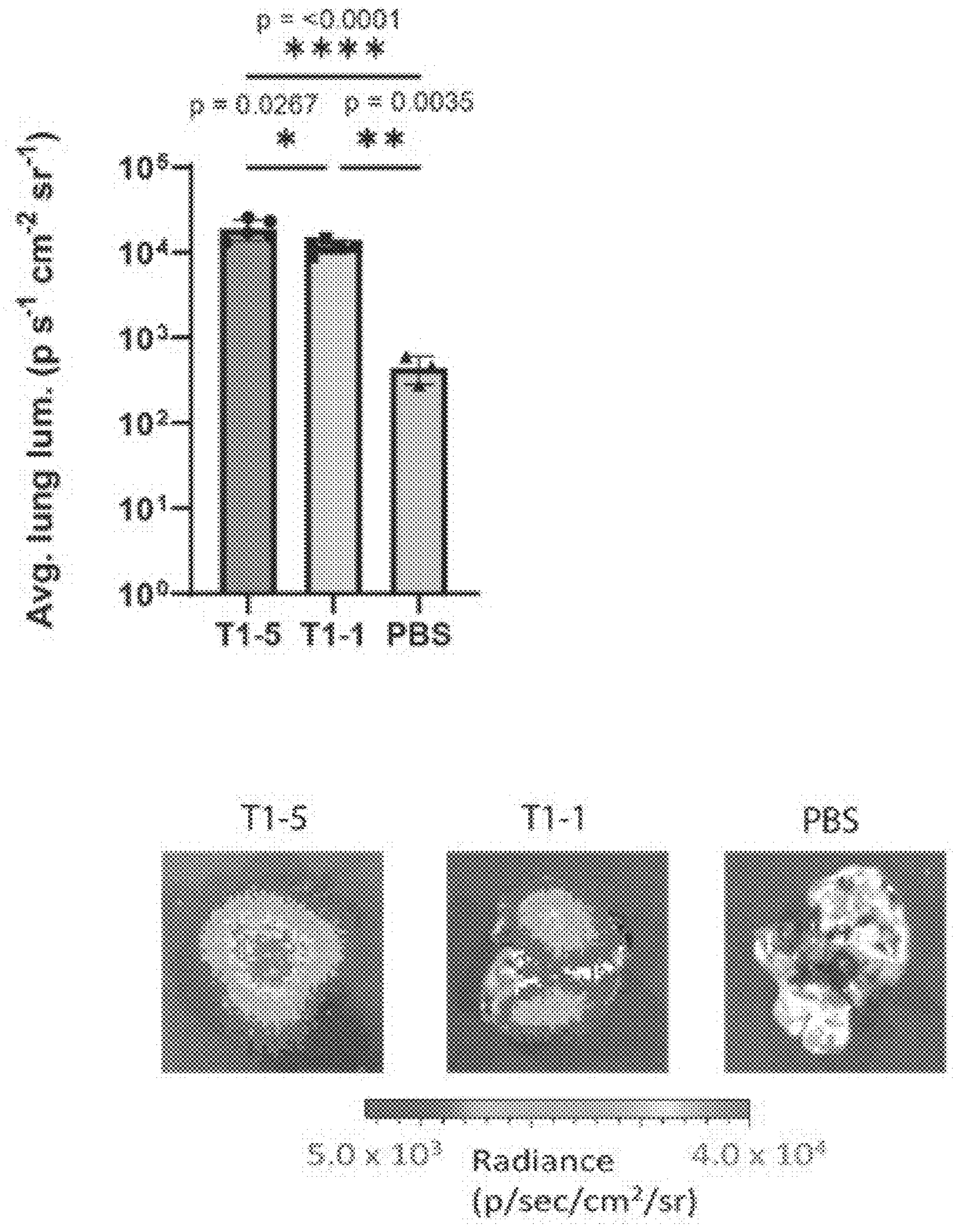

Based on these promising characteristics of T1-5, its in vivo performance was evaluated in delivering FFL mRNA to mice via nebulization. Luminescence was significantly higher in lungs transfected with T1-5 ($1.88\times10^4$ p $s^{-1}$ $cm^{-2}$ $sr^{-1}$) compared to T1-1 ($1.18\times10^4$ p $s^{-1}$ $cm^{-2}$ $sr^{-1}$) (FIG. 10E). Although promising, the potential of the T1-5 formulation was hindered by its increase in size following nebulization. Such an increase was observed for all the LNPs tested but not for a hPBAE PNP that was the first published, nebulized mRNA delivery formulation for the lungs (FIG. 19).[53] This nebulization induced aggregation of LNPs suggested further opportunities to improve LNP stability during nebulization and potentially improve in vivo efficacy.

Figure 11A:
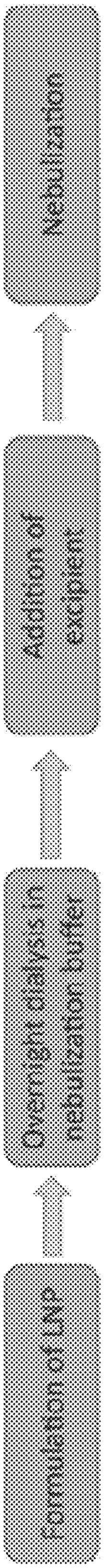
FIG. 11A shows a schematic of workflow for evaluating addition of excipients and buffer modifications to improve LNP nebulization.
Figure 11B:
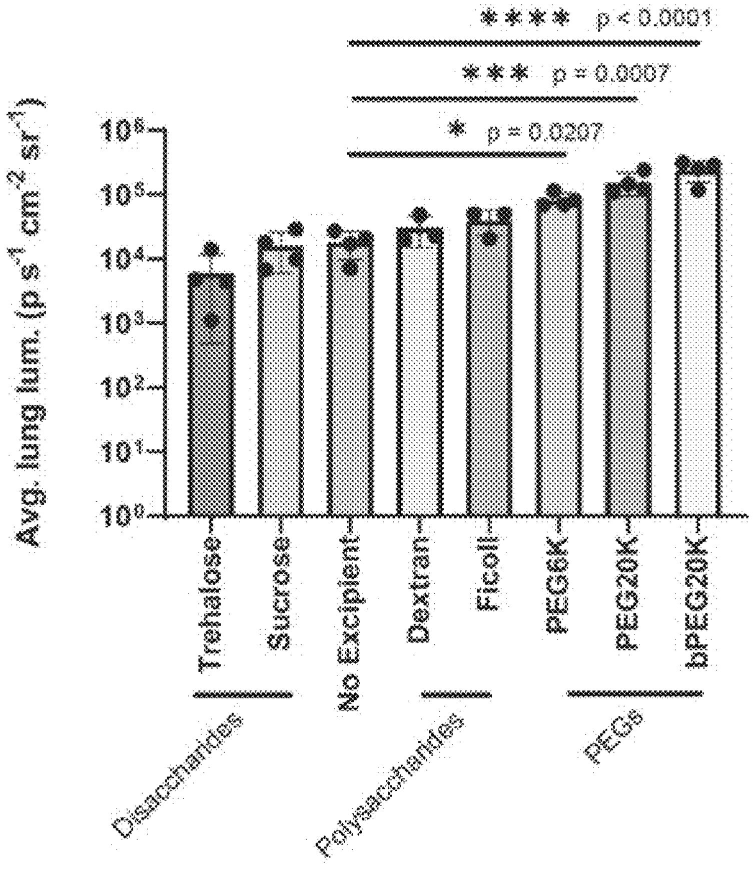
FIGS. 11B-D show bioluminescence in lung 6 h after nebulized administration of T1-5 with (FIG. 11B) PEG excipients showing significant increase over no excipients, (FIG. 11C) nose-only exposure to aerosols generated from nebulized T1-5 and bPEG20K excipient increasing luminescence compared to whole-body exposure, and (FIG. 11D) overnight dialysis of T1-5 into 100 mM NaAc buffer, pH 5.2, improving luminescent signal over dialysis into 0.9% saline or PBS. $*p<0.05$, $*p<0.001$, $p<0.0001$, one-way ANOVA for B) and D), two-tailed, unpaired t-test for C), average±SD, biological replicates shown.
Figure 21:
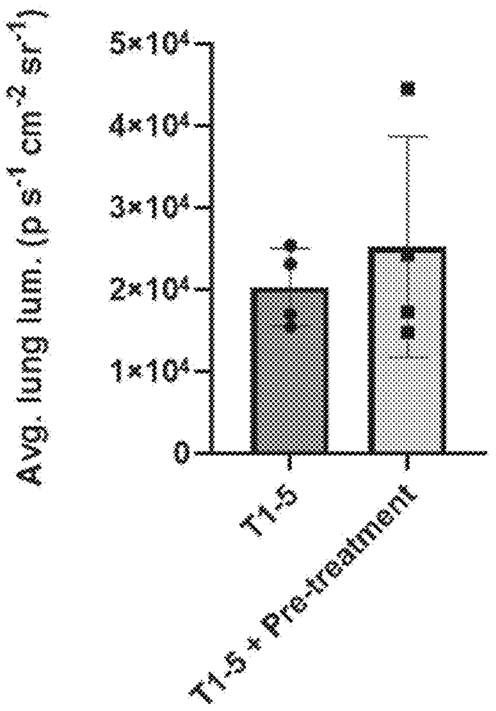
FIG. 21 shows a comparison of luminescence 6 h after nebulized delivery of 0.5 mg FFL mRNA with T1-5 in lungs either without or with nebulized pre-treatment of 2% bPEG20K solution. For pre-treatment, mice were nebulized 3 mL of 2% bPEG20K solution immediately prior to nebulized delivery of T1-5. Average t SD, biological replicates shown.

Example 2: Excipients and Buffer Modifications for Improved LNP Stability and Delivery A rationally designed screen of stabilizing excipients and buffer modifications was performed (FIG. 11A). To evaluate the effects of additional excipients on nebulized delivery efficiency, excipients were added to T1-5 LNP formulations following overnight dialysis in PBS and immediately before nebulization. Based on previous data demonstrating that the addition of disaccharide lyoprotectants such as trehalose and sucrose helped to prevent LNP aggregation and loss of LNP efficacy following multiple freeze-thaw cycles,[72] these two sugars were evaluated in our LNP formulation at a final concentration of 20% (w/v) before nebulized delivery of the resultant LNP solution to mice. However, it was found that neither sugar improved the nebulized performance of T1-5 in mice when compared to T1-5 nebulized without any excipient (FIG. 11B). It was reasoned that addition of an inert hydrophilic polymeric excipient could provide steric hindrance between LNPs that could prevent LNP aggregation and improve nebulized LNP performance in vivo. Polysaccharides (Dextran and Ficoll) were evaluated, as well as linear (PEG6K and PEG20k) and branched (bPEG20K) PEGs by adding these polymers to the LNP formulation at a final concentration of 2% (w/v) before nebulizing. All polymers evaluated were able to improve the nebulized performance of T1-5 in mice, with all three PEGs significantly improving luminescence in the lung over T1-5 with no excipient (FIG. 11B), bPEG20K in particular led to a ~13-fold increase in lung luminescence when compared to T1-5 with no excipient. To evaluate whether bPEG20K improved in vivo performance of T1-5 due to changes in lung physiology upon exposure to bPEG20K, a solution of 2% bPEG20K without LNPs was nebulized to mice immediately followed by T1-5 LNPs without an excipient. Pre-treatment of the mice with the bPEG20K solution did not improve T1-5 performance compared to T1-5 delivered without pre-treatment (FIG. 21), suggesting that the effect of bPEG20K on in vivo nebulized performance is directly related to its presence in the nebulization formulation.

Figure 11C:
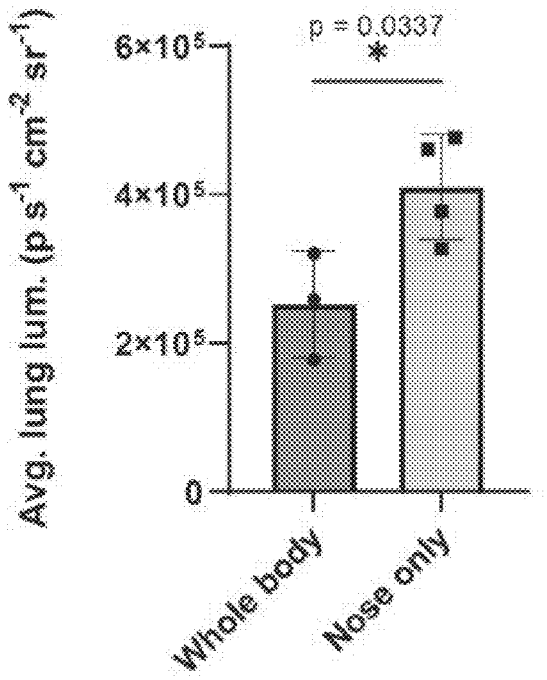

While performing nebulization experiments, mice would sometimes huddle together while in the whole-body chamber, which may lead to varied exposure to aerosol. To remove this potential issue. mRNA formulations were administered to mice that are restrained such that only their noses are exposed to a central chamber. Aerosol generated from the nebulizer is directed into this chamber via air flow. Using this nose-only exposure system, nebulized delivery of T1-5 with 2% bPEG20K leads to significantly higher lung luminescence when compared to the same formulation delivered in the whole-body exposure chamber (FIG. 11C). The nose-only exposure system was used for all subsequent experiments.

Figure 11D:
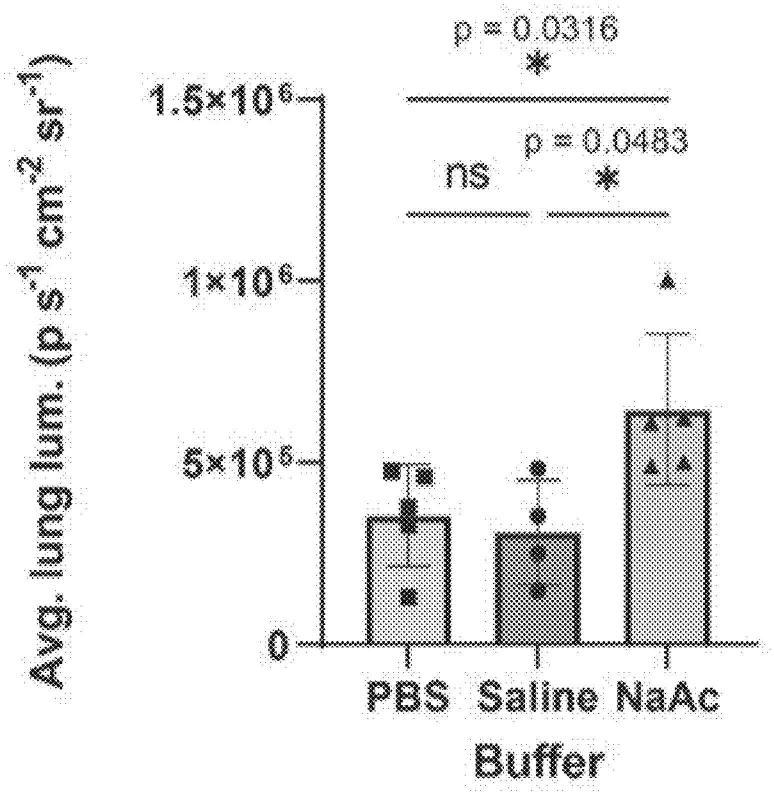

During the process of excipient evaluation, all nebulization experiments were performed in PBS. It was hypothesized that modifications to the LNP buffer may further improve the in vivo nebulized delivery efficacy of the T1-5 formulation with bPEG20K excipient. Two additional buffers were tested: 0.9% saline, pH 7.0, which has been previously explored in nebulized delivery of liposomal formulations,[73] and 100 mM sodium acetate (NaAc) at pH 5.2. It was reasoned that the slightly acidic NaAc buffer would protonate the ionizable lipids present in LNPs. This would lead both to tighter mRNA binding which could improve resistance to nebulization-based shear forces, and to a more positive surface charge that could reduce LNP aggregation via electrostatic repulsion. Additionally, 100 mM NaAc buffer has been used in the nebulized delivery of hPBAEs with no observed toxicity.[53] To evaluate the buffers, T1-5 LNPs were microfluidically mixed,[68] initially dialyzed into PBS before overnight dialysis in the selected buffer, and 2% bPEG20K excipient was added before nebulization to mice in the nose only exposure system. NaAc buffer, but not 0.9% saline, significantly improved nebulized delivery efficacy compared to PBS (FIG. 11D).

To test the hypothesis that addition of the bPEG20K stabilizing excipient and use of the NaAc buffer improved nebulized delivery of T1-5 through reduction of LNP aggregation during nebulization, the size of LNPs was measured before and after nebulization in the presence or absence of the excipient and buffer modification. From DLS measurements, incorporating bPEG20K into the PBS buffer attenuated the increase in LNP size following nebulization. An even greater reduction was observed for LNPs nebulized with bPEG20K in NaAc buffer when comparing both nebulization formulations to PBS buffer without excipient (FIG. 11E) These sequential reductions in LNP size increase following nebulization are consistent with the sequential increase in lung luminescence observed in vivo. However, nebulization of LNPs in NaAc buffer alone did not reduce the size increase following nebulization.

Figure 1B:
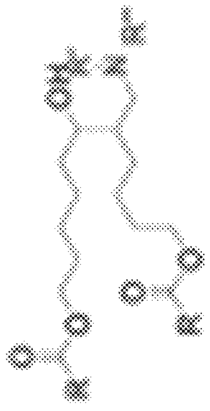
Figure 1C:
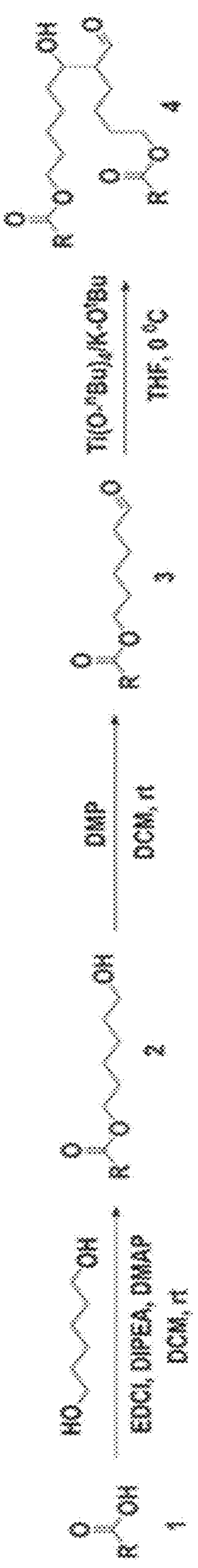
Figure 22:
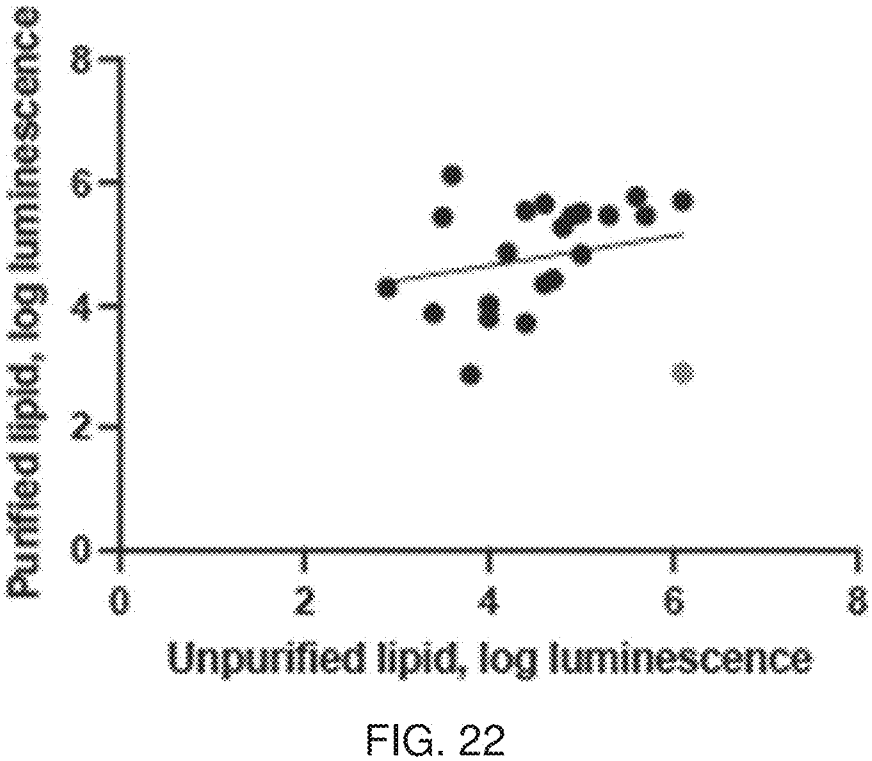
FIG. 22 shows a correlation between FFL delivery of T1-5 LNPs generated from purified and unpurified lipids. Correlation is not significant (p=0.66) and removal of outlier (red) does not yield a significant correlation (p=0.15).

Example 3: Synthesis and In Vitro Screening of Combinatorial, Biodegradable Lipid Library Conventional ionizable lipids for RNA delivery conform to a general model comprising an amine head group linked to tails via a linker (FIG. 1A). An ionizable lipid library was rationally designed in which various tails were linked to amine head groups by biodegradable ester bonds (FIG. 1B). A unique feature of this library was the presence of biodegradable tails and a hydroxyl group two carbons away from the carbon attached to the amine head group. This hydroxyl group was afforded by the Aldol chemistry used in the "linker-tail" synthesis as shown in FIG. 1C. The "linker-tail" synthesis proceeded by esterification of a commercially available fatty acid with 1,6-hexane diol and gave ester 2, which was then oxidized to the aldehyde 3 using Dess-Martin oxidation. Aldol reaction, facilitated by a (1:1) mixture of $Ti(O\text{-}n\text{-}Bu)_4$/t-BuOK was used to dimerize the aldehyde to give the respective "linker-tail" as an aldol. To test whether the lipids could be screened without individual purification, 22 lipids both purified and unpurified were prepared, and LNPs were synthesized from these lipids using the T1-5 formulation. The FFL mRNA delivery was tested in A549 cells (an immortalized alveolar epithelial cell line). There was a slight but not statistically significant positive correlation between purified and unpurified lipids with this chemistry (FIG. 22, correlation coefficient $\rho=0.14$, $p=0.66$; $\rho=0.47$, $p=0.15$ even after removal of an outlier), suggesting that a screen of unpurified lipids would not be informative.

Figure 1D:
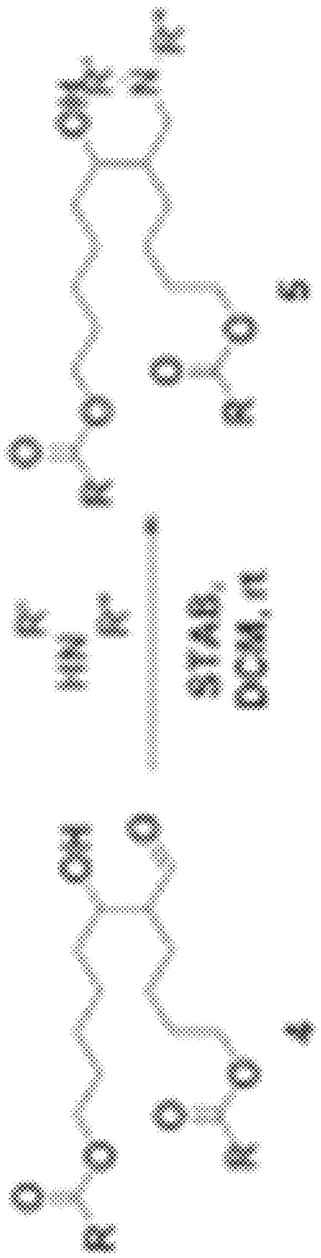

Utilizing the reactivity of the aldehyde group in the "linker-tail", thirty different amines (FIG. 2) were reacted with appropriate tails to make to make ionizable lipids by reductive amination (FIG. 1D). Structures of lipids made using this chemistry are shown in FIGS. 3A-3D.

Figure 4A:
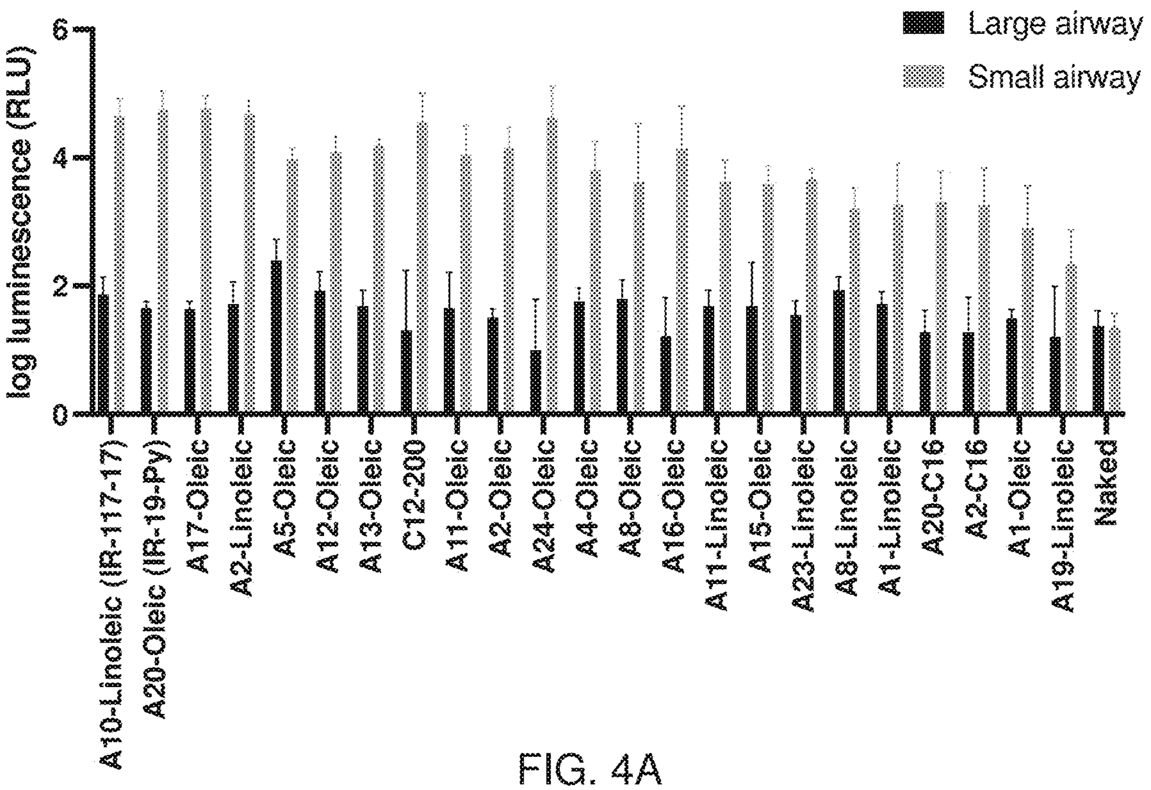
FIGS. 4A-4C show the ionizable lipid screening in primary ALI cultures.

It was predicted that unsaturated tails would have optimal activity so lipids with oleic and linoleic acid tails were primarily synthesized (FIG. 3B), though lipids with $C_{16}$ (palmitic acid) tail were also synthesized. Purified lipids were screened in A549 cells, several of which had comparable efficiency to C12-200 (FIG. 4A). Of the 4 $C_{16}$-tail lipids, 3/4 had worse activity than headgroup-matched unsaturated tail variants, while the $4^{th}$ was not in the top 20 lipids by activity, thus preliminarily validating a focus on unsaturated tails.

Figure 12A:
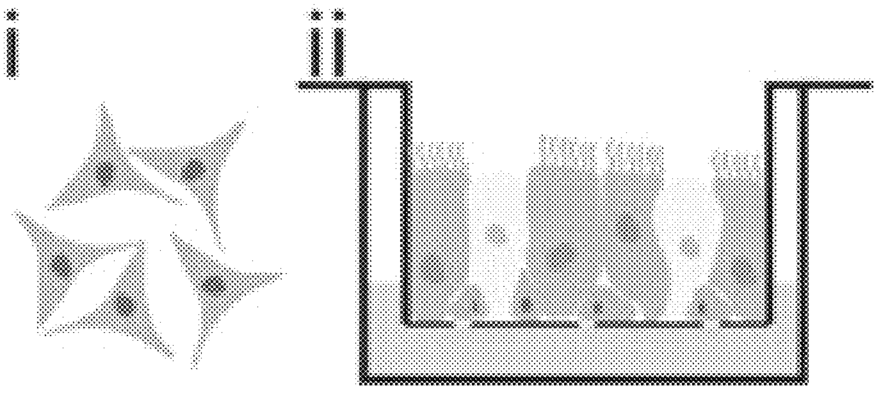
FIG. 12A shows a schematic of difference between (i) classic submerged culture (undifferentiated cells, no tight junctions, non-physiological environment) and (ii) ALI cultures.

Example 4: Screening of Ionizable Lipids for Epithelial Delivery in Air-Liquid Interface Cultures Because nebulization is a low throughput approach and in vitro mRNA delivery assays with classic cell culture techniques can be unreliable, a medium throughput screening approach with good capacity to predict lung epithelial delivery was sought. For such an assay, a model system was desired that recapitulated the primary known barriers to apically delivered lung gene therapy. Air-liquid interface (ALI) cultures derived from primary human bronchial epithelial cells were selected. ALI cultures are grown on porous Transwell inserts such that, upon reaching confluence, media can be removed from the top (apical) side of the insert and the cells can be fed from the bottom, basolateral, side (FIG. 12A). This enables recapitulation of the conditions of the native bronchial epithelium, where the apical side of the cells is exposed to the air while the basolateral side is bathed in nutrients.

Figure 12B:
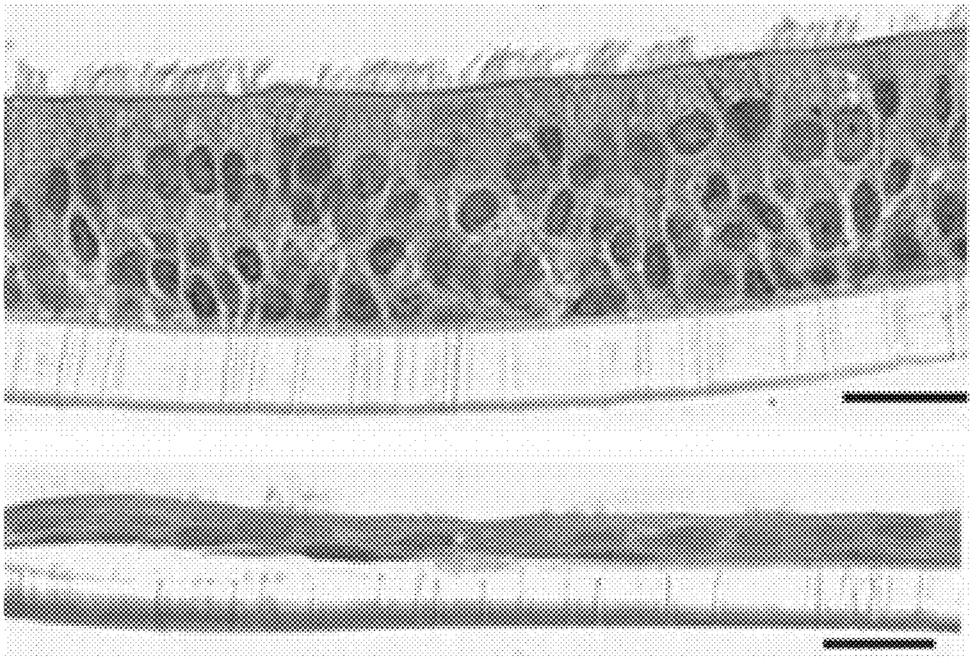
FIG. 12B shows representative H&E stained histology images of 3-week old large (top) and small (bottom) airway ALI cultures. Scale bars: 50 um.
Figure 23A:
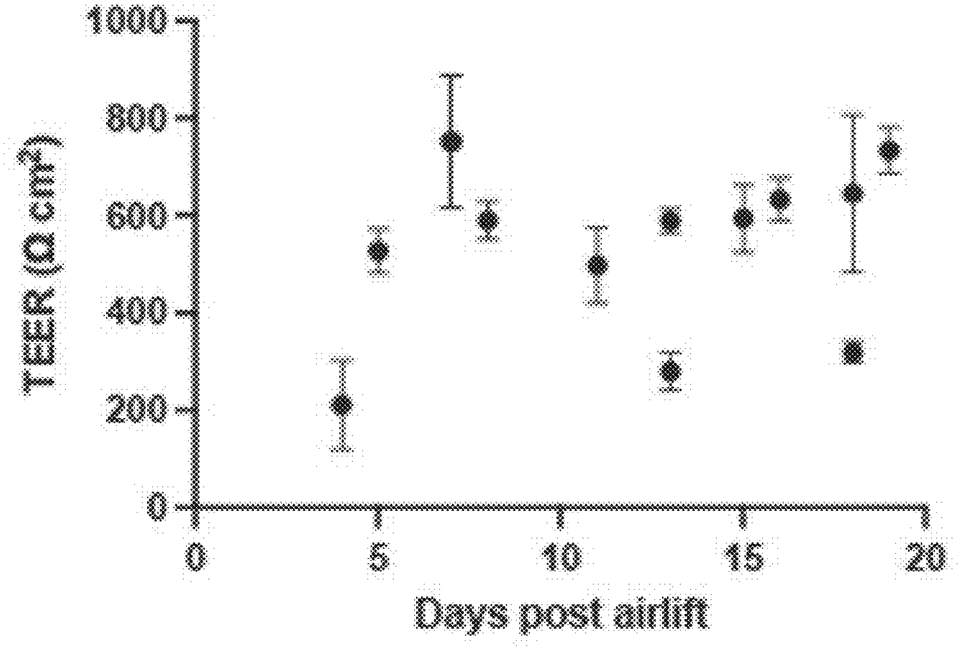
FIG. 23A shows TEER of ALI cultures generated from primary large airway cells (n>3 per measurement, ALI cultures from 3 different donors included).
Figure 23B:
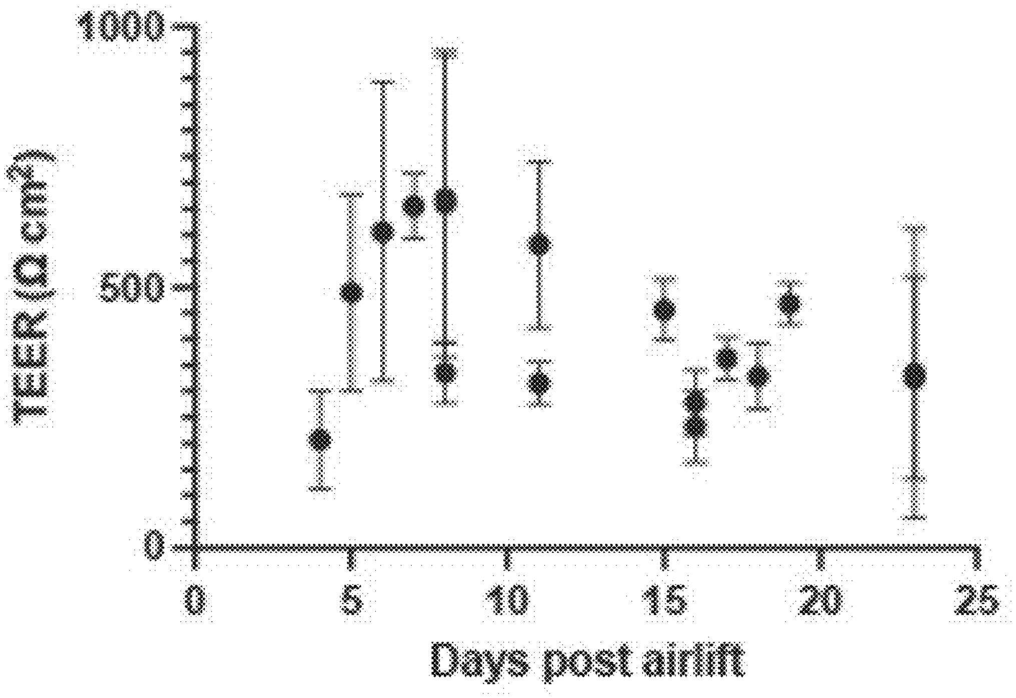
FIG. 23B shows TEER of ALI cultures generated from primary small airway cells (n>3 per measurement. ALI cultures from 2 different donors included).

ALI cultures can be used to examine bronchial epithelial biology and share characteristics of the in vivo bronchial epithelium including differentiation, mucus secretion, periciliary layer formation, and tight junctions.[65-67,74] ALI cultures can be difficult to transfect,[74] likely due to these in vivo-like characteristics, which suggested that these cultures would be a suitable model for screening LNPs for mRNA delivery. Both primary large airway (LA) and small airway (SA) ALI cultures were generated. While large airway ALI cultures are more commonly studied, both large and small airway are important for respiratory diseases including CF. COPD, and asthma.[75-78] Both small and large airway cultures formed tight junctions (FIGS. 23A-23B) as measured by transepithelial electrical resistance,[79] and large airway cultures grew more thickly, with dense visible ciliation (FIG. 12B).

Figure 12C:
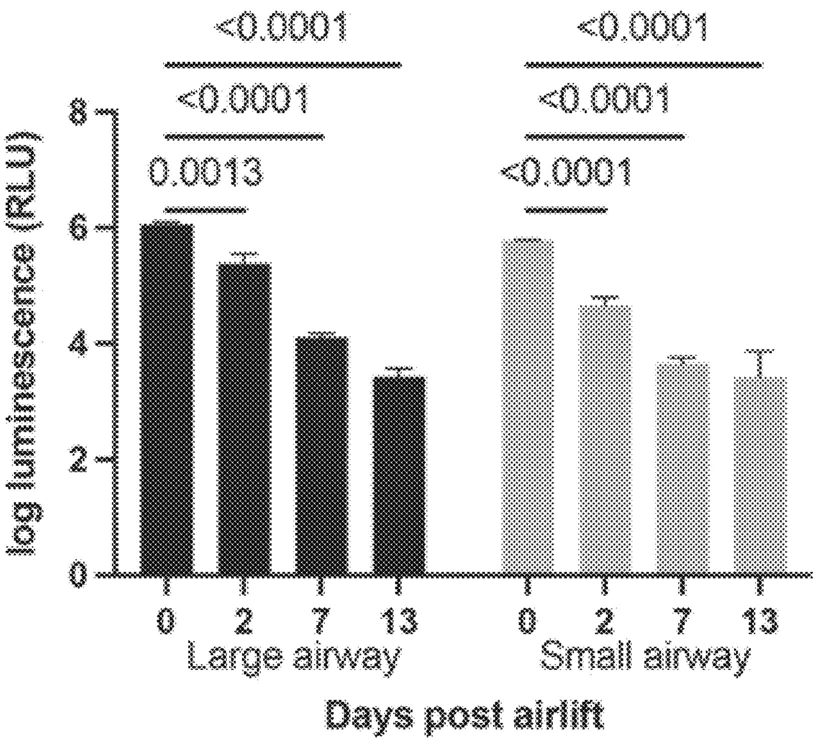
FIG. 12C shows FFL delivery using T1-5-formulated C12-200 LNPs, 2-13 days after airlift (n=3 per day and airway cell line type, 2-way ANOVA).
Figure 12D:
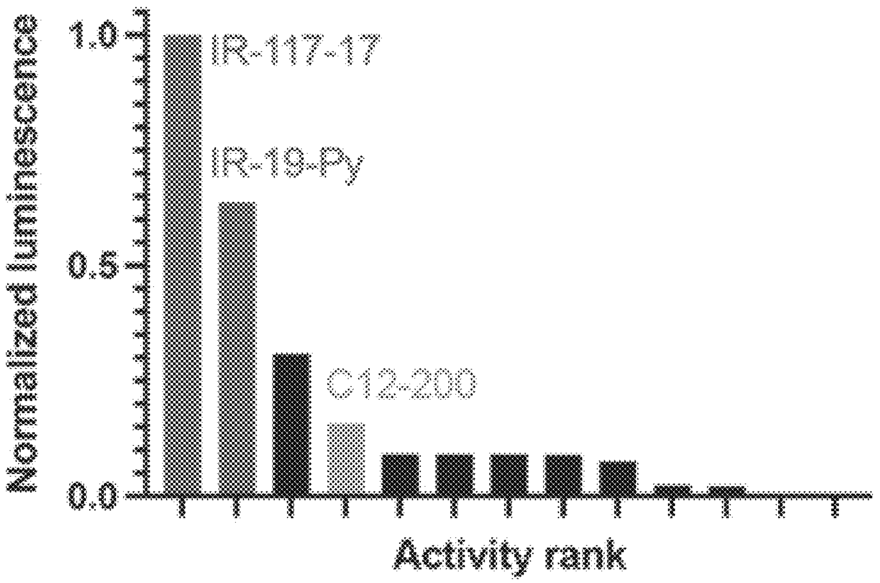
FIG. 12D shows a screen of top A549 delivery hits for delivery to small airway ALI cultures (n=1), normalized to delivery of top lipid. IR-117-17.
Figure 12E:
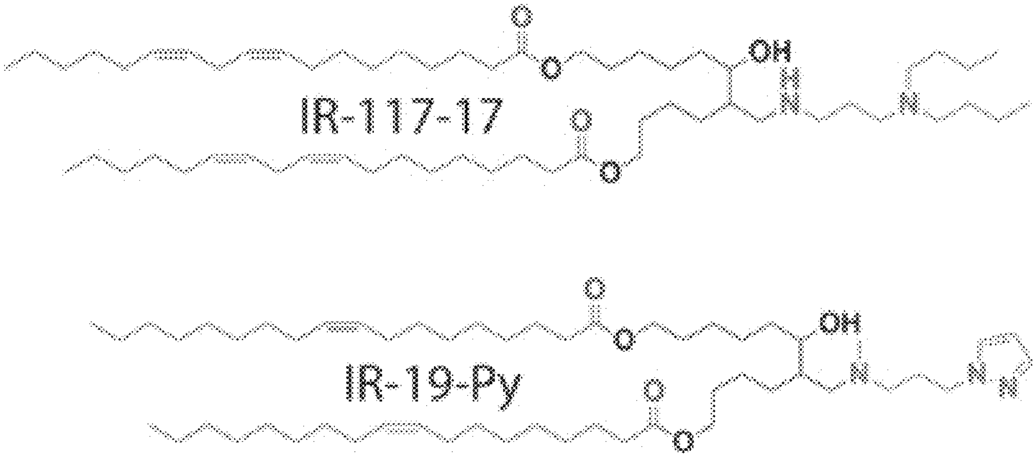
FIG. 12E shows structures of 2 top hits, IR-117-17 and IR-19-Py.

To validate ALI cultures as a model for LNP delivery, T1-5 formulated C12-200 LNPs were tested for FFL delivery to ALI cultures up to two weeks after airlift. Transfection efficiency dropped over that period by 2.5-3 orders of magnitude (FIG. 12C), consistent with the previous observation that siRNA delivery by traditional in vitro transfection reagents decreases sharply over the first week of ALI culture.[74] Next, 12 top-performing (in the A549 assay) LNPs were screened for mRNA delivery to small airway ALI cultures (FIG. 12D), leading to identification of two LNPs in particular with excellent performance. IR-117-17 and IR-19-Py (FIG. 12E).

Figure 4B:
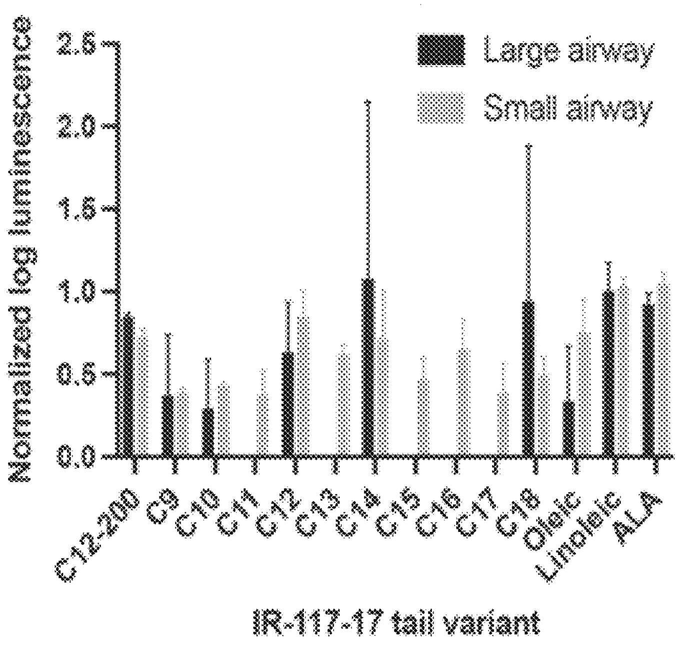
Figure 4C:
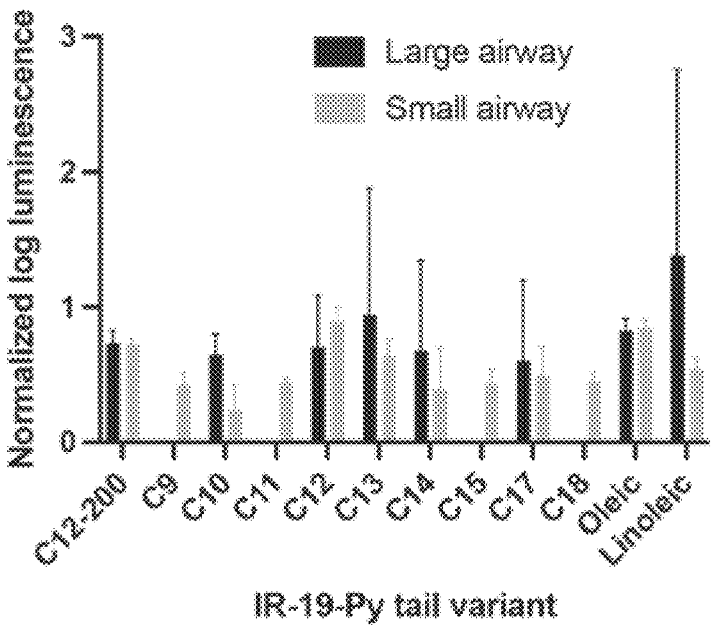

To optimize these top structures and identify structure-activity relationships, 21 and 14 tail- and headgroup variants of IR-117-17 and IR-19-Py were synthesized and screened, respectively, in both small and large airway ALI cultures, along with A549 cells. First, saturated tails of lengths 9-18 were screened for each lipid, and in both cases intermediate tail lengths in the range of $C_2$-$C_{14}$ tended to be optimal, though none of the saturated tails outperformed unsaturated versions (FIGS. 4B-4C). For IR-117-17 in particular, it was reasoned that because linoleic tails (2 unsaturations) outperformed oleic tails (1 unsaturation), adding a third unsaturation may further improve delivery. However, the alpha-linolenic acid (ALA) tailed variant was merely comparable to the linoleic tail.

Figure 24A:
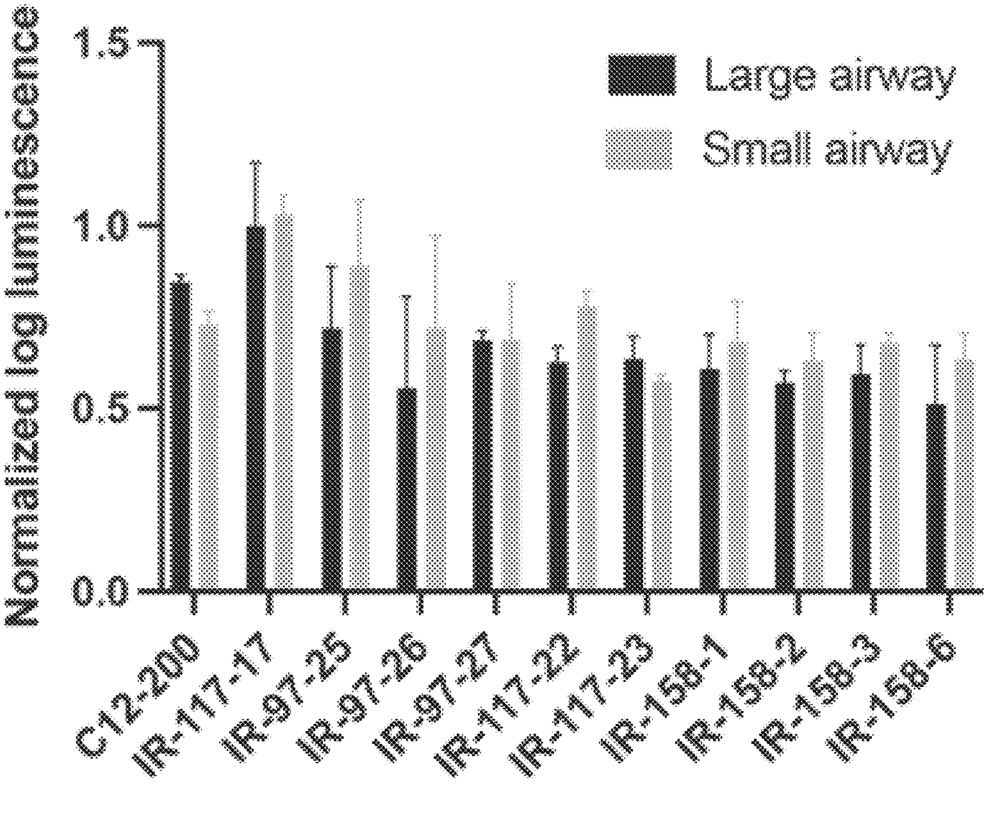
FIGS. 24A-24D show a screen of headgroup variants (plus tailgroup variants of the headgroup variants themselves) of IR-117-17 (FIG. 24A, structures shown in FIG. 24B) and IR-19-Py (FIG. 24C, structures shown in FIG. 24D) (n=2 per airway cell line type). Each value for a lipid and cell type is normalized to IR-117-17's delivery to that cell type. All error bars+/−SEM.
Figure 24B:
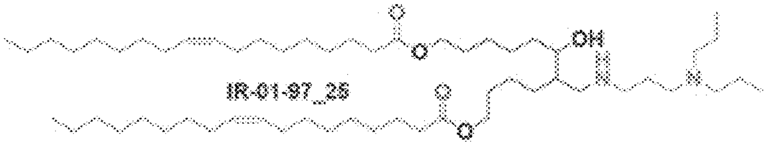
Figure 24B:
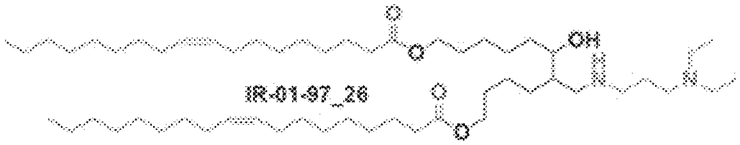
Figure 24B:
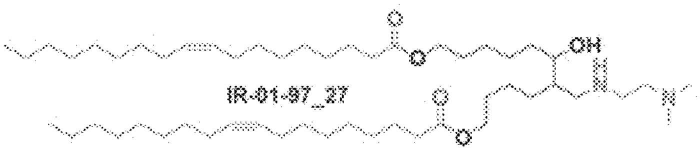
Figure 24B:
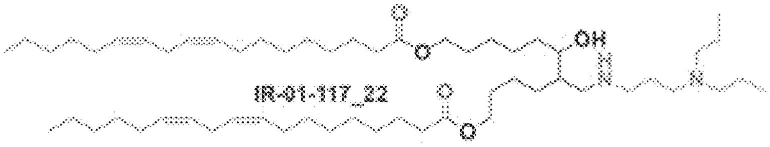
Figure 24B:
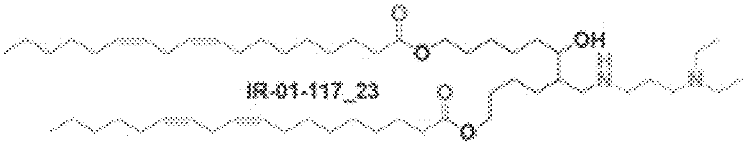
Figure 24B:
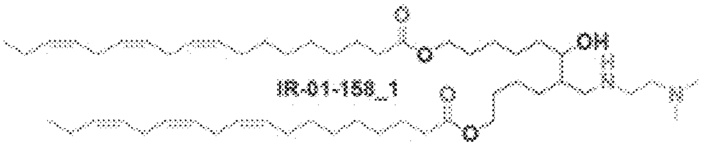
Figure 24B:
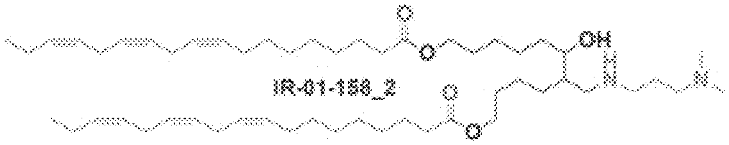
Figure 24B:
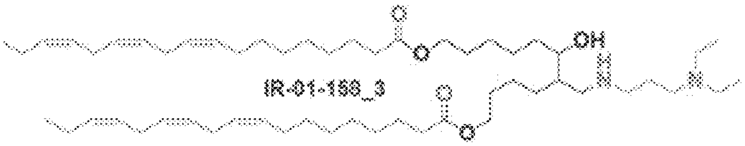
Figure 24B:
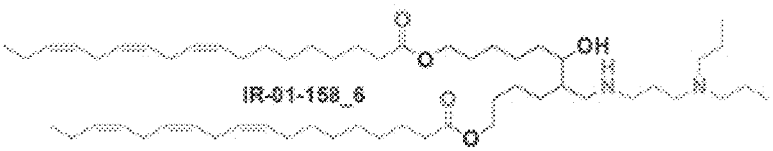
Figure 24C:
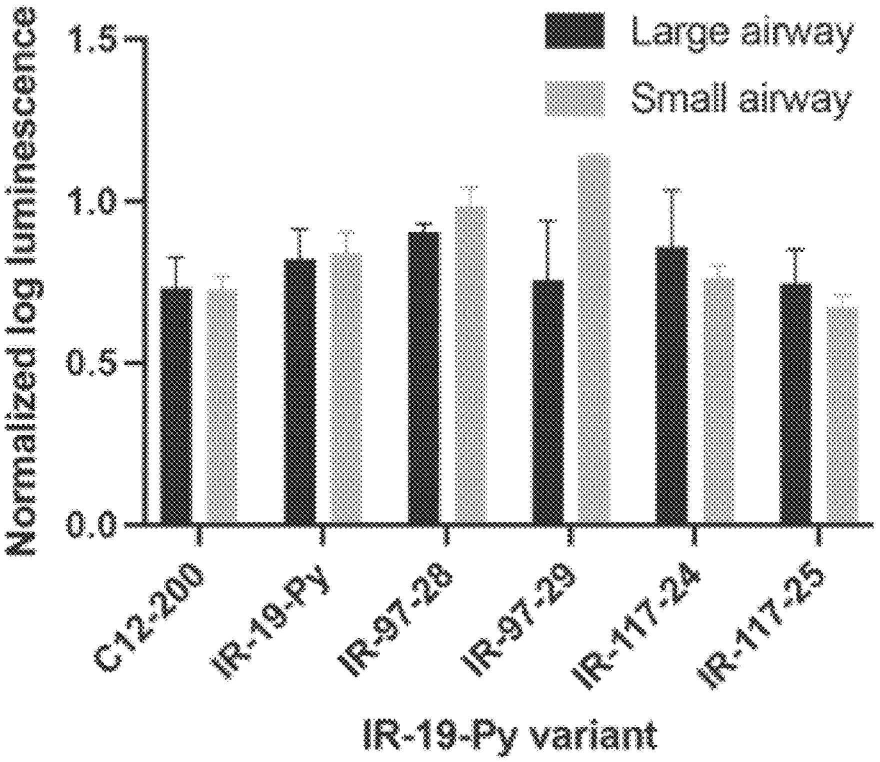
Figure 24D:
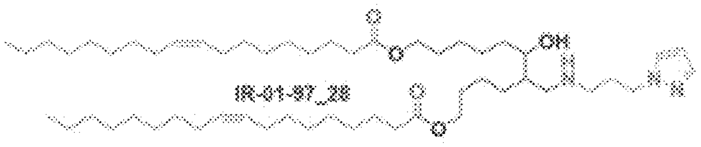
Figure 24D:
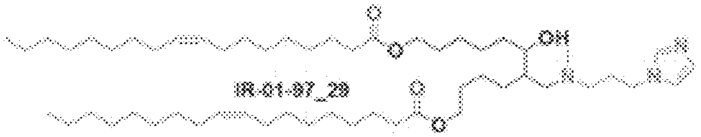
Figure 24D:
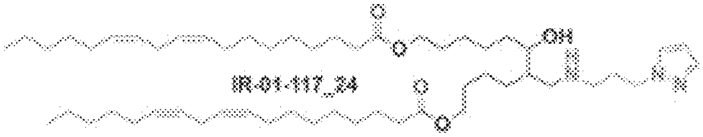
Figure 24D:
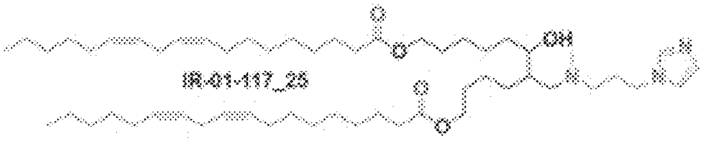

To further elucidate IR-117-17's structure-activity relationship, headgroup variants of IR-117-17 with oleic, linoleic, and/or ALA tails were tested, to determine whether shortening the alkyl chains branching off from the tertiary amine would improve performance. Shortening the alkyl chains significantly impaired activity for the linoleic and ALA tails, while activity for the oleic tails was unaffected or improved by tail shortening, though not to the level of the original IR-117-17 (FIGS. 24A-24B). Headgroup variants of IR-19-Py were also tested, and the activity was relatively insensitive to replacement of the pyrazole group with an imidazole, and to demethylation of one of the headgroup nitrogens (FIGS. 24C-24D).

Figure 5A:
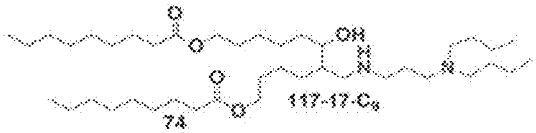
FIGS. 5A-5B show the structures of analogs of 117-17 and 19-Pyrazole synthesized. Eleven analogs of each hit with varying tail lengths were synthesized.
Figure 5A:
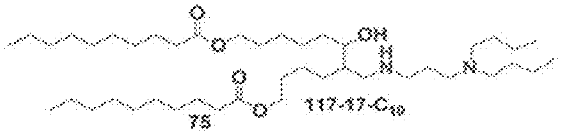
Figure 5A:
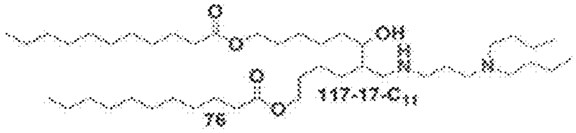
Figure 5A:
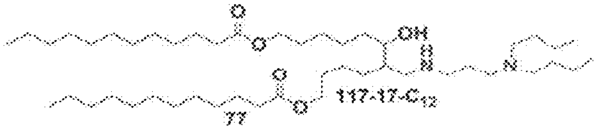
Figure 5A:
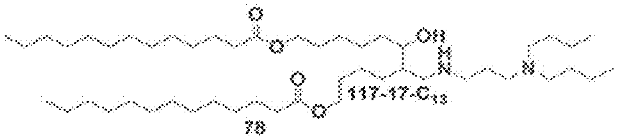
Figure 5A:
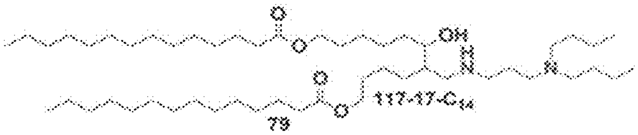
Figure 5A:
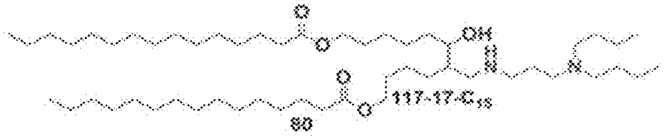
Figure 5A:
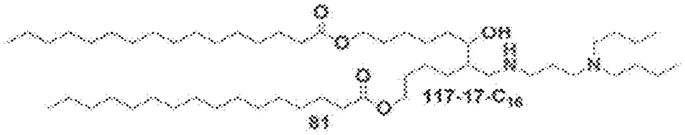
Figure 5A:
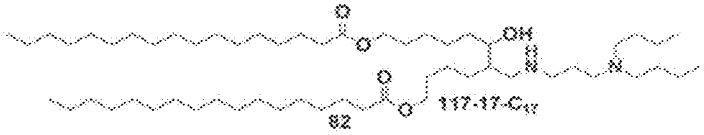
Figure 5A:
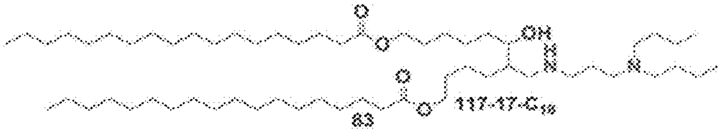
Figure 5A:
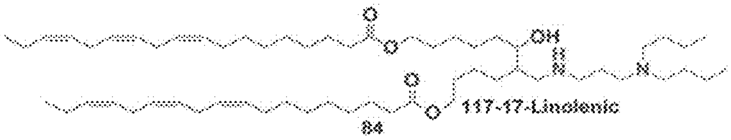
Figure 5B:
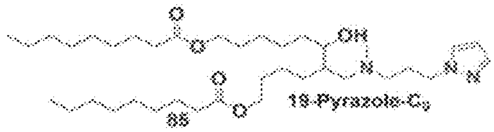
Figure 5B:
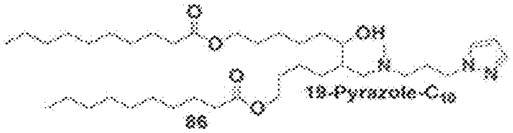
Figure 5B:
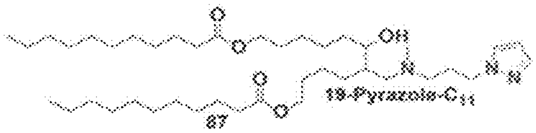
Figure 5B:
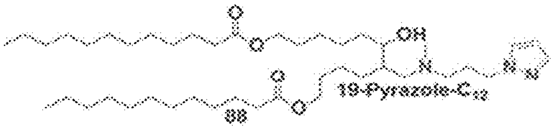
Figure 5B:
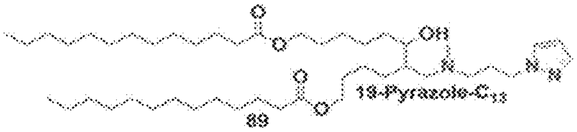
Figure 5B:
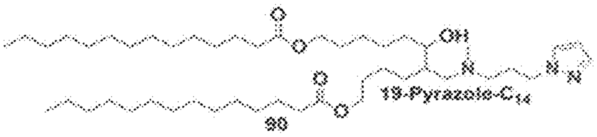
Figure 5B:
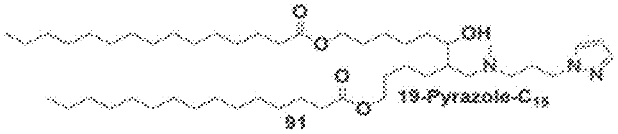
Figure 5B:
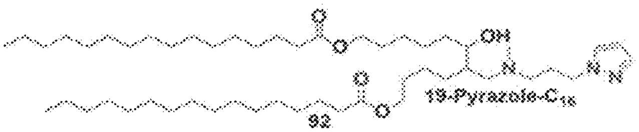
Figure 5B:
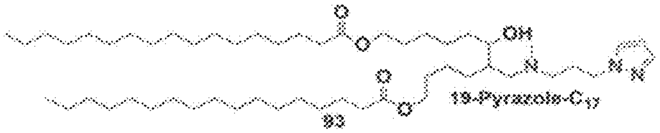
Figure 5B:
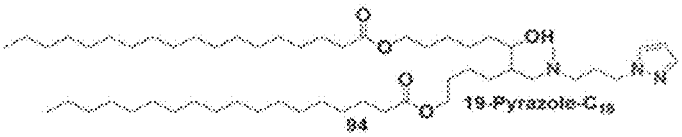
Figure 5B:
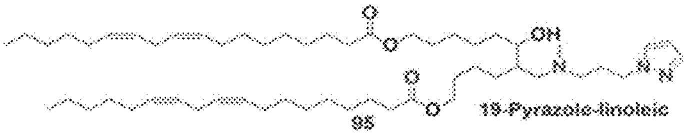

Lipids were screened as part of LNPs that contained 50.1% ionizable lipid, 24.6% DOTAP, 16.8% cholesterol, and 8.5% PEG-lipid by mass, and a 10:1 ionizable lipid: mRNA weight ratio. LNPs generated using the 117-17 and 19-Pyrazole ionizable lipids outperformed other screened lipids in ALI cultures (FIG. 4A-4C). Subsequently, analogs of 117-17 and 19-Pyrazole were synthesized with varying tail lengths (FIGS. 5A-5B), formulated into LNPs and screened in ALI cultures. Some of them performed well in ALI cultures (FIG. 4A-4C), though none better than the original 117-17 and 19-Pyrazole. In particular, C12 tail variants were comparably effective to original lipids (original 117-17 has linoleic tail; original 19-Pyrazole has oleic tail).

Figure 13A:
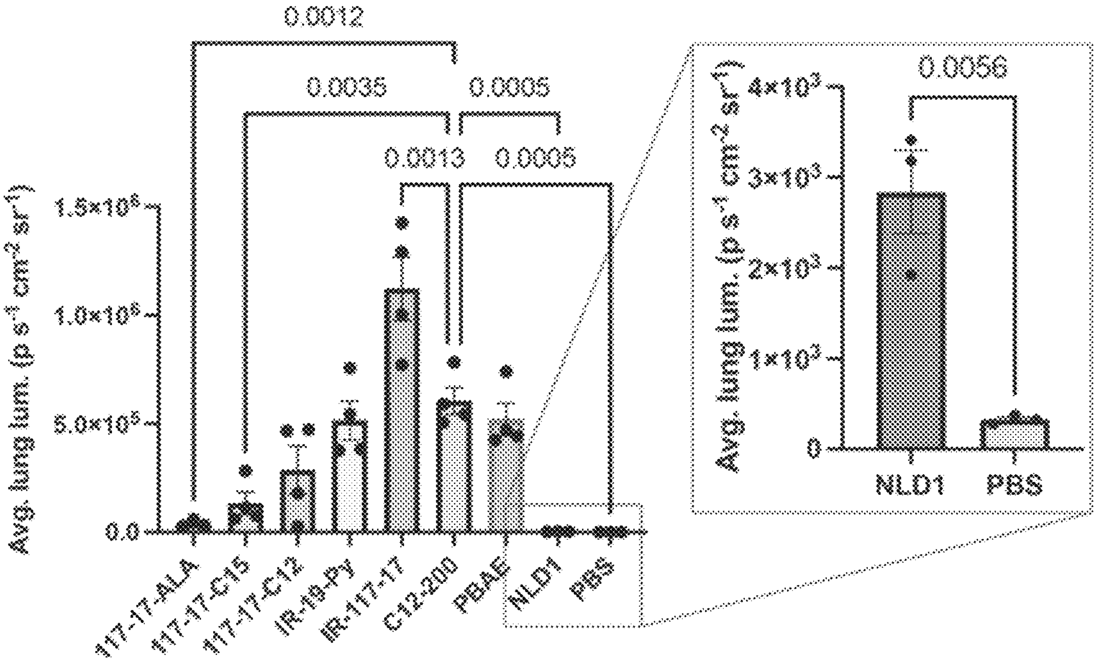
FIG. 13A shows nebulized mRNA delivery to mouse lung, 6 hr after 1 mg dose delivered via nose cone (average±SD, biological replicates shown, 1-way ANOVA). Left: all nebulized NPs, right: zoomed-in image showing significant NLD1 delivery compared to PBS.
Figure 13B:
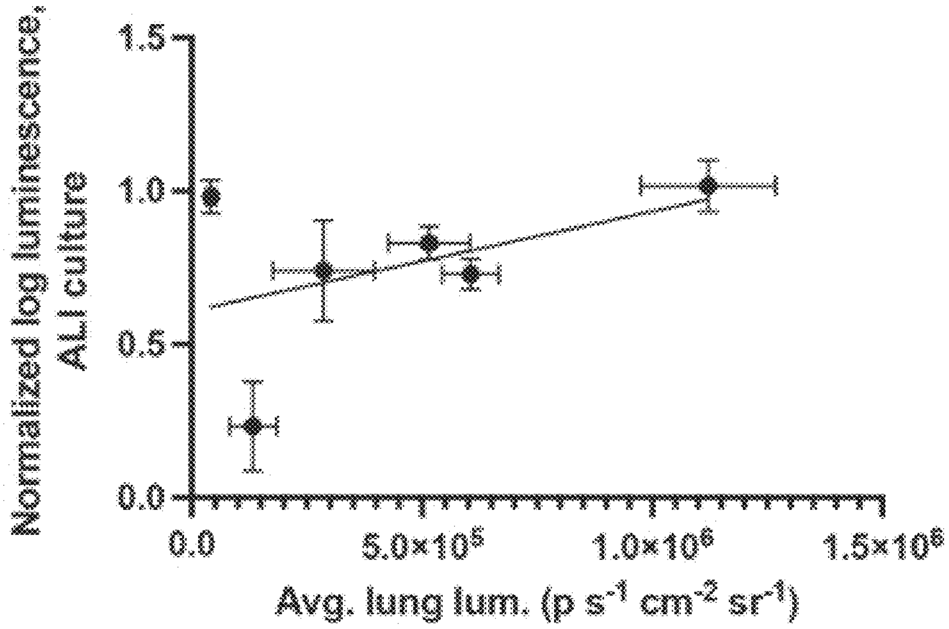
FIGS. 13B-13E show correlation of in vivo nebulized lung delivery data from FIG. 13A to: FFL delivery to ALI cultures using handmixed LNPs (no significant correlation, p=0.37) (FIG. 13B). FFL delivery to A549 cells using handmixed LNPs (no significant correlation, p=0.85) (FIG. 13C). FFL delivery to ALI cultures using microfluidically mixed post-nebulized LNPs (p=0.64, p=0.0022) (FIG. 13D). FFL delivery to A549 cells using microfluidically mixed post-nebulized LNPs (p=0.658, p=0.0076) (FIG. 13E). FFL delivery to ALI cultures generated from a CF patient (W1282X/R1162X genotype) using microfluidically mixed T1-5 formulated C12-200, IR-117-17, and IR-19-Py LNPs (FIG. 13F).
Figure 13C:
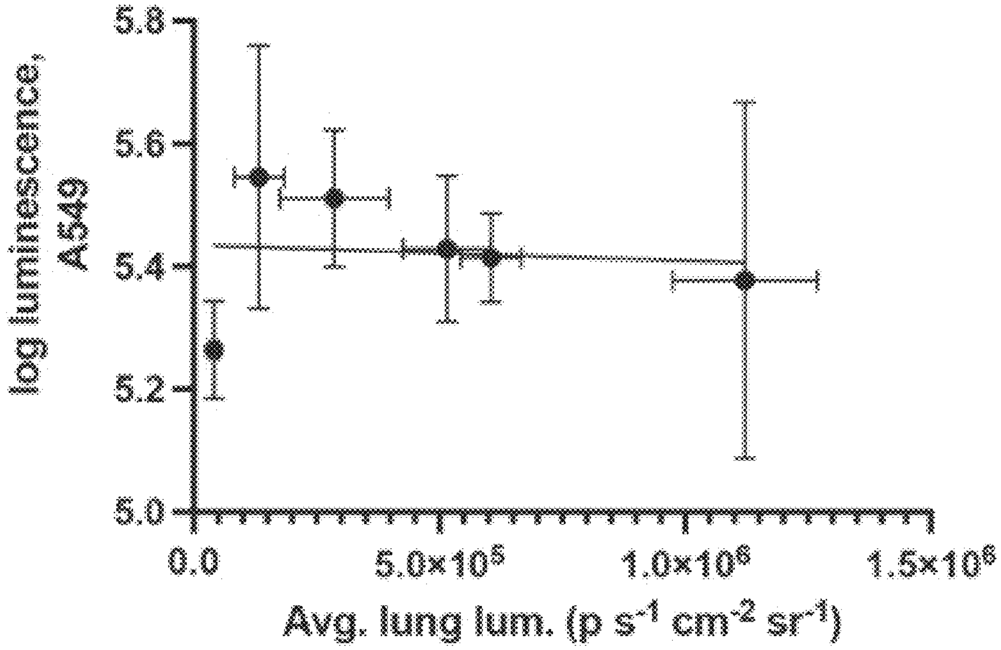

Example 5: In Vivo Evaluation of Lead Ionizable Lipid LNPs Combined with Optimized Nebulization Formulations Next, to confirm the efficacy of the identified top lipids in vivo and test the ability of ALI cultures and A549 cells to predict lung delivery, T1-5 formulated IR-117-17 and IR-19-Py (with bPEG20K and NaAc excipients) were nebulized to mice, along with IR-117-17's $C_{12}$, $C_{15}$, and ALA tail variants. As controls, previously reported lung delivery-optimized hPBAE[53] and NLD1, an LNP that has been reported to have good stability to nebulization and lung mRNA delivery,[54] were also nebulized. As observed in ALI cultures, IR-117-17 ($1.1\times10^6$ p $s^{-1}$ $cm^{-2}$ $sr^{-1}$) significantly outperformed C12-200 ($6.1\times10^5$ p $s^{-1}$ $cm^{-2}$ $sr^{-1}$) (FIG. 13A). Of note, IR-117-17 also outperformed the polymeric PBAE nanoparticle ($5.2\times10^5$ p $s^{-1}$ $cm^{-2}$ $sr^{-1}$) by two-fold and NLD1 ($2.8\times10$ p $s^{-1}$ $cm^{-2}$ $sr^{-1}$) by 300-fold. Results from the ALI culture experiments also correctly predicted that IR-117-17-C15 would perform poorly relative to IR-117-17-C12 and the original IR-117-17. However, the ALI cultures incorrectly predicted good IR-117-17-ALA activity, as it performed the worst of all tested lipids. Overall, there was not a statistically significant correlation between the ALI culture and in vivo data (FIG. 13B). However, the A549 data was substantially worse, predicting nearly everything incorrectly and notably showing C12-200 as the top-performing lipid (FIG. 13C).

Figure 13D:
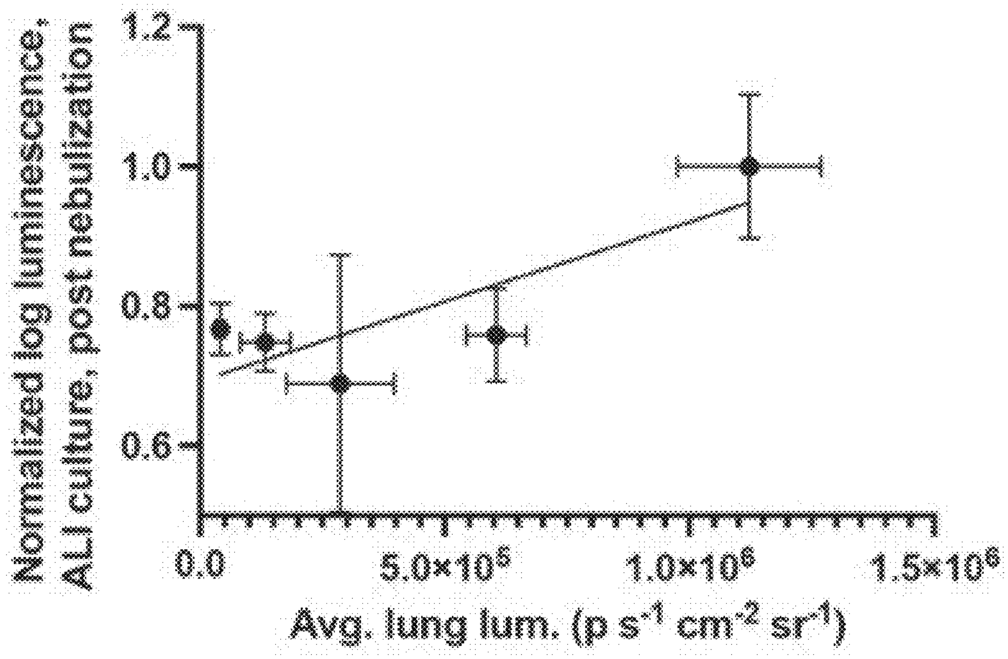
Figure 13E:
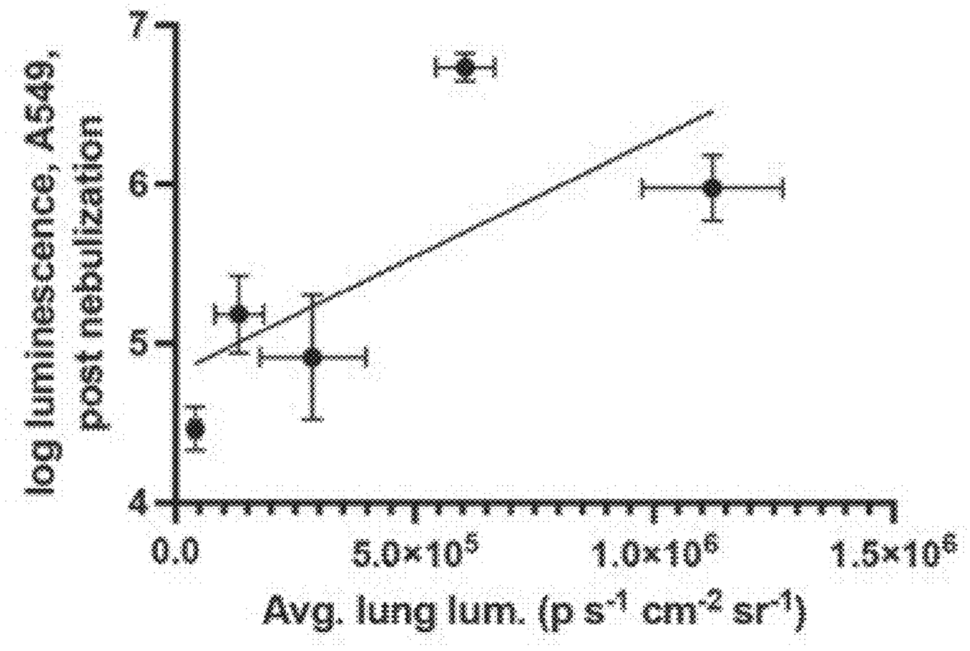

One possible explanation for the lack of correlation between ALI culture and in vivo results was that the ALI culture screens used hand mixed lipids that were not nebulized. LNPs were therefore generated from C12-200 and the IR-117-17 variants via microfluidic synthesis, in which the LNPs were nebulized using bPEG20K and NaAc excipients, and then A549 cells and ALI cultures were treated with the post-nebulized LNPs. For post-nebulized LNPs, both A549 cells ($p=0.0076$) and ALI cultures ($p=0.0022$) showed significant correlations between in vitro and in vivo activity (FIGS. 13D-13E), primarily because both predicted IR-117-17 to be effective and IR-117-17-ALA no longer performed well. However, C12-200 continued to be the most effective lipid for A549 cell transfection, while ALI cultures correctly identified IR-117-17 as the top lipid.

Figure 13F:
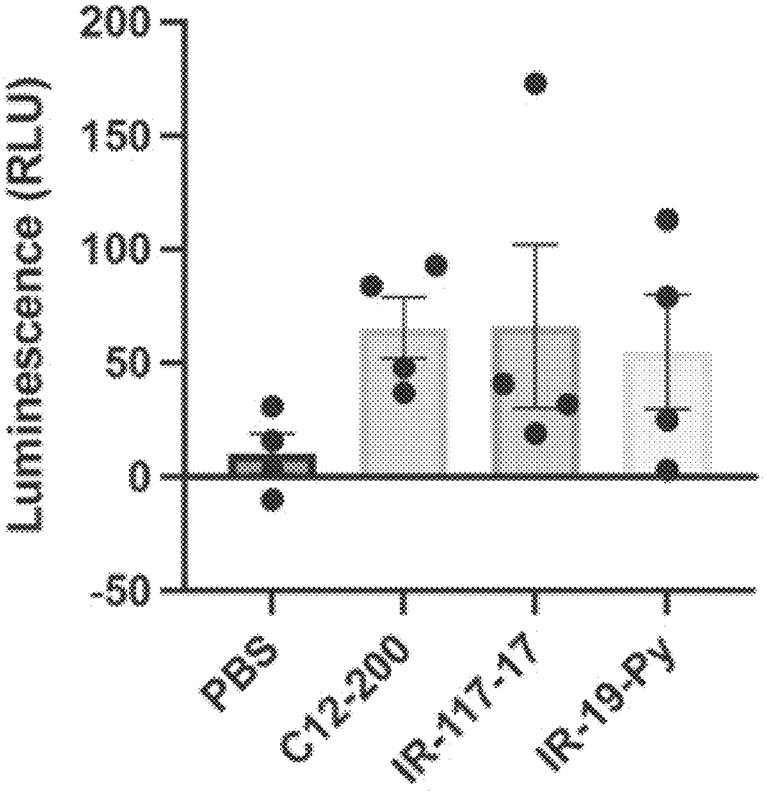
Figure 23C:
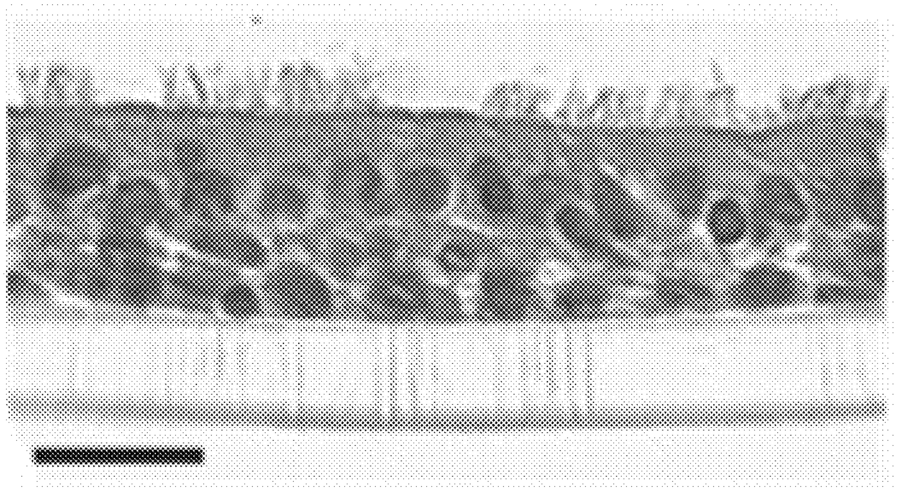
FIG. 23C shows representative H&E stained histology image of ALI culture generated from primary cells from a CF patient (W1282X/R1162X genotype).
Figure 23D:
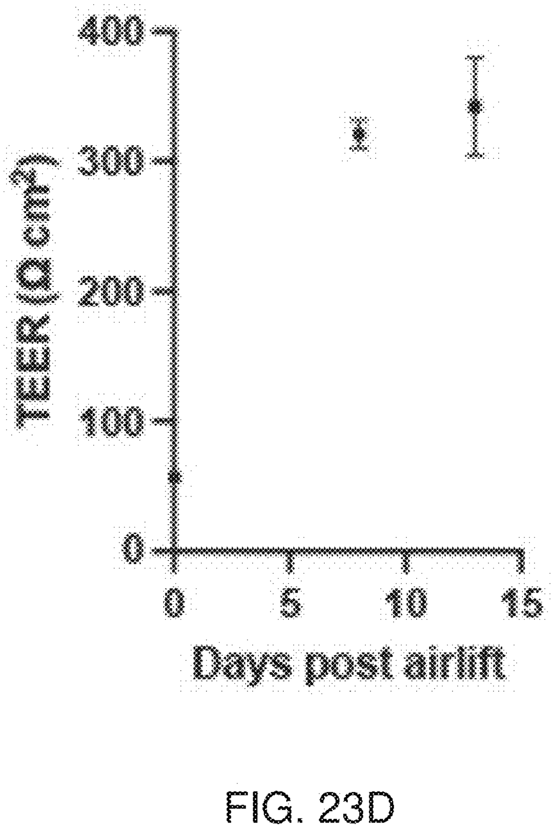
FIG. 23D shows TEER of ALI culture generated from primary cells from a CF patient (W1282X/R1162X genotype, n=12 wells per measurement).

Based on these results, IR-117-17, the top-performing lipid, and IR-19-Py, which had statistically comparable delivery to C12-200 and a more chemically distinct headgroup than IR-117-17-C12, were further characterized. The three lipids were tested in ALI cultures generated from a person with CF (W1282X/R1162X genotype), finding comparable delivery between the three lipids (FIGS. 13F and 23C-23D). To understand if nebulization with bPEG20K and NaAc improved in vivo performance of T1-5 LNPs formulated with IR-117-17 and IR-19-Py as they did for C12-200, the in vivo nebulized delivery of the two biodegradable lipids in either the optimized nebulization formulation or in PBS buffer with no excipient was compared.

Figure 11E:
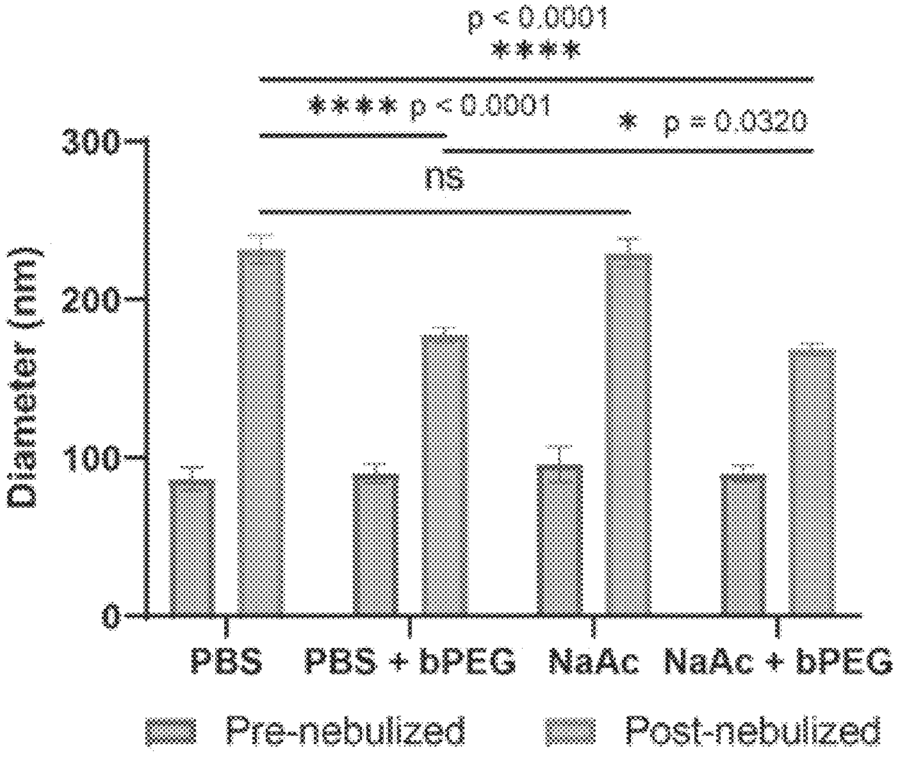
FIG. 11**E shows DLS measurements of LNP size before and after nebulization demonstrating reduction in size increase following nebulization for T1-5 formulation when bPEG20K is added to PBS and further reduction when PBS is replaced with NaAc buffer in the presence of bPEG20K. Two-way ANOVA, Average±SEM, n=10 repeated measurements.
Figure 25:
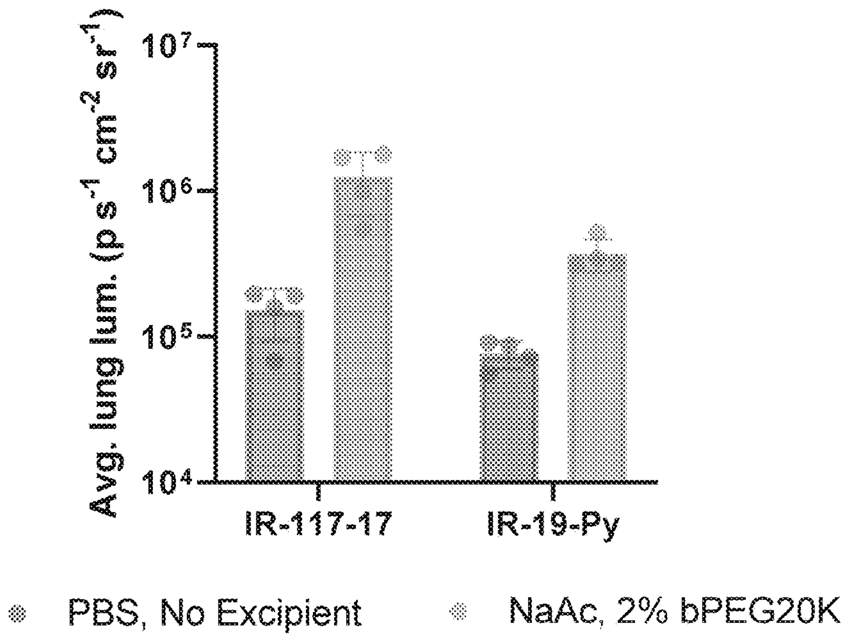
FIG. 25 shows a comparison of in vivo nebulized performance of LNPs comprising the biodegradable lipids IR-117-17 and IR-19-Py. Addition of NaAc buffer and bPEG20K improves nebulized delivery of both LNPs compared to PBS. Average±SD, biological replicates shown.
Figure 26:
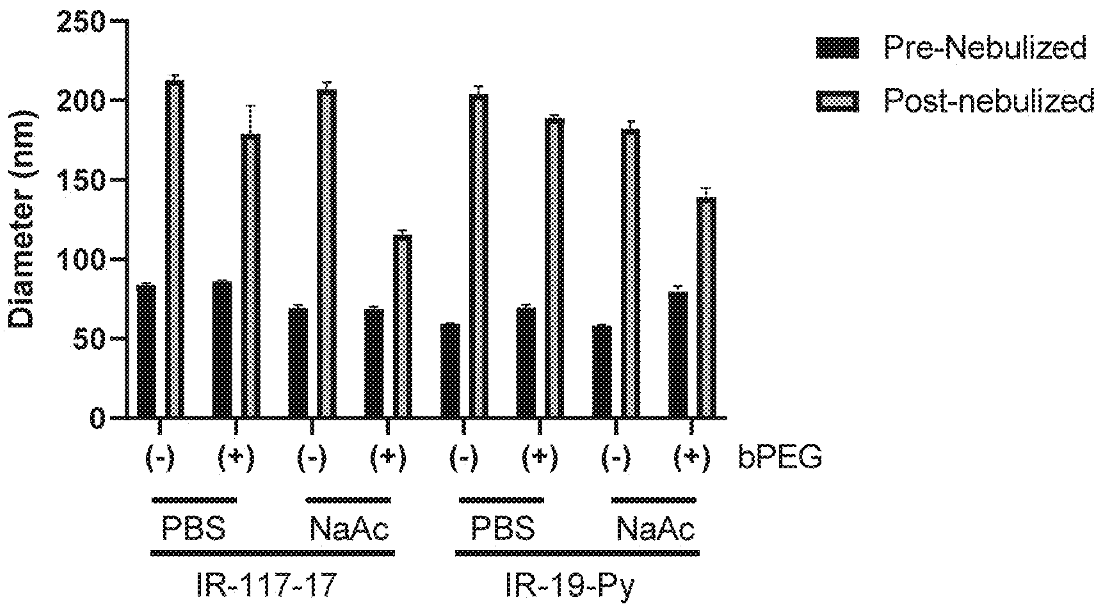
FIG. 26 shows DLS measurements of LNP size before and after nebulization in the presence or absence of bPEG20K and in either PBS or NaAc buffer. Average±SEM, n=10 repeated measurements.

Nebulization in the optimized formulation improved delivery of LNPs formulated with either biodegradable lipid (FIG. 25). These improvements in nebulized delivery are consistent with the observation that nebulization in the presence of bPEG20K and NaAc buffer significantly limited LNP size increase when compared to PBS alone for the biodegradable lipids, similar to the trends in nebulization size and efficacy observed for C12-200 (FIG. 26. FIG. 11E). Of note, when IR-117-17 LNPs were nebulized in the presence of bPEG20K and NaAc buffer, the resultant LNPs had an average diameter of only 116 nm, the smallest size observed for any LNP following nebulization.

Example 6: Pharmacokinetics and Pharmacodynamics of Top Performing LNPs

Figure 6A:
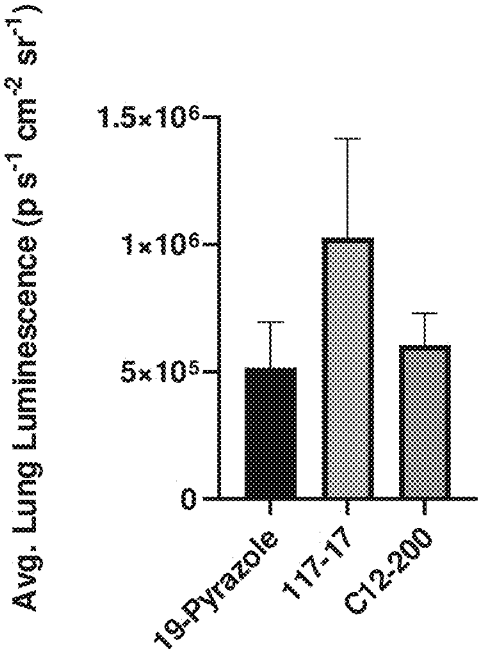
FIGS. 6A-6E show nebulized mRNA delivery of 117-17, 19-Pyrazole, and C12-200 (1 mg mRNA dose; only a fraction of the dose is inhaled).
Figure 6B:
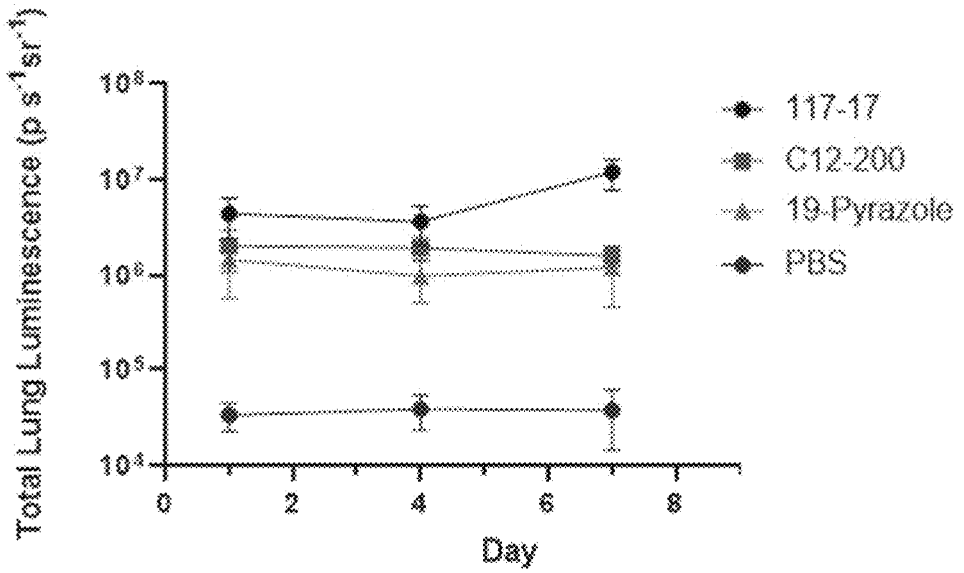
Figure 6C:
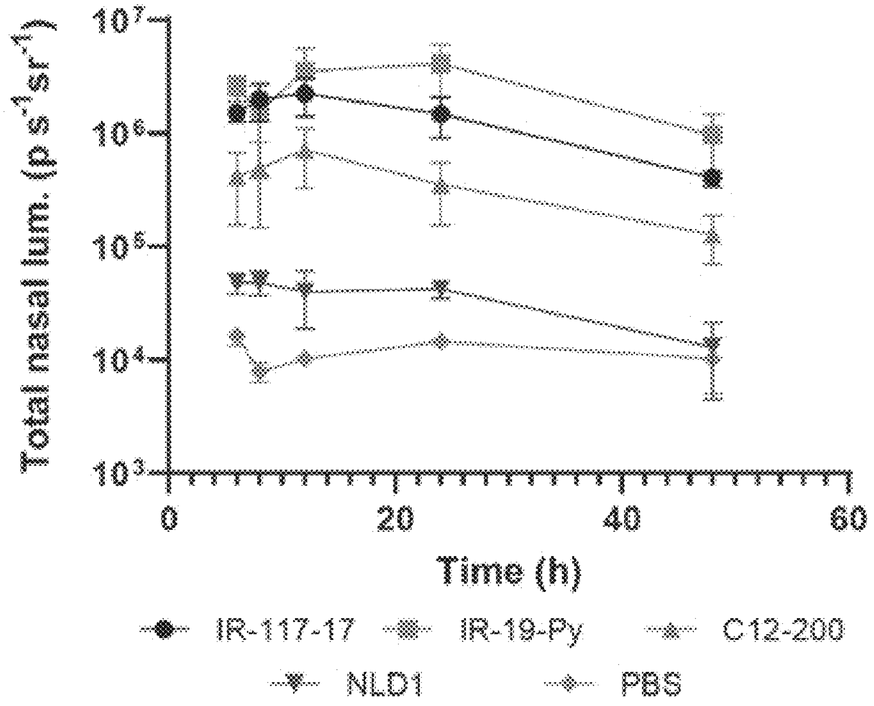
Figure 6D:
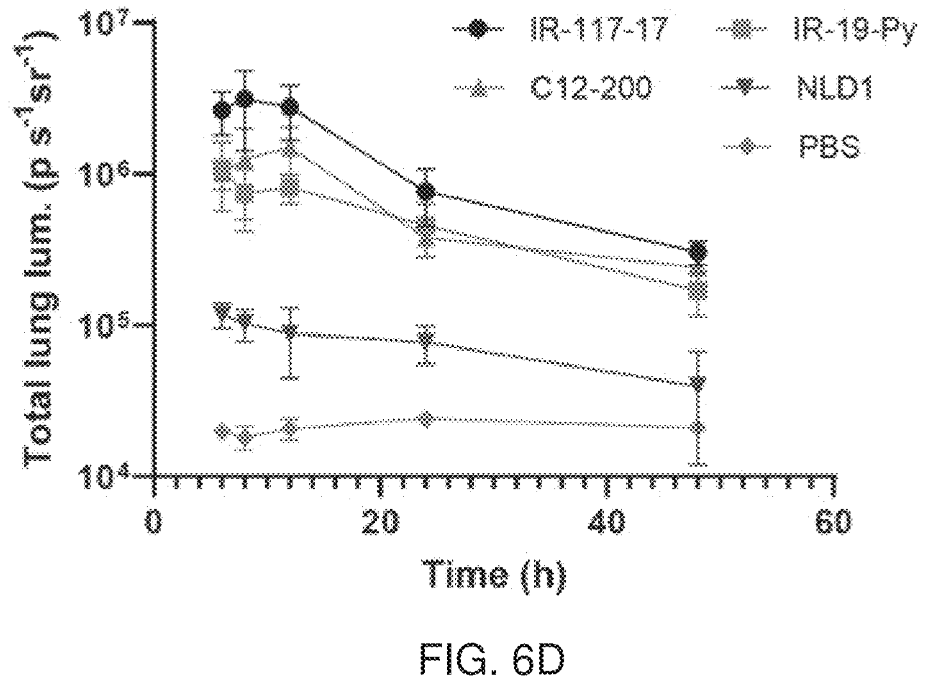
Figure 6E:
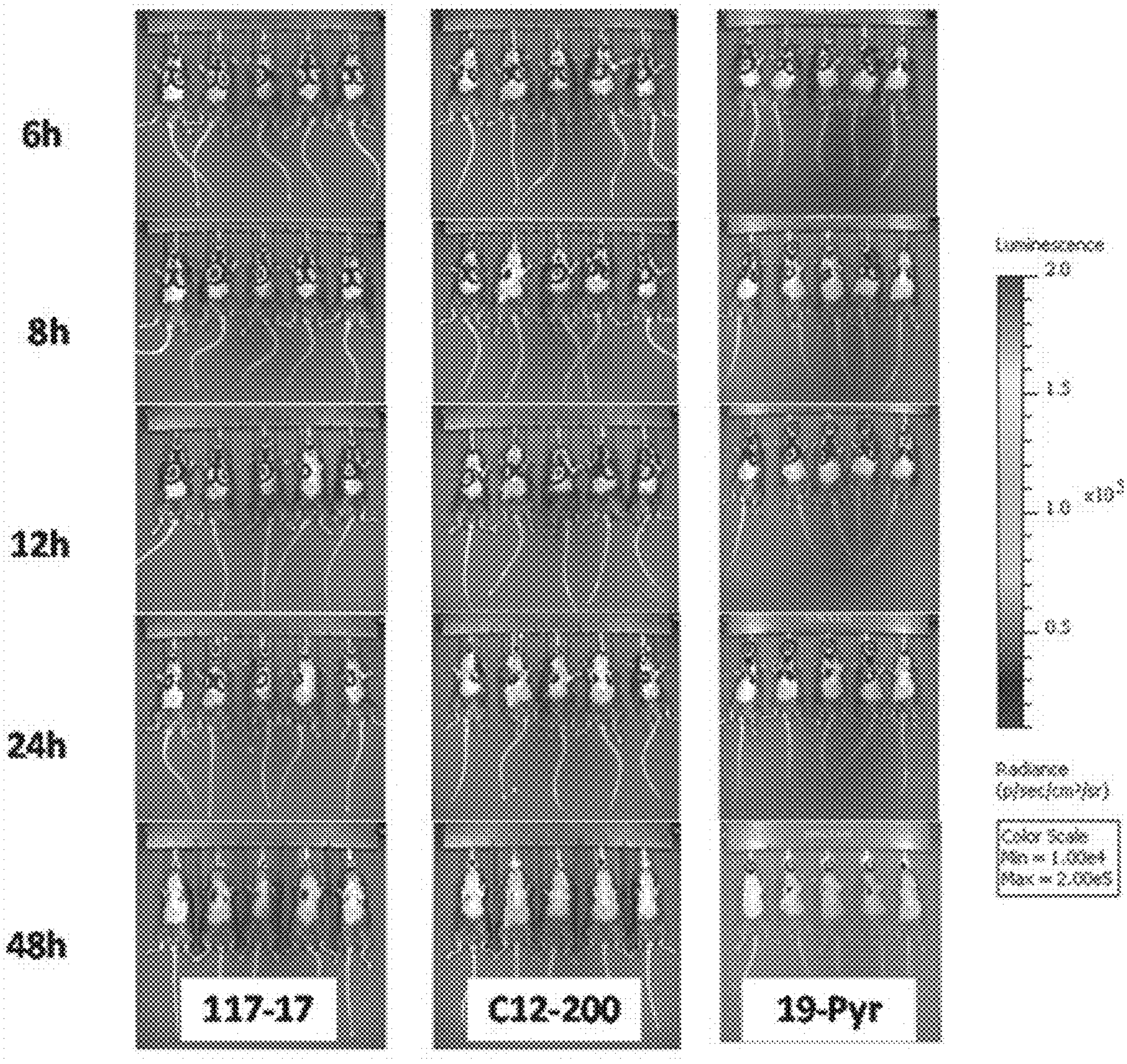
Figure 14A:
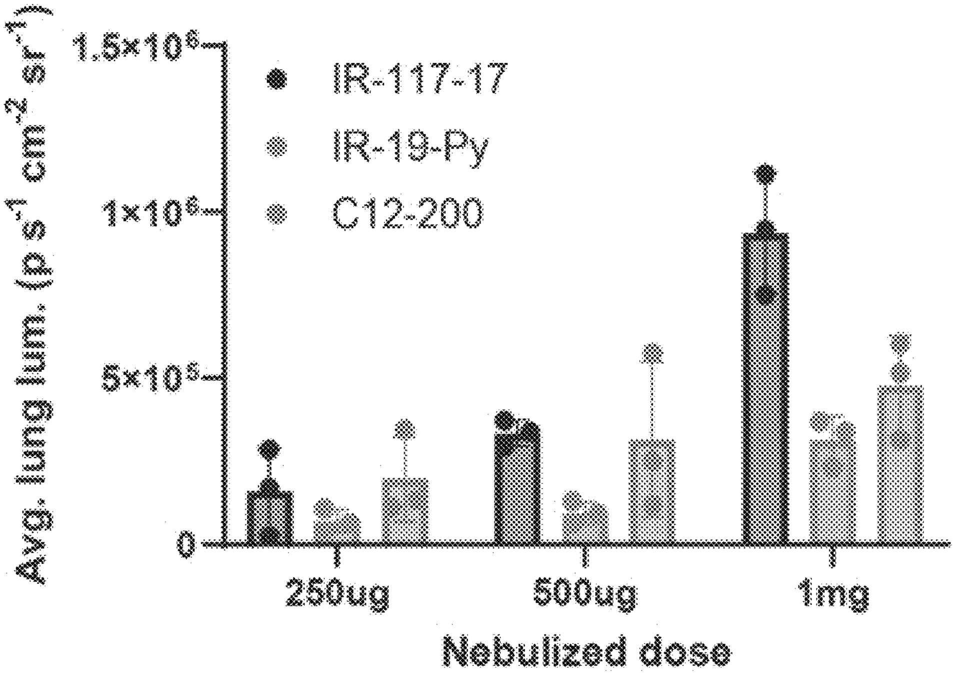
FIG. 14A shows a dose-response study of T1-5 LNPs comprising the two biodegradable ionizable lipids, IR-117-17 and IR-19-Py, compared to the non-biodegradable lipid C12-200. Average±SD, biological replicates shown.
Figure 14B:
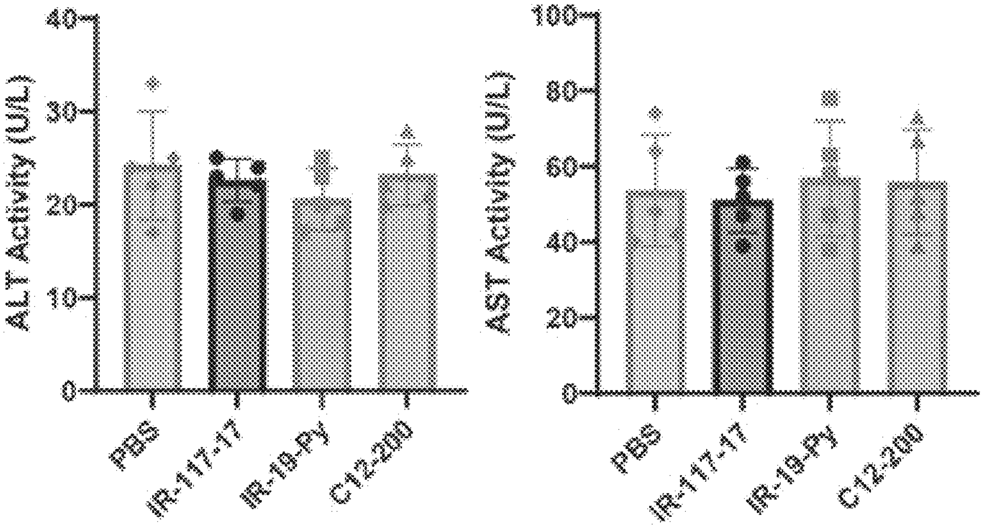
FIG. 14B shows levels of liver enzymes aspartate aminotransferase (AST) and alanine aminotransferase (ALT) in serum following three doses of LNP formulations or PBS. Average±SD, n=5 mice per experimental group.
Figure 27:
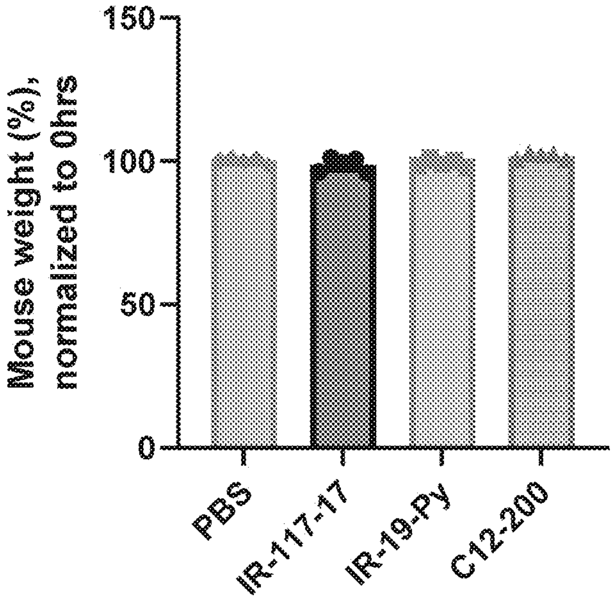
FIG. 27 shows mouse weights 48 h after third dose of 1 mg FFL mRNA normalized to weight immediately prior to nebulized delivery of $3^{rd}$ dose. Average±SD, n=5.

The top candidates, 117-17 and 19-Pyrazole, were tested in vivo via nebulization, 117-17 outperformed C12-200 while 19-Pyrazole performed comparably to C12-200. (FIG. 6A). C12-200 was reported as an aminoalcohol lipoloid in International Application No. PCT/US2009/006018. The lipids provided herein have an additional advantage of being biodegradable, which would likely make them less toxic compared to C12-200. To determine whether the protein expression in the lung could be controlled by nebulized dose, a dose-response study of the three LNPs was performed, whereby mice were nebulized with 0.25, 0.5, or 1 mg of mRNA. For all three LNPs, there was an increase in lung luminescence corresponding to increasing dose (FIG. 14A). A time-course study of protein-expression in mice following nebulized delivery of the LNPs showed that nebulized delivery of these LNPs led to protein-expression in both the lungs (FIG. 6B, 6D, 6E) and nose (FIG. 6C, 6E) of mice lasting at least 48 h after nebulized dosing. For IR-19-Py, particularly high and extended protein expression was observed in the nose, suggesting that application of this LNP as a nasal vaccine may be of interest. For mRNA protein-replacement therapies to treat pulmonary diseases like cystic fibrosis, repeat dosing of the therapeutic will be required unless genome editing is possible. Therefore, the ability to repeat-dose nebulized LNPs was characterized by administration of 1 mg of FFL mRNA every 72 h, with measurement of lung luminescence 6 h after each nebulization. For all LNPs, no loss in lung luminescence was observed over the course of the three administrations (FIG. 6B). Additionally, repeated delivery of the nebulized LNPs was well tolerated as evidenced by the lack of weight loss (FIG. 27) and normal liver enzyme levels (FIG. 14B) in mice.

The ability to efficiently deliver mRNA to the lung epithelium represents a significant advance in treatment of lung diseases such as cystic fibrosis via RNA-based gene editing or via direct delivery of mRNA encoding therapeutic proteins. Likewise, efficient delivery of mRNA to the nasal epithelium is significant in the development of mucosal vaccines. The use of biodegradable lipids may allow for repeat dosing without toxic bioaccumulation of ionizable lipids.

Figure 7:
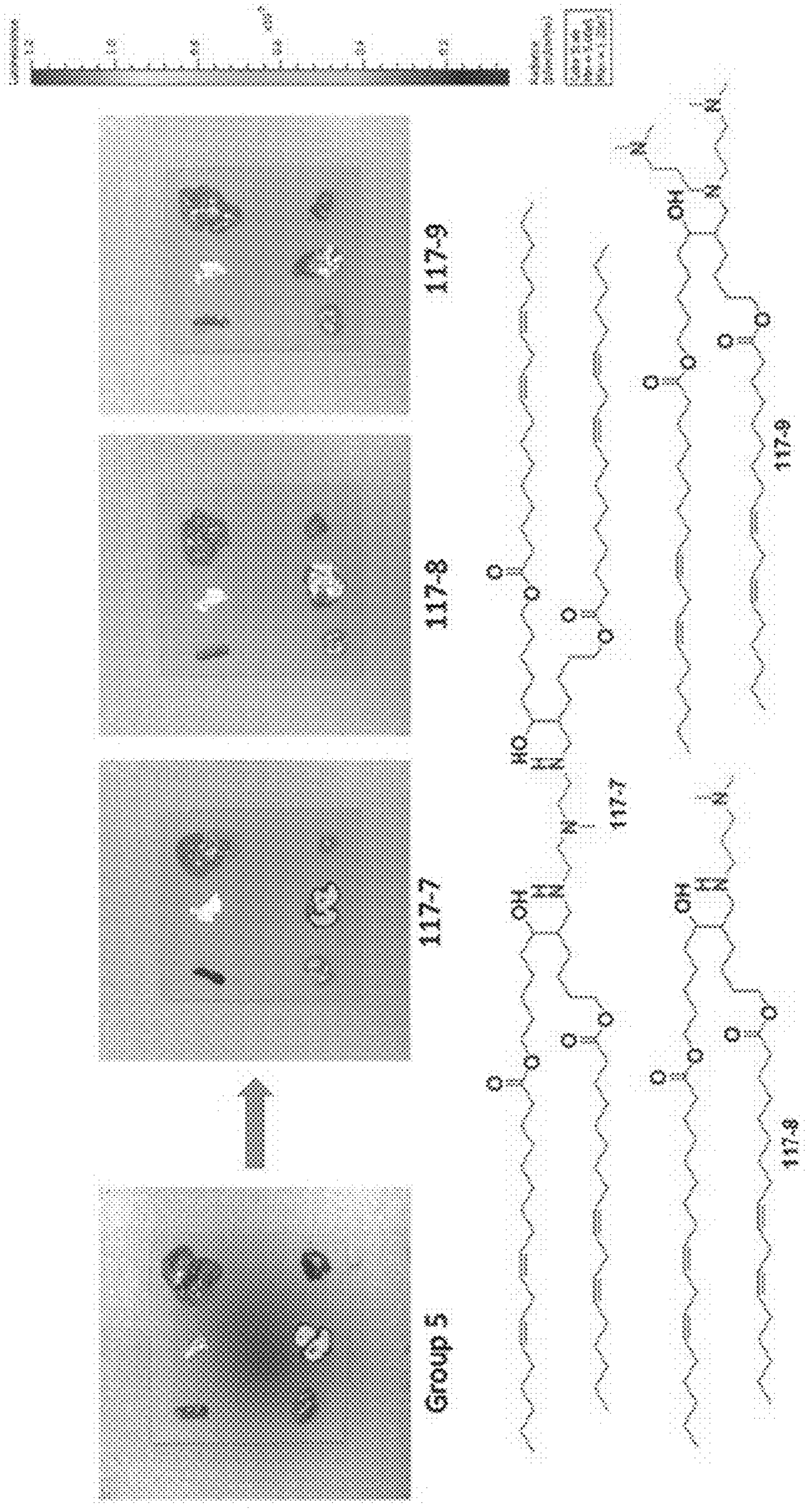
FIG. 7 shows representative images of major organs 24 hours post-injection of individual members (117-7, 117-8, and 117-9) of pooled group 5 lipids. In each image, the organs shown are (top left) spleen, (top center) pancreas, (top right) liver, (bottom left) kidneys, (bottom center) lungs, and (bottom right) heart.

Unlike the epithelium, the lung endothelium is more accessible by intravenously administered nanomedicines. To identify lipids that can potently facilitate delivery of mRNA to pulmonary endothelial cells, the entire lipid library was formulated into LNPs, and their performance was evaluated in vivo using a pooled firefly luciferase analysis following IV administration. From this analysis, it was observed that 117-7, when formulated with helper lipids (mole percentages of 35% 117-7, 16% DOPE, 46.5% cholesterol, 2.5% C14-PEG2000, 10:1 weight ratio of 117-7 to mRNA) was able to effectively deliver mRNA to the lung at a dose of 0.5 mg/kg of mRNA (FIG. 7).

Figure 8:
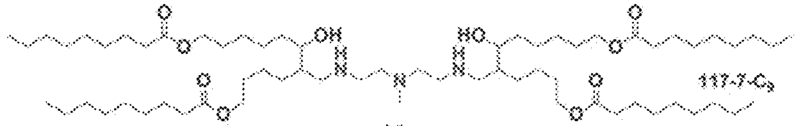
FIG. 8 shows the structures of analogs of 117-7 with varying tail lengths.
Figure 8:
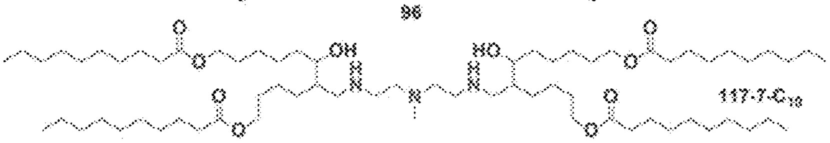
Figure 8:
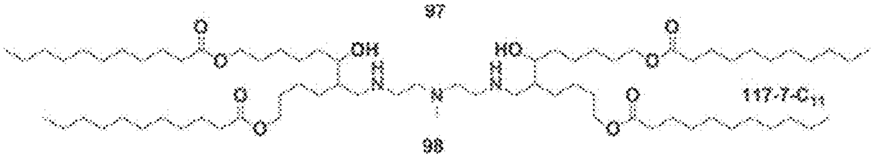
Figure 8:
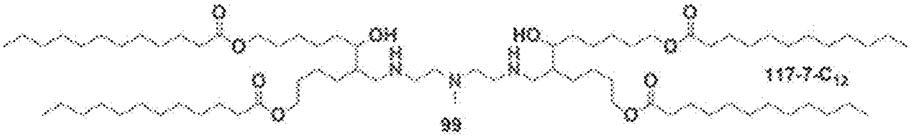
Figure 8:
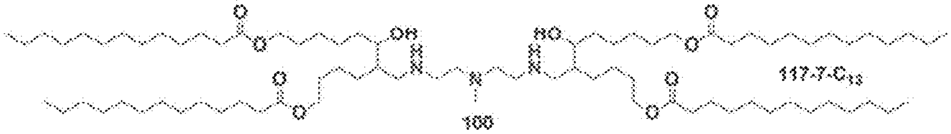
Figure 8:
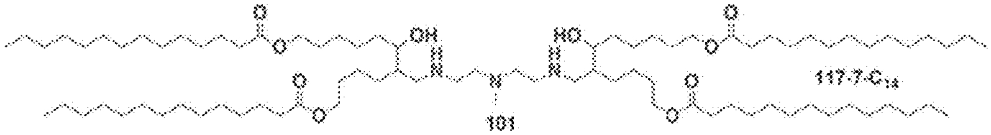
Figure 8:
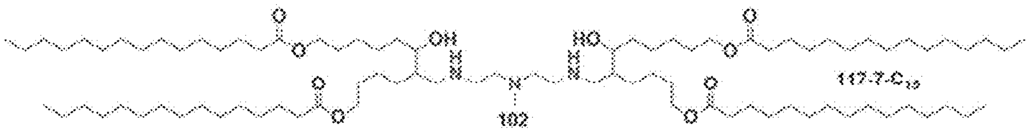
Figure 8:
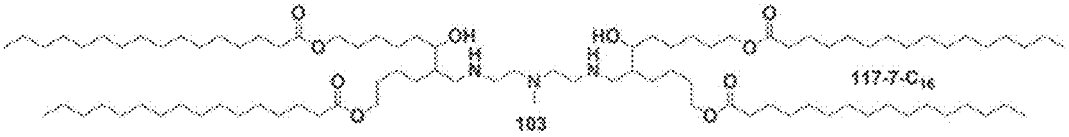
Figure 8:
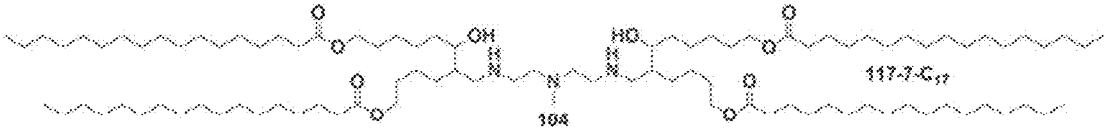
Figure 8:
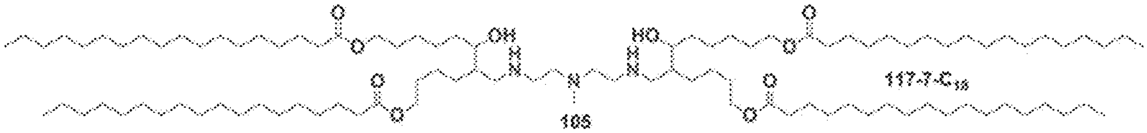
Figure 8:
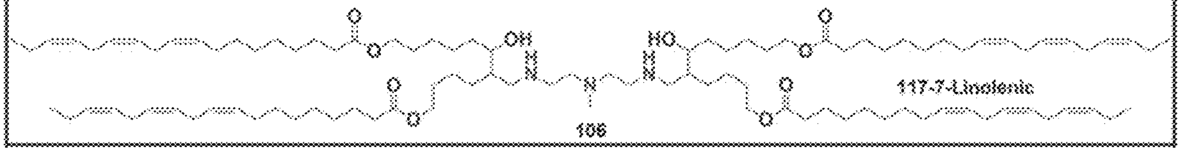
Figure 9:
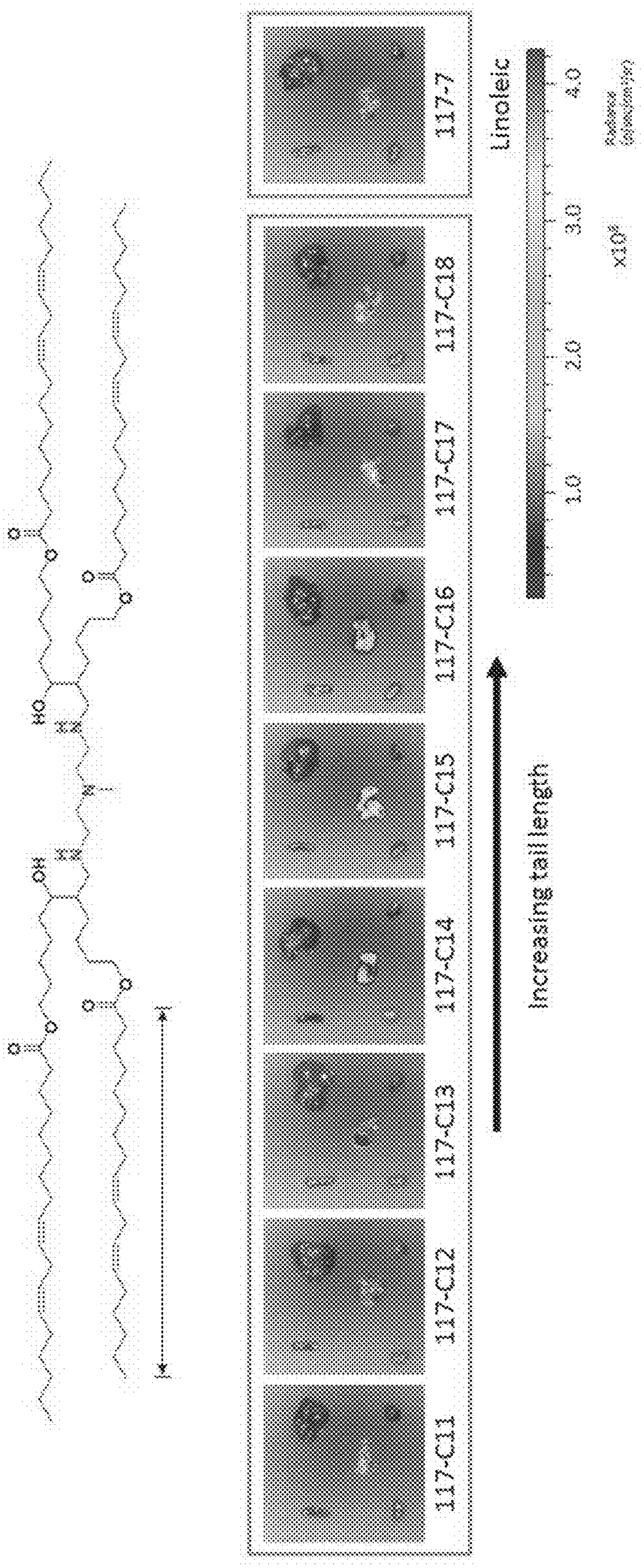
FIG. 9 shows the representative images of major organs 24 hours post-injection of analogs of 117-7. In each image, the organs shown are (top left) spleen, (top right) liver, (center) lungs, (bottom left) kidneys, and (bottom right) heart.

Further optimization of the structure of 117-7 by varying the tail length led to the identification of 117-7-C15 (FIG. 8), which was found to be roughly an order of magnitude more potent than 117-7 at the same dose of mRNA (FIG. 9).

Figure 15A:
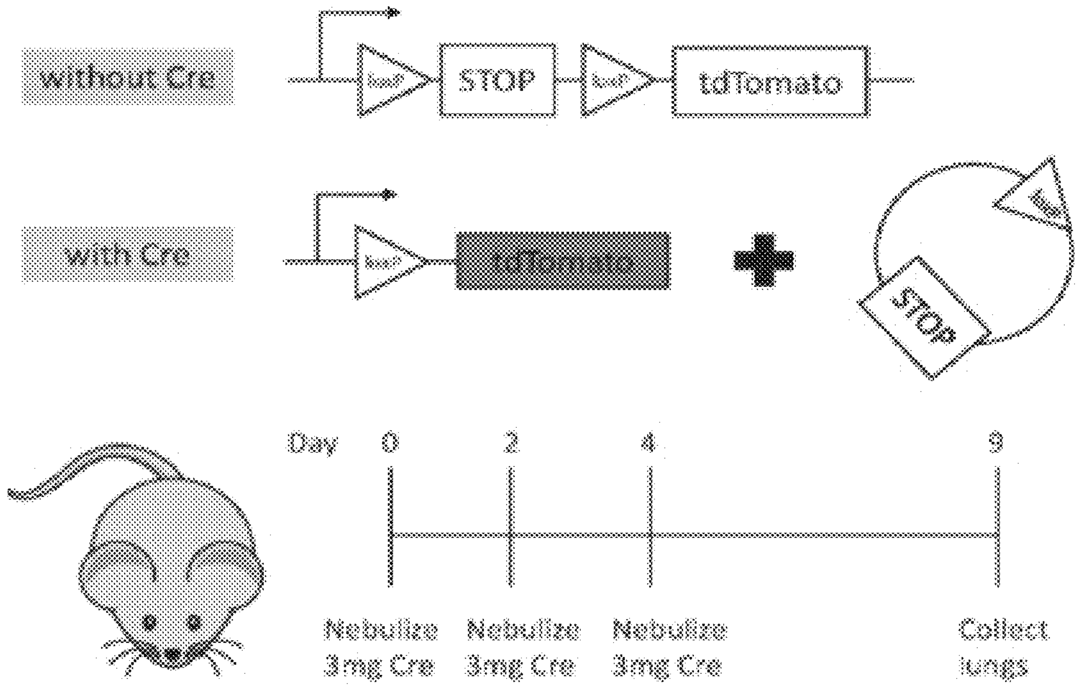
FIG. 15A shows a schematic of Cre delivery experiment to quantify transfected cells.
Figure 15B:
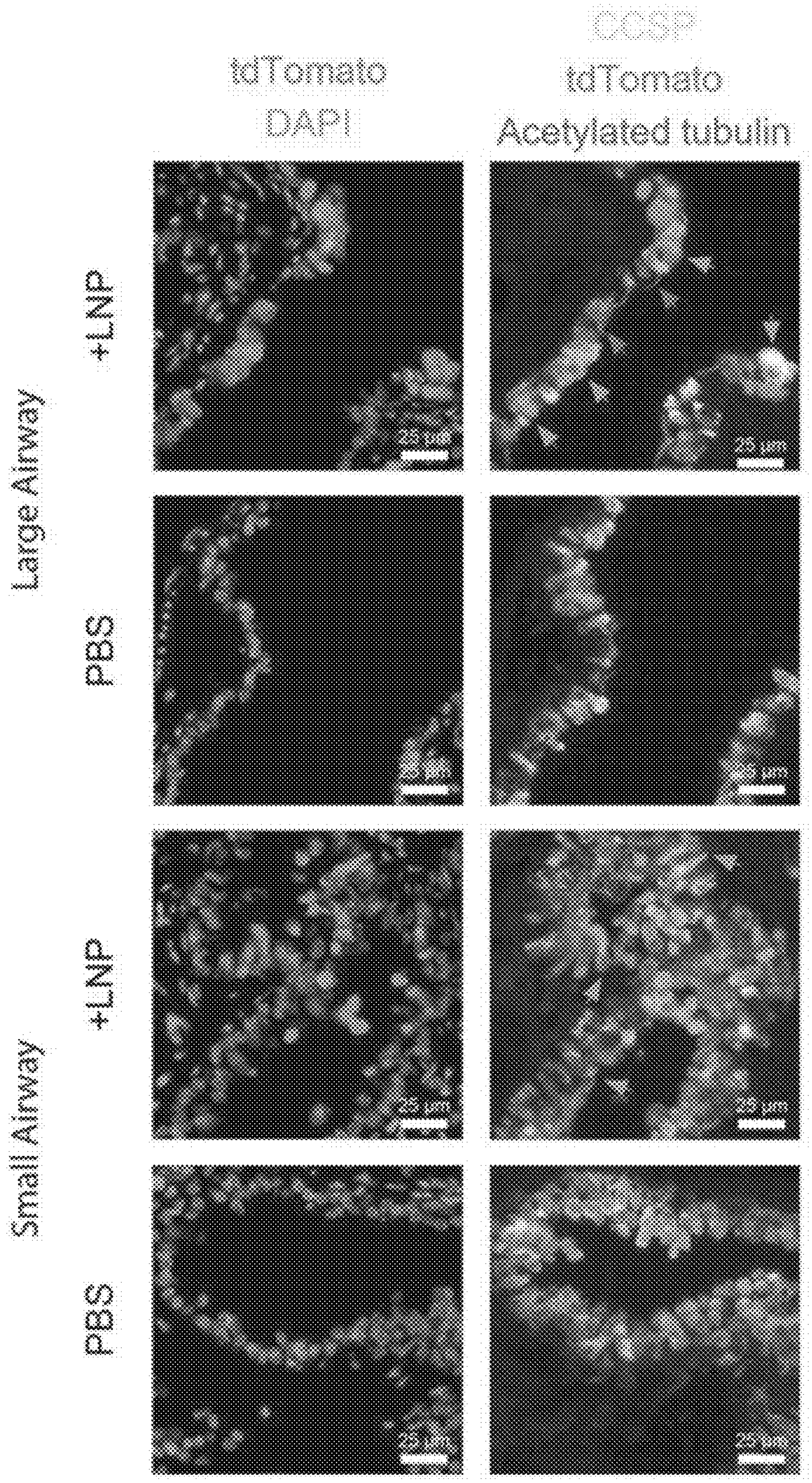
FIG. 15B shows representative images of large and small airways+/−nebulized LNP treatment. Left column: co-visualization of transfected cells (tdTomato+) with DAPI. Right column: Co-visualization of transfected cells (tdTomato+), club cells (CCSP+) and ciliated cells (acetylated tubulin [AcTub]+, AcTub is membrane-localized hence color is not present throughout the cell). Green arrows indicate transfected club cells (tdTomato+CCSP+), purple arrows indicate transfected ciliated cells (tdTomato+AcTub+).

Example 7. Evaluating Functional mRNA Delivery to Lung Epithelium with IR-117-17 LNPs in Ai14 Mouse Model To identify which cells in particular were transfected, nebulized delivery of Cre recombinase mRNA to the Ai14 mouse model was tested. Cells in these mice express tdTomato only upon Cre activity (FIG. 15A).[70] 10 mg of Cre mRNA was nebulized to mice over the course of 3 doses, and lung transfection was measured in large and small airways using histology. FIG. 15B shows representative images of the large and small airways respectively; transfected (tdTomato+) club and ciliated cells are indicated with arrows.

Figure 15C:
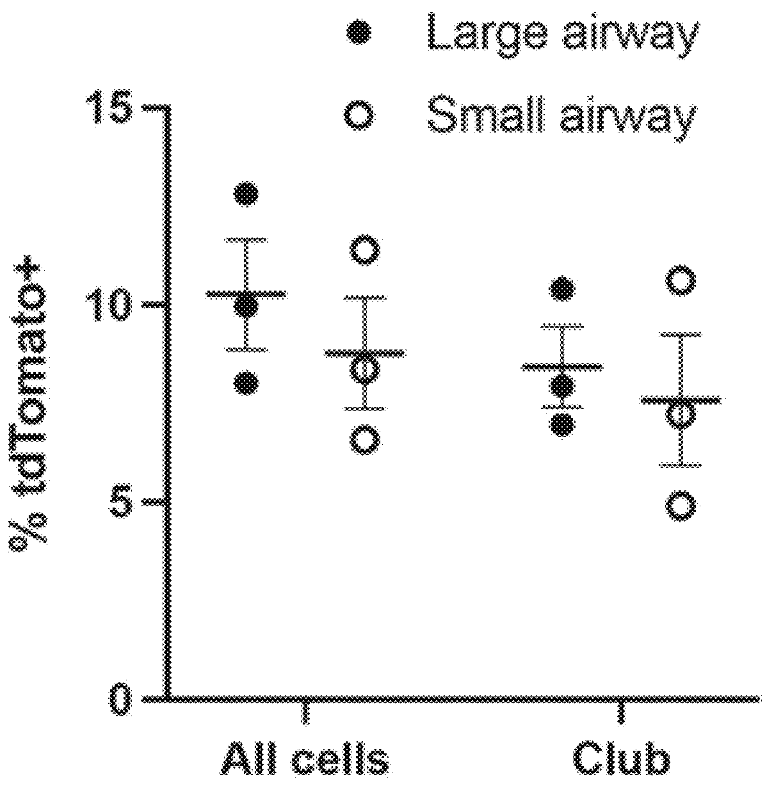
FIG. 15C shows quantification of transfection of large and small airways for all cells and club cells (n=3 mice; individual points are averages over >=5 large airways/mouse and >=27 small airways/mouse).
Figure 28A:
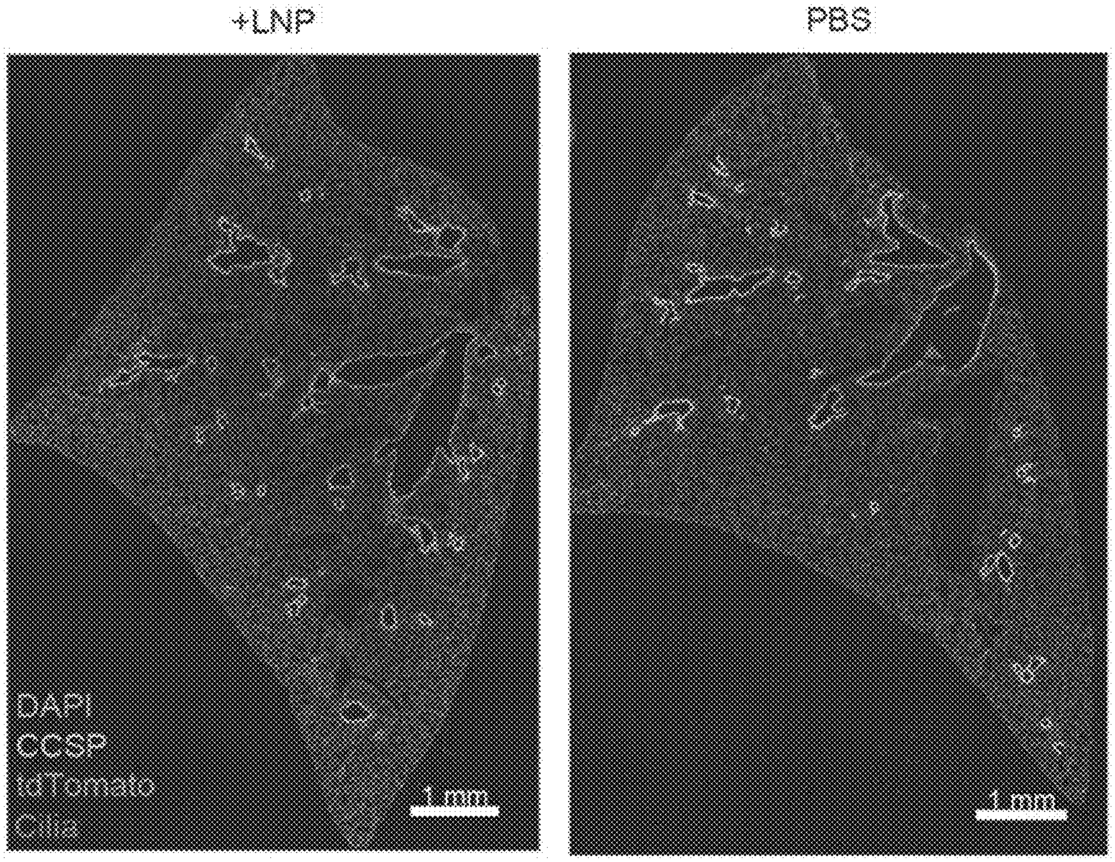
FIG. 28A shows representative whole slides that were quantified for tdTomato delivery. Transfected cells (tdTomato+) are visible in the LNP-treated mice but not the PBS treated mice.

Next, the images were quantified, indicating averages of 10.3% and 8.8% transfection of large and small airway cells respectively (FIGS. 15C & 28A). Club cell transfection was also quantified because club cells collectively are the largest source of CFTR in the lung[80,81] (while individual pulmonary ionocytes highly express CFTR.[80-83] they are rare). They can also act as progenitor cells and are easier to target via nebulization than basal cells[84] so they are excellent candidates for both gene therapy and gene editing for cystic fibrosis. Slightly smaller percentages of club cells (8.4% and 7.6%) were transfected (FIG. 15C), though the difference between club cell transfection and all cell transfection was not significant (p=0.35 for large, p=0.61 for small airway, t-test) respectively.

Figure 15D:
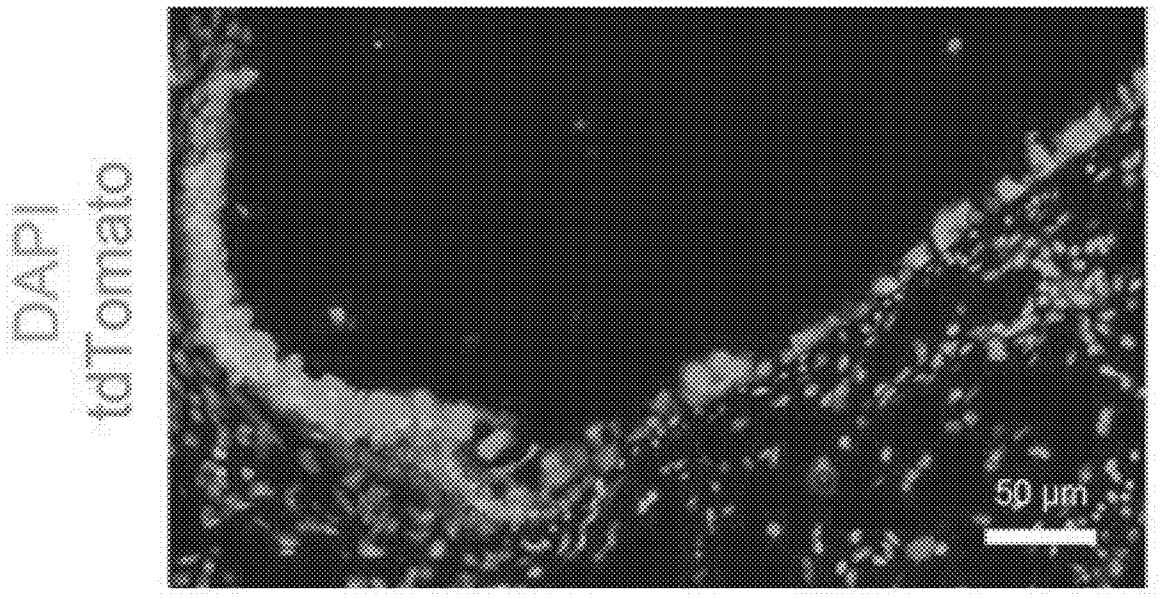
FIG. 15D shows some epithelial regions in the lung had near 100% transfection.
Figure 16A:
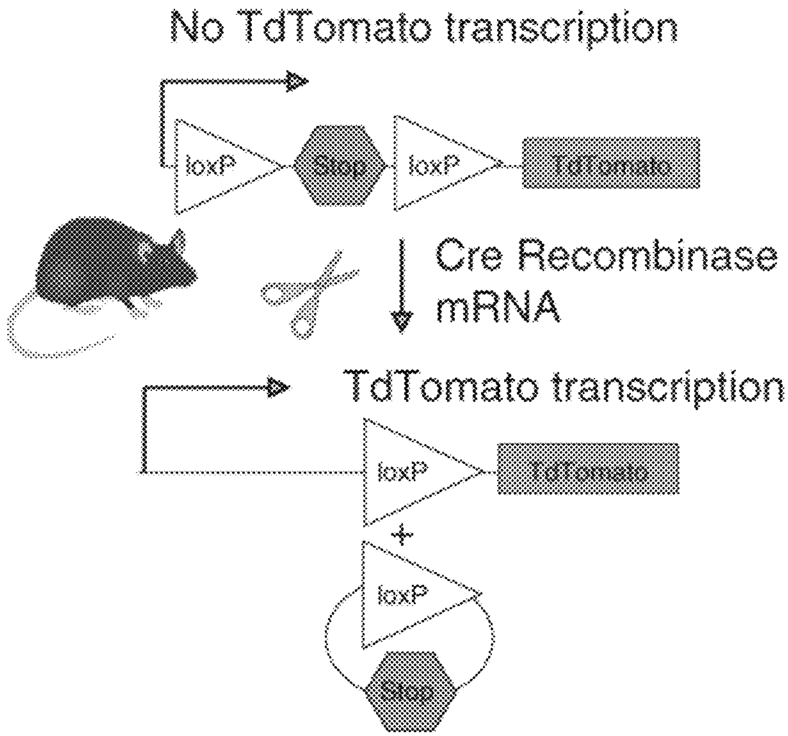
FIGS. 16A-16F show IR-117-7-C15 delivers mRNA exclusively to the lunGS.
Figure 16B:
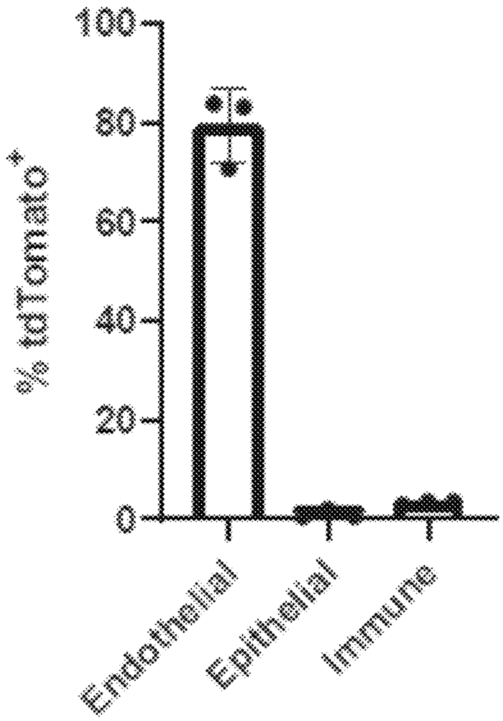
Figure 16C:
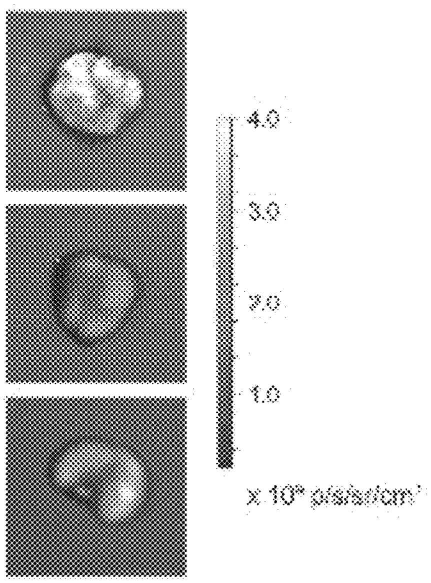
Figure 16D:
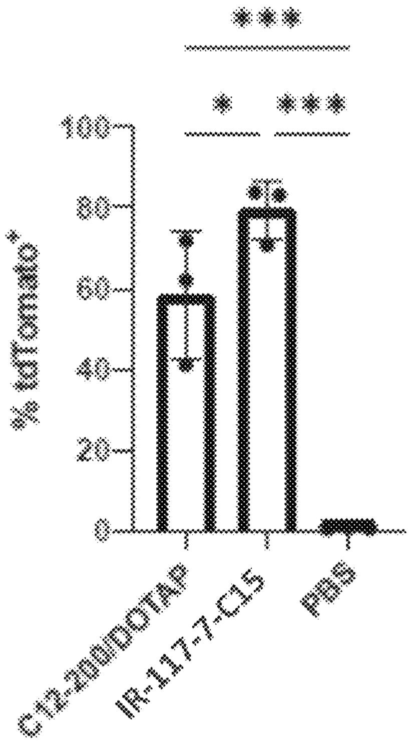
Figure 16E:
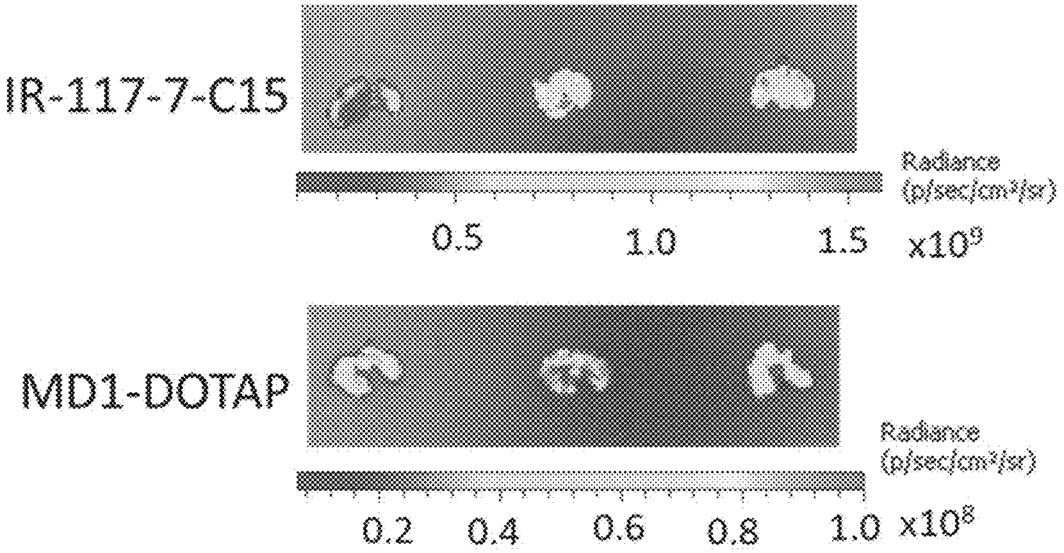
Figure 16F:
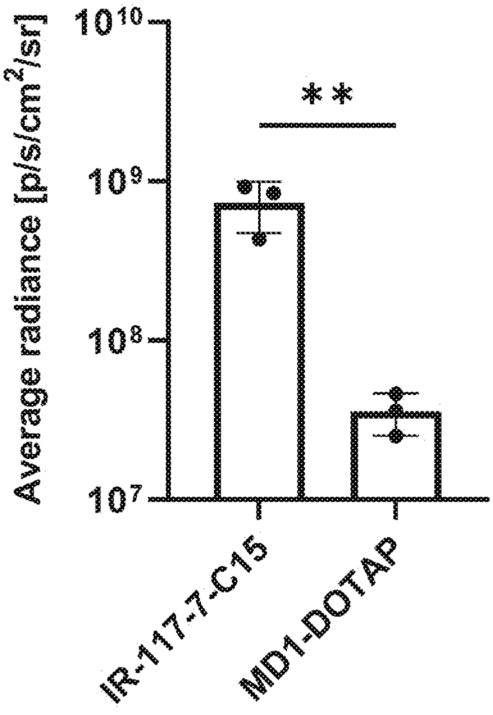
Figure 28B:
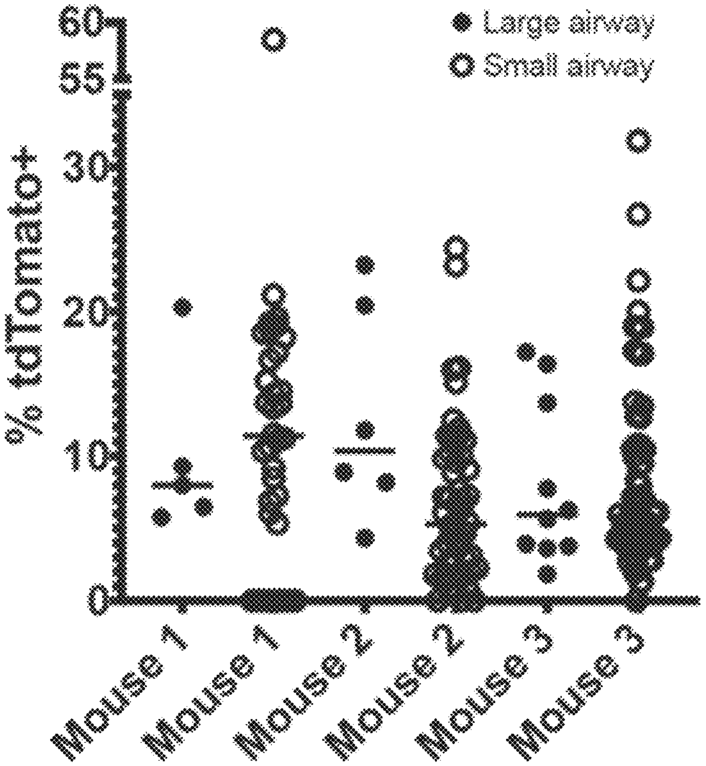
FIGS. 28B-28C show quantification of transfected cells in individual airways for all airway cells (FIG. 28B) and club cells (CCSP+) (FIG. 28C).
Figure 28C:
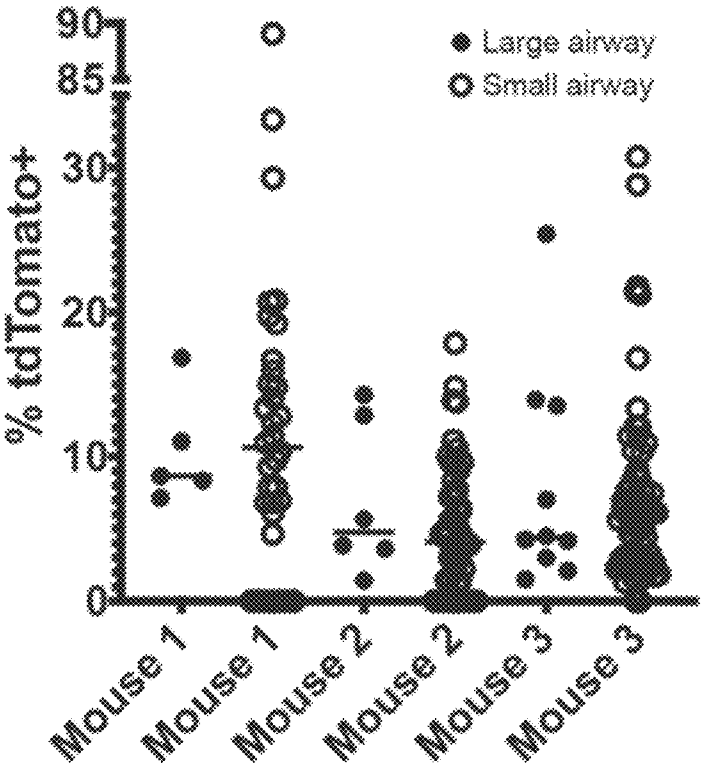

Additionally, all 21 large airways were quantified, and 140/151 (93%) of small airways had at least 1 transfected cell (FIG. 28B). However, microscale heterogeneity was observed in transfection in some images (FIGS. 28B-28C), while some individual stretches of airway showed near-complete transfection (FIG. 15D). Heterogeneity may be due to differences in transfectability and/or particle deposition.

Example 8

It is disclosed herein that novel excipients and a novel formulation were rationally designed to improve LNP stability during nebulization. The use of the excipients and DOTAP allowed the avoidance of high PEG-lipid content to stabilize LNPs to nebulization as was done previously,[54] and likely contributed to the improved potency of the formulations, as high PEG-lipid content often reduces transfection efficiency.[85] Furthermore, given that the NaAc buffer and bPEG improved delivery for LNPs containing three highly chemically distinct lipids, this buffer-excipient combination is generalizable to other LNPs.

Additionally, in vitro screens based on primary ALI cultures were shown to be an effective means of evaluating mRNA delivery LNPs for the lung. These screens are higher throughput than nebulization and require much less material, while being substantially more accurate than submerged cell culture assays. ALI cultures can be a valuable tool for screening of future delivery vehicles to the lung epithelium or of alternative strategies to improve epithelial mRNA delivery.

Further, the combination of formulation, excipient, our combinatorial lipid library, and ALI culture-based screening yielded optimized biodegradable lipids for nebulized mRNA delivery—IR-117-17 and IR-19-Py. Optimized LNPs using these two biodegradable lipids have state-of-the-art nebulized delivery to the lung and nose, respectively, substantially outperforming previously published work on nebulized LNP delivery. These nebulized LNPs also drive protein expression in multiple epithelial cell types and for multiple days, allow for multiple dosing, and have no apparent toxicity. A further advantage relative to IR-117-17's closest competitor, PBAEs, is that lipids are monodisperse, while PBAEs generated with step-growth polymerization are polydisperse polymers.[86]. To the knowledge of Applicant, the technology described here is the most potent mRNA delivery formulation reported for nebulized, in vivo mRNA delivery.

Example 9: Methods

Nanoparticle formulation. LNPs were synthesized by mixing an aqueous phase containing the mRNA with an ethanol phase containing the lipids either by pipetting or in a microfluidic chip device.[87] The aqueous phase was prepared in a 10 mM citrate buffer with corresponding mRNA (firefly luciferase and Cre recombinase mRNA provided by Translate Bio). The ethanol phase was prepared by solubilizing a mixture of ionizable lipid, helper phospholipid (DOTAP, DOPE, or DSPC [Avanti]), cholesterol (Chol, Sigma-Aldrich), and C14-$PEG_{2000}$ (Avanti) at pre-determined molar ratios with an ionizable lipid/mRNA weight ratio of 10 to 1. For microfluidically prepared LNPs, the aqueous and ethanol phases were mixed in a microfluidic device at a 3:1 ratio by syringe pumps to a final mRNA concentration of 0.1 mg/mL for in vitro studies or 0.2 mg/mL for in vivo studies. The resultant formulation was dialyzed against PBS, unless otherwise specified, overnight in a 20K MWCO dialysis cassette (ThermoFisher) at 4° C. For formulations in other buffers. LNPs were first dialyzed against PBS for 4 h followed by overnight dialysis against 0.9% saline. pH 7.0 or 100 mM NaAc buffer prepared by diluting 3M. pH 5.2 NaAc with DI $H_2O$. Following dialysis, LNPs were concentrated using Amicon 100K MWCO centrifugation filters (Sigma) at 4° C. For pipette mixed LNPs, the two phases were mixed by repeated pipetting and immediately diluted in PBS to specified concentrations.

For screening of ionizable lipids generated by reductive amination, screening took place holding mass ratios from the T1-5 formulation (with C12-200 as the ionizable lipid) constant. This corresponded to mass ratios of 50.1:24.6:16.8:8.5 Ionizable lipid:DOTAP:Cholesterol:C14-PEG2000. This constant mass ratio formulation was used in all subsequent experiments.

NLD1 LNPs and hPBAE PNPs were prepared as previously described.[53,54]

LNP characterization. mRNA encapsulation efficiencies were measured by a modified Quanti-iT Ribogreen RNA assay (Invitrogen) as previously described.[88] The diameter of the LNPs was measured using dynamic light scattering (Dyna Pro Plate Reader. Wyatt). LNPs were diluted to 0.5 ng mRNA/uL in PBS for DLS measurements. LNP diameters are reported as the largest intensity mean peak average, constituting>90% of the nanoparticles present in the sample.

Nebulization of nanoparticles. For characterizing effects of nebulization on LNP size, encapsulation efficiency, and transfection efficiency, 100 uL of LNPs at 150 ng/uL were loaded into an Aeroneb vibrating mesh nebulizer (Aerogen) and nebulized into 1.5 mL microcentrifuge tubes. Where specified, 2% w/v of excipients were added to the LNP formulation following dialysis and immediately prior to nebulization.

Cell culture. A549 lung epithelial cells (ATCC) were grown in DMEM high glucose+sodium pyruvate+GlutaMax (Gibco no. 10569-010)+10% FBS.

Primary large airway cells (University of North Carolina at Chapel Hill MLI Tissue Procurement and Cell Culture Core) and primary small airway cells (ATCC) were expanded using PneumaCult-ExPlus (StemCell) according to the instructions for the media and plated for ALI cultures at P3 and P4 respectively.

ALI cultures were plated either onto 0.4 μm pore, 6.5 mm diameter PET Transwell inserts for 24-well plates (Corning) or 0.4 μm pore polycarbonate inserts for 96-well plates (Corning). The 24-well plates were used for histology, the two-week transfection timecourse, and TEER measurements; 96-well plates were used for all other experiments, 33,000 cells/well were seeded in the 24 well inserts and 15,000 cells/well were seeded in the 96-well plate inserts.

Per manufacturer instructions, cultures were grown to confluence with both apical and basolateral (ExPlus) media for 2-4 days before airlift. Because polycarbonate inserts are opaque so confluence was not observable, each time cells were thawed and plated on a 96-well insert plate, the same cells were plated on 6.5 mm PET inserts, 96-well insert plates were airlifted one day after the concurrently plated PET inserts because initial experiments showed that the extra day helped tight junctions form more consistently. Upon airlift, apical media was removed and basolateral media was changed to PneumaCult-ALI (for large airway cells) or ALI-S (for small airway cells) media (StemCell). Qualitative tight junction formation, as measured by a lack of leakage of media overnight into the apical space, was observed for both 24-well and 96-well ALI cultures within a week of airlift. Media was changed 3 times/week and cells were not transfected until at least 20 days of ALI culture.

In vitro transfection experiments. For DOE screening and optimization of the IR-117-17 and IR-19-Py leads, 10,000 A549 cells/well were plated in white-sided, clear bottom 96-well plates. After 24 h of incubation, FFL mRNA encapsulated in either LNPs diluted in PBS or RNAiMAX (ThermoFisher) were added at 50 ng/well except for post-nebulized LNP samples which were added at the same volume as the respective pre-nebulized sample. For the initial reductive amination lipid screen, 2,000 A549 cells/well were plated in a white 384-well plate and allowed to grow overnight. The next day. LNPs were generated by pipette mixing (except where otherwise noted) to a final concentration of 100 ng/uL mRNA, diluted in PBS to 10 ng/uL mRNA, and wells were treated with 20 ng mRNA/well. For ALI cultures. LNPs were likewise generated by pipette mixing or microfluidic mixing as noted in the main text, and diluted to 50 ng/uL total mRNA with PBS, 10 μL of this 50 ng solution was added apically to 96-well inserts, or 20 uL to 24-well inserts.

Bioluminescence was measured 24 h after transfection using Bright-Glo (Promega) according to the manufacturer's instructions. Bioluminescence was quantified using the Tecan Infinite M200 Pro plate reader (Tecan).

Animal studies. All procedures were performed under an animal protocol approved by the Massachusetts Institute of Technology Committee on Animal Care (CAC) and the guidelines for animal care in an MIT animal facility.

In vivo nebulized delivery. In vivo nebulized delivery of mRNA to C57BL/6 mice (Jackson Laboratory) was performed either in a whole-body exposure chamber or a nose-only exposure chamber (CH Technologies) where specified. LNPs at 0.3 mg/mL of mRNA were loaded into the nebulizer at required volumes with 2% w/v excipients where specified. For the whole-body exposure chamber, the nebulizer was connected to the chamber via a tee and an oxygen flow rate of 15 SCFH was used to direct aerosol into the chamber. For the nose-only exposure chamber, mice were immobilized in restrainers and the restrainers connected to the chamber. A flow rate of 2 SLPM of oxygen was used and pressure within the chamber was maintained at −0.1 din. $H_2O$. Nebulizations were performed until no more aerosol was observed in the chamber.

In vivo bioluminescence, 6 h after nebulization, unless otherwise noted, mice were injected intraperitoneally with 0.2 ml XenoLight D-luciferin (10 mg/mL in DPBS, PerkinElmer). For whole-body imaging, mice were anesthetized in a ventilated anesthesia chamber with 2.5% isofluorane in oxygen and imaged 10 min after luciferin injection. Otherwise, mice were sacrificed 10 min after luciferin injection and organs were collected for imaging. Luminescence was measured with an in vivo imaging system (IVIS, PerkinElmer) and quantified using the Living Image software (PerkinElmer).

Toxicity study, 48 h after the third nebulization of FFL mRNA in the repeat dosing study, mice were bled and sera was isolated using microcentrifugation in BD SST microtainers. Serum was analyzed for ALT and AST levels (Custom lipid panel 62149, IDEXX Bioanalytics).

Histology study with Ai14 mice. B6.Cg-$Gt(ROSA)_{26}Sor^{tm14(CAG-tdTomato)Hze}$/J mice (Jackson Laboratory) were administered three 3 mg doses of Cre mRNA via nebulization in the nose-only exposure chamber. Control Ai14 mice were administered PBS. Nebulizations were separated by 48 h and mice were sacrificed 5 days after the final dose. Upon $CO_2$ euthanasia, the mouse lungs were first perfused with PBS via the right ventricle. The right lobes of the lung were tied off and removed for flow cytometry. The left lobe was inflated through the trachea with 0.25 mL of fresh 4% PFA and then placed in 4% PFA overnight. The following day, the left lobe was submitted for paraffin processing. The lobe was then embedded with the ventral side down and serial sections (5 μm each) were obtained until the middle of the lung was reached. For each mouse, two slides were taken for immunofluorescent imaging. One section was taken from the middle of the lung where more large airways are present and one section was taken from a quarter of the way into the lung where many small airways are present. The slides were deparaffinized, permeabilized, blocked, and then stained with rabbit anti-RFP antibody (abcam, ab62341, 1:200) for 1 hr. The slides were then washed and labeled with Dylight 594 goat anti-rabbit antibody (Vector Labs. DI-1594, 1:200). Alexa Fluor 647 anti-acetylated tubulin antibody (Santa Cruz, SC-23950, 1:200), and Alexa Fluor 488 anti-Uteroglobin/SCGB1A1/CC10 antibody (Santa Cruz, SC-390313, 1:200) for 1 hr. Autofluorescence was blocked with Vector Labs autofluorescence quencher and then slides were mounted with DAPI mounting media. Slides were imaged on a Nikon Spinning-disk confocal microscope. The number of tdTomato positive cells in all airways on these sections were counted manually using FIJI.

Statistics analysis. Design of experiment (DOE) was performed using JMP 13 software (JMP, SAS Institute).

Example 10: Synthesis of Lipids

All solvents and reagents were obtained commercially and used as such unless noted otherwise. $^1H$ and $^{13}C$ NMR spectra were recorded in $CDCl_3$ at room temperature using a Bruker Ultrashield 400 MHz instrument. Spectra were processed with Chemical shifts reported as parts per million (ppm) relative to TMS (0.00) for $^1H$. Silica gel chromatography was performed on ISCO CombiFlash Rf+ Lumen Instruments using ISCO RediSep Rf Gold Flash Cartridges (particle size: 20-40 microns). All final compounds were confirmed by mass spectrometry using direct injection method on QTOF-HRMS (Agilent) coupled to an Agilent Infinity 1260 LC system. Only top performing lipids after screening were fully characterized by $^1H$ and $^{13}C$ NMR.

Scheme 1: synthesis of tails used in reductive amination library synthesis.

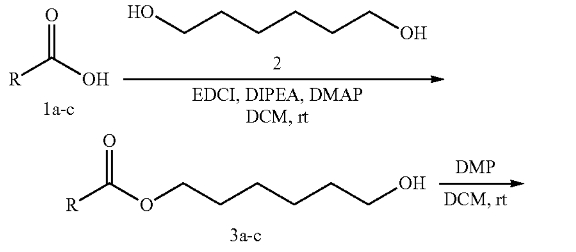

-continued

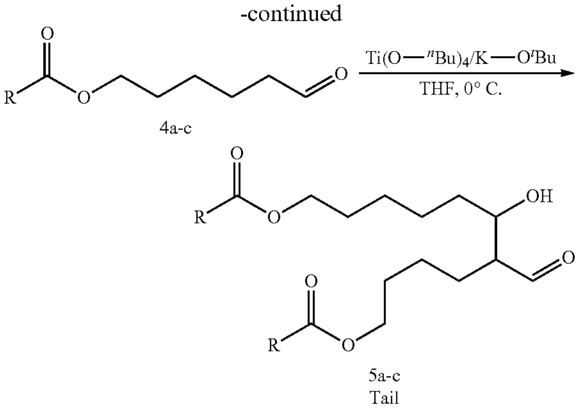

a = oleic acid,
b = linoleic acid,
c = palmitic acid

Synthesis of 6-hydroxyhexyl oleate, 3a: Oleic acid (5 g, 17.7 mmol). N-(3-dimethylaminopropyl)-N'-ethylcarbodiimide hydrochloride (EDC HCl, 5.1 g, 26.6 mmol), hexane-1,6-diol (10.5 g, 88.5 mmol), 4-(dimethylamino) pyridine (DMAP, 1.1 g, 8.9 mmol) and N, N-diisopropylethylamine (DIPEA, 6.2 ml, 35.4 mmol) were dissolved in dichloromethane (200 ml). The reaction was stirred at room temperature under nitrogen for 18 h, then washed with a saturated aqueous sodium bicarbonate solution. The organic layer was separated, washed with brine, dried over $Na_2SO_4$, filtered, and the filtrate was evaporated under vacuum. The residue was purified by silica gel chromatography (0-50% ethyl acetate in hexanes) to give 6-hydroxyhexyl oleate, 3a (5.8 g, 15.2 mmol, 86%) as a colorless oil. $^1H$ NMR (400 MHz, $CDCl_3$) δ 5.43-5.29 (m, 2H), 4.09 (t, J=6.7 Hz, 2H), 3.67 (t, J=6.5 Hz, 2H), 2.31 (t, J=7.5 Hz, 2H), 2.03 (q, J=6.5 Hz, 4H), 1.73-1.53 (m, 6H), 1.49-1.17 (m, 24H), 0.95-0.83 (m, 3H).

Synthesis of 6-oxohexyl oleate, 4a: 6-hydroxyhexyl oleate, 3a (5.8 g, 15.2 mmol) was dissolved in dichloromethane (300 ml) followed by Dess-Martin Periodinane (9.6 g, 22.8 mmol). The reaction was stirred under nitrogen at room temperature for 2 hr. After confirmation of reaction completion by thin layer chromatography, sodium thiosulfate pentahydrate (50% w/v, 200 ml) was added to the reaction and left to stir for additional 15 mins. Organic layer was thereafter separated, washed with brine, dried over $Na_2SO_4$, filtered, and the filtrate was evaporated under vacuum. The residue obtained was purified by silica gel chromatography (0-50% ethyl acetate in hexanes) to give 6-oxohexyl oleate, 4a (3.5 g, 9.2 mmol, 61%) as a colorless oil. $^1H$ NMR (400 MHz, $CDCl_3$) δ 9.79 (s, J=1.8 Hz, 1H), 5.42-5.33 (m, 2H), 4.09 (t, J=6.6 Hz, 2H), 2.47 (td, J=7.3, 1.7 Hz, 2H), 2.31 (t, J=7.5 Hz, 2H), 2.03 (q, J=6.5 Hz, 4H), 1.67 (dp, J=15.1, 7.8 Hz, 7H), 1.48-1.21 (m, 23H), 0.90 (t. J=6.8 Hz, 3H).

Synthesis of 5-formyl-6-hydroxyundecane-1,11-diyl dioleate, 5a: Titanium (IV) butoxide (3.1 g, 9.2 mmol) and potassium tert-butoxide (1.0 g, 9.2 mmol) were dissolved in anhydrous tetrahydrofuran (200 ml) and left to stir under nitrogen for 5 mins at room temperature. The mixture was then cooled to 0° C. Thereafter, (6-oxohexyl oleate, 11 (3.5 g, 9.2 mmol) was added to the reaction and stirring was continued for another 45 mins. The reaction was quenched with 1N HCl (100 ml), and then extracted with ethyl acetate (250 ml). Organic layer was separated, dried over $Na_2SO_4$, filtered, and the filtrate was evaporated under vacuum. The residue was purified by silica gel chromatography (0-50% ethyl acetate in hexanes) to give 5-formyl-6-hydroxyundecane-1,11-diyl dioleate, 5a (1.7 g, 2.3 mmol, 25%) as a brown oil. $^1$H NMR (400 MHz, $CDCl_3$) δ 9.79 (dd, J=7.1, 2.3 Hz, 1H), 5.45-5.32 (m, 4H), 4.09 (td, J=6.6, 3.3 Hz, 4H), 2.31 (t, J=7.6 Hz, 4H), 2.05 (dq, J=12.8, 6.5, 5.7 Hz, 7H), 1.87 (d, J=5.3 Hz, 2H), 1.74-1.46 (m, 15H), 1.46-1.07 (m, 42H), 0.90 (t, J=6.7 Hz, 6H).

Synthesis of 6-hydroxyhexyl (9Z,12Z)-octadeca-9,12-dienoate, 3b: 6-hydroxyhexyl (9Z,12Z)-octadeca-9,12-dienoate, 3b was made using the same procedure for the synthesis of 6-hydroxyhexyl oleate, 3a above. $^1$H NMR (500 MHz, $CDCl_3$) δ 5.47-5.26 (m, 4H), 4.09 (t, J=6.7 Hz, 2H), 3.67 (t, J=6.5 Hz, 2H), 2.80 (t. J=6.7 Hz, 2H), 2.31 (t, J=7.6 Hz, 2H), 2.07 (q, J=7.0 Hz, 4H), 1.74-1.53 (m, 7H), 1.49-1.18 (m, 18H), 0.91 (t, J=6.8 Hz, 3H).

Synthesis of 6-oxohexyl (9Z,12Z)-octadeca-9,12-dienoate, 4b: 6-oxohexyl (9Z,12Z)-octadeca-9,12-dienoate, 4b was made using the same procedure for the synthesis of 6-oxohexyl oleate, 4a above. $^1$H NMR (400 MHz, $CDCl_3$) δ 9.79 (s, 1H), 5.59-5.15 (m, 4H), 4.09 (t, J=6.6 Hz, 2H), 2.79 (t, J=6.4 Hz, 2H), 2.31 (t, J=7.6 Hz, 2H), 2.06 (dd, J=8.1, 5.7 Hz, 4H), 1.68 (dq, J=14.4, 7.2 Hz, 8H), 1.44-1.22 (m, 16H), 0.91 (t. J=6.7 Hz, 3H).

Synthesis of 5-formyl-6-hydroxyundecane-1,11-diyl (9Z,9'Z,12Z,12'Z)-bis octadeca-9,12-dienoate), 5b: 5-formyl-6-hydroxyundecane-1,11-diyl (9Z,9'Z,12Z,12'Z)-bis(octadeca-9,12-dienoate), 5b was made using the same procedure for the synthesis of 5-formyl-6-hydroxyundecane-1,1-diyl dioleate, 5a. $^1$H NMR (400 MHz, $CDCl_3$) δ 9.78 (dd. J=7.0, 2.3 Hz, 1H), 5.47-5.24 (m, 8H), 4.09 (td, J=6.6, 3.0 Hz, 4H), 3.86 (t, J=6.1 Hz, 1H), 2.79 (t. J=6.4 Hz, 4H), 2.31 (t, J=7.5 Hz, 4H), 2.06 (dd, J=7.9, 5.9 Hz, 9H), 1.74-1.60 (m, 10H), 1.48-1.16 (m, 36H), 0.91 (t, J=6.8 Hz, 6H).

Synthesis of 6-hydroxyhexyl palmitate, 3c: 6-hydroxyhexyl palmitate 3c (octadecanoic acid) was made using the same procedure for the synthesis of 6-hydroxyhexyl oleate, 3a above. $^1$H NMR (500 MHz, $CDCl_3$) δ 4.09 (t. J=6.7 Hz, 2H), 3.67 (q, J=6.2 Hz, 2H), 2.31 (t, J=7.6 Hz, 2H), 1.64 (tp, J=21.2, 6.7 Hz, 7H), 1.48-1.36 (m, J=3.6, 3.0 Hz, 4H), 1.36-1.20 (m, 22H), 0.90 (t. J=6.9 Hz, 3H).

Synthesis of 6-oxohexyl palmitate, 4c: 6-oxohexyl palmitate 4c was made using the same procedure for the synthesis of 6-oxohexyl oleate, 4a above. $^1$H NMR (500 MHz, $CDCl_3$) δ 9.79 (s, 1H), 4.09 (t, J=6.6 Hz, 2H), 2.48 (td, J=7.3, 1.7 Hz, 2H), 2.31 (t, J=7.5 Hz, 2H), 1.75-1.53 (m, 7H), 1.28 (s, 24H), 0.90 (t, J=6.9 Hz, 3H).

Synthesis of 5-formyl-6-hydroxyundecane-1,1-diyl dipalmitate, 5c: 5-formyl-6-hydroxyundecane-1,1-diyl dipalmitate, 5c was made using the same procedure for the synthesis of 5-formyl-6-hydroxyundecane-1,11-diyl dioleate, 5a. $^1$H NMR (500 MHz, $CDCl_3$) δ 9.79 (s, 1H), 4.09 (qd, J=6.7, 5.8, 2.4 Hz, 4H), 3.91-3.78 (m, 1H), 2.31 (t, J=7.6 Hz, 5H), 2.07 (d, J=5.6 Hz, 2H), 1.91-1.75 (m, 3H), 1.75-1.49 (m, 16H), 1.46-1.21 (m, 43H), 0.90 (t, J=6.9 Hz, 6H).

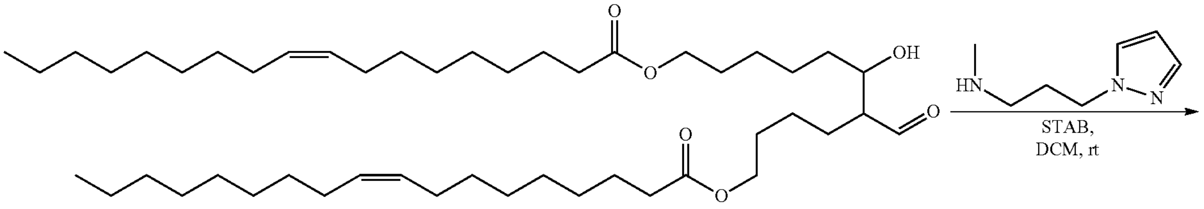

5a

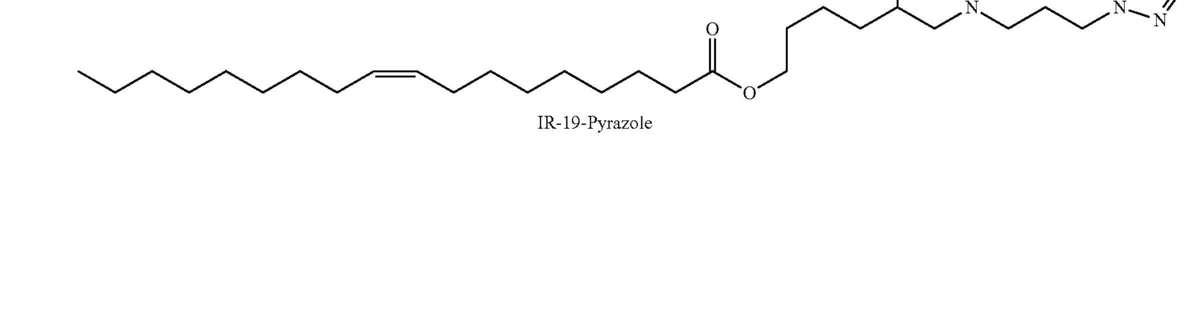

IR-19-Pyrazole

Synthesis of 5-(((3-(1H-pyrazol-1-yl)propyl)(methyl)amino)methyl)-6-hydroxyundecane-1,11-diyl dioleate, IR-19-pyrazole: N-methyl-3-(1H-pyrazol-1-yl)propan-1-amine (0.18 g, 1.30 mmol) was added to a solution of 5-formyl-6-hydroxyundecane-1,11-diyl dioleate, 5a (0.5 g, 0.66 mmol) in dichloromethane (100 ml) and left to stir under nitrogen at room temperature for 1 hr. Sodium triacetoxyborohydride (0.42 g, 1.97 mmol) was then added and the reaction was left to stir at room temperature overnight. Solvent was evaporated off, and the residue was purified by silica gel chromatography (10% methanol in dichloromethane with 0.1% $NH_4OH$) to give IR-19-Pyrazole as a colorless oil (0.37 g, 0.42 mmol, 63%). QTOF MS (ESI): m/z calcd for $C_{55}H_{102}N_3O_5^+$ (M+H), 884.78140; found, 884.7847. $^1H$ NMR (400 MHz, $CDCl_3$) δ 7.52 (d. J=1.8 Hz, 1H), 7.45 (dd. J=5.6, 2.3 Hz, 1H), 6.24 (t, J=2.0 Hz, 1H), 5.42-5.31 (m, 4H), 4.24-4.12 (m, 2H), 4.07 (q, J=7.1 Hz, 4H), 3.52 (t, J=8.3 Hz, 1H), 2.76-2.38 (m, 3H), 2.37-2.18 (m, 8H), 2.17-1.92 (m, 11H), 1.62 (tdd, J=14.3, 12.1, 10.1, 5.0 Hz, 10H), 1.48-1.20 (m, 46H), 1.14-1.00 (m, 1H), 0.94-0.83 (m, 6H). $^{13}C$ NMR (101 MHz, $CDCl_3$) δ 173.98, 173.91, 173.89, 139.42, 130.02, 129.99, 129.76, 129.71, 105.22, 64.39, 63.97, 63.93, 63.59, 60.39, 59.87, 54.89, 49.52, 49.46, 41.92, 41.86, 39.41, 39.22, 35.24, 34.37, 34.33, 31.90, 29.76, 29.70, 29.52, 29.32, 29.30, 29.19, 29.15, 29.12, 29.04, 28.86, 28.81, 27.22, 27.17, 26.23, 26.20, 24.99, 22.68, 14.12.

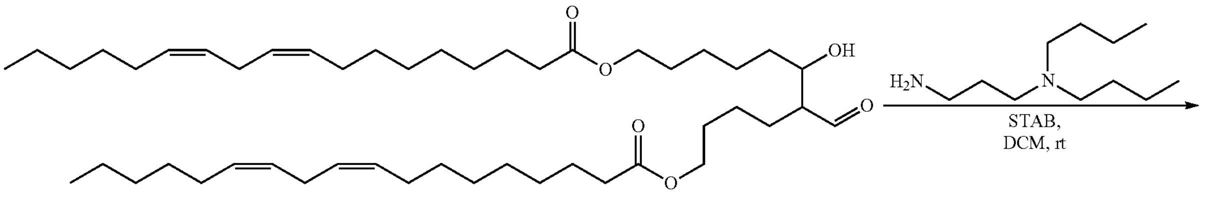

5b

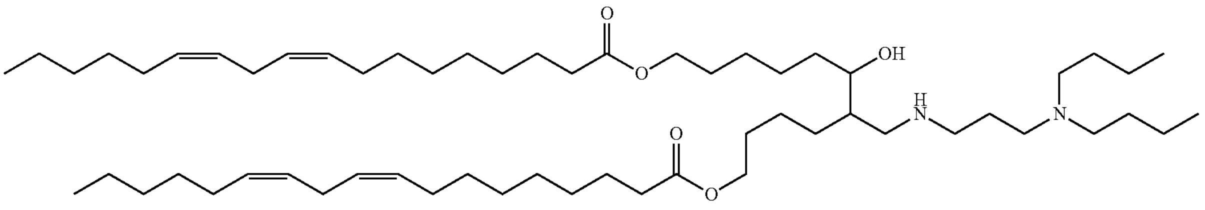

IR-117-17

Synthesis of 5-(((3-(dibutylamino) propyl) amino) methyl)-6-hydroxyundecane-1,11-diyl (9Z,9'Z,12Z,12'Z)-bis(octadeca-9,12-dienoate) IR-117-17: $N^1,N^1$-dibutylpropane-1,3-diamine (0.1 g, 0.0.54 mmol) was added to a solution of 5-formyl-6-hydroxyundecane-1,11-diyl (9Z,9'Z,12Z,12'Z)-bis(octadeca-9,12-dienoate), 5b (0.21 g, 0.28 mmol) in dichloromethane (50 ml) and left to stir under nitrogen at room temperature for 1 hr. Sodium triacetoxyborohydride (0.18 g, 0.84 mmol) was then added and the reaction was left to stir at room temperature overnight. Solvent was evaporated off, and the residue was purified by silica gel chromatography (10% methanol in dichloromethane with 0.1% $NH_4OH$) to give 5-(((3-(dibutylamino) propyl) amino) methyl)-6-hydroxyundecane-1,11-diyl (9Z,9'Z,12Z,12'Z)-bis(octadeca-9,12-dienoate). IR-117-17 as a light brown oil (0.16 g, 0.17 mmol, 61%). QTOF MS (ESI): m/z calcd for $C_{59}H_{111}N_2O_5^+$ (M+H), 927.84875; found, 927.8491. $^1H$ NMR (500 MHz, $CDCl_3$) δ 5.45-5.29 (m, 8H), 4.08 (t, J=6.7 Hz, 4H), 3.75 (dt, J=9.5, 2.9 Hz, 1H), 3.56 (td, J=7.6, 2.8 Hz, 1H), 2.96-2.86 (m, 1H), 2.79 (t, J=6.7 Hz, 4H), 2.76-2.59 (m, 3H), 2.55-2.36 (m, 6H), 2.31 (td, J=7.6, 2.2 Hz, 4H), 2.07 (q, J=7.0 Hz, 8H), 1.80-1.58 (m, 12H), 1.51-1.15 (m, 46H), 0.93 (dq, J=11.3, 8.0, 7.0 Hz, 12H). $^{13}C$ NMR (126 MHz, $CDCl_3$) δ 173.97, 173.91, 130.23, 130.22. 130.07, 130.03, 128.07, 128.04, 127.92, 127.90, 75.95, 64.41, 64.39, 64.05, 64.03, 53.76, 53.73, 52.84, 52.78, 49.54, 49.30, 42.00, 41.80, 36.11, 34.38, 34.34, 32.90, 31.53, 31.51, 31.50, 29.65, 29.62, 29.35, 29.21, 29.20, 29.16, 29.13, 29.08, 29.04, 28.97, 28.81, 28.79, 27.24, 27.21, 26.81, 26.36, 26.22, 26.20, 25.67, 25.66, 25.64, 25.34, 25.00, 24.12, 23.54, 22.58, 20.72, 14.11, 14.08, 14.06.

REFERENCES

1. Kowalski, P. S., Rudra, A., Miao, L. & Anderson, D. G. Delivering the Messenger: Advances in Technologies for Therapeutic mRNA Delivery. *Mol. Ther.* 27, 710-728 (2019).

2. Hajj, K. A. & Whitehead, K. A. Tools for translation: non-viral materials for therapeutic mRNA delivery. *Nat. Rev. Mater.* 2, 1-17 (2017).
3. Han, X. et al. An ionizable lipid toolbox for RNA delivery. *Nat. Commun.* 12, 7233 (2021).
4. Qiu, M. et al. Lipid nanoparticle-mediated codelivery of Cas9 mRNA and single-guide RNA achieves liver-specific in vivo genome editing of Angpt13. *Proc. Natl. Acad. Sci.* 118. (2021).
5. Swingle, K. L., Hamilton, A. G. & Mitchell, M. *J. Lipid* Nanoparticle-Mediated Delivery of mRNA Therapeutics and Vaccines. *Trends Mol. Med.* 27, 616-617 (2021).
6. Miao, L. et al. Delivery of mRNA vaccines with heterocyclic lipids increases anti-tumor efficacy by STING-mediated immune cell activation. *Nat. Biotechnol.* 37, 1174-1185 (2019).
7. Zhang, X. et al. Functionalized lipid-like nanoparticles for in vivo mRNA delivery and base editing. *Sci. Adv.* 6, eabc2315.
8. Billingsley, M. M. et al. Ionizable Lipid Nanoparticle-Mediated mRNA Delivery for Human CAR T Cell Engineering. *Nano Lett.* 20, 1578-1589 (2020).
9. Riley. R. S. et al. Ionizable lipid nanoparticles for in utero mRNA delivery. *Sci. Adv.* 7, eaba1028.
10. Sabnis, S. et al. A Novel Amino Lipid Series for mRNA Delivery: Improved Endosomal Escape and Sustained Pharmacology and Safety in Non-human Primates. *Mol. Ther.* 26, 1509-1519 (2018).
11. Fenton, O. S. et al. Synthesis and Biological Evaluation of Ionizable Lipid Materials for the In Vivo Delivery of Messenger RNA to B Lymphocytes. *Adv. Mater.* 29, 1606944 (2017).
12. Liu, J. et al. Fast and Efficient CRISPR/Cas9 Genome Editing In Vivo Enabled by Bioreducible Lipid and Messenger RNA Nanoparticles. *Adv. Mater.* 31, 1902575 (2019).
13. Polack, F. P. et al. Safety and Efficacy of the BNT162b2 mRNA Covid-19 Vaccine. *N. Engl. J. Med.* 383, 2603-2615 (2020).
14. Baden, L. R. et al. Efficacy and Safety of the mRNA-1273 SARS-CoV-2 Vaccine. *N. Engl. J. Med.* 384.403-416 (2021).
15. Gillmore, J. D. et al. CRISPR-Cas9 In Vivo Gene Editing for Transthyretin Amyloidosis. *N. Engl. J. Med.* 385, 493-502 (2021).
16. Cornebise, M. et al. Discovery of a Novel Amino Lipid That Improves Lipid Nanoparticle Performance through Specific interactions with mRNA. *Adv. Funct. Mater*, n/a, 2106727.
17. Barbier, A. J., Jiang, A. Y., Zhang, P., Wooster, R. & Anderson. D. G. The clinical progress of mRNA vaccines and immunotherapies. *Nat. Biotechnol.* 40, 840-854 (2022).
18. Chakraborty, C., Sharma, A. R., Bhattacharya, M. & Lee, S.-S. From COVID-19 to Cancer mRNA Vaccines: Moving From Bench to Clinic in the Vaccine Landscape. *Front. Immunol.* 12, 2648 (2021).
19. Cafri, G. et al. mRNA vaccine-induced neoantigen-specific T cell immunity in patients with gastrointestinal cancer. *J. Clin. Invest.* 130, 5976-5988 (2020).
20. Oberli, M. A. et al. Lipid Nanoparticle Assisted mRNA Delivery for Potent Cancer Immunotherapy. *Nano Lett.* 17, 1326-1335 (2017).
21. Espeseth, A. S. et al. Modified mRNA/lipid nanoparticle-based vaccines expressing respiratory syncytial virus F protein variants are immunogenic and protective in rodent models of RSV infection. *Npj Vaccines* 5, 1-14 (2020).
22. Aliprantis, A. O. et al. A phase 1, randomized, placebo-controlled study to evaluate the safety and immunogenicity of an mRNA-based RSV prefusion F protein vaccine in healthy younger and older adults. *Hum. Vaccines Immunother.* 17, 1248-1261 (2021).
23. Bahl, K. et al. Preclinical and Clinical Demonstration of Immunogenicity by mRNA Vaccines against $H10N_8$ and $H7N_9$ Influenza Viruses. *Mol. Ther.* 25, 1316-1327 (2017).
24. Feldman, R. A. et al. mRNA vaccines against $H10N_8$ and $H7N_9$ influenza viruses of pandemic potential are immunogenic and well tolerated in healthy adults in phase 1 randomized clinical trials. *Vaccine* 37, 3326-3334 (2019).
25. John, S. et al. Multi-antigenic human cytomegalovirus mRNA vaccines that elicit potent humoral and cell-mediated immunity. *Vaccine* 36, 1689-1699 (2018).
26. Medina-Magües, L. G. et al. mRNA Vaccine Protects against Zika Virus. *Vaccines* 9, 1464 (2021).
27. Mu, Z., Haynes, B. F. & Cain, D. W. HIV mRNA Vaccines—Progress and Future Paths. *Vaccines* 9, 134 (2021).
28. Zabaleta, N., Torella, L., Weber. N. D. & Gonzalez-Aseguinolaza, G. mRNA and gene editing: Late breaking therapies in liver diseases. Hepatology n/a.
29. Robinson, E. et al. Lipid Nanoparticle-Delivered Chemically Modified mRNA Restores Chloride Secretion in Cystic Fibrosis. *Mol. Ther.* 26, 2034-2046 (2018).
30. Da Silva Sanchez, A., Paunovska, K., Cristian, A. & Dahlman, J. E. Treating Cystic Fibrosis with mRNA and CRISPR. *Hum. Gene Ther.* 31, 940-955 (2020).
31. Lai, M. et al. Gene editing of DNAH11 restores normal cilia motility in primary ciliary dyskinesia. *J. Med. Genet.* 53, 242-249 (2016).
32. Paff, T., Omran, H., Nielsen. K. G. & Haarman, E. G. Current and Future Treatments in Primary Ciliary Dyskinesia. *Int. J. Mol. Sci.* 22, 9834 (2021).
33. Guan, S., Darmstädter, M., Xu, C. & Rosenecker, J. In Vitro Investigations on Optimizing and Nebulization of IVT-mRNA Formulations for Potential Pulmonary-Based Alpha-1-Antitrypsin Deficiency Treatment. *Pharmaceutics* 13, 1281 (2021).
34. Zeyer, F. et al. mRNA-Mediated Gene Supplementation of Toll-Like Receptors as Treatment Strategy for Asthma In Vivo. *PLOS ONE* 11, e0154001 (2016).
35. Mays, L. E. et al. Modified Foxp3 mRNA protects against asthma through an IL-10-dependent mechanism. *J. Clin. Invest.* 123, 1216-1228 (2013).
36. Rakhra, K. et al. Exploiting albumin as a mucosal vaccine chaperone for robust generation of lung-resident memory T cells. *Sci. Immunol.* 6, eabd8003 (2021).
37. Bivas-Benita, M. et al. Pulmonary delivery of chitosan-DNA nanoparticles enhances the immunogenicity of a DNA vaccine encoding HLA-A*0201-restricted T-cell epitopes of *Mycobacterium tuberculosis. Vaccine* 22, 1609-1615 (2004).
38. Rajapaksa, A. E. et al. Effective pulmonary delivery of an aerosolized plasmid DNA vaccine via surface acoustic wave nebulization. *Respir. Res,* 15, 60 (2014).
39. Wu, M. et al. Intranasal Vaccination with Mannosylated Chitosan Formulated DNA Vaccine Enables Robust IgA and Cellular Response Induction in the Lungs of Mice and Improves Protection against Pulmonary Mycobacterial Challenge. *Front. Cell. Infect. Microbiol.* 7, 445 (2017).

40. King, R. G. et al. Single-Dose Intranasal Administration of AdCOVID Elicits Systemic and Mucosal Immunity against SARS-CoV-2 and Fully Protects Mice from Lethal Challenge. *Vaccines* 9, 881 (2021).
41. An, X. et al. Single-dose intranasal vaccination elicits systemic and mucosal immunity against SARS-CoV-2. *iScience* 24, 103037 (2021).
42. Kim, Y. C. et al. Strategy to Enhance Dendritic Cell-Mediated DNA Vaccination in the Lung. *Adv. Ther.* 3, 2000013 (2020).
43. Lu, D. & Hickey, A. J. Pulmonary vaccine delivery. *Expert Rev. Vaccines* 6, 213-226 (2007).
44. Sou, T. et al. New developments in dry powder pulmonary vaccine delivery. *Trends Biotechnol.* 29, 191-198 (2011).
45. Huang, J. et al. A novel dry powder influenza vaccine and intranasal delivery technology: induction of systemic and mucosal immune responses in rats. *Vaccine* 23, 794-801 (2004).
46. Minne, A. et al. The delivery site of a monovalent influenza vaccine within the respiratory tract impacts on the immune response. *Immunology* 122, 316-325 (2007).
47. Wang, Z. et al. Exosomes decorated with a recombinant SARS-CoV-2 receptor-binding domain as an inhalable COVID-19 vaccine. *Nat. Biomed. Eng.* 1-15 (2022) doi: 10.1038/s41551-022-00902-5.
48. Cheng, Q. et al. Selective organ targeting (SORT) nanoparticles for tissue-specific mRNA delivery and CRISPR-Cas gene editing. *Nat. Nanotechnol.* 15, 313-320 (2020).
49. Kaczmarek, J. C. et al. Optimization of a Degradable Polymer-Lipid Nanoparticle for Potent Systemic Delivery of mRNA to the Lung Endothelium and Immune Cells. *Nano Let.* 18, 6449-6454 (2018).
50. Kaczmarek, J. C. et al. Polymer-Lipid Nanoparticles for Systemic Delivery of mRNA to the Lungs. *Angew. Chem. Int. Ed.* 55, 13808-13812 (2016).
51. Kaczmarek, J. C. et al. Systemic Delivery of mRNA and DNA to the Lung using Polymer-Lipid Nanoparticles. *Biomaterials* 120966 (2021) doi:10.1016/j.biomaterials.2021.120966.
52. Kim, N., Duncan, G. A., Hanes. J. & Suk, J. S. Barriers to inhaled gene therapy of obstructive lung diseases: A review. *J. Controlled Release* 240, 465-488 (2016).
53. Patel, A. K. et al. Inhaled Nanoformulated mRNA Polyplexes for Protein Production in Lung Epithelium. *Adv. Mater.* 31, 1805116 (2019).
54. Lokugamage, M. P. et al. Optimization of lipid nanoparticles for the delivery of nebulized therapeutic mRNA to the lungs. *Nat. Biomed. Eng.* 5, 1059-1068 (2021).
55. Wilson, C. Future therapies for cystic fibrosis. *Lancet Respir. Med.* 0, (2022).
56. Witten, J., Samad, T. & Ribbeck, K. Selective permeability of mucus barriers. *Curr. Opin. Biotechnol.* 52, 124-133 (2018).
57. Witten, J. & Ribbeck, K. The particle in the spider's web: transport through biological hydrogels. *Nanoscale* 9, 8080-8095 (2017).
58. Cone, R. A. Barrier properties of mucus. *Adv. Drug Deliv. Rev.* 61, 75-85 (2009).
59. Lieleg, O. & Ribbeck, K. Biological hydrogels as selective diffusion barriers. *Trends Cell Biol.* 21, 543-551 (2011).
60. Coyne, C. B., Kelly, M. M., Boucher, R. C. & Johnson, L. G. Enhanced Epithelial Gene Transfer by Modulation of Tight Junctions with Sodium Caprate. *Am. J. Respir. Cell Mol. Biol.* 23, 602-609 (2000).
61. Hou, X., Zaks, T., Langer, R. & Dong, Y. Lipid nanoparticles for mRNA delivery. *Nat. Rev. Mater.* 6, 1078-1094 (2021).
62. Andries, O. et al. Comparison of the Gene Transfer Efficiency of mRNA/GL67 and pDNA/GL67 Complexes in Respiratory Cells. *Mol. Pharm,* 9.2136-2145 (2012).
63. Paunovska, K. et al. A Direct Comparison of in Vitro and in Vivo Nucleic Acid Delivery Mediated by Hundreds of Nanoparticles Reveals a Weak Correlation. *Nano Lett.* 18, 2148-2157 (2018).
64. Whitehead, K. A. et al. In Vitro—in Vivo Translation of Lipid Nanoparticles for Hepatocellular siRNA Delivery. *ACS Nano* 6, 6922-6929 (2012).
65. Hill, D. B. & Button, B. Establishment of Respiratory Air-Liquid Interface Cultures and Their Use in Studying Mucin Production. Secretion, and Function, in *Mucins: Methods and Protocols* (eds. McGuckin, M. A. & Thornton, D. J.) 245-258 (Humana Press, 2012). doi:10.1007/978-1-61779-513-8_15.
66. Ramachandran, S. et al. Efficient delivery of RNA interference oligonucleotides to polarized airway epithelia in vitro. *Am. J. Physiol.—Lung Cell. Mol. Physiol.* 305. L23-L32 (2013).
67. Pezzulo, A. A. et al. The air-liquid interface and use of primary cell cultures ae important to recapitulate the transcriptional profile of in vivo airway epithelia. *Am. J. Physiol.—Lung Cell. Mol. Physiol.* 300, L25-L31 (2011).
68. Kauffman, K. J. et al. Optimization of Lipid Nanoparticle Formulations for mRNA Delivery in Vivo with Fractional Factorial and Definitive Screening Designs. *Nano Lett.* 15, 7300-7306 (2015).
69. Billingsley, M. M. et al. Orthogonal Design of Experiments for Optimization of Lipid Nanoparticles for mRNA Engineering of CAR T Cells. *Nano Lett.* 22, 533-542 (2022).
70. Kauffman, K. J. et al. Rapid. Single-Cell Analysis and Discovery of Vectored mRNA Transfection In Vivo with a loxP-Flanked tdTomato Reporter Mouse. *Mol. Ther.—Nucleic Acids* 10, 55-63 (2018).
71. Numata, M. et al. Phosphatidylglycerol provides short-term prophylaxis against respiratory syncytial virus infection. *J. Lipid Res,* 54, 2133-2143 (2013).
72. Ball, R. L., Bajaj, P. & Whitehead, K. A. Achieving long-term stability of lipid nanoparticles: examining the effect of pH, temperature, and lyophilization. *Int. J. Nanomedicine* 12, 305-315 (2017).
73. Eastman, S. J. et al. Optimization of formulations and conditions for the aerosol delivery of functional cationic lipid:DNA complexes. *Hum. Gene Ther.* 8, 313-322 (1997).
74. Krishnamurthy, S. et al. Manipulation of Cell Physiology Enables Gene Silencing in Well-differentiated Airway Epithelia. *Mol. Ther.—Nucleic Acids* 1, e41 (2012).
75. Burgel, P.-R., Montani, D., Danel, C., Dusser, D. J. & Nadel, J. A. A morphometric study of mucins and small airway plugging in cystic fibrosis. *Thorax* 62, 153-161 (2007).
76. Ratjen, F. Cystic Fibrosis: The Role of the Small Airways. *J. Aerosol Med. Pulm. Drug Deliv.* 25, 261-264 (2012).
77. van den Berge, M., ten Hacken, N. H. T., Cohen, J., Douma, W. R. & Postma, D. S. Small Airway Disease in Asthma and COPD: Clinical Implications. *Chest* 139, 412-423 (2011).
78. Tiddens, H. A. W. M., Donaldson, S. H., Rosenfeld, M. & Paré, P. D. Cystic fibrosis lung disease starts in the small airways: Can we treat it more effectively? *Pediatr. Pulmonol.* 45, 107-117(2010).

79. Tatsuta, M. et al. Effects of cigarette smoke on barrier function and tight junction proteins in the bronchial epithelium: protective role of cathelicidin LL-37. *Respir. Res,* 20, 251 (2019).

80. Okuda, K. et al. Secretory Cells Dominate Airway CFTR Expression and Function in Human Airway Superficial Epithelia. *Am. J. Respir. Crit. Care Med.* 203, 1275-1289 (2021).

81. Carraro, G. et al. Transcriptional analysis of cystic fibrosis airways at single-cell resolution reveals altered epithelial cell states and composition. *Nat. Med.* 27, 806-814 (2021).

82. Montoro, D. T. et al. A revised airway epithelial hierarchy includes CFTR-expressing ionocytes. *Nature* 560, 319 (2018).

83. Plasschaert, L. W. et al. A single-cell atlas of the airway epithelium reveals the CFTR-rich pulmonary ionocyte. *Nature* 560, 377 (2018).

84. Hodges, C. A. & Conlon. R. A. Delivering on the promise of gene editing for cystic fibrosis. *Genes Dis.* 6, 97-108 (2019).

85. Ryals, R. C. et al. *The effects of PEGylation on LNP based mRNA delivery to the eye. PLOS ONE* 15, e0241006 (2020).

86. Eltoukhy, A. A. et al. Effect of molecular weight of amine end-modified poly(p-amino ester)s on gene delivery efficiency and toxicity. *Biomaterials* 33, 3594-3603 (2012).

87. Chen, D. et al. Rapid Discovery of Potent siRNA-Containing Lipid Nanoparticles Enabled by Controlled Microfluidic Formulation. *J. Am. Chem. Soc.* 134, 6948-6951 (2012).

88. Heyes, J., Palmer, L., Bremner, K. & MacLachlan, I. Cationic lipid saturation influences intracellular delivery of encapsulated nucleic acids. *J. Control. Release Off. J. Control. Release Soc.* 107, 276-287 (2005).

89. Maier, M. A.; Jayaraman, M.; Matsuda, S.; Liu. J.; Barros, S.; Querbes, W.; Tam, Y. K.; Ansell, S. M.; Kumar, V.; Qin, J.; et al. Biodegradable Lipids Enabling Rapidly Eliminated Lipid Nanoparticles for Systemic Delivery of RNAi Therapeutics. *Mol. Ther.* 2013, 21 (8), 1570-1578, https://doi.org/https://doi.org/10.1038/mt.2013.124.

90 Reddy Guduru, S. K.; Chamakuri, S.; Raji, I. O.; MacKenzie, K. R.; Santini, C.; Young, D. W. Synthesis of Enantiomerically Pure 3-Substituted Piperazine-2-Acetic Acid Esters as Intermediates for Library Production. *J. Org. Chem,* 2018, 83 (19). https://doi.org/10.1021/acs.joc.8b01708.

91 Han, Z.; Yorimitsu, H.; Shinokubo, H.; Oshima, K. A Highly Effective Aldol Reaction Mediated by Ti(O-n-Bu)$_4$/t-BuOK Combined Reagent. *Tetrahedron Lett.* 2000, 41 (22), 4415-4418. https://doi.org/https://doi.org/10.1016/S0040-4039(00)00642-0.

92 Abdel-Magid, A. F.; Carson, K. G.; Harris, B. D.; Maryanoff, C. A.; Shah. R. D. Reductive Amination of Aldehydes and Ketones with Sodium Triacetoxyborohydride. Studies on Direct and Indirect Reductive Amination Procedures1. *J. Org. Chem,* 1996, 61 (11), 3849-3862. https://doi.org/10.1021/jo960057x.

93. Ghanem, R.; Laurent, V.; Roquefort, P.; Haute, T.; Ramel, S.; Le Gall, T.; Aubry, T.; Montier, T. Optimizations of In Vitro Mucus and Cell Culture Models to Better Predict In Vivo Gene Transfer in Pathological Lung Respiratory Airways: Cystic Fibrosis as an Example. Pharmaceutics, 2021. https://doi.org/10.3390/pharmaceutics13010047.

94. Yin, H.; Song, C.-Q.; Suresh, S.; Wu. Q.; Walsh, S.; Rhym, L. H.; Mintzer, E.; Bolukbasi, M. F.; Zhu. L. J.; Kauffman, K.; et al. Structure-Guided Chemical Modification of Guide RNA Enables Potent Non-Viral in Vivo Genome Editing. Nat. Biotechnol. 2017, 35 (12), 1179-1187. https://doi.org/10.1038/nbt.4005.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The present disclosure includes embodiments in which exactly one member of the group is present in, employed in, or otherwise relevant to a given product or process. The present disclosure includes embodiments in which more than one, or all of the group members are present in, employed in, or otherwise relevant to a given product or process.

Furthermore, the present disclosure encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the present disclosure, or aspects of the present disclosure, is/are referred to as comprising particular elements and/or features, certain embodiments of the present disclosure or aspects of the present disclosure consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the present disclosure, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present disclosure that falls within the prior art may be explicitly excluded from any one or more of the claims. Because such embodiments are deemed to be known to one of ordinary skill in the art, they may be excluded even if the exclusion is not set forth explicitly herein. Any particular embodiment of the present disclosure can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present disclosure, as defined in the following claims.

What is claimed is:

1. A compound of Formula (I):

(I)

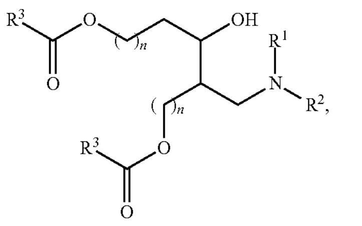

or a pharmaceutically acceptable salt, solvate, tautomer, stereoisomer, or isotopically labeled derivative thereof, wherein:

$R^1$ is —H, optionally substituted alkyl, optionally substituted alkenyl, optionally substituted alkynyl, optionally substituted heteroalkyl, optionally substituted heteroalkenyl, optionally substituted heteroalkynyl, optionally substituted aryl, optionally substituted heteroaryl, optionally substituted carbocyclyl, optionally substituted heterocyclyl, or a nitrogen protecting group;

$R^2$ is —H, optionally substituted alkyl, optionally substituted alkenyl, optionally substituted alkynyl, optionally substituted heteroalkyl, optionally substituted heteroalkenyl, optionally substituted heteroalkynyl, optionally substituted aryl, optionally substituted heteroaryl, optionally substituted carbocyclyl, optionally substituted heterocyclyl, or a nitrogen protecting group; or $R^1$ and $R^2$ are joined together with the intervening atoms to form an optionally substituted heterocyclyl;

each $R^3$ independently is optionally substituted $C_6$-$C_{25}$ aliphatic; and each n independently is 0-15, inclusive.

2. The compound of claim 1, or a pharmaceutically acceptable salt, solvate, tautomer, stereoisomer, or isotopically labeled derivative thereof, wherein each n is 4.

3. The compound of claim 1, or a pharmaceutically acceptable salt, solvate, tautomer, stereoisomer, or isotopically labeled derivative thereof, wherein $R^2$ is —H, optionally substituted $C_1$-$C_{10}$ alkyl, optionally substituted $C_1$-$C_{10}$ heteroalkyl, optionally substituted $C_3$-$C_{14}$ carbocyclyl, optionally substituted 3- to 14-membered heterocyclyl, or a nitrogen protecting group.

4. The compound of claim 1, or a pharmaceutically acceptable salt, solvate, tautomer, stereoisomer, or isotopically labeled derivative thereof, wherein $R^2$ is optionally substituted heteroalkyl comprising one or more N atoms substituted with

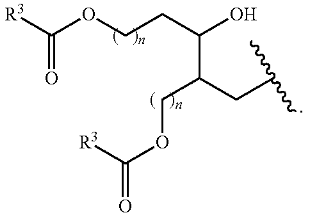

5. The compound of claim 1, or a pharmaceutically acceptable salt, solvate, tautomer, stereoisomer, or isotopically labeled derivative thereof, wherein $R^1$ and $R^2$ are joined together with the intervening atoms to form an optionally substituted heterocyclyl.

6. The compound of claim 1, or a pharmaceutically acceptable salt, solvate, tautomer, stereoisomer, or isotopically labeled derivative thereof, wherein each $R^3$ independently is optionally substituted $C_6$-$C_{25}$ alkyl, optionally substituted $C_6$-$C_{25}$ alkenyl, or optionally substituted $C_6$-$C_{25}$ alkynyl.

7. The compound of claim 1, selected from

1

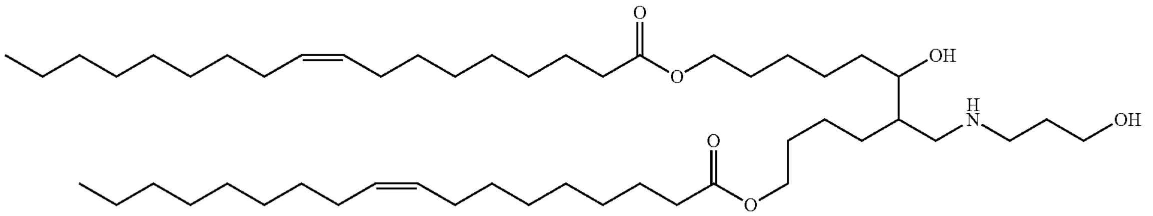

2

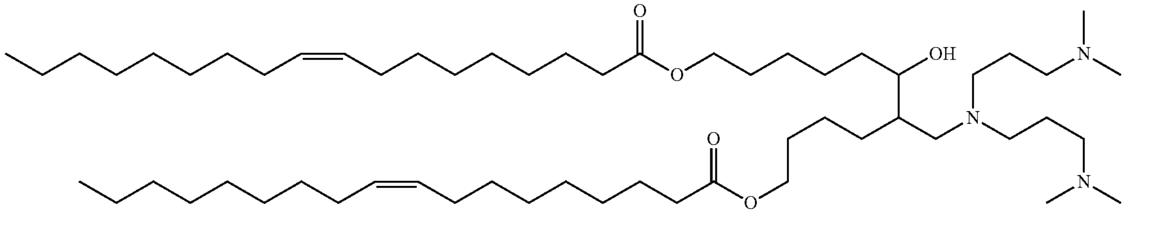

-continued
3
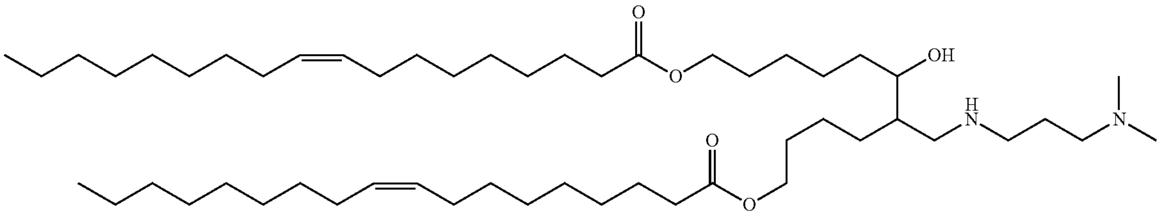
4
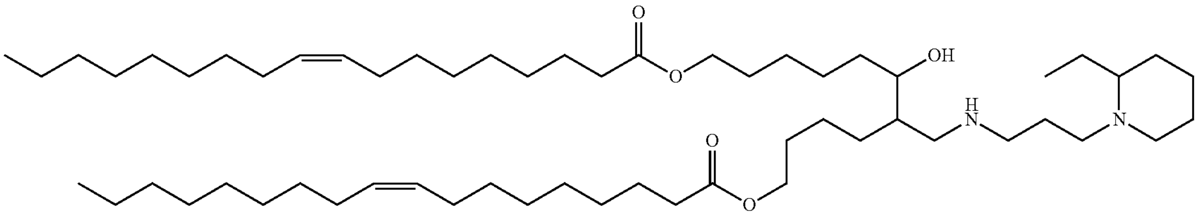
5
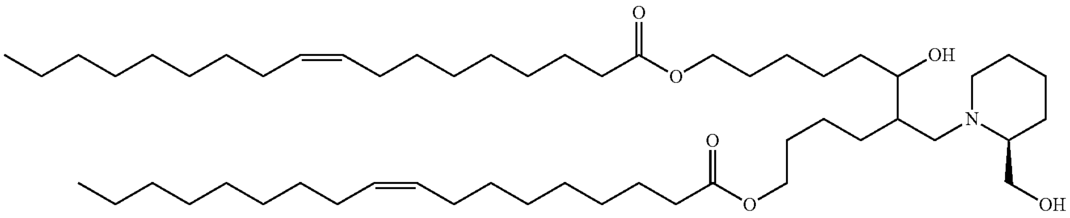
6
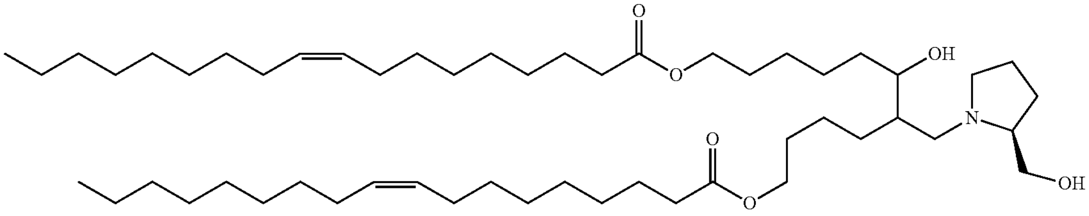
7
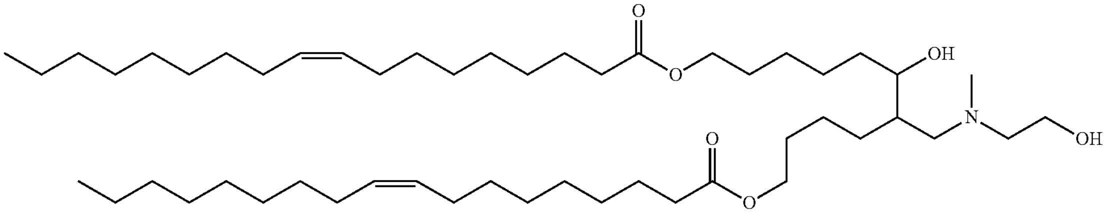
8
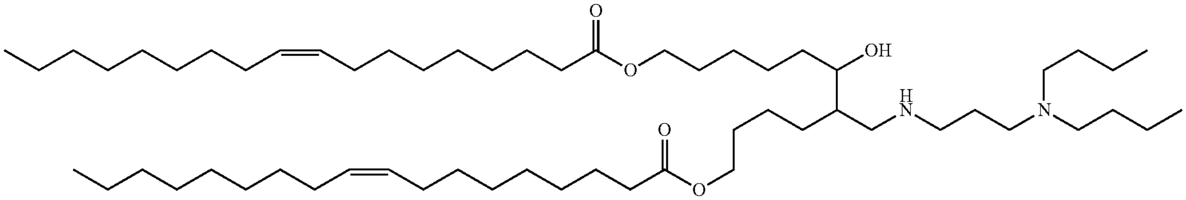
9
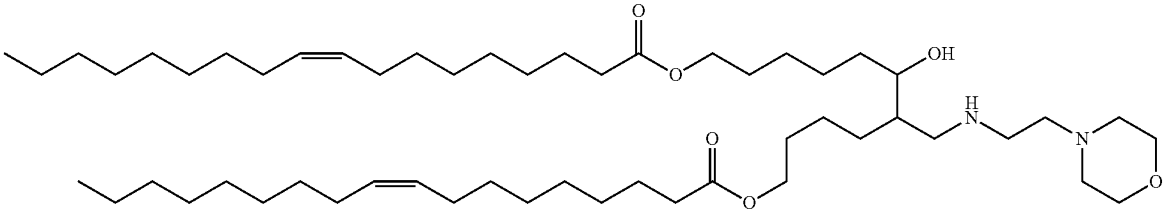

-continued
10
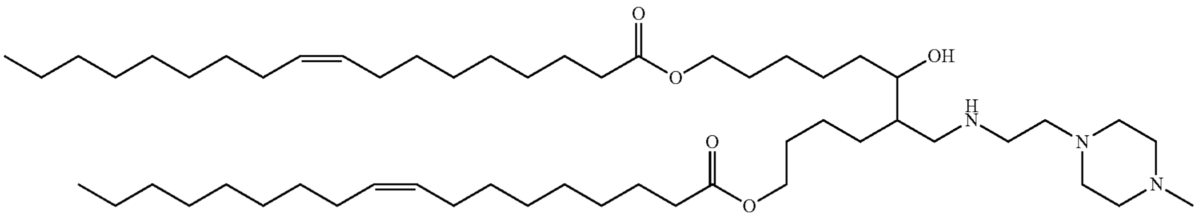
11
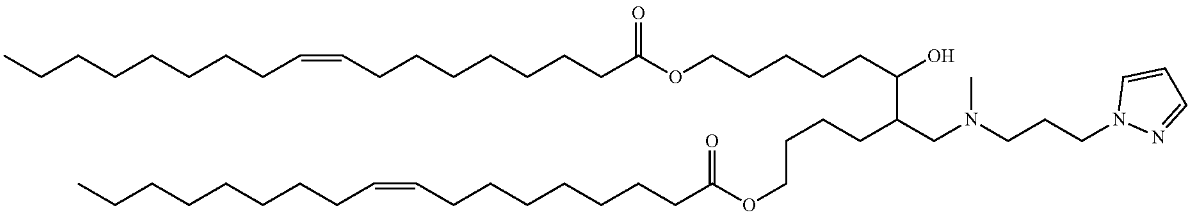
12
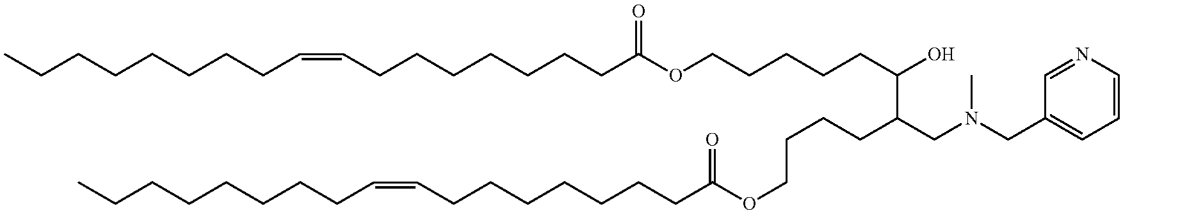
13
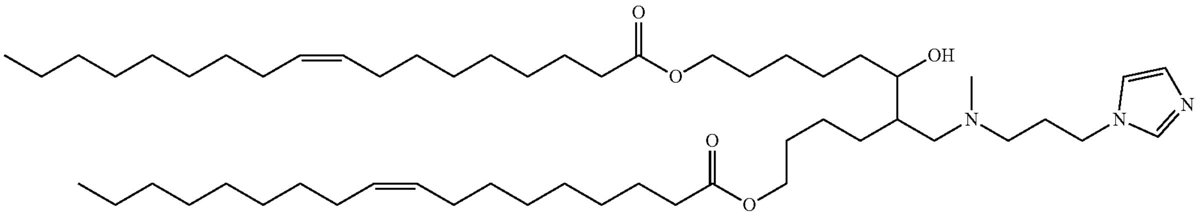
14
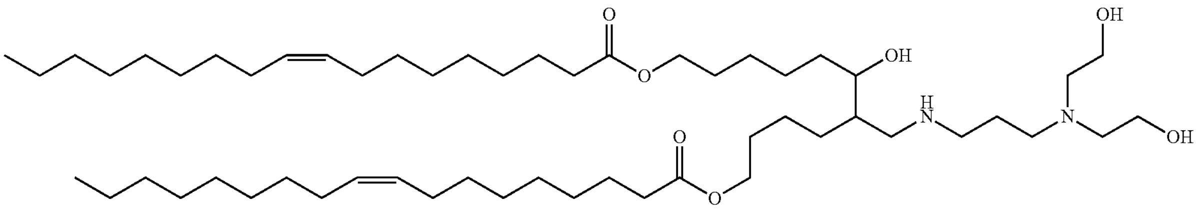
15
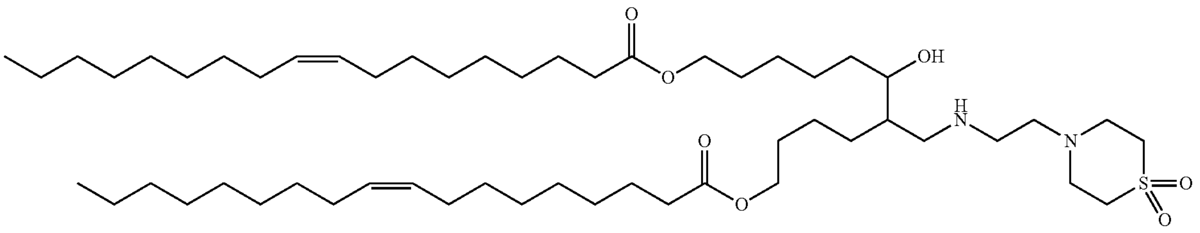

-continued
16
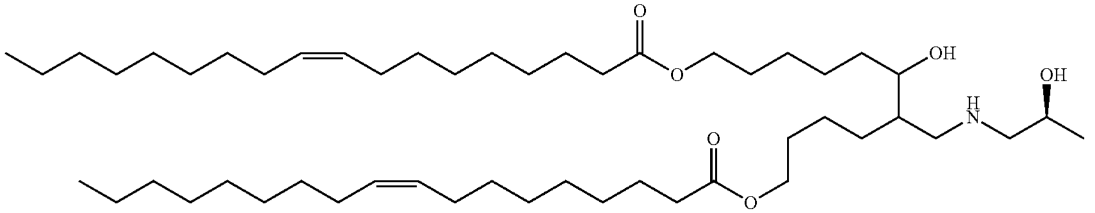
17
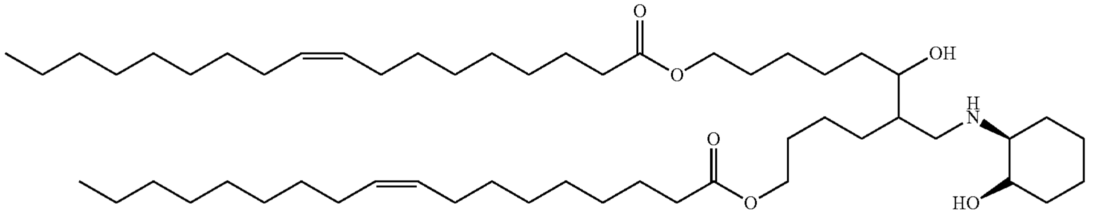
18
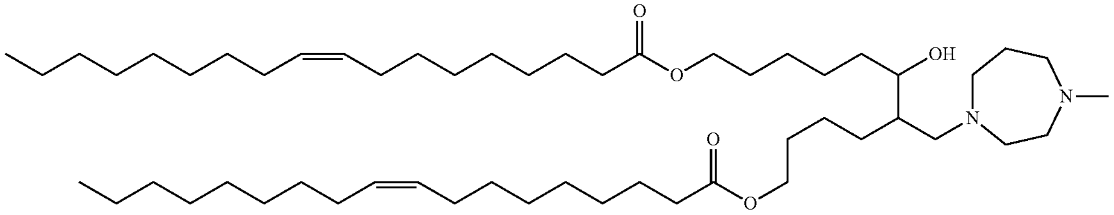
19
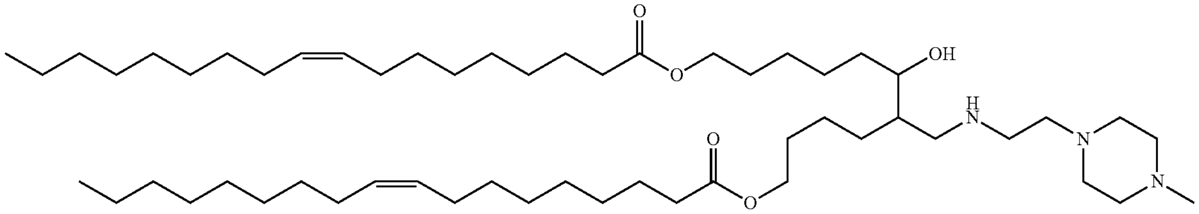
20
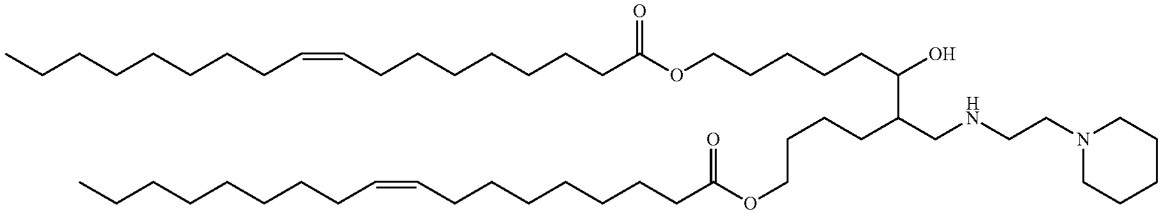
21
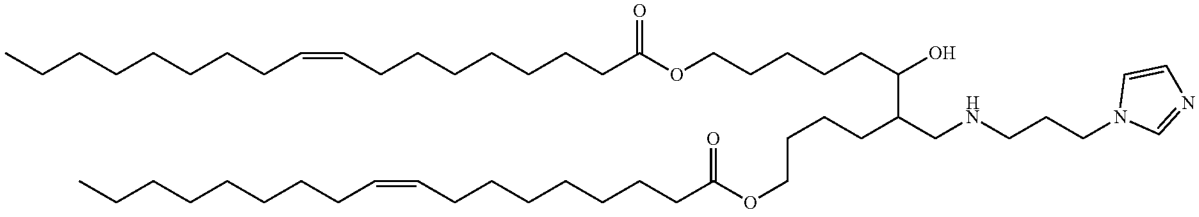
22
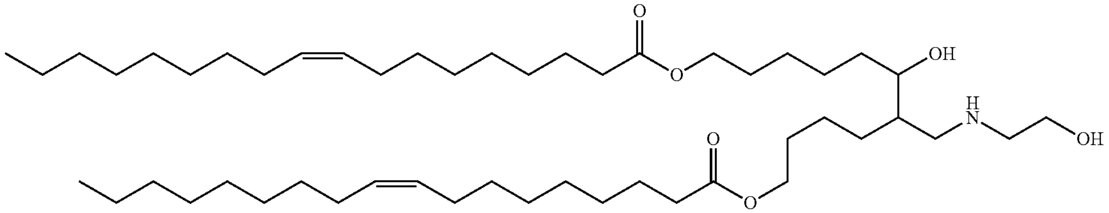

-continued
23
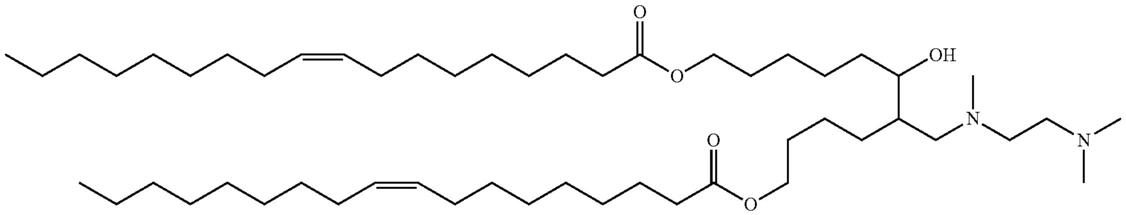
24
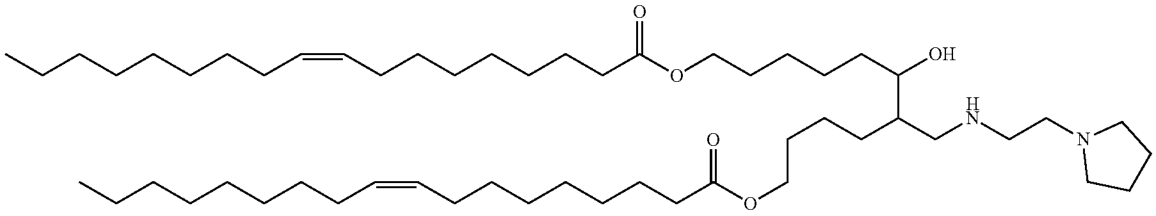
25
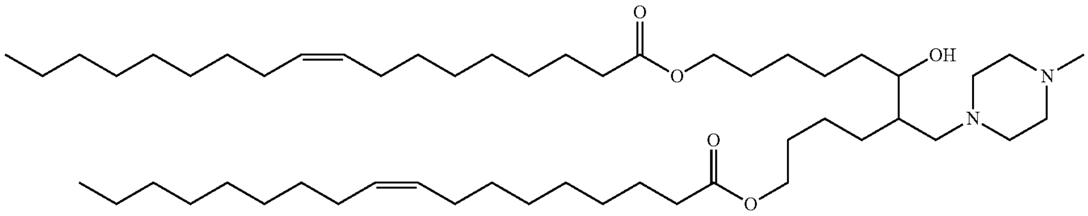
26
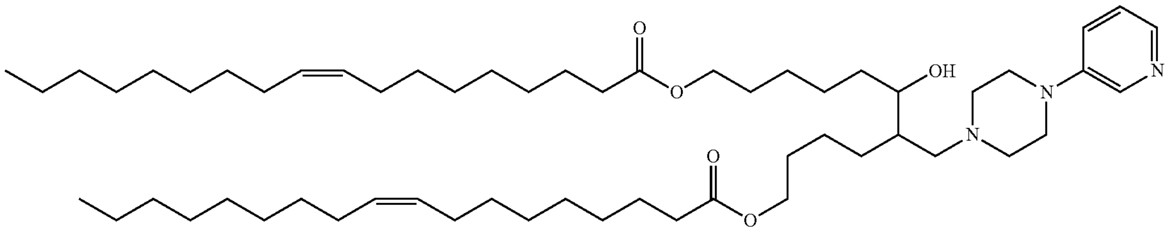
27
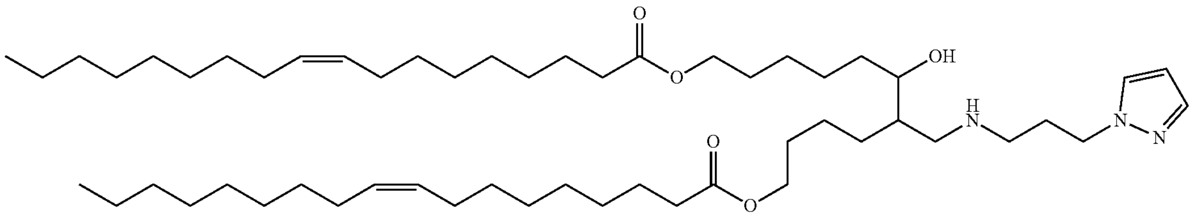
28
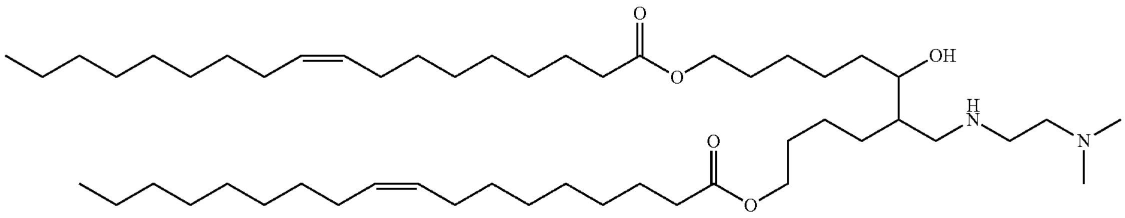
29
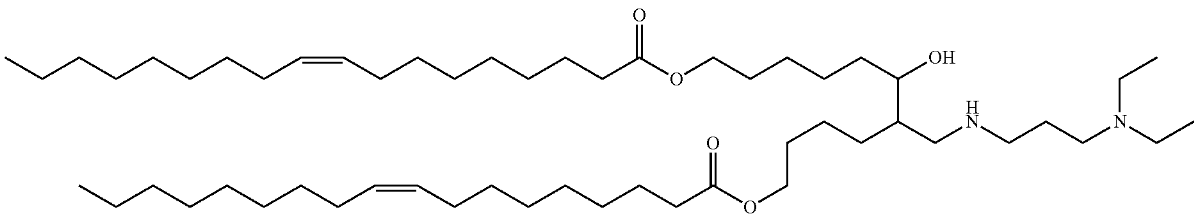

-continued
30
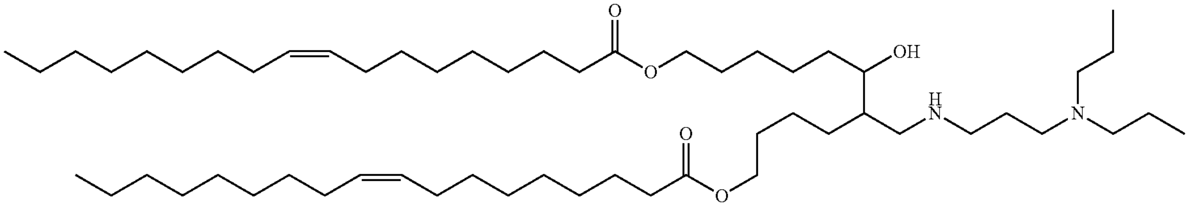
31
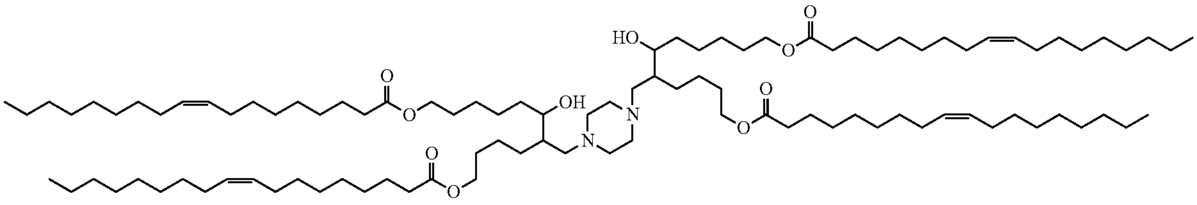
32
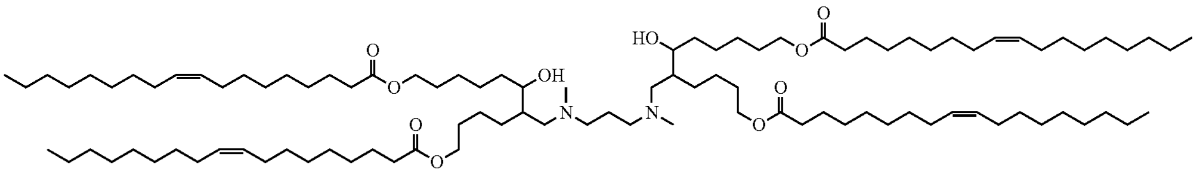
33
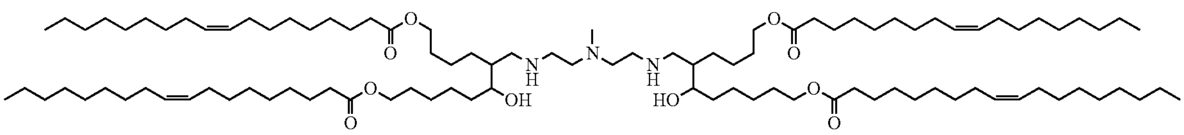
34
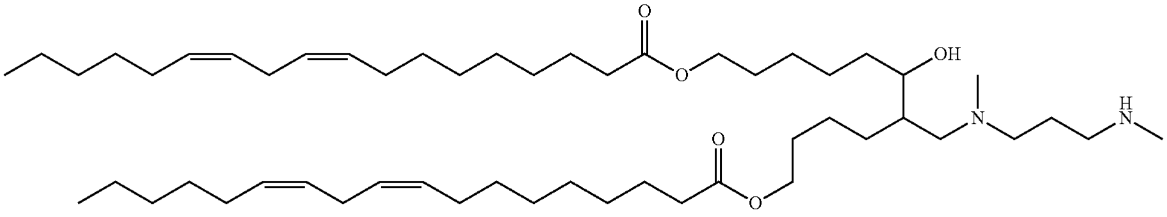
35
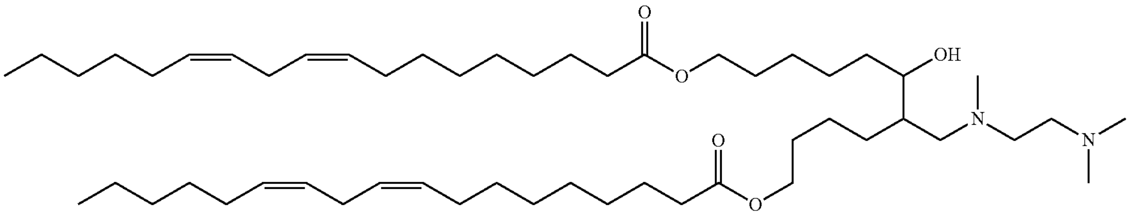
36
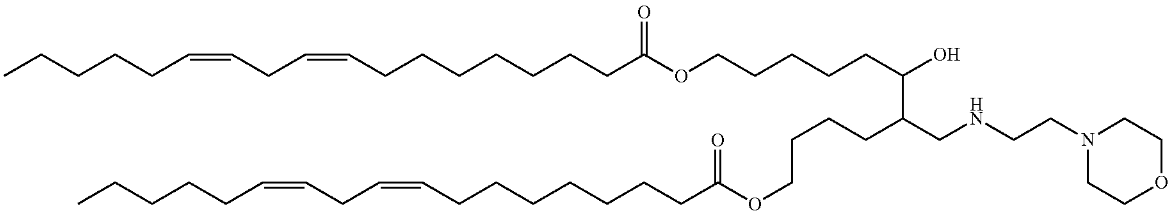

-continued
37
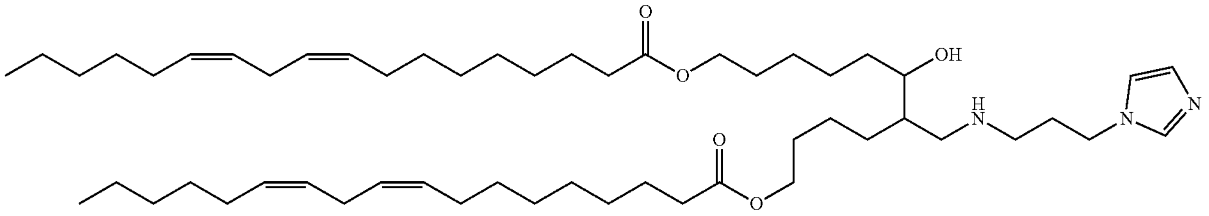
38
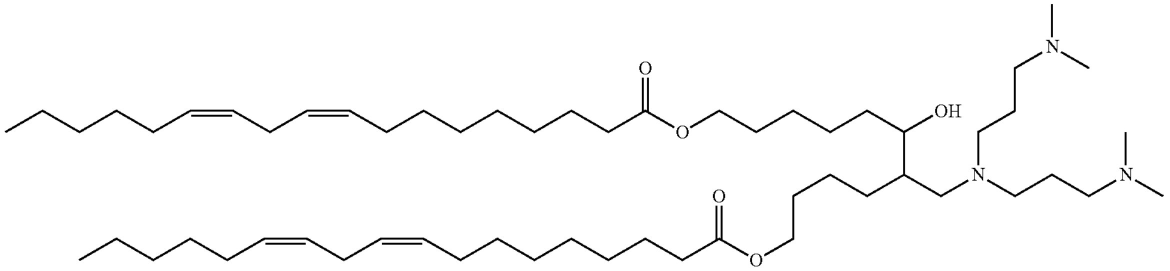
39
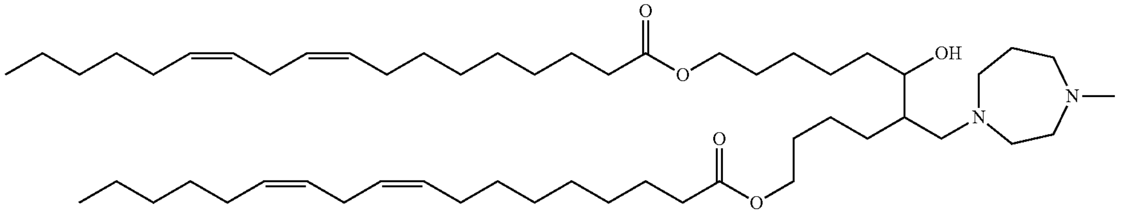
40
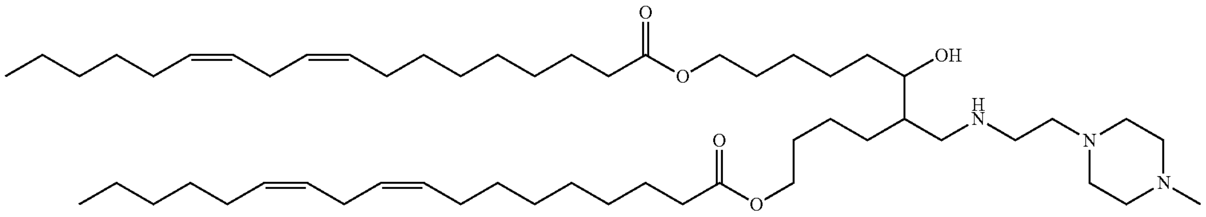
41
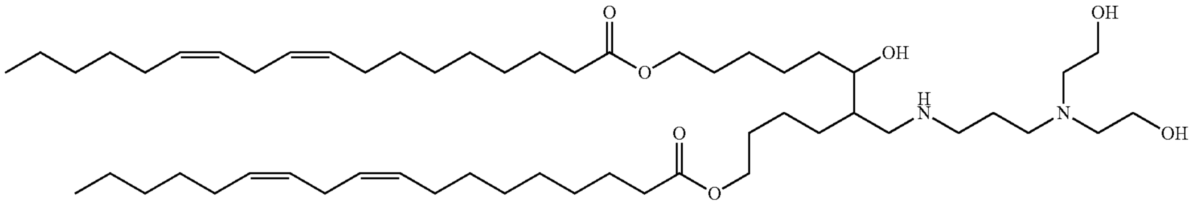
42
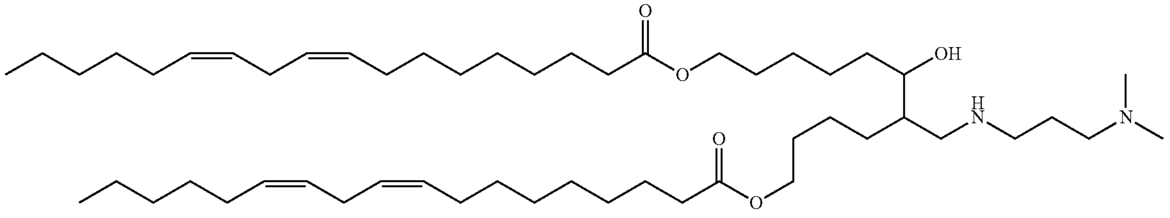

-continued
43
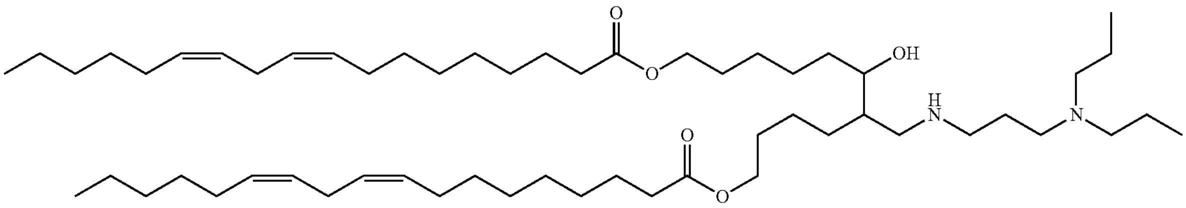
44
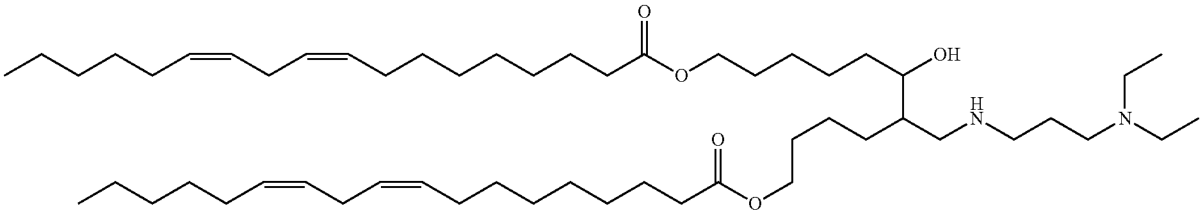
45
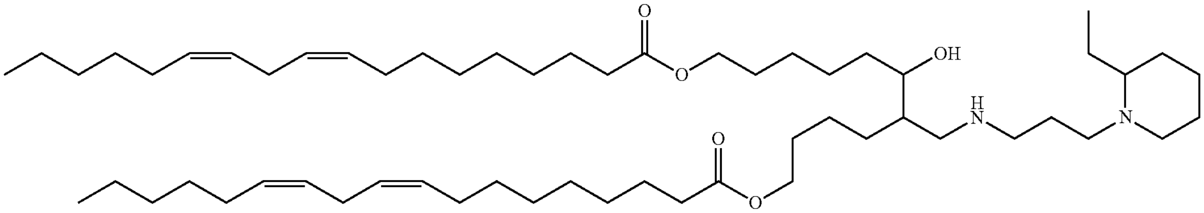
46
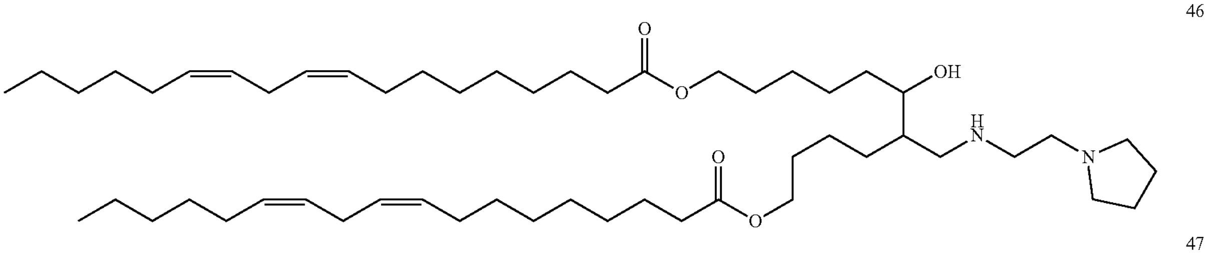
47
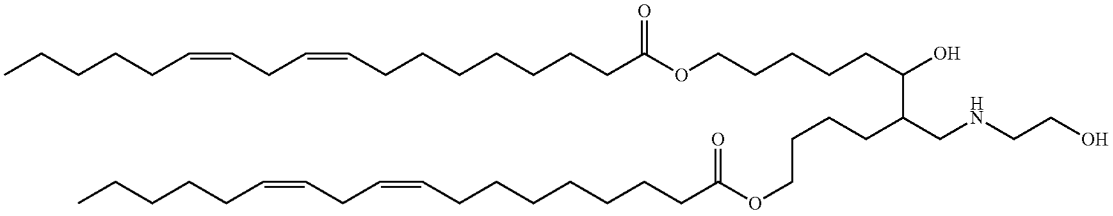
48
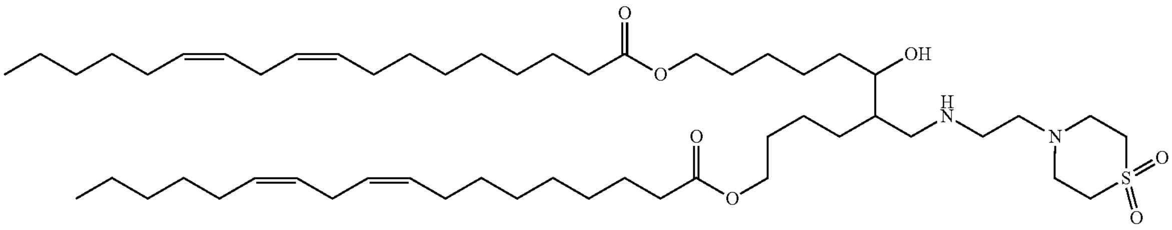
49
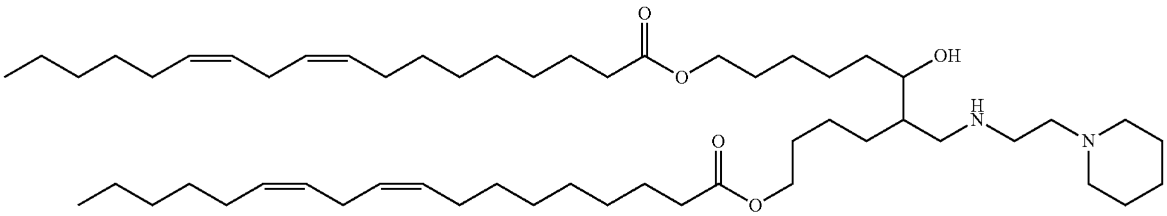

-continued
50
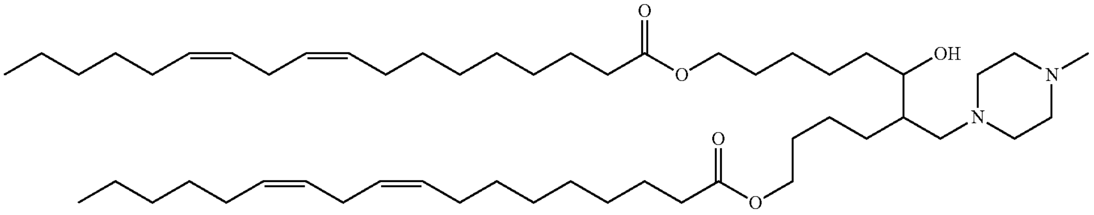
51
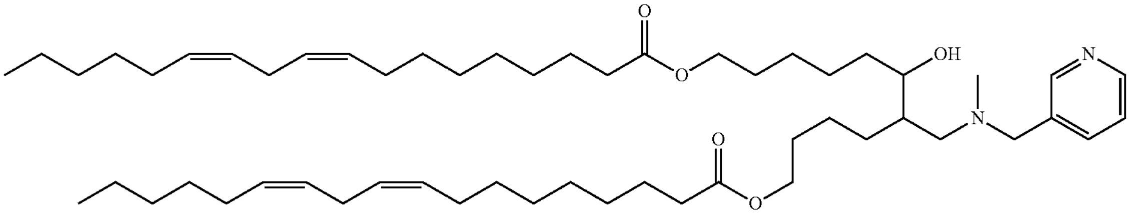
52
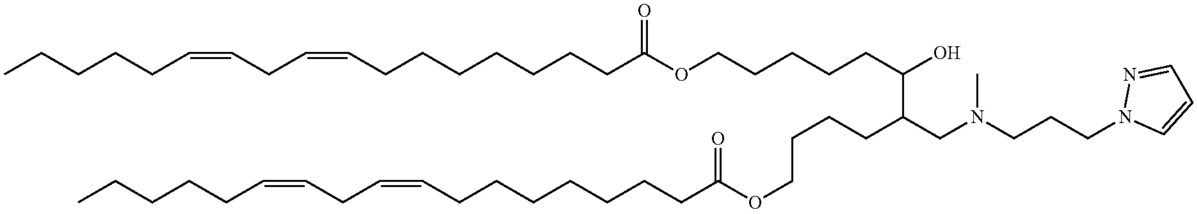
53
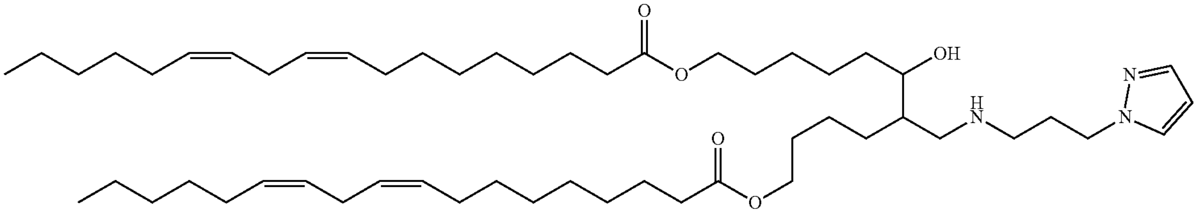
54
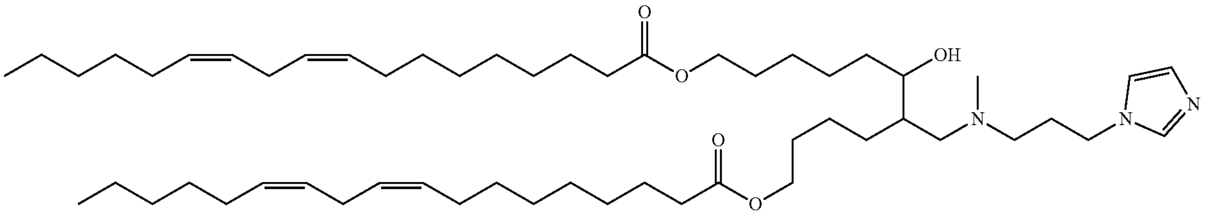
55
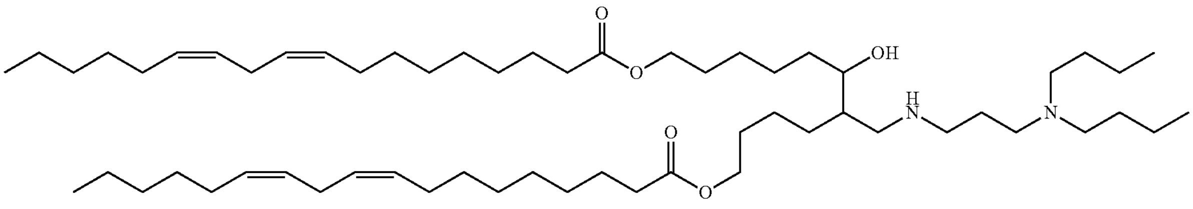
56
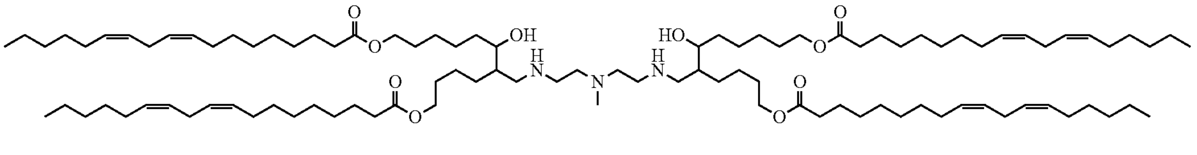

-continued
62
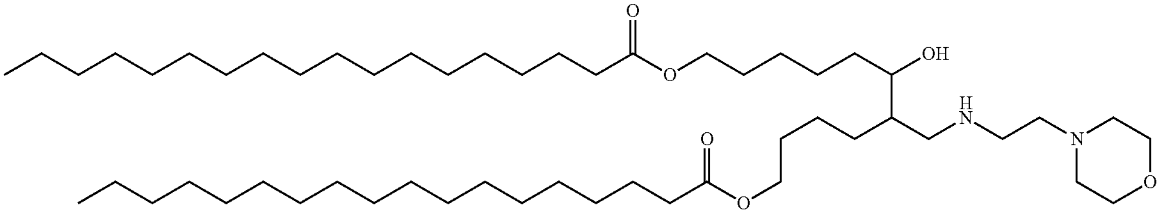
63
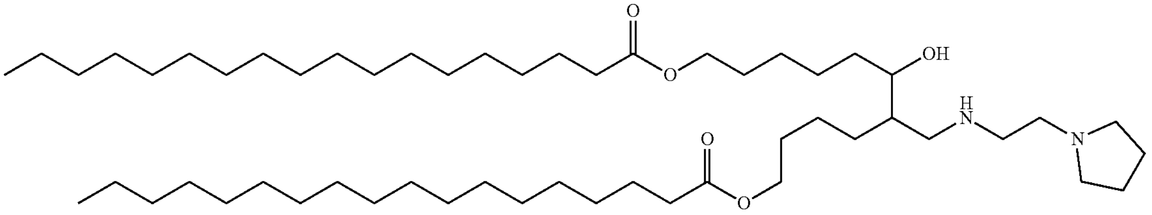
64
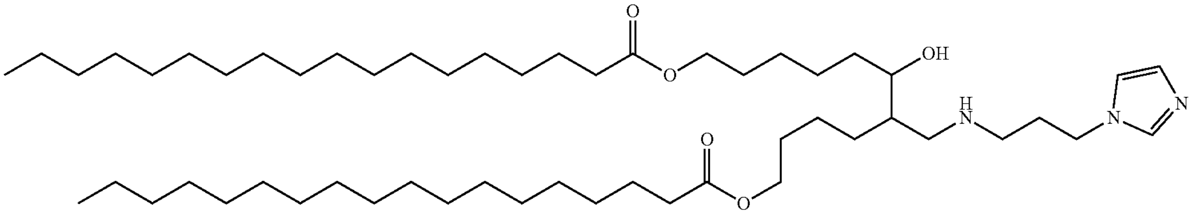
65
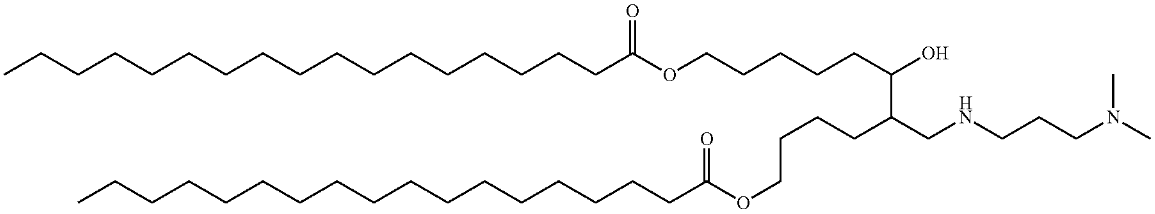
66
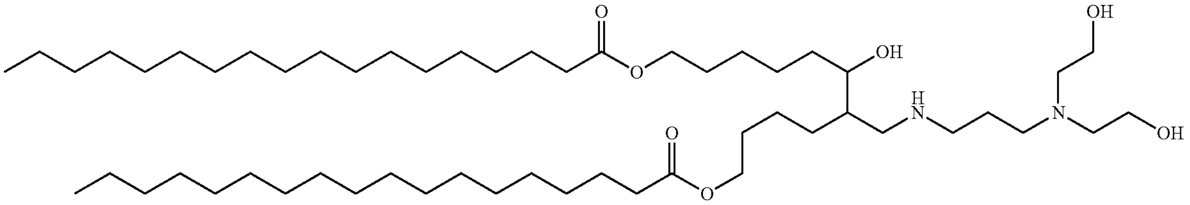
67
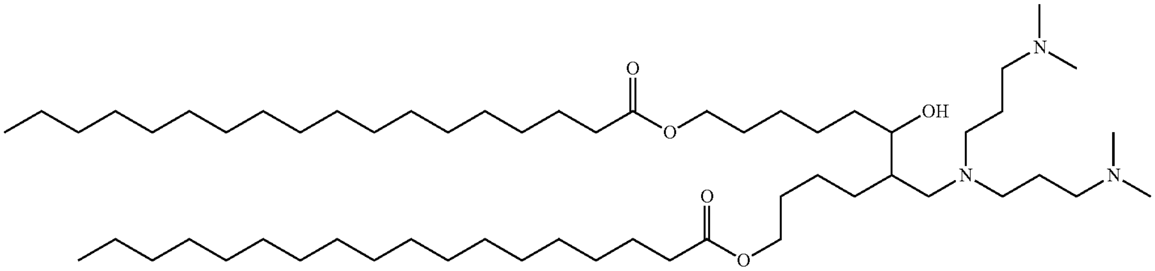

-continued
68
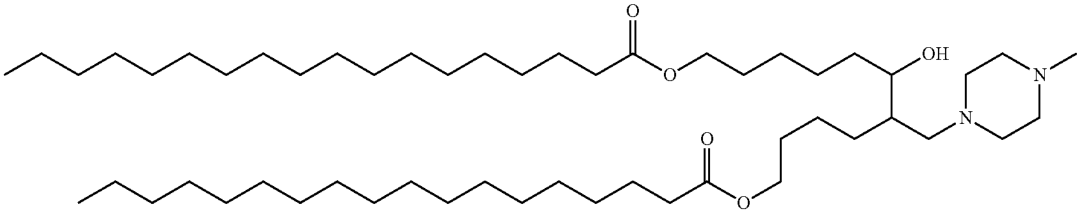
69
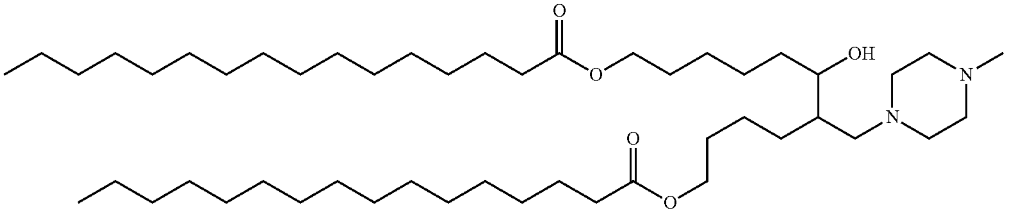
70
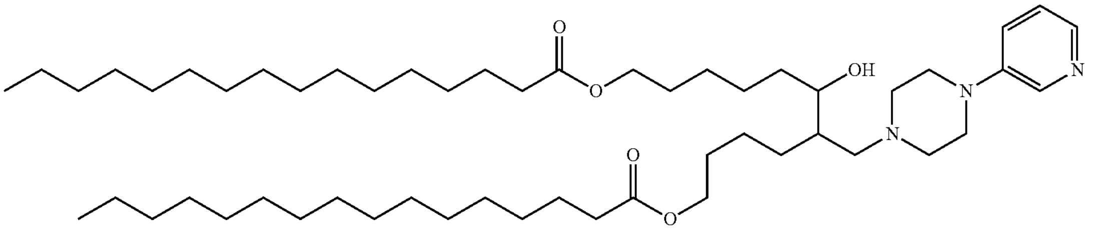
71
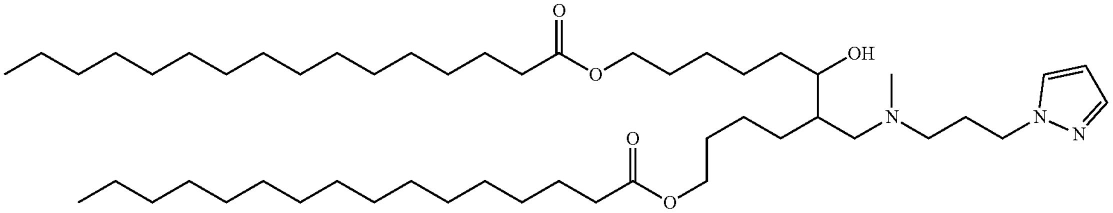
72
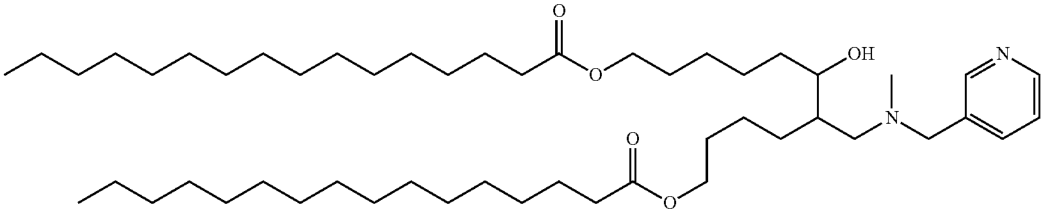
73
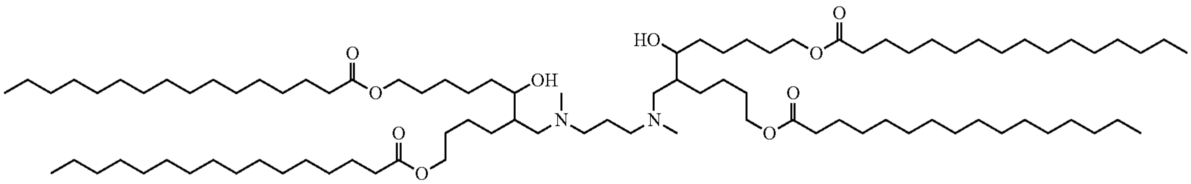
74
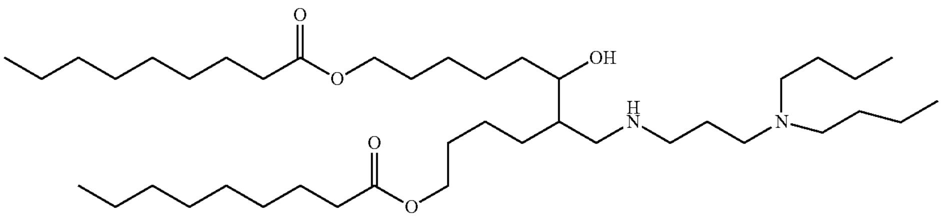
117-17-$C_9$ -continued
75
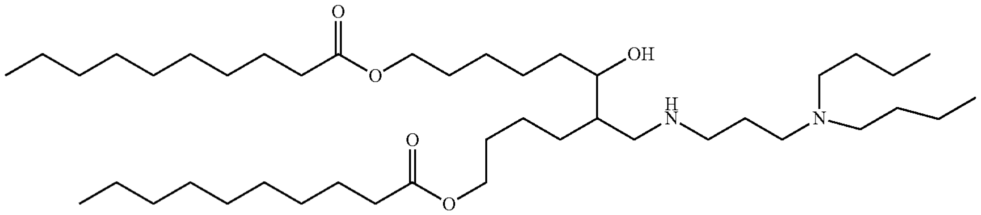
117-17-$C_{10}$
76
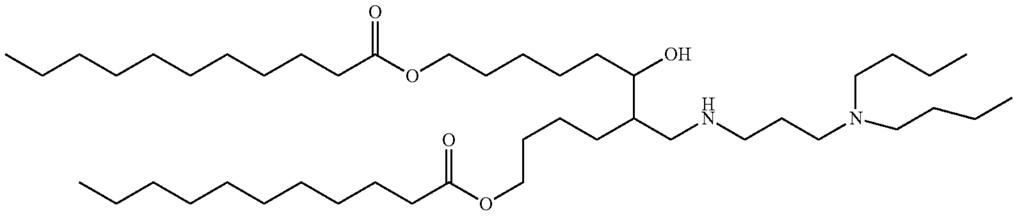
117-17-$C_{11}$
77
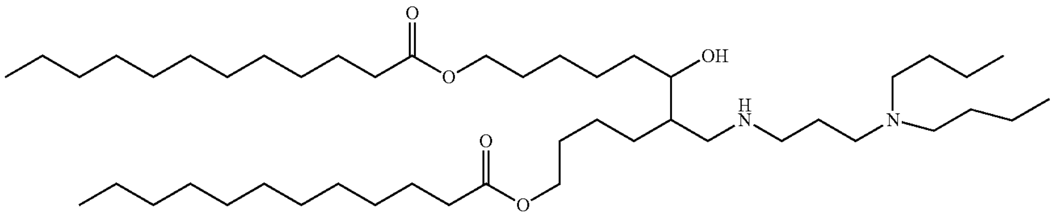
117-17-$C_{12}$
78
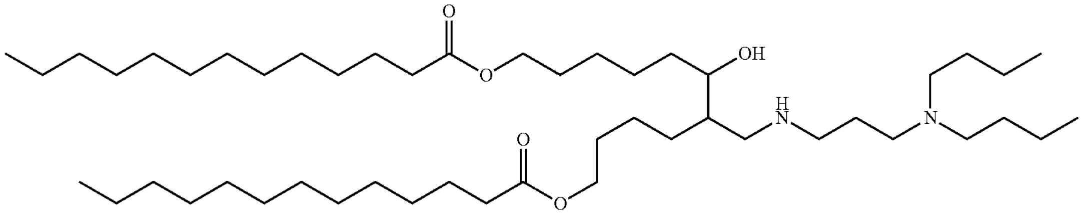
117-17-$C_{13}$
79
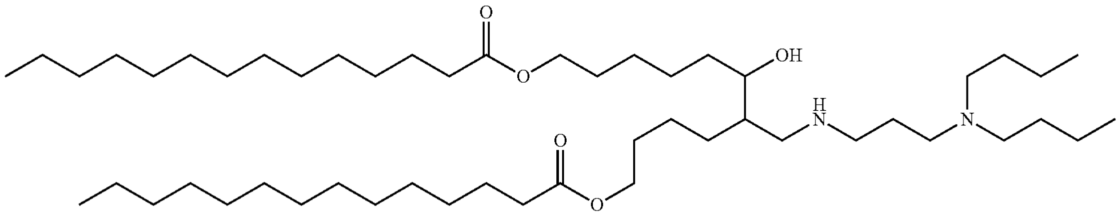
117-17-$C_{14}$
80
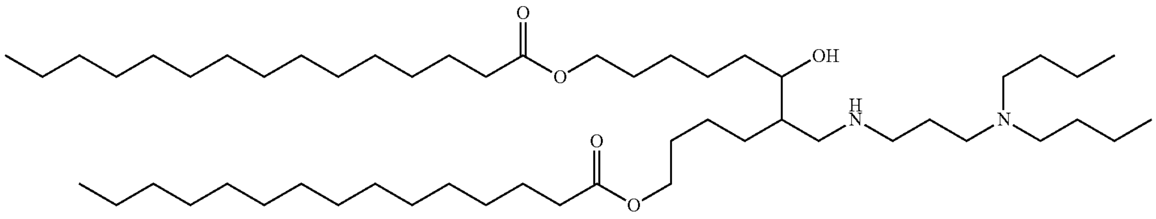
117-17-$C_{15}$ -continued
81
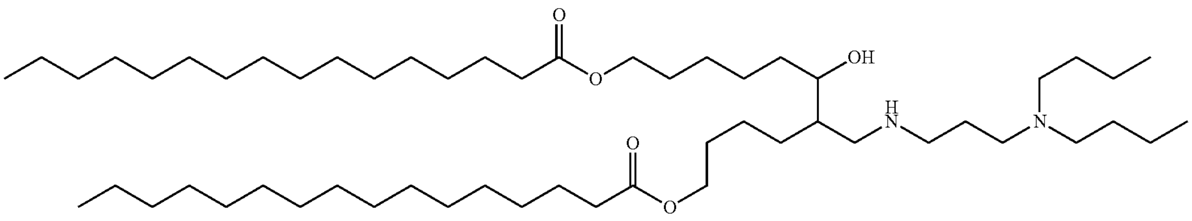
117-17-$C_{16}$
82
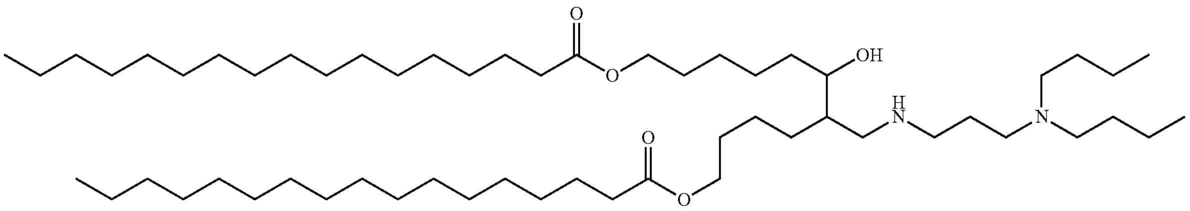
117-17-$C_{17}$
83
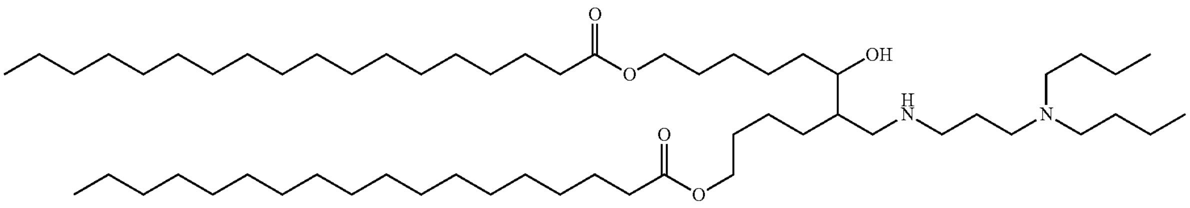
117-17-$C_{18}$
84
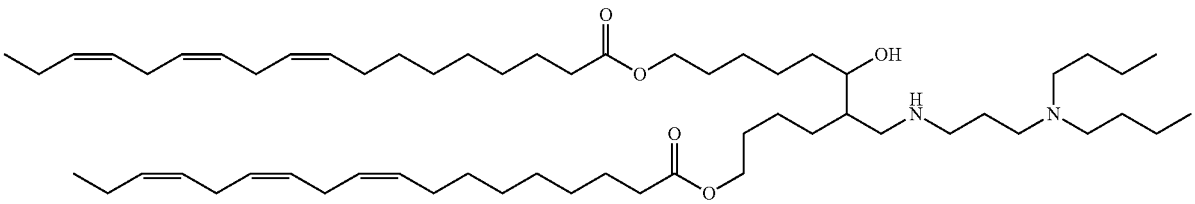
117-17-Linolenic
85
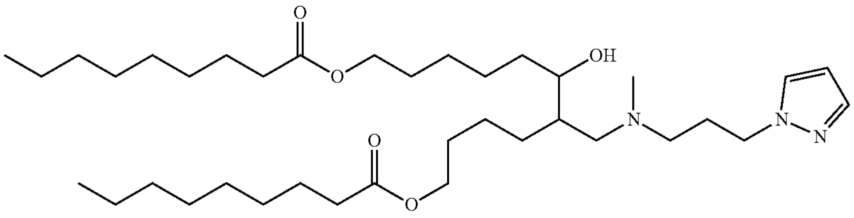
19-Pyrazole-$C_9$
86
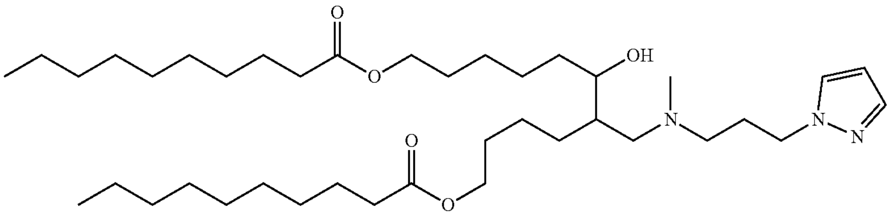
19-Pyrazole-$C_{10}$ -continued
87
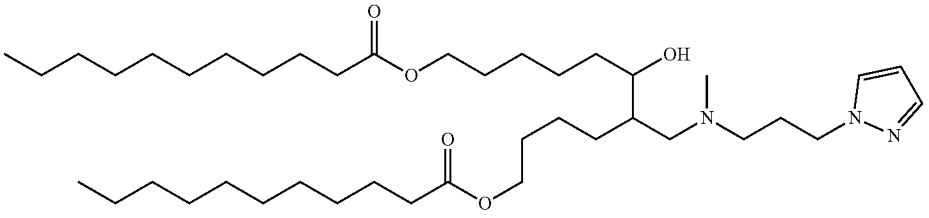
19-Pyrazole-$C_{11}$
88
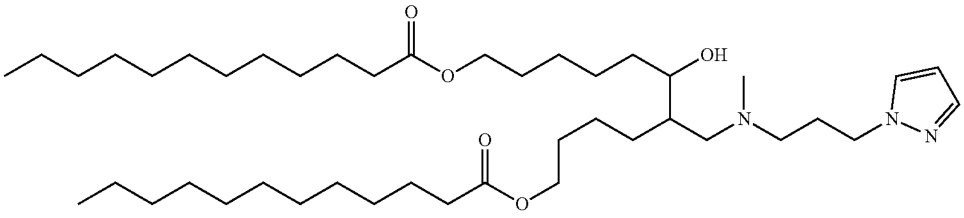
19-Pyrazole-$C_{12}$
89
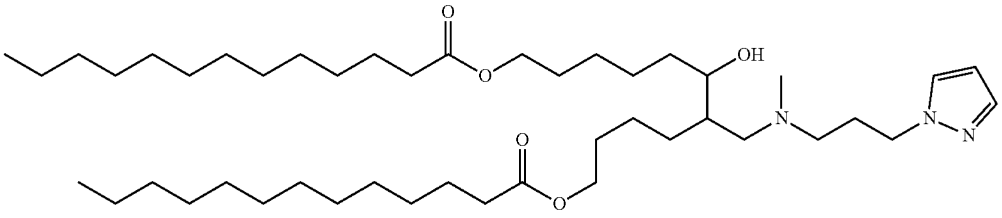
19-Pyrazole-$C_{13}$
90
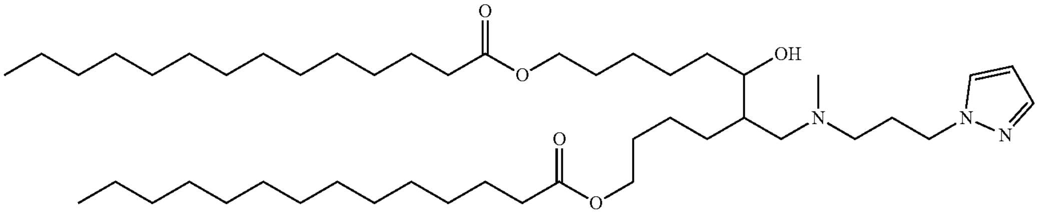
19-Pyrazole-$C_{14}$
91
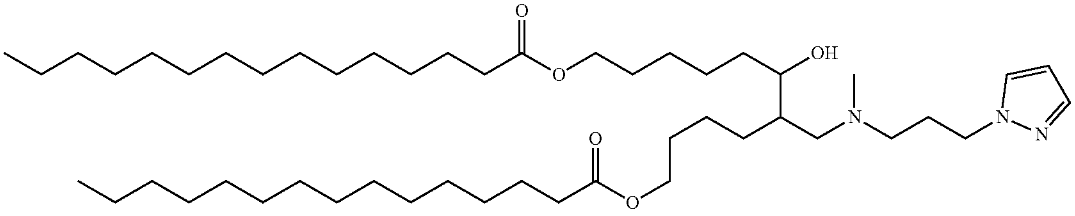
19-Pyrazole-$C_{15}$
92
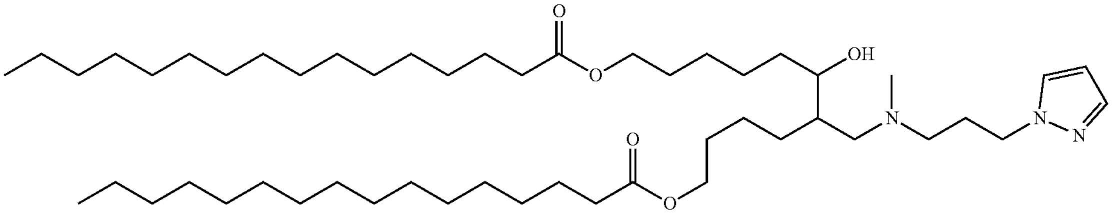
19-Pyrazole-$C_{16}$ -continued
93
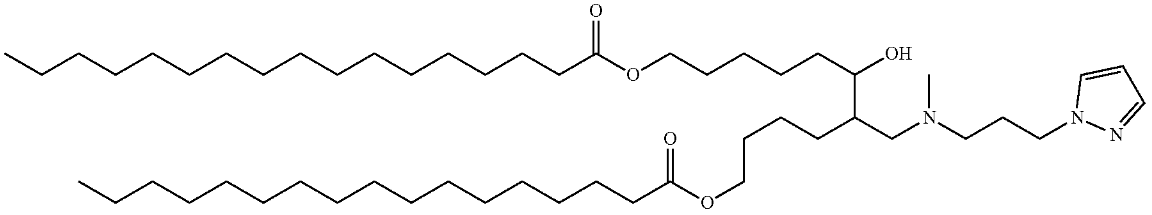
19-Pyrazole-$C_{17}$
94
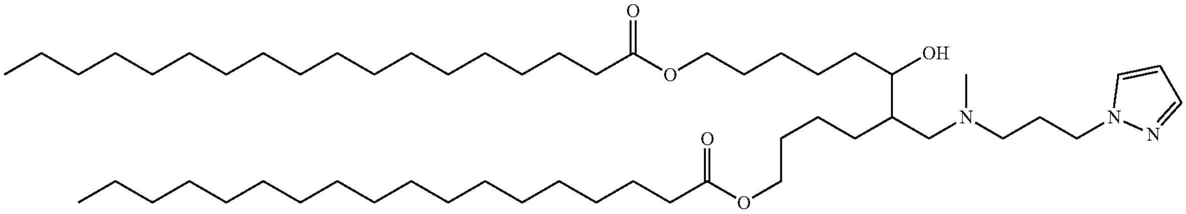
19-Pyrazole-$C_{18}$
95
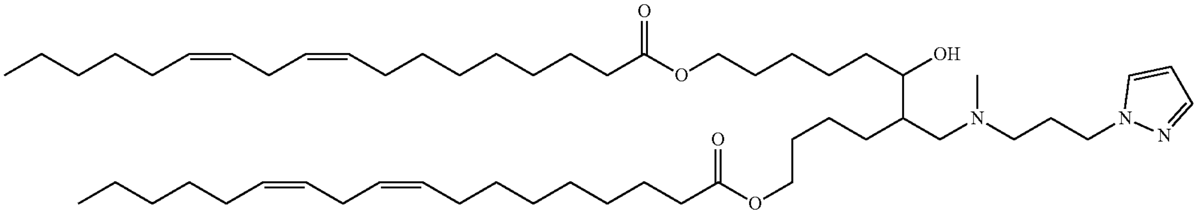
19-Pyrazole-linoleic
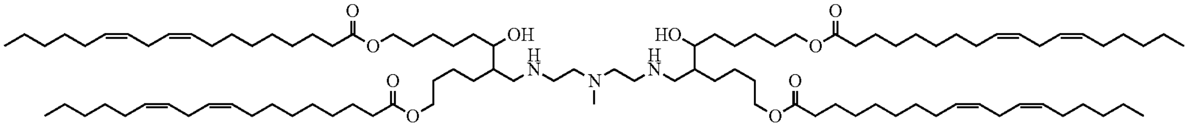
117-7
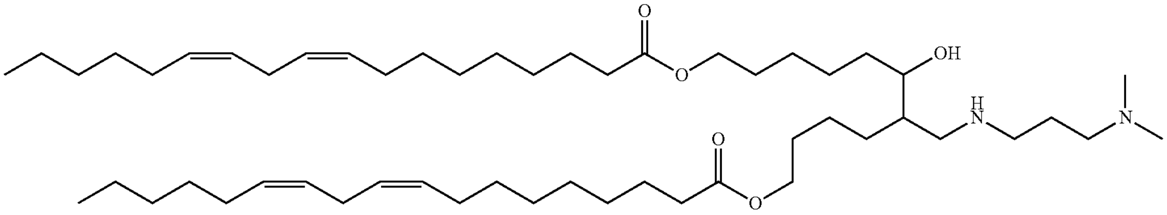
117-8
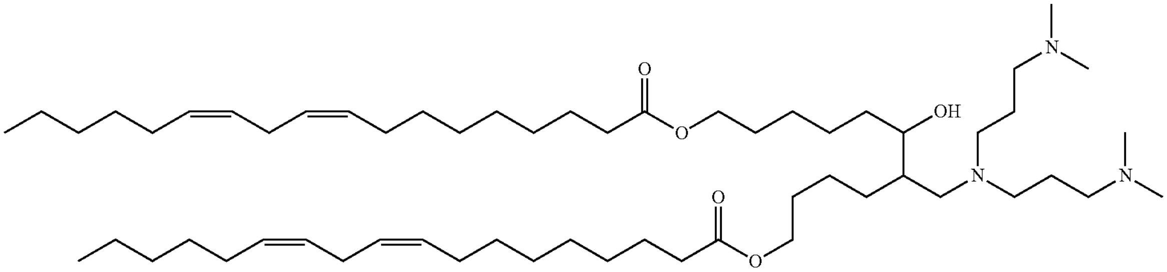
117-9

-continued
96
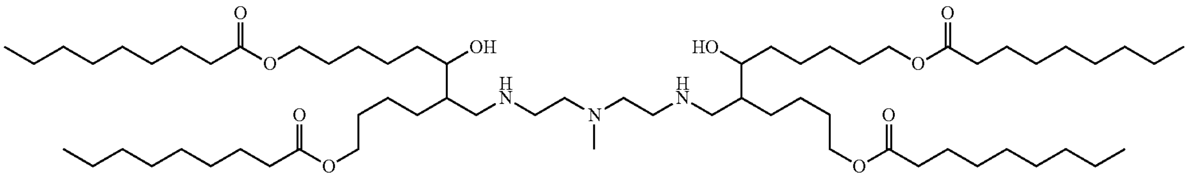
117-7-$C_9$
97
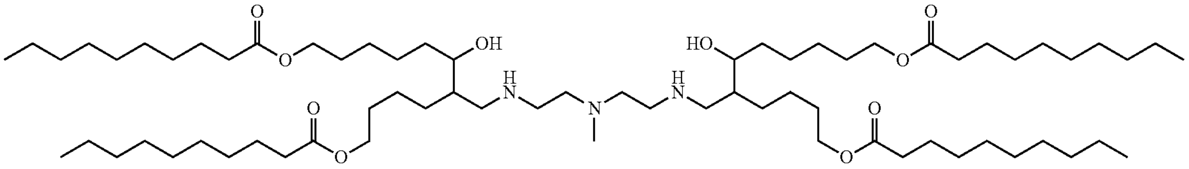
117-7-$C_{10}$
98
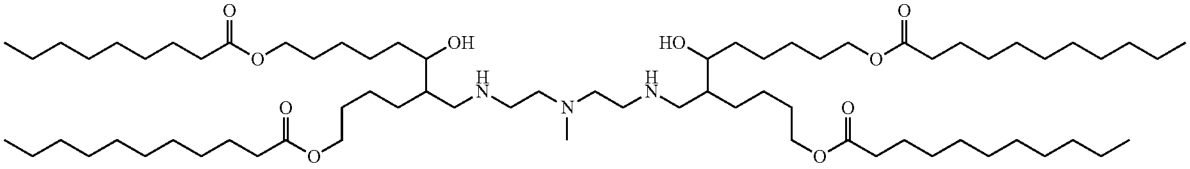
117-7-$C_{11}$
99
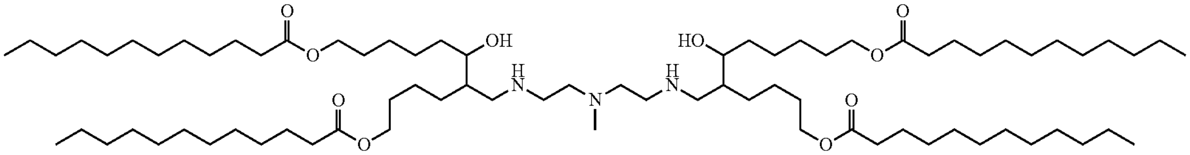
117-7-$C_{12}$
100
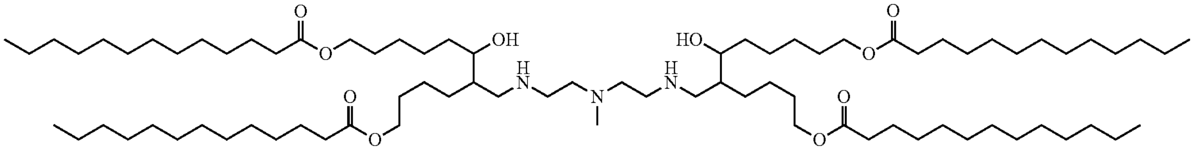
117-7-$C_{13}$
101
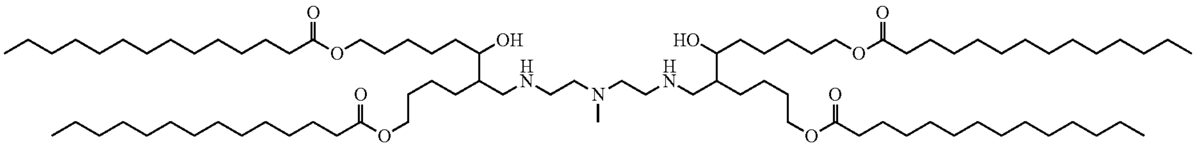
117-7-$C_{14}$
102
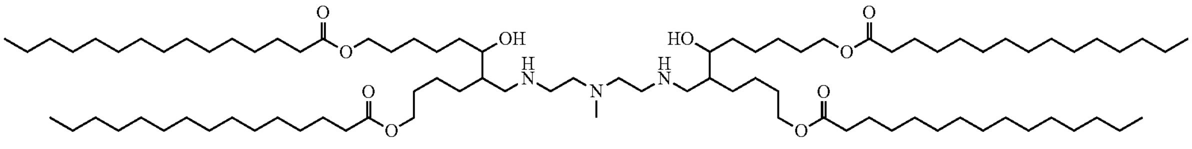
117-7-$C_{15}$ -continued

103

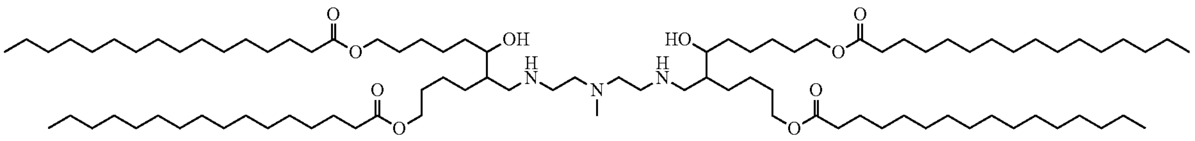

117-7-$C_{16}$

104

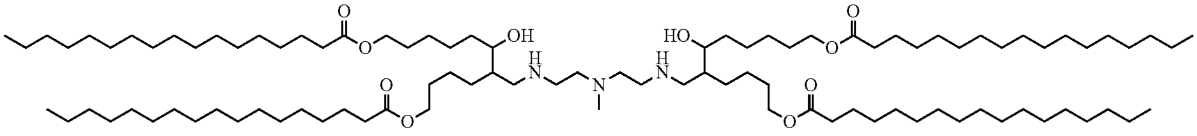

117-7-$C_{17}$

105

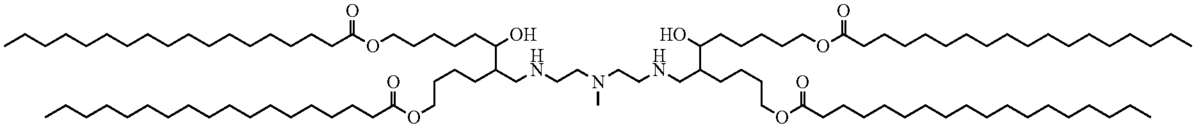

117-7-$C_{18}$

106

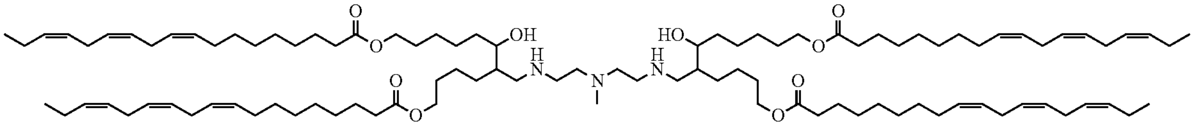

117-7-Linolenic or a pharmaceutically acceptable salt, solvate, tautomer, stereoisomer, or isotopically labeled derivative thereof.

8. A composition comprising a compound of claim 1, or a pharmaceutically acceptable salt, solvate, tautomer, stereoisomer, or isotopically labeled derivative thereof, and an agent.

9. The composition of claim 8, wherein the agent is a protein, peptide, polynucleotide, vaccine, or an immunological agent.

10. The composition of claim 8, wherein the agent is a polynucleotide.

11. The composition of claim 10, wherein the polynucleotide is an RNA.

12. The composition of claim 11, wherein the RNA is RNA is messenger RNA (mRNA), single-stranded RNA (ssRNA), double-stranded RNA (dsRNA), small interfering RNA (siRNA), precursor messenger RNA (pre-mRNA), small hairpin RNA or short hairpin RNA (shRNA), microRNA (miRNA), guide RNA (gRNA), transfer RNA (tRNA), antisense RNA (asRNA), heterogeneous nuclear RNA (hnRNA), coding RNA, non-coding RNA (ncRNA), long non-coding RNA (long ncRNA or lncRNA), satellite RNA, viral satellite RNA, signal recognition particle RNA, small cytoplasmic RNA, small nuclear RNA (snRNA), ribosomal RNA (rRNA), Piwi-interacting RNA (piRNA), polyinosinic acid, ribozyme, flexizyme, small nucleolar RNA (snoRNA), spliced leader RNA, viral RNA, or viral satellite RNA.

13. The composition of claim 12, wherein the RNA is mRNA.

14. The composition of claim 10, wherein the polynucleotide is a DNA.

15. The composition of claim 14, wherein the DNA is a plasmid DNA (pDNA).

16. The composition of claim 8, wherein the composition further comprises one or more of a PEG-lipid, sterol, phospholipid, or helper lipid.

17. A kit comprising:

a compound of claim 1, or a pharmaceutically acceptable salt, solvate, tautomer, stereoisomer, or isotopically labeled derivative thereof; and instructions for using the compound, or pharmaceutically acceptable salt, solvate, tautomer, stereoisomer, or isotopically labeled derivative thereof, or composition.

18. The compound of claim 1, or a pharmaceutically acceptable salt, solvate, tautomer, stereoisomer, or isotopically labeled derivative thereof, wherein $R^1$ is —H or -Me.

19. The compound of claim 3, or a pharmaceutically acceptable salt, solvate, tautomer, stereoisomer, or isotopically labeled derivative thereof, wherein $R^2$ is

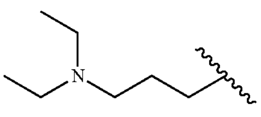,
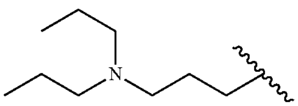,
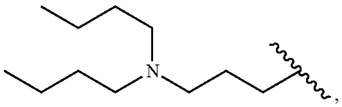,

-continued

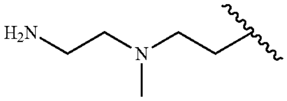,
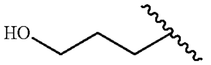,
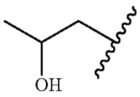,
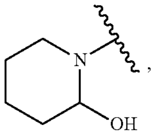, or
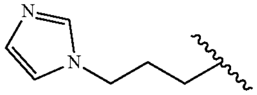.

20. The compound of claim 5, or a pharmaceutically acceptable salt, solvate, tautomer, stereoisomer, or isotopically labeled derivative thereof, wherein —$NR^1R^2$ is

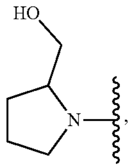,
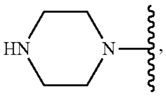,
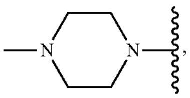,
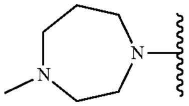,
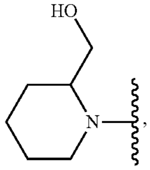, or
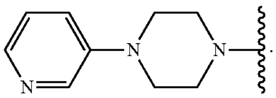.

21. The compound of claim 6, or a pharmaceutically acceptable salt, solvate, tautomer, stereoisomer, or isotopically labeled derivative thereof, wherein each $R^3$ is independently

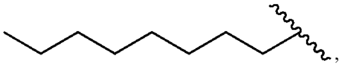,
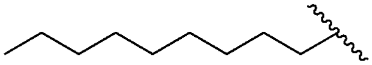,

-continued

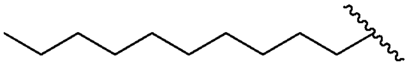,
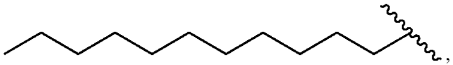,
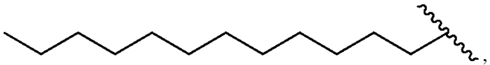,
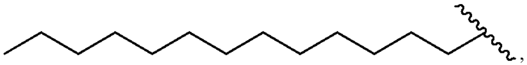,
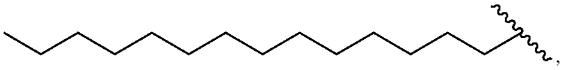,
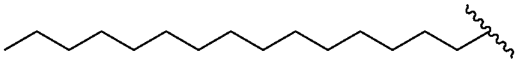,
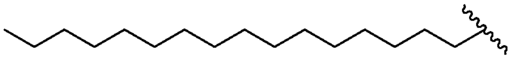,
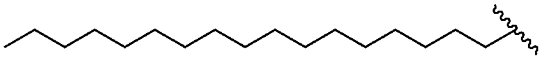,
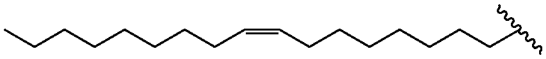,
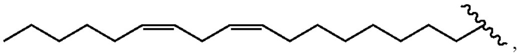, or
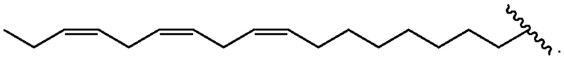.

22. The compound of claim 1, wherein $R^1$ is —H or optionally substituted $C_1$-$C_{10}$ alkyl, and $R^2$ is optionally substituted $C_1$-$C_{10}$ alkyl, optionally substituted $C_1$-$C_{10}$ heteroalkyl, optionally substituted $C_3$-$C_{14}$ carbocyclyl, or optionally substituted 3- to 14-membered heterocyclyl; or $R^1$ and $R^2$ are joined together with the intervening atoms to form an optionally substituted heterocyclyl comprising one or two nitrogen atoms.

23. The compound of claim 1, wherein $R^1$ is —H or optionally substituted $C_1$-$C_{10}$ alkyl, and each $R^3$ independently is optionally substituted $C_6$-$C_{25}$ alkyl or optionally substituted $C_6$-$C_{25}$ alkenyl.

24. The compound of claim 1, wherein $R^2$ is optionally substituted $C_1$-$C_{10}$ alkyl, optionally substituted $C_1$-$C_{10}$ heteroalkyl, optionally substituted $C_3$-$C_{14}$ carbocyclyl, or optionally substituted 3- to 14-membered heterocyclyl, and each $R^3$ independently is optionally substituted $C_6$-$C_{25}$ alkyl or optionally substituted $C_6$-$C_{25}$ alkenyl.

25. The compound of claim 1, or a pharmaceutically acceptable salt thereof.

* * * * *